United States Patent [19]

Martin et al.

[11] Patent Number: 5,658,956
[45] Date of Patent: Aug. 19, 1997

[54] BIOADHESIVE-WOUND HEALING COMPOSITIONS AND METHODS FOR PREPARING AND USING SAME

[75] Inventors: Alain Martin, Ringoes; Sau-Hung S. Leung, Parsippany, both of N.J.

[73] Assignee: Warner-Lambert Company, Morris Plains, N.J.

[21] Appl. No.: 445,824

[22] Filed: May 22, 1995

Related U.S. Application Data

[63] Continuation-in-part of Ser. No. 298,521, Aug. 30, 1994, abandoned, which is a continuation-in-part of Ser. No. 53,922, Apr. 26, 1993, abandoned, which is a continuation of Ser. No. 663,500, Mar. 1, 1991, abandoned.

[51] Int. Cl.$^6$ .......................... A61K 31/045; A61K 31/07; A61K 31/355; A61L 15/00
[52] U.S. Cl. .......................... 514/724; 514/725; 514/458; 514/904; 514/969; 514/887; 514/886; 514/943; 424/DIG. 13; 424/445; 424/446; 424/447
[58] Field of Search .......................... 514/725, 724, 514/943, 886, 887, 904, 969, 458; 424/DIG. 13, 445, 446, 447

[56] References Cited

U.S. PATENT DOCUMENTS

| | | |
|---|---|---|
| 3,887,702 | 6/1975 | Baldwin .......................... 424/61 |
| 3,920,835 | 11/1975 | Van Scott et al. .......................... 424/311 |
| 3,984,566 | 10/1976 | Van Scott et al. .......................... 424/283 |
| 3,988,470 | 10/1976 | Van Scott et al. .......................... 424/283 |
| 4,105,783 | 8/1978 | Yu et al. .......................... 424/283 |
| 4,158,057 | 6/1979 | Stanko .......................... 424/252 |
| 4,170,821 | 10/1979 | Booth .......................... 30/41 |
| 4,197,316 | 4/1980 | Yu et al. .......................... 424/317 |
| 4,234,599 | 11/1980 | Van Scott et al. .......................... 424/279 |
| 4,246,261 | 1/1981 | Van Scott et al. .......................... 424/240 |
| 4,284,630 | 8/1981 | Yu et al. .......................... 424/241 |
| 4,294,852 | 10/1981 | Wildnauer et al. .......................... 424/317 |
| 4,351,835 | 9/1982 | Stanko .......................... 424/252 |
| 4,363,815 | 12/1982 | Yu et al. .......................... 424/274 |
| 4,415,576 | 11/1983 | Stanko .......................... 424/252 |
| 4,416,982 | 11/1983 | Tsuda et al. .......................... 435/11 |
| 4,451,482 | 5/1984 | Cagen .......................... 424/284 |
| 4,454,159 | 6/1984 | Musher .......................... 424/258 |
| 4,496,536 | 1/1985 | Moller .......................... 424/70 |
| 4,521,375 | 6/1985 | Houlsby .......................... 422/29 |
| 4,533,637 | 8/1985 | Yamane .......................... 435/240 |
| 4,548,937 | 10/1985 | Stanko .......................... 514/251 |
| 4,615,697 | 10/1986 | Robinson .......................... 604/890 |
| 4,645,764 | 2/1987 | Stanko .......................... 514/251 |
| 4,663,166 | 5/1987 | Veech .......................... 424/146 |
| 4,696,917 | 9/1987 | Lindstrom et al. .......................... 514/54 |
| 4,725,586 | 2/1988 | Lindstrom et al. .......................... 514/54 |
| 4,734,276 | 3/1988 | Ziegler .......................... 424/10 |
| 4,812,479 | 3/1989 | Stanko .......................... 514/557 |
| 4,847,069 | 7/1989 | Bissett et al. .......................... 424/47 |
| 4,847,071 | 7/1989 | Bissett et al. .......................... 424/59 |
| 4,847,072 | 7/1989 | Bissett et al. .......................... 424/59 |
| 4,874,603 | 10/1989 | Fratzer .......................... 424/10 |
| 5,084,482 | 1/1992 | Hirsch et al. .......................... 514/562 |
| 5,296,307 | 3/1994 | Martin et al. .......................... 435/252.1 |

FOREIGN PATENT DOCUMENTS

| | | | |
|---|---|---|---|
| 0348627A1 | 4/1989 | European Pat. Off. | ........ B26B 21/44 |
| 0345082A | 6/1989 | European Pat. Off. | ........ A61K 31/19 |
| 0347056A1 | 12/1989 | European Pat. Off. | ........ A61K 31/20 |
| 0371421 | 6/1990 | European Pat. Off. | . |
| 0410696A1 | 7/1990 | European Pat. Off. | ......... A61K 9/70 |
| 3719097C1 | 6/1988 | Germany | ..................... A61K 31/355 |
| 51-032738 | 3/1976 | Japan . | |
| 2009017 | 11/1978 | United Kingdom | ............ B26B 21/44 |
| 2196348 | 9/1987 | United Kingdom | ............. C12N 5/02 |

OTHER PUBLICATIONS

Bauer, G., et al, "Reversal of Doxorubicin–Impaired Wound Healing Using Triad Compound," *The American Surgeon*, vol. 60, No. 6, Jun. 1994, pp. 455–459.

Duchene, D., et al., "Pharmaceutical and Medical Aspects of Bioadhesive Systems from Drug Administration," *Drug Development and Industrial Pharmacy*, vol. 14, No. 2–3, 1988, pp. 283–318.

Giannelli, S. Jr., et al. (May 1976). Prevention of increased hemoglobin–oxygen affinity in open–heart operations with inosine–phosphate–pyruvate solution. *Annals of Thoracic Surgery*, vol. 21, No. 5, pp. 386–396.

Freese, E., et al. (1971). Molecular mechanisms of mutations. In *Chemical Mutations* (A. Hollander, ed.), Plenum Press, New York–London, pp. 46–48.

Marchek, A. C., et al. (Jun. 1977) Increased in vito growth capacity of tracheal epithelium exposed in vivo to 7, 12 dimethylbenz(a)anthracene. *Cancer Research*, vol. 37, pp. 1811–1921.

Schwartz, C., et al. (May 7, 1979). Antagonism of cyanide intoxication with sodium pyruvate. *Toxicology and Applied Pharmacology*, vol. 50, pp. 437–441.

Ahmed, A. M. et al. (1979). Effects of ascorbic acid and various keto–acids on the glyoxalase enzyme system in mouse and rat liver. *IRCS Medical Science*, vol. 7, pp. 505.

Mochizuki, S., et al. (1980). Energy metabolism during reperfusion following ischemia. *J. Physiol.*, Paris, vol. 76, pp. 805–812.

(List continued on next page.)

*Primary Examiner*—Theodore J. Criares
*Attorney, Agent, or Firm*—Jean B. Barish

[57] ABSTRACT

The present invention pertains to therapeutic bioadhesive-wound healing compositions useful for treating wounds and increasing the proliferation and resuscitation rate of mammalian cells. The compositions comprise a bioadhesive agent and a therapeutically effective amount of a wound healing composition. In one embodiment the wound healing composition comprises (a) pyruvate; (b) an antioxidant; and (c) a mixture of saturated and unsaturated fatty acids. The therapeutic bioadhesive-wound healing compositions may further comprise medicaments such as antiviral agents, antikeratolytic agents, anti-inflammatory agents, antifungal agents, antibacterial agents, immunostimulating agents, and the like. The bioadhesive-wound healing compositions may be utilized in a wide variety of pharmaceutical products. This invention also relates to methods for preparing and using the bioadhesive-wound healing compositions and the pharmaceutical products in which the compositions may be used.

32 Claims, 77 Drawing Sheets

OTHER PUBLICATIONS

Cohen, M. H., (Spring, 1981). Cure of Advanced L1210 leukemia after correction of abnormal red blood cell deformability. *Cancer Chemother, Pharmacol.*, vol. 5, pp. 175–179.

Regitz, V., et al. (1981). Biochemical mechanism of infarct size reduction by pyruvate. *Cardiovascular Res.* vol. 15, pp. 652–658.

Wolters, M., et al. (1982). The effect of x irradiation on survival of mammalian cells substituted by poly unsaturated fatty–acids. *Radiat. Res.*, vol. 93 (3), pp. 474–482.

Puschmann, V. M. (1983). Animal experimental examinations of the gastric mucosa and demonstration of the analgetic and antipyretic effect after combined application of acetylsalicylic acid and sodium pyruvate. *Arzneim–Forsch/Drug Res.* vol. 33 (I), nr. 3, pp. 410–415.

Puschmann, V. M., et al. (1983). Double–blind controlled gastroscopic comparative study on lesions of the gastric mucosa in healthy volunteers after treatment with acetylsalicylic acid or acetylsalicylic acid/sodium pyruvate. *Arzneim–Forsch/Drug Res.*, vol. 33(I) nr. 33, pp. 415–416.

Subramanyam, K. (Sep. 1984). Effects of Preparation–H on wound healing in the rectum of man. *Digestive Diseases and Sciences*, vol. 29, No. 9, pp. 829–832.

Bunger, R., et al. (1986). Pyruvate attenuation of hypoxia damage in isolated working guinea–pig heart. *J. Mol Cell Cardiol*, vol. 18, pp. 234–438.

Andrae, U., et al. (1985). Pyruvate and related a–ketoacids protect mammaliancells in culture against hydrogen peroxide–induced cytotoxicity. *Toxicology Letters*, vol. 28, pp. 93–98.

Cohen, J., et al. (Jun. 1985). Pregnancies following the frozen storage of expanding human blastocycsts. *J. of in Vitro Fertilization and Embryo Transfer*, vol. 2, No. 2, pp. 59–64.

Davis, D. L. (1985). Culture and storage of pig embryos. *J. Reprod. Fert. Suppl.*, vol. 33, pp. 115–124.

Ogawa, Y., et al. (Sep. 1986). Comparative study of the effects of pyruvate and CG–120 in preventing experimental oxalate urolithiasis in rats. *Acta Urol. Jpn.*, vol. 32, No. 9, pp. 1341–1347.

Shacter, E. (1987). Serum–free medium for growth factor–dependent and independent plasmacytomas and hybridomas. *J. of Immunological Methods*, vol. 99, pp. 259–270.

Varma, S. D., et al. (1988). Peroxide damage to the eye lens in vitro prevention by pyruvate. *Free Rad. Res. Comms.*, vol. 4, No. 5, pp. 283–290.

O'Donnell–Tormey, J., et al., (Feb. 1967). Secretion of pyruvate, an antioxidant defense of mammalian cells. *J. Exp. Med.*, vol. 165, pp. 500–514.

Sabri, M. I., et al. (1989). Effect of exogenous pyruvate on acrylamide neuropathy in rats. *Brain Research*, vol. 483, pp. 1–11.

Mentzer, R. M., et al. (Apr. 1988). Effect of pyruvate on regional ventricular function in normal and stunned myocardium. *Ann. of Surgery*, vol. 209, No. 4, pp. 629–634.

Martin, A., et al. (1990). A resuscitation/selection system for rapid determination of salmonella in foods. *J. Assoc Off. Anal. Chem.*, vol. 74, No. 3, pp. 522–525.

Martin, A., et al. (1990). A resuscitation medium for rapid recovery and isolation of injured Salmonella, *Escherichia coli, Staphylococcus aureus*, and listeria in food. (unpublished Ph.D. dissertation, Rutgers Univ., N.J.).

Salahudeen, A. K., et al. (1991). Hydrogen peroxide–induced renal injury, a protective role for pyruvate in vitro and in vivo. *J. Clin. Invest.*, vol. 88, pp. 1886–1893.

FIG-13A
FIG-13B
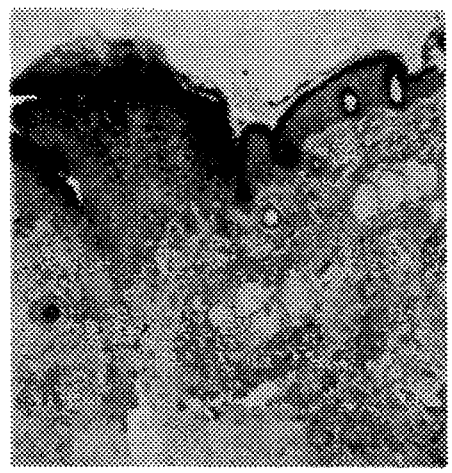

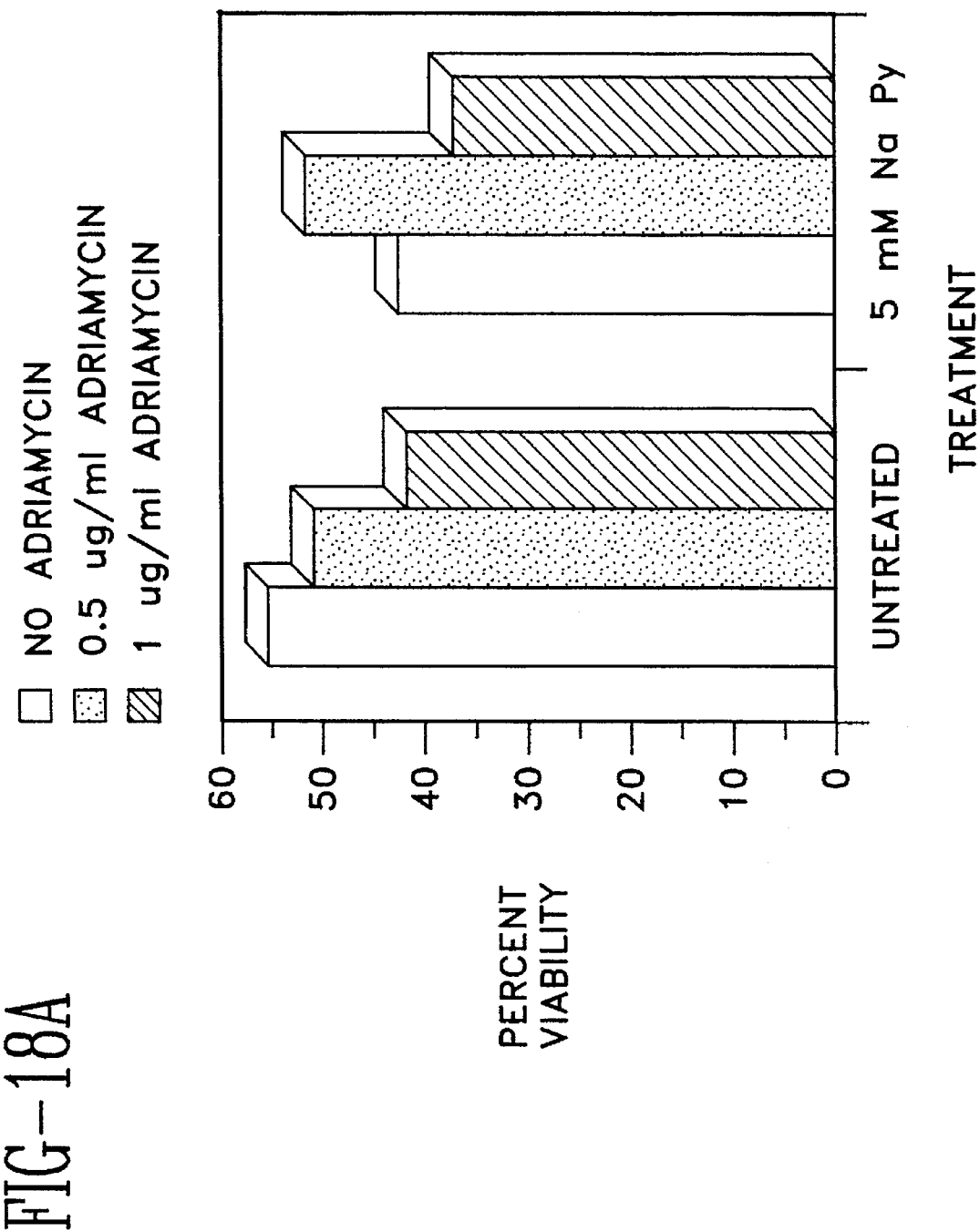

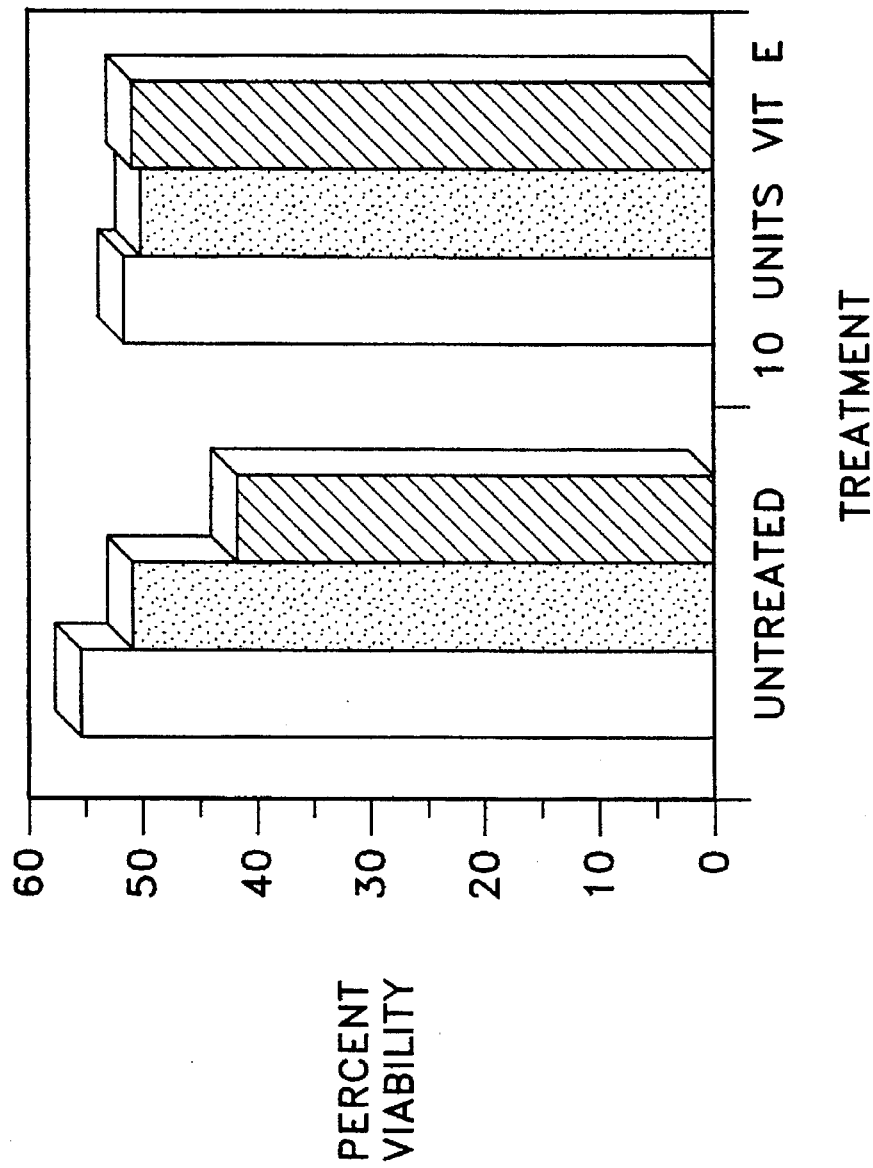

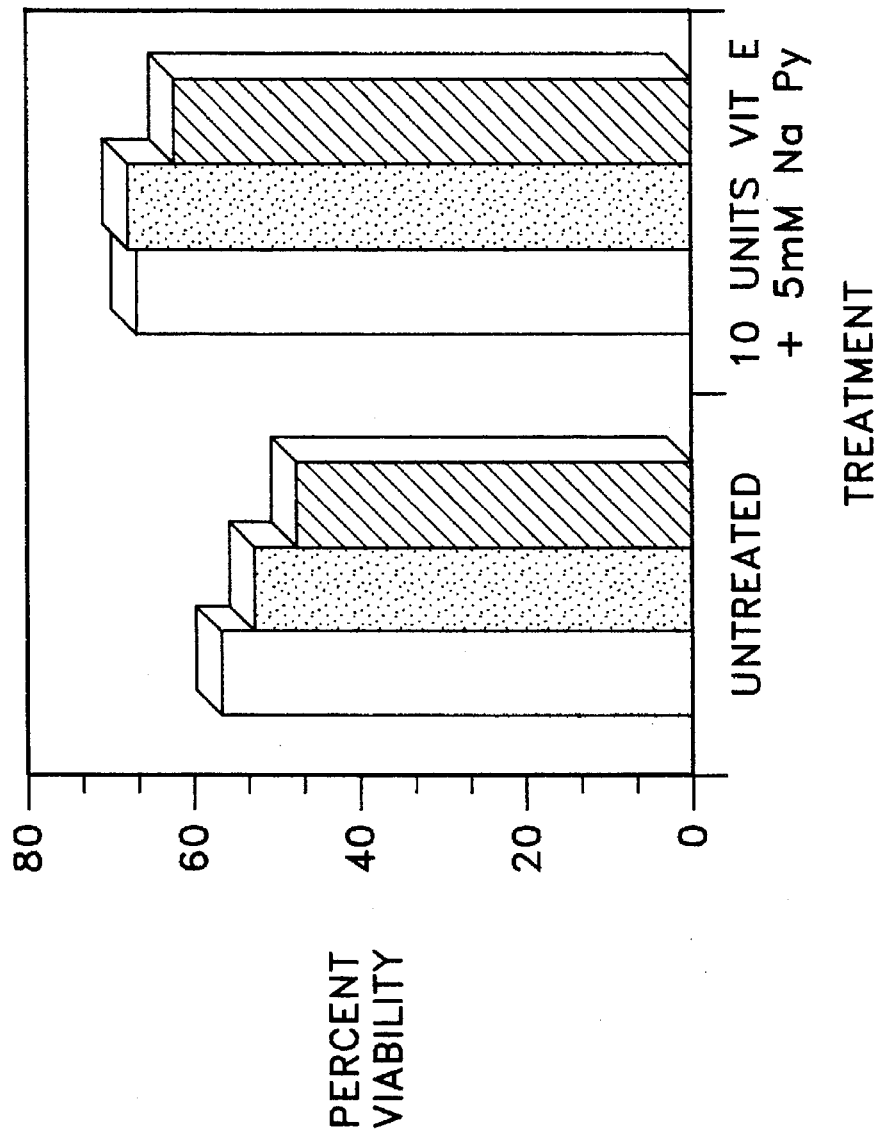

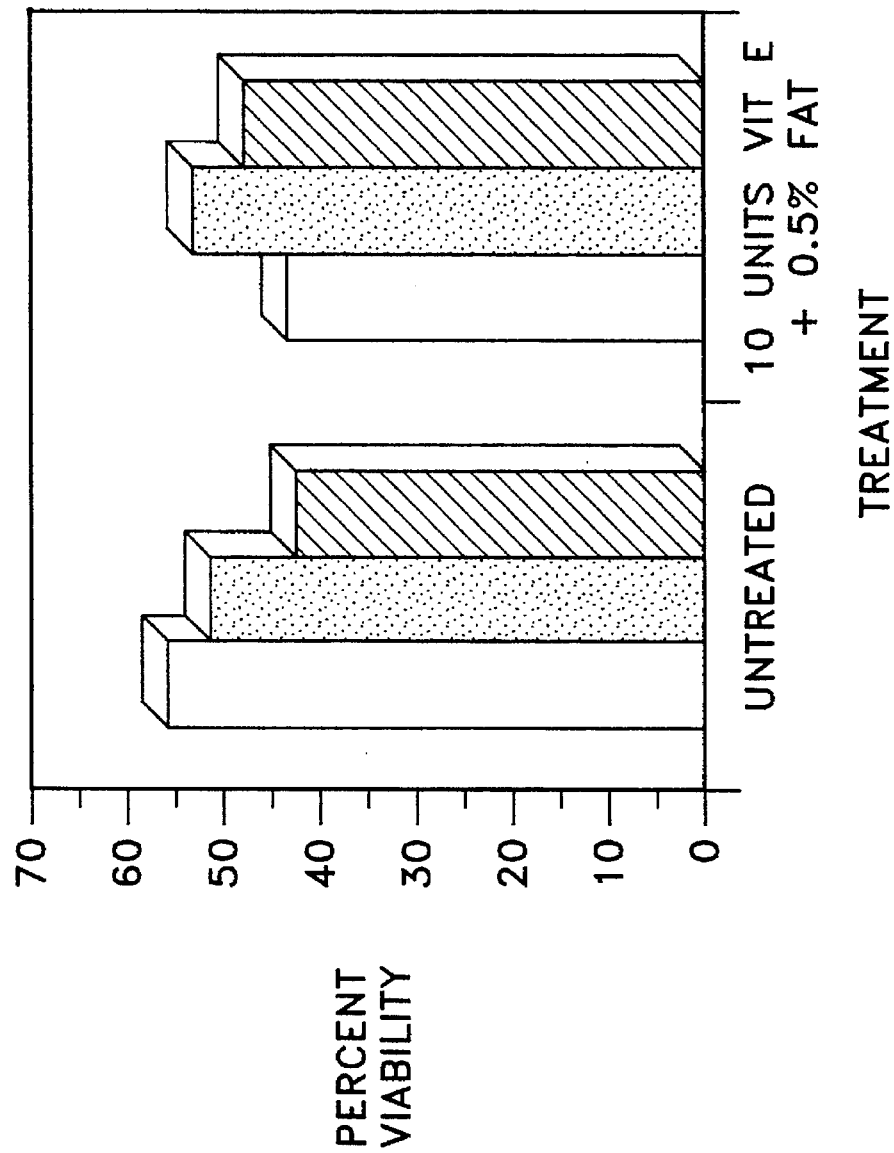

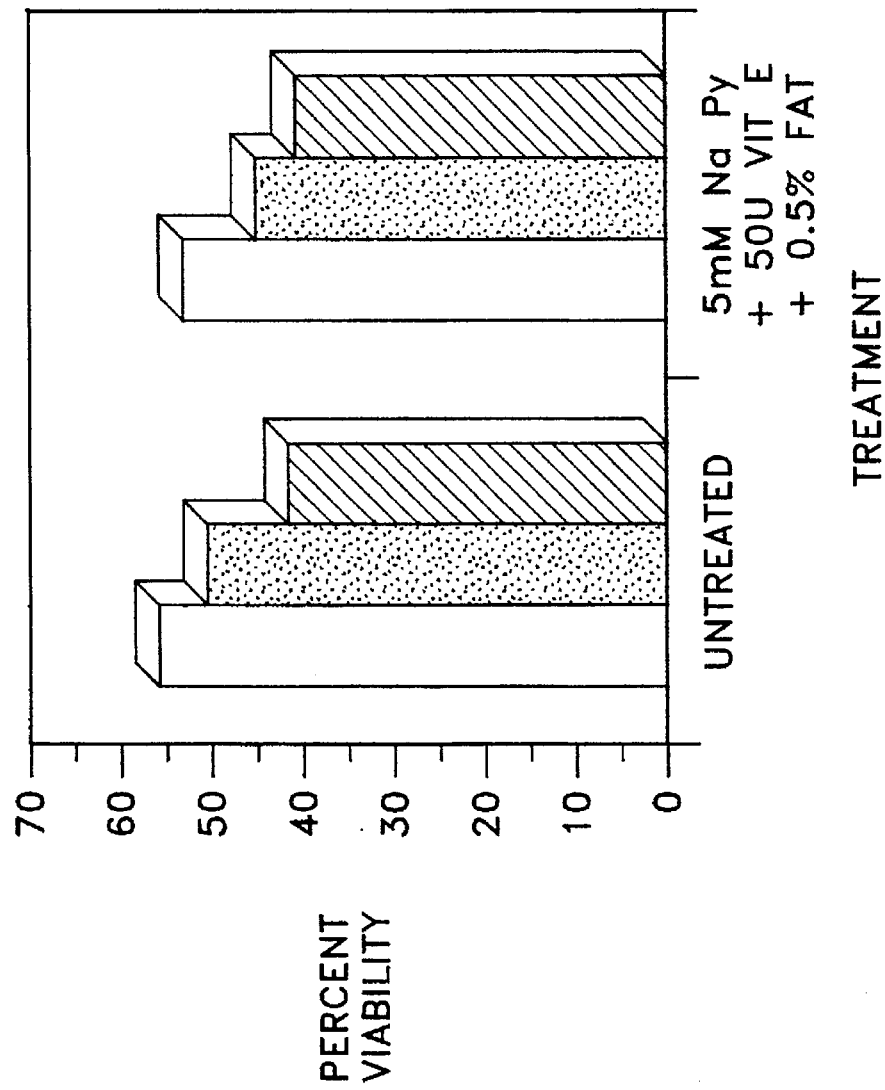

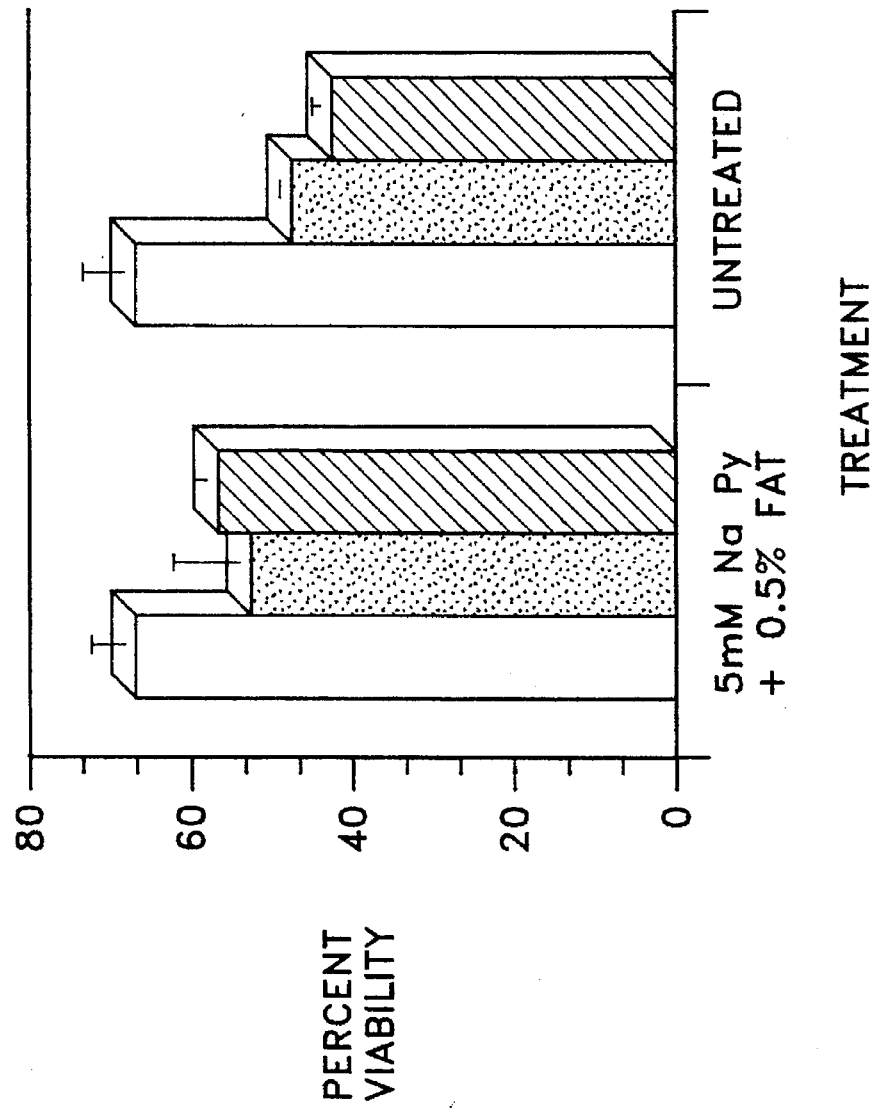

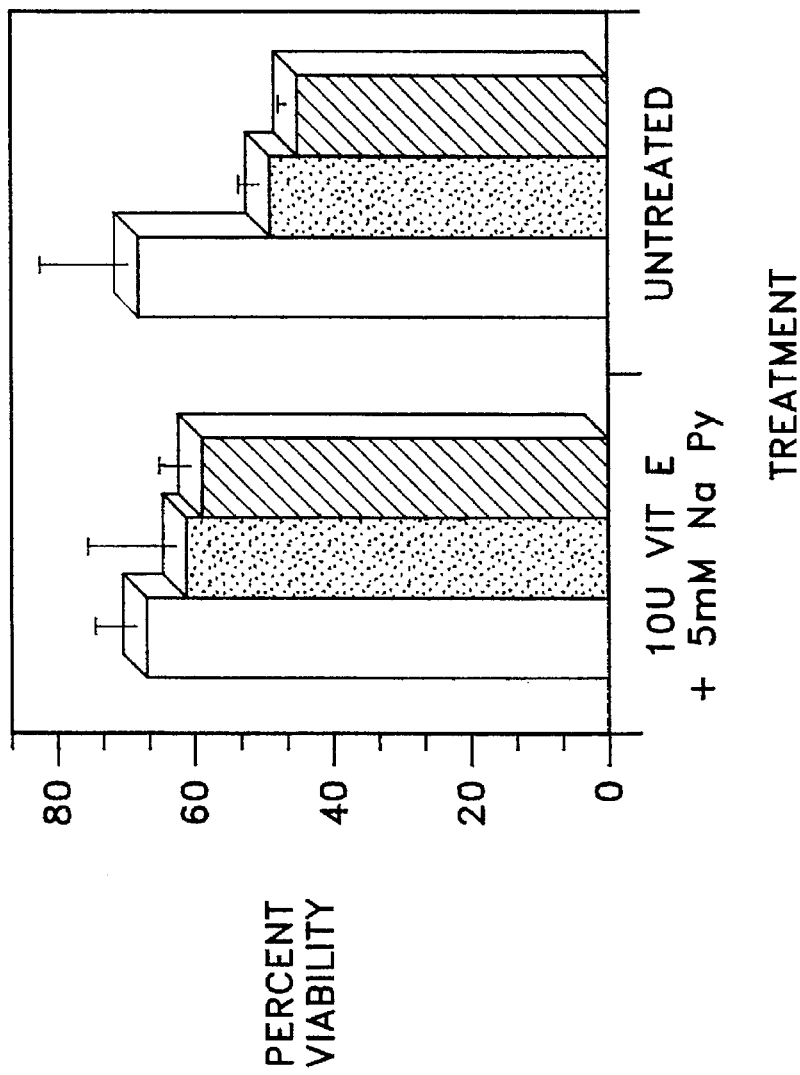

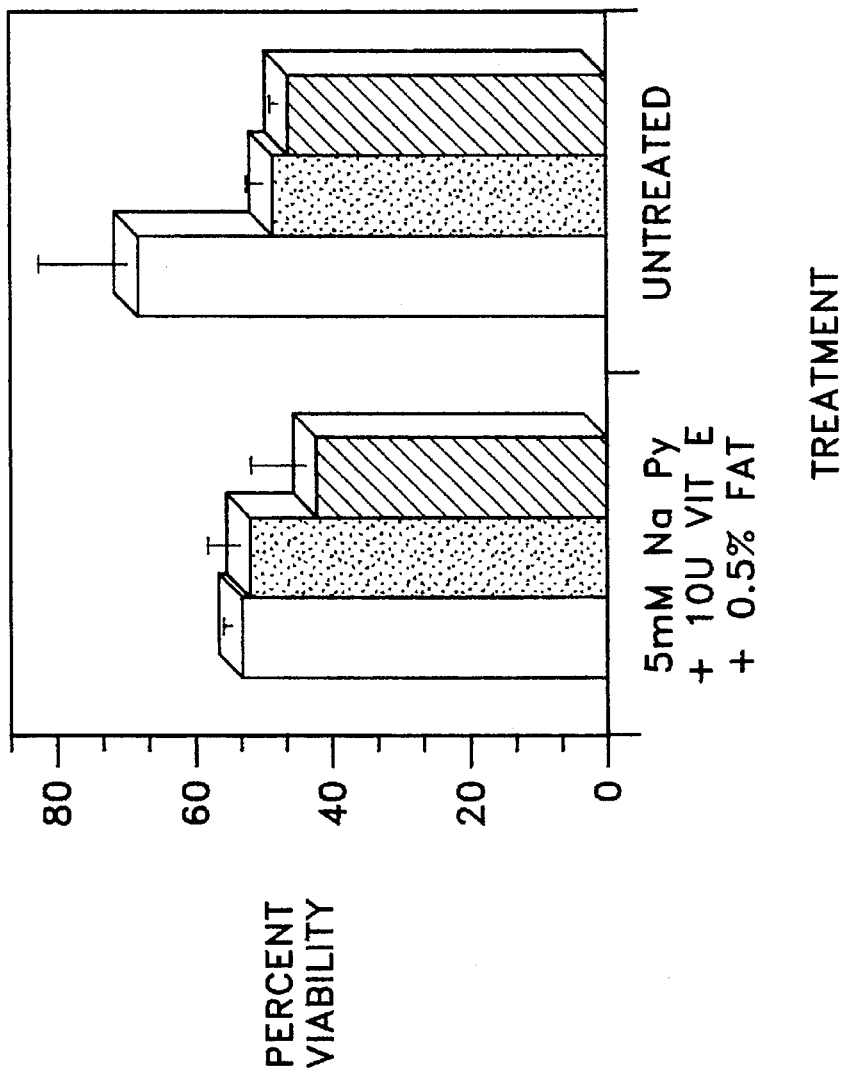

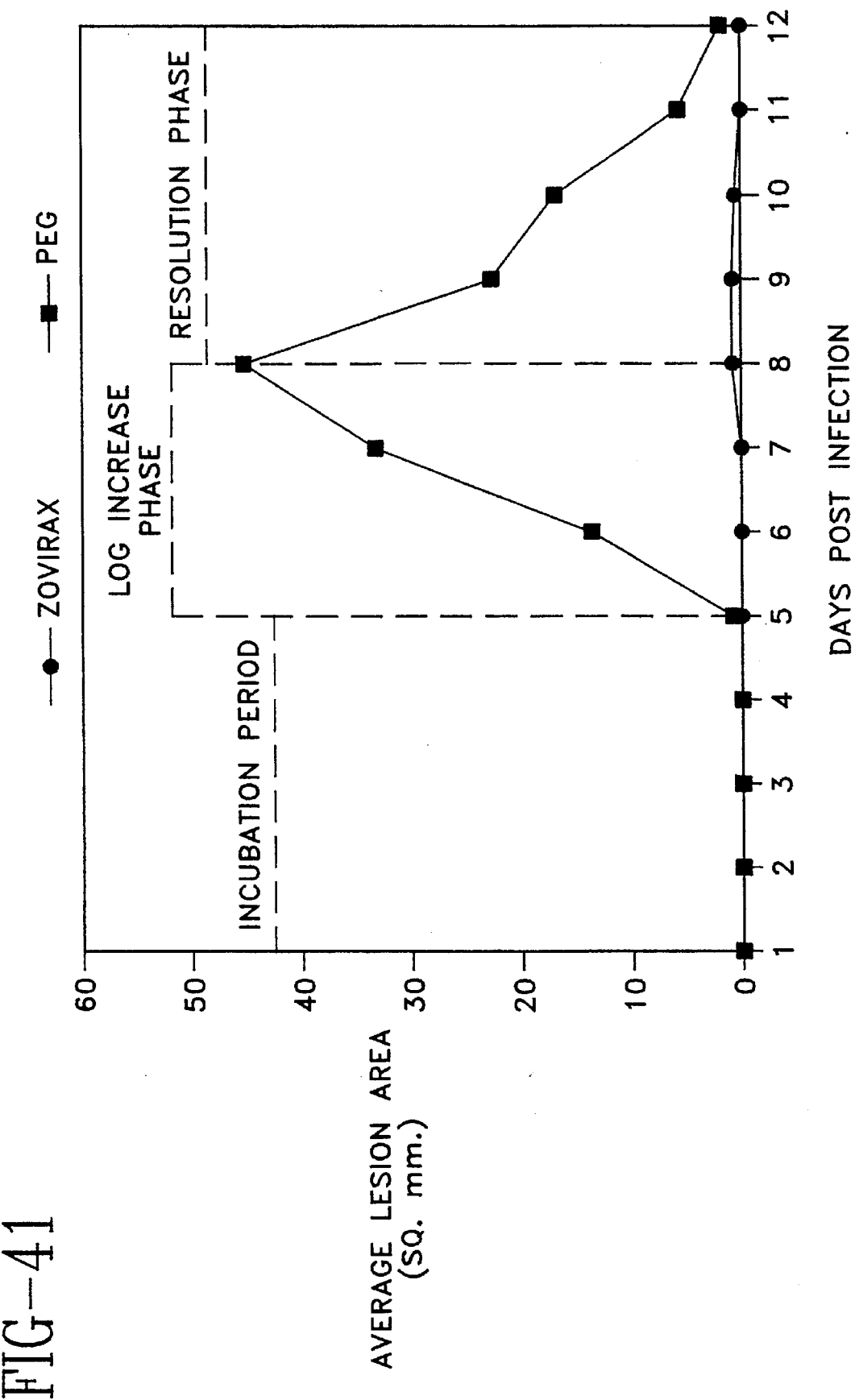

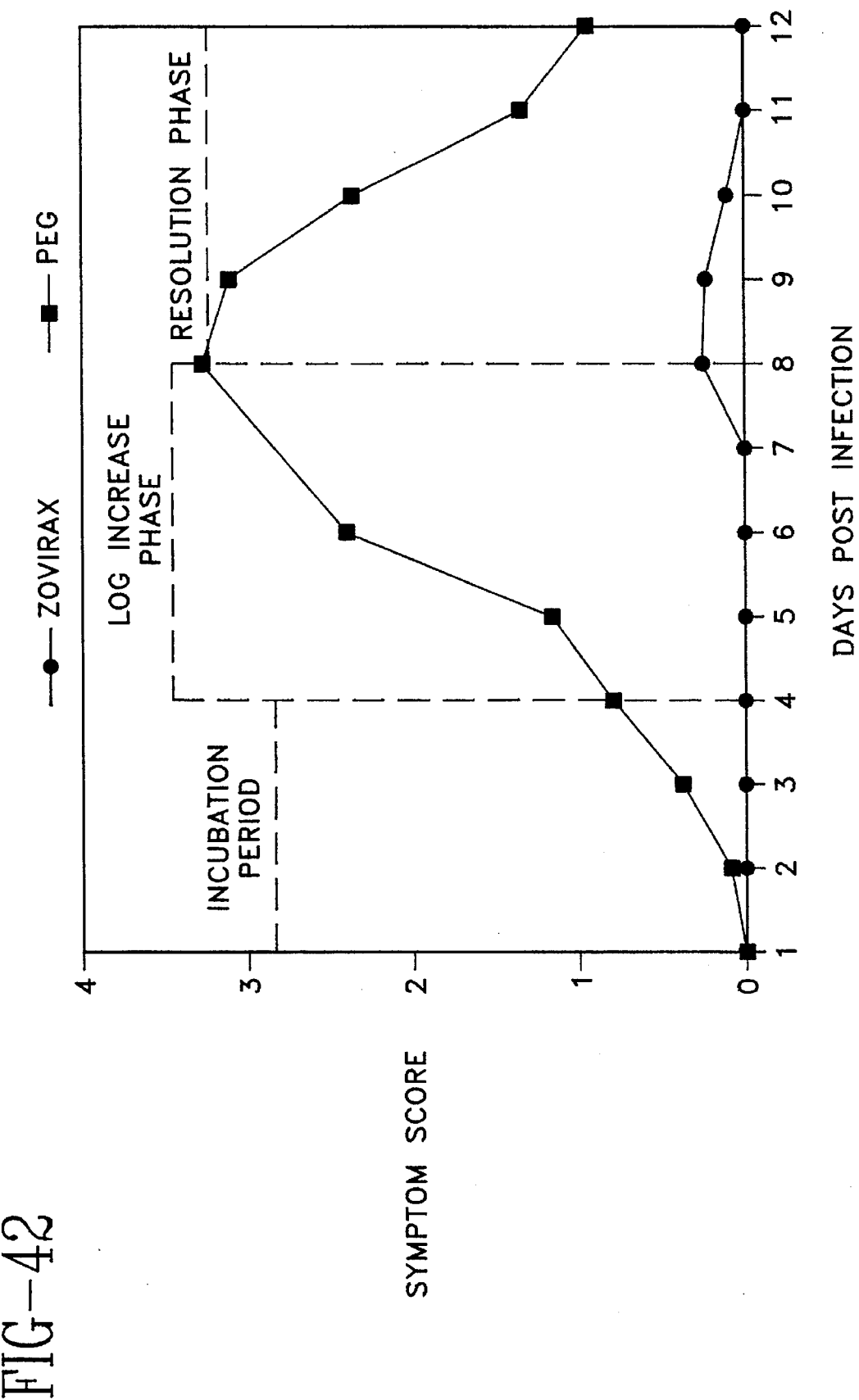

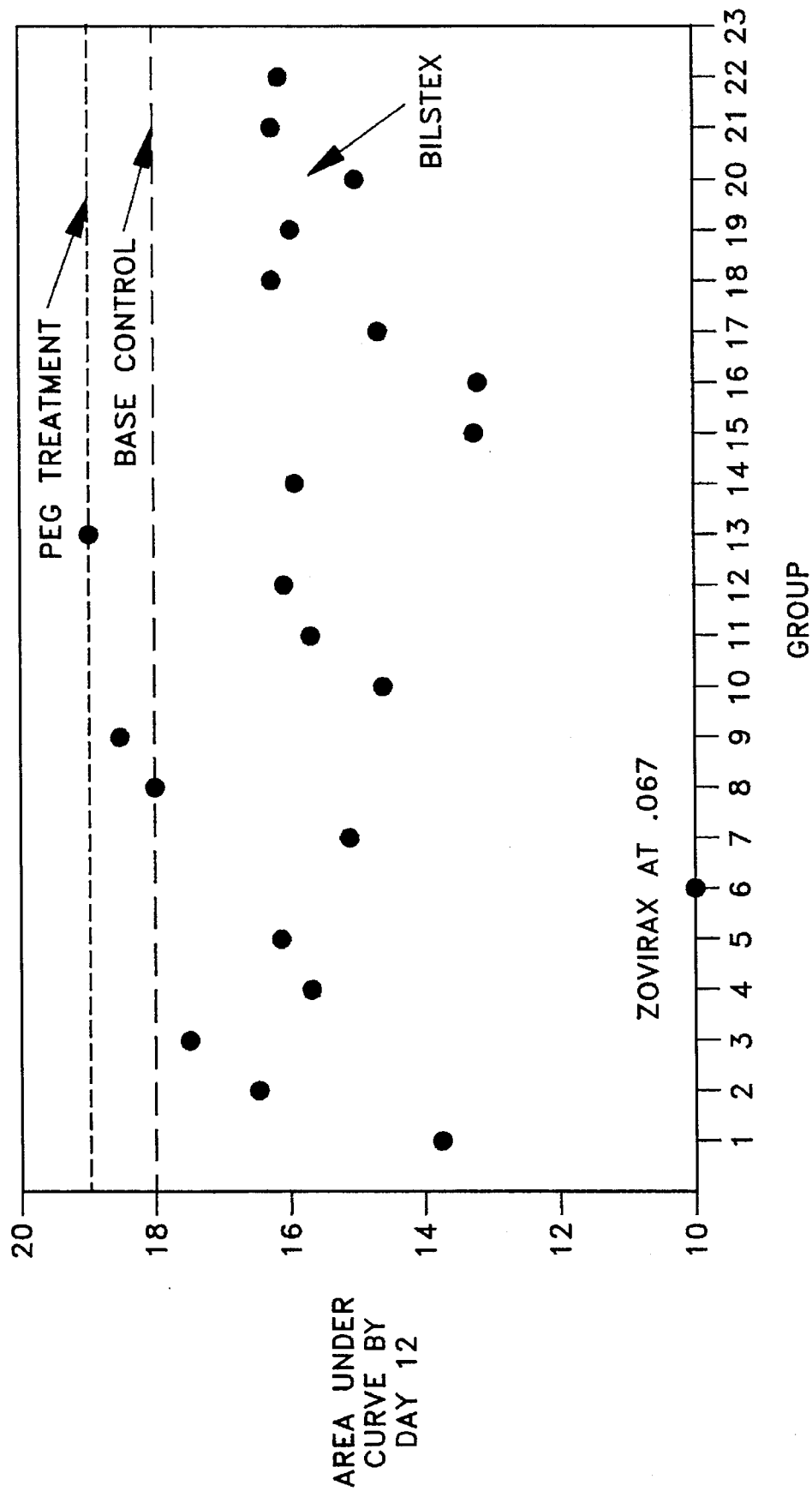

FIG-44A
FIG-44B
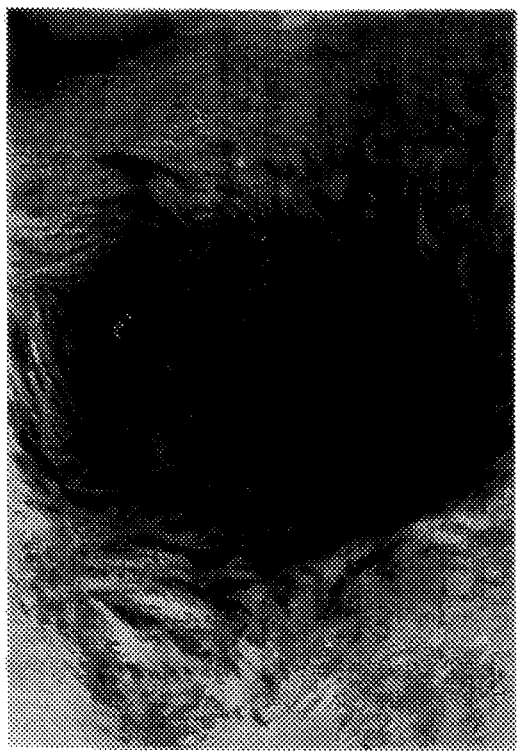
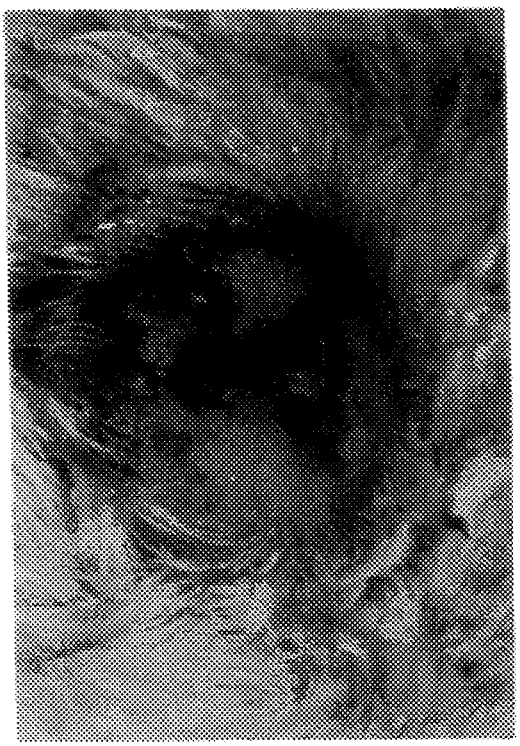

FIG-45A
FIG-45B
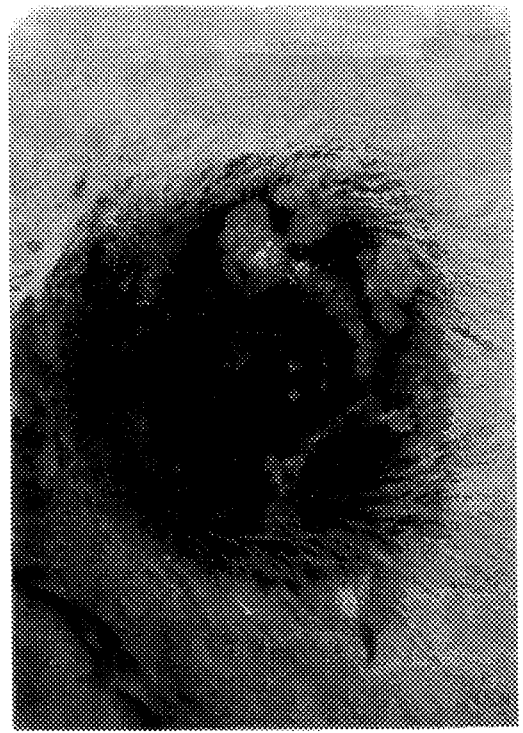

FIG-46A
FIG-46B

FIG-47A
FIG-47B
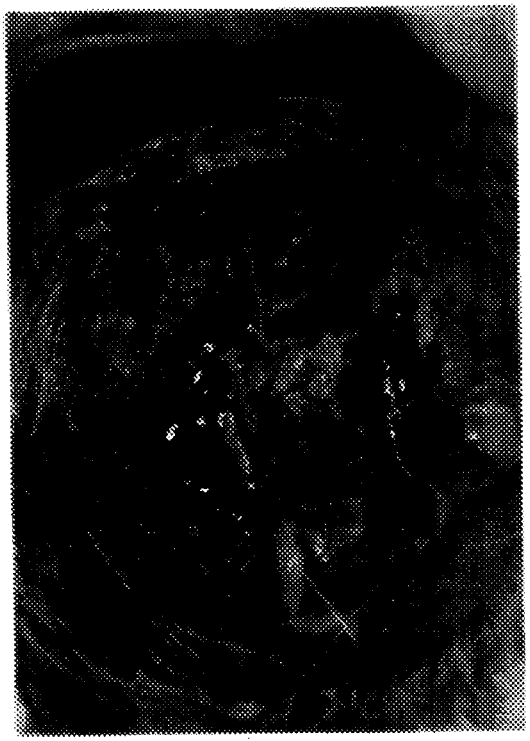

BIOADHESIVE-WOUND HEALING COMPOSITIONS AND METHODS FOR PREPARING AND USING SAME

REFERENCE TO RELATED U.S. APPLICATIONS

This application is a continuation-in-part of application Ser. No. 08/298,521 filed Aug. 30, 1994, now abandoned, which is a continuation-in-part of application Ser. No. 08/053,922, filed Apr. 26, 1993, now abandoned, which is a continuation of application Ser. No. 07/663,500, filed Mar. 1, 1991, now abandoned.

BACKGROUND OF THE INVENTION

1. Field of the Invention

This invention pertains to therapeutic bioadhesive-wound healing compositions useful for treating wounds. More particularly, the bioadhesive-wound healing compositions comprise a bioadhesive agent and a wound healing composition and/or its metabolites. This invention also pertains to methods for preparing and using the bioadhesive-wound healing compositions and the pharmaceutical products in which the therapeutic compositions may be used.

A preferred embodiment of the therapeutic wound healing composition of this invention comprises (a) pyruvate selected from the group consisting of pyruvic acid, pharmaceutically acceptable salts of pyruvic acid, and mixtures, thereof, (b) an antioxidant, and (c) a mixture of saturated and unsaturated fatty acids wherein the fatty acids are those fatty acids required for the repair of cellular membranes and resuscitation of mammalian cells.

2. Description of the Background

Wound Healing

Wounds are internal or external bodily injuries or lesions caused by physical means, such as mechanical, chemical viral, bacterial, or thermal means, which disrupt the normal continuity of structures. Such bodily injuries include contusions, wounds in which the skin is unbroken, incisions, wounds in which the skin is broken by a cutting instrument, and lacerations, wounds in which the skin is broken by a dull or blunt instrument. Wounds may be caused by accidents or by surgical procedures.

Wound healing consists of a series of processes whereby injured tissue is repaired, specialized tissue is regenerated, and new tissue is reorganized. Wound healing consists of three major phases: a) an inflammation phase (0–3 days), b) a cellular proliferation phase (3–12 days), and (c) a remodeling phase (3 days–6 months).

During the inflammation phase, platelet aggregation and clotting form a matrix which traps plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

When cells are injured or killed as a result of a wound, a wound healing step is desirable to resuscitate the injured cells and produce new cells to replace the dead cells. The healing process requires the reversal of cytotoxicity, the suppression of inflammation, and the stimulation of cellular viability and proliferation. Wounds require low levels of oxygen in the initial stages of healing to suppress oxidative damage and higher levels of oxygen in the later stages of healing to promote collagen formation by fibroblasts.

Mammalian cells are continuously exposed to activated oxygen species such as superoxide ($O_2$—), hydrogen peroxide ($H_2O_2$), hydroxyl radical (OH.), and singlet oxygen ($^1O_2$). In vivo, these reactive oxygen intermediates are generated by cells in response to aerobic metabolism, catabolism of drugs and other xenobiotics, ultraviolet and x-ray radiation, and the respiratory burst of phagocytic cells (such as white blood cells) to kill invading bacteria such as those introduced through wounds. Hydrogen peroxide, for example, is produced during respiration of most living organisms especially by stressed and injured cells.

These active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5,6-double bond, which reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material.

Antioxidants have been shown to inhibit damage associated with active oxygen species. For example, pyruvate and other Alpha-ketoacids have been reported to react rapidly and stoichiometrically with hydrogen peroxide to protect cells from cytolytic effects, O'Donnell-Tormey et al., J. Exp. Med., 165, pp. 500–514 (1987).

U.S. Pat. Nos. 3,920,835, 3,984,556, and 3,988,470, all issued to Van Scott et al., disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of Alpha-hydroxyacids, Alpha-ketoacids and esters thereof, and 3-hydroxybutryic acid in a pharmaceutically acceptable carrier. The aliphatic compounds include pyruvic acid and lactic acid.

U.S. Pat. Nos. 4,105,783 and 4,197,316, both issued to Yu et al., disclose a method and composition, respectively, for treating dry skin which consists of applying to the affected area a topical composition comprising from about 1% to about 20% of a compound selected from the group consisting of amides and ammonium salts of Alpha-hydroxyacids, β-hydroxyacids, and Alpha-ketoacids in a pharmaceutically acceptable carrier. The compounds include the amides and ammonium salts of pyruvic acid and lactic acid.

U.S. Pat. No. 4,234,599, issued to Van Scott et al, discloses a method for treating actinic and nonactinic skin keratoses which consists of applying to the affected area a topical composition comprising an effective amount of a compound selected from the group consisting of Alpha-hydroxyacids, β-hydroxyacids, and Alpha-ketoacids in a pharmaceutically acceptable carrier. The acidic compounds include pyruvic acid and lactic acid.

U.S. Pat. No. 4,294,852, issued to Wildnauer et al., discloses a composition for treating skin which comprises the Alpha-hydroxyacids, β-hydroxyacids, and Alpha-ketoacids disclosed above by Van Scott et al. in combination with $C_3$–$C_8$ aliphatic alcohols.

U.S. Pat. No. 4,663,166, issued to Veech, discloses an electrolyte solution which comprises a mixture of L-lactate and pyruvate in a ratio from 20:1 to 1:1, respectively, or a mixture of D-β-hydroxybutyrate and acetoacetate, in a ratio from 6:1 to 0.5:1, respectively.

Sodium pyruvate has been reported to reduce the number of erosions, ulcers, and hemorrhages on the gastric mucosa in guinea pigs and rats caused by acetylsalicylic acid. The analgesic and antipyretic properties of acetylsalicylic acid were not impaired by sodium pyruvate, Puschmann, Arzneimittelforschung, 33, pp. 410–415 and 415–416 (1983).

Pyruvate has been reported to exert a positive inotropic effect in stunned myocardium, which is a prolonged ventricular dysfunction following brief periods of coronary artery occlusions which does not produce irreversible damage, Mentzer et al., Ann. Surg., 209, pp. 629–633 (1989).

Pyruvate has been reported to produce a relative stabilization of left ventricular pressure and work parameter and to reduce the size of infarctions. Pyruvate improves resumption of spontaneous beating of the heart and restoration of normal rates and pressure development, Bunger et al., J. Mol. Cell. Cardiol., 18, pp. 423–438 (1986), Mochizuki et al., J. Physiol. (Paris), 76, pp. 805–812 (1980), Regitz et al., Cardiovasc. Res., 15, pp. 652–658 (1981), Giannelli et al., Ann. Thorac. Surg., 21, pp. 386–396 (1976).

Sodium pyruvate has been reported to act as an antagonist to cyanide intoxication (presumably through the formation of a cyanohydrin) and to protect against the lethal effects of sodium sulfide and to retard the onset and development of functional, morphological, and biochemical measures of acrylamide neuropathy of axons, Schwartz et al., Toxicol. Appl. Pharmacol., 50, pp. 437–442 (1979), Sabri et al., Brain Res., 483, pp. 1–11 (1989).

A chemotherapeutic cure of advanced L1210 leukemia has been reported using sodium pyruvate to restore abnormally deformed red blood cells to normal. The deformed red blood cells prevented adequate drag delivery to tumor cells, Cohen, Cancer Chemother. Pharmacol., 5, pp. 175–179 (1981).

Primary cultures of heterotopic tracheal transplant exposed in vivo to 7,12-dimethyl-benz(a)anthracene were reported to be successfully maintained in enrichment medium supplemented with sodium pyruvate along with cultures of interleukin-2 stimulated peripheral blood lymphocytes, and plasmacytomas and hybridomas, pig embryos, and human blastocysts, Shacter, J. Immunol. Methods, 99, pp. 259–270 (1987), Marchok et al., Cancer Res., 37, pp. 1811–1821 (1977), Davis, J. Reprod. Fertil. Suppl., 33, pp. 115–124 (1985), Okamoto et al., No To Shinkei, 38, pp. 593–598 (1986), Cohen et al., J. In Vitro Fert. Embryo Transfer, 2, pp. 59–64 (1985).

U.S. Pat. Nos. 4,158,057, 4,351,835, 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively. The methods comprise administering to the mammal a therapeutic mixture of pyruvate and dihydroxyacetone, and optionally riboflavin. U.S. Pat. No. 4,548,937, issued to Stanko, discloses a method for controlling the weight gain of a mammal which comprises administering to the mammal a therapeutically effective amount of pyruvate, and optionally riboflavin. U.S. Pat. No. 4,812,479, issued to Stanko, discloses a method for controlling the weight gain of a mammal which comprises administering to the mammal a therapeutically effective amount of dihydroxyacetone, and optionally riboflavin and pyruvate.

Rats fed a calcium-oxalate lithogenic diet including sodium pyruvate were reported to develop fewer urinary calculi (stones) than control rats not given sodium pyruvate, Ogawa et al., Hinyokika Kiyo, 32, pp. 1341–1347 (1986).

U.S. Pat. No. 4,521,375, issued to Houlsby, discloses a method for sterilizing surfaces which come into contact with living tissue. The method comprises sterilizing the surface with aqueous hydrogen peroxide and then neutralizing the surface with pyruvic acid.

U.S. Pat. No. 4,416,982, issued to Tauda et al., discloses a method for decomposing hydrogen peroxide by reacting the hydrogen peroxide with a phenol or aniline derivative in the presence of peroxidase.

U.S. Pat. No. 4,696,917, issued to Lindstrom et al., discloses an eye irrigation solution which comprises Eagle's Minimum Essential Medium with Earle's salts, chondroitin sulfate, a buffer solution, 2-mercaptoethanol, and a pyruvate. The irrigation solution may optionally contain ascorbic acid and Alpha-tocopherol. U.S. Pat. No. 4,725,586, issued to Lindstrom et al., discloses an irrigation solution which comprises a balanced salt solution, chondroitin sulfate, a buffer solution, 2-mercaptoethanol, sodium bicarbonate or dextrose, a pyruvate, a sodium phosphate buffer system, and cystine. The irrigation solution may optionally contain ascorbic acid and gamma-tocopherol.

U.S. Pat. No. 3,887,702 issued to Baldwin, discloses a composition for treating fingernails and toenails which consists essentially of soybean oil or sunflower oil in combination with Vitamin E.

U.S. Pat. No. 4,847,069, issued to Bissett et al., discloses a photoprotective composition comprising (a) a sorbohydroxamic acid, (b) an anti-inflammatory agent selected from steroidal anti-inflammatory agents and a natural anti-inflammatory agent, and (c) a topical carrier. Fatty acids may be present as an emollient. U.S. Pat. No. 4,847,071, issued to Bissett et al., discloses a photoprotective composition comprising (a) a tocopherol or tocopherol ester radical scavenger, (b) an anti-inflammatory agent selected from steroidal anti-inflammatory agents and a natural anti-inflammatory agent, and (c) a topical carrier. U.S. Pat. No. 4,847,072, issued to Bissett et al., discloses a topical composition comprising not more than 25% tocopherol sorbate in a topical carrier.

U.S. Pat. No. 4,533,637, issued to Yamane et al., discloses a culture medium which comprises a carbon source, a nucleic acid source precursor, amino acids, vitamins, minerals, a lipophilic nutrient, and serum albumin, and cyclodextrins. The lipophilic substances include unsaturated fatty acids and lipophilic vitamins such as Vitamin A, D, and E. Ascorbic acid may also be present.

United Kingdom patent application no. 2,196,348A, to Kovar et al., discloses a synthetic culture medium which comprises inorganic salts, monosaccharides, amino acids, vitamins, buffering agents, and optionally sodium pyruvate adding magnesium hydroxide or magnesium oxide to the emulsion. The oil phase may include chicken fat.

U.S. Pat. No. 4,284,630, issued to Yu et al, discloses a method for stabilizing a water-in-oil emulsion which comprises adding magnesium hydroxide or magnesium oxide to the emulsion. The oil phase may include chicken fat.

Preparation H™ has been reported to increase the rate of wound healing in artificially created rectal ulcers. The active ingredients in Preparation H™ are skin respiratory factor and shark liver oil, Subramanyam et al., Digestive Diseases and Sciences, 29, pp. 829-832 (1984).

The addition of sodium pyruvate to bacterial and yeast systems has been reported to inhibit hydrogen peroxide production, enhance growth, and protect the systems against the toxicity of reactive oxygen intermediates. The unsaturated fatty acids and saturated fatty acids contained within chicken fat enhanced membrane repair and reduced cytotoxicity. The antioxidants glutathione and thioglycollate reduced the injury induced by oxygen radical species, Martin, Ph. D. thesis, (1987-89).

U.S. Pat. No. 4,615,697, issued to Robinson, discloses a controlled release treatment composition comprising a treating agent and a bioadhesive agent comprising a water-swellable but water-insoluble, fibrous cross-linked carboxy-functional polymer.

European patent application no. 0410696A1, to Kellaway et al., discloses a mucoadhesive delivery system comprising a treating agent and a polyacrylic acid cross-linked with from about 1% to about 20% by weight of a polyhydroxy compound such as a sugar, cyclitol, or lower polyhydric alcohol.

Viral Infections

Herpes simplex virus type 1 (HSV-1) is a common viral infection in humans which commonly causes epidermal lesions in and around the oral cavity. The hallmark of an HSV infection is the ability of the virus to establish a latent infection in the nervous system, and to reactivate and cause recrudescent lesions. Recurrent disease can be a rather unsightly, painful, and unpleasant episode, Overall J. C., Dermatologic Viral Diseases; In: Galasso, G. I., Merigan, T. C., Buchanan, R. A., Eds.; Antiviral Agents and Viral Diseases in Man. 2nd ed., New York; Raven Press; 1984; 247-312.

The vast majority of perioral infections are caused by HSV type I and serologic studies indicate that 50% to 100% of the population has contacted the virus by adulthood, Nahmias, A. J., Roizman, B., Infection with Herpes-Simplex Virus 1 and 2, N. Engl. J. Med., 289:781-789, 1973. More important, it is estimated that 20% to 45% of the population have reoccurring perioral HSV infections, most commonly in the form of fever blisters, Young S. K., Rowe, N. H., Buchanan R. A., A Clinical Study For the Control Of Facial Mucocutaneous Herpes Virus Infections; I. Characterization of Natural History in a Professional School Population, Oral Surg. Oral Med. Oral Pathol., 41:498-507, 1976, Embil, J. A., Stephens K. G., Manuel F. R., Prevalence of Recurrent Herpes Labialis and Aphthous Ulcers Among Young Adults on Six Continents, Can. Med. Assoc. 113: 627-30, 1975, Ship I. I., Brightman V. J., Laster L. L.; The Patient with Recurrent Aphthous Ulcers and the Patient with Recurrent Herpes Labialis; A Study of Two Population Samples, J. Am. Dent. Assoc., 75:645-54, 1967. Fever blisters are more than a minor annoyance; an estimated 98 million cases occur each year in the U.S., Spruance S. L., Overall J. C. Jr, Kern E. K. et al., The Natural History of Recurrent Herpes Simplex Labialis: Implications for Anti-vital Therapy, N. Eng. J. Med., 197:69-75, 1977. Fever blisters cause considerable discomfort and are aesthetically annoying to patients.

The Herpes group of viruses is composed of seven human viruses and multiple animal viruses. The human herpes viruses consist of herpes simplex virus type I and II, varicella-zoster, cytomegalovirus, Epstein-barr, and human herpes virus types 6 and 7. The viruses are similar in size and morphology, and are characterized by a double-stranded DNA core and a lipoprotein envelope with glycoprotein projections. All the human herpes viruses replicate primarily in the cell nuclei. HSV-I and HSV-2 can be distinguished by a variety of properties, including clinical and epidemiologic patterns, antigenicity, DNA base composition, biologic characteristics, and sensitivity to various physical and chemical stresses, Rodu B., Russell C., Mattingly G., Determining Therapeutic Efficacy in Recurrent Herpes Labialis by Lesion Size analysis, Oral Surg. Oral Med. Oral Pathol., August 1991, 178-182; Fox J. D., Briggs M., et al., Human Herpes Virus 6 in Salivary Glands, Lancet 336: 590, 1990; Cory L., Spear P. G., Infection with Herpes Simplex Viruses (pts 1 and 2). N. Engl. J. of Med., 314:686,749, 1986; Hammer S. M., et al.: Temporal Cluster of Herpes Simplex Encephalitis; Investigation by Restriction Endonuclease Cleavage of Viral DNA, J. Infect. Dis., 141: 436, 1980; Johnson R. E., Nahmias A. J., et al.: A Seroepidemiologic Survey of the Prevalence of Herpes Simplex Virus Type 2 Infection in the United States, N. Engl. J. Med., 321: 7, 1989.

HSV-I primary infections occur mainly in childhood. The herpes virus is a contact infectious agent that invades the moist membranes of the lips, mouth, or throat. The herpes virus is most frequently transmitted by kissing. Although virus titers are higher and transmission is more likely when lesions are present, a symptomatic excretion of the virus is common. Thus, the virus may be transmitted even in the absence of lesions.

On entry into the skin sites, the virus replicates in epithelial cells, which results in lysis of infected cells and the instigation of a local inflammatory response. After primary infection, the virus may become latent within sensory nerve ganglion sites, Bonneau R. H., Sheridan J. F., et al., Stress-Induction Suppression of Herpes Simplex Virus (HSV)-Specific Cytotoxic T Lymphocyte and Natural Killer Cell Activity and Enhancement of Acute Pathogenesis Following Local HSV Infection, Brain, Behavior and Immunity, 5: 170192, 1991; Rooney J. F., et al. Prevention of Ultraviolet-Light-Induced Herpes Labialis by Sunscreen, The Lancet, 338: 1419-1422, 1991; Bastian F. O., Rabson A. S., Yee CL, et al., Herpes Virus Hominis: Isolation From Human Trigeminal Ganglion, Science, 1972; 178; 306. In humans, the virus remains in a dormant state in the trigeminal ganglion near the cheek bone. The virus can remain dormant in these nerve cells for extended periods of time. The virus can emerge from latency, track along the neural pathway back to the site of the original infection causing the formation of a cold sore blister. A variety of humoral and cell-mediated immune mechanisms are recruited in response to primary and recurrent HSV infections including the production of antibodies, interferon, activation of macrophages, the induction of T-Lymphocyte-mediated reactivity, and the development of antibody dependent lymphocyte cytotoxicity, Bonneau R. H., Sheridan J. F., et al., Stress-induction Suppression of Herpes Simplex Virus (HSV)-Specific Cytotoxic T Lymphocyte and Natural Killer Cell Activity and Enhancement of Acute Pathogenesis Following Local HSV Infection, Brain, Behavior and Immunity, 5: 170-192, 1991.

Once infected, the cold sore manifests itself in the form of a fluid filled blister inside or outside the mouth. Other possible symptoms which occur three to five days after exposure to the virus include: fever, swollen neck glands, and general aches and pain. As time passes, the fever blister will collapse followed by the formation of yellow crust over the sore. The entire sore usually heals without scaring within two weeks, Bonneau R. H., Sheridan J. F., et al. Stress-Induction Suppression of Herpes Simplex Virus (HSV)-Specific Cytotoxic T Lymphocyte and Natural Killer Cell Activity and Enhancement of Acute Pathogenesis Following Local HSV Infection, Brain, Behavior and Immunity, 5, 170–192, 1991; Rooney J. F., et al., Prevention of Ultraviolet-Light-Induced Herpes Labialis by Suncreen, The Lancet, 338:1419–1422 (1991).

Recurrent infections are generally less severe than the primary attack. Recurrent infections decline in frequency after the age of 35. Signals of recurrent infections include: itching, tingling, burning in the lip area, one to three days before the blister forms. In the United States, lip or perioral recurrences develop in 20 to 40% of the population. Recurrences vary in frequency from more than one attack per month to less than one attack every six months. Factors triggering recurrence are: emotional stress, fever, illness, injury, overexposure to the sun, and menses. Sunlight triggers herpes labialis in approximately 25% of people with recurrent infections.

The key to prevention is to eliminate exposure to the virus. When cold sores are present, one can prevent against autoinoculation by not touching the sores. One can prevent against spreading the virus by not kissing other individuals. Currently cold sores cannot be cured. Treatment exists for relief of pain and discomfort. Antiseptic creams, emollients, and antiseptic ingredients reduce the discomfort through their cooling and protective actions. Sun blocks with UVB protection act as a prophylaxis for people prone to recurrent cold sore sun blisters.

Several drugs are currently available for the treatment of HSV infections. Acyclovir (trade name Zovirax) is a prescription compound that interferes with viral DNA replication through its action on viral thymidine kinase. Although extremely effective when given orally or intravenously for the treatment of primary or encephalitic HSV infections, Acyclovir has little effectiveness, and is not generally prescribed, for recurrent disease. A variety of over-the-counter medications are also available. Most of these medications rely on the weak antiviral properties of chemicals such as phenol which has a low level of effectiveness against recurrent HSV infections, Whitley R. J., Gnann J. W., Acyclovir a Decade Later, N. Eng. J. of Med., September 1992, 782–89.

Psoriasis

Psoriasis is a common chronic and recurrent scaling papular disease characterized by dry, well-circumscribed silvery, scaling papules and plaques of various sizes. The severity of psoriasis may vary from 1 or 2 lesions to a widespread dermatosis with disabling arthritis or exfoliation. The cause of psoriasis is not known but the thick scaling is believed to be caused by an increased rate of epidermal cell proliferation. The onset of psoriasis is usually gradual followed by chronic remissions and recurrences which may vary in frequency and duration. Factors which precipitate psoriatic eruptions include local trauma, severe sunburn, irritation, topical medications, and withdrawal of systemic corticosteroids. Psoriasis characteristically involves the scalp, the extensor surface of the extremities (particularly at elbows and knees), the back, the buttocks, and sometimes the nails, eyebrows, axillas, umbilicus, and anogenital region.

Acute attacks usually clear up but complete permanent remission is rare. Early lesions are more amenable to treatment than are longstanding ones, but no known therapeutic method assures a cure. The simplest forms of treatment are lubricants, antikeratolytics, and topical corticosteroids. Lubricating creams, hydrogenated vegetable (cooking) oils, or white petrolatum may be applied, alone or with added corticosteroids, salicylic acid, crude coal tax, or anthralin (dithranol). Alternatively, crude coal tar ointment or cream may be applied. Topical corticosteroids may be used as an alternative or adjunct to anthralin or coal tar treatment. Methotrexate taken orally is the most effective treatment in severe disabling psoriasis unresponsive to topical therapy, especially severe psoriatic arthritis or widespread pustular or exfoliative psoriasis. Methotrexate seems to act by interfering with the rapid proliferation of epidermal cells.

Inflammation

Intimation is a nonspecific response caused by several kinds of injury, including penetration of the host by infectious agents. The distinguishing feature of inflammation is dilation and increased permeability of minute blood vessels. Direct injury, such as that caused by toxins elaborated by microorganisms, leads to destruction of vascular endothelium and increased permeability to plasma proteins, especially in the venules and venular capillaries. Mediators of secondary injury are liberated from the site of direct injury. As a result, gaps form between vascular endothelial cells through which plasma proteins escape. Granulocytes, monocytes, and erythrocytes may also leave vascular channels. Mediators of secondary injury include unknown substances and histamine, peptides (kinins), kinin-forming enzymes (kininogenases), and a globulin permeability factor. These mediators are blocked from action by antihistamines and sympathoamines, and are most pronounced in effect on venules, although lymphvascular endothelium also becomes more porous as a part of secondary injury.

The beneficial effect of the inflammatory response is the production of: (1) leukocytes in great numbers; (2) plasma proteins, nonspecific and specific humoral agents, fibrinogen that on conversion to fibrin aids in localization of the infectious process while acting as a matrix for phagocytosis; and (3) increased blood and lymph flow that dilutes and flushes toxic materials while causing a local increase in temperature.

In the early stages of inflammation, the exudate is alkaline and neutrophilic polymorphonuclear leukocytes predominate. As lactic acid accumulates, presumably from glycolysis, the pH drops and macrophages become the predominant cell type. Lactic acid and antibodies in the inflammatory exudate may inhibit parasites, but the major anti-infectious effect of the inflammatory response is attributable to phagocytic cells.

The inflammatory response consists of three successive phases: (a) increased vascular permeability with resulting edema and swelling, (b) cellular infiltration and phagocytoses, and (c) proliferation of the fibroblasts, synthesizing new connective tissue to repair the injury. A large number of so-called mediators of inflammation have been implicated in the inflammatory process primarily in terms of their capacity to induce vasodilation and increase permeability.

The initial increase in capillary permeability and vasodilation in an inflamed joint is followed by an increase in metabolism of the joint tissues. Leakage of fibrinogen into the wound, where proteolytic enzymes convert it into fibrin, establishes a capillary and lymphatic blockade. The concentrations of components of the ground substance of connective tissue collagen, mucopolysaccharides, glycoproteins, and nonfibrous proteins are greatly increased during this process. As the exudative phase of the inflammation subsides, the fibroblast is found to be the dominant cell in the wounded zone. It first proliferates, then synthesizes extracellular material, including new collagen fibers and acid mucopolysaccharides, which are laid down to form the new tissue matrix.

The inflammatory phenomenon includes fenestration of the microvasculature, leakage of the elements of blood into the interstitial spaces, and migration of leukocytes into the inflamed tissue. On a macroscopic level, this is usually accompanied by the familiar clinical signs of erythema, edema tenderness (hyperalgesia), and pain. During this complex response, chemical mediators such as histamine, 5-hydroxytryptamine (5-HT), slow-reacting substance of anaphylaxis (SRS-A), various chemotactic factors, bradykinin, and prostaglandins are liberated locally. Phagocytic cells migrate into the area, and cellular lysosomal membranes may be ruptured, releasing lyric enzymes. All these events may contribute to the inflammatory response.

Fungal Infections

Opportunistic fungal infections are generally caused by normally nonpathogenic organisms in patients whose host defense mechanisms have been compromised. Host defense mechanisms, physiologic, anatomic, or immunologic, may be altered or breached by disease or trauma, or by procedures or agents used for diagnosis or therapy. Thus, opportunistic infection may occur if antimicrobial therapy alters the normal relationship between host and microbe, or if the host defense mechanisms have been altered by burns, anemia, neoplasms, metabolic disorders, irradiation, foreign bodies, immunosuppressive or cytotoxic drugs, corticosteroids, or diagnostic or therapeutic instrumentation. The underlying alteration predisposes the patient to infections from endogenous microflora or-from organisms acquired by contact with other individuals.

Postmenopausal women often suffer from atrophy in the vaginal area. This atrophy generally leads to cellular thinning of tissue which causes the tissue to break easily, to form scabs, and to lose elasticity. Postmenopausal women also suffer with a diminished rate and amount of vaginal lubrication and decreased acidity of the vaginal environment which permits undesirable bacteria and pathogens to flourish. Furthermore, conventional douches contain strong antimicrobials that kill normal flora allowing pathogens to grow and invade the genital area. As a consequence, many women suffer with Candida infections, caused primarily by the yeast *Candida albicans*. Candida infections are generally treated with vaginal inserts or suppositories containing an antifungal agent such as miconazole or clotrimazole.

Tretinoin

Tretinoin (Retin-A™) is indicated for the topical treatment of acne vulgaris. Although the exact mode of action of tretinoin is unknown, it is believed that tretinoin decreases the cohesiveness of follicular epithelial cells with decreased microcomedo formation. Tretinoin also stimulates mitotic activity and increases the turnover of follicular epithelial cells causing extrusion of the comedones. Because tretinoin decreases the cohesiveness of follicular epithelial cells, tretinoin is also used to decrease wrinkles.

Topical use of tretinoin is known to cause the skin of some individuals to become excessively red, edematous blistered, or crusted. Topical use may also induce severe local erythema and peeling at the site of application. When these effects occur, the medication is either discontinued or the dosage lowered to a level the patient can tolerate. Topical use of tretinoin may also cause a heightened susceptibility to sunlight as well as to weather extremes such as wind or cold. In addition, drug interactions with other topical medications such as abrasive soaps and cleansers and soaps and cosmetics having a strong drying effect are also a concern.

Sunburn

Sunburn is an acute reaction by the skin to excessive exposure to sunlight. Ordinary sunburn results from overexposure of the skin to ultraviolet waves of about 3000 Angstroms. Sunburn symptoms appear in 1 to 24 hours and, except in severe reactions, pass their peak in 72 hours. Following exposure to sunlight, the epidermis thickens and the melanocytes produce melanin at an increased rate, providing some natural protection against further exposure. Skin changes range from a mild erythema with subsequent evanescent scaling, to pain, swelling, skin tenderness, and blisters from more prolonged exposure. Fever, chills, weakness, and shock may appear if a large portion of the body surface is affected. Secondary infection, particularly furunculosis, is the most common late complication. The skin may remain hypervulnerable to sunlight for one to several weeks when pronounced exfoliation has occurred.

Sunscreen agents are very effective for preventing sunburn. A useful sunscreen agent formulation is 5% para-aminobenzoic acid (PABA) in ethyl alcohol or in a gel. The esters of para-aminobenzoic acid in an alcohol base are only slightly less effective. Patients who do not tolerate para-aminobenzoic acid or its esters may use a benzophenone or titanium dioxide sunscreen agent. Early treatment of extensive and severe sunburn with a topical or systemic corticosteroid decreases discomfort considerably.

Chronic exposure to sunlight has an aging effect on the skin. Wrinkling and elastosis (yellow discoloration with small yellow nodules) are the most common consequences of long-term exposure. Precancerous keratotic lesions (actinic keratoses) are a frequent, disturbing consequence of years of overexposure. Squamous and basal cell carcinoma of the skin are especially common in people who work outdoors.

Diaper Dermatitis

Diaper dermatitis, or diaper rash, is an irritant contact dermatitis localized to the skin area in contact with the diaper in infants. Diaper dermatitis occurs in about 65% of infants ranging from one to 20 months of age. The manifestations of diaper dermatitis vary from diffuse erythema to nodular lesions. Prolonged contact of the skin with urine-soaked diapers results in maceration of the epidermis. Occlusive robber or plastic pants further aggravates the injury. Diaper dermatitis is caused by ammonia from the urine raising the pH of the skin and combining with constituents of skin off to form irritants. Bacterial or yeast infections may further complicate diaper dermatitis by causing persistent and severe inflammation.

Diaper dermatitis is generally treated by keeping the skin dry by changing diapers frequently and applying talcum powder to the irritated area. In severe cases, robber pants and plastic disposable diaper coverings should be avoided.

Cytotoxicity

Cancer is a group of neoplastic diseases affecting different organs and systems in the body. A common feature in all cancers is cellular mutation and abnormal and uncontrolled cell growth usually at a rate greater than that of normal body cells. Neither the etiology of cancer nor the manner in which cancer causes death is completely understood.

Significant advances have been made in the chemotherapeutic treatment of cancer. Most anticancer agents act at specific phases of the cell cycle and are therefore only active against cells in the process of division. Although differences in the duration of the cell cycle occur between different types of cells, all cells show a similar pattern during the division process which may be characterized as follows: (1) a presynthetic phase; (2) a DNA synthesis phase; (3) a postsynthetic phase following termination of DNA synthesis; and (4) a mitosis phase, wherein the cell containing a double complement of DNA divides into two daughter cells. Most antineoplastic agents act specifically on processes such as the DNA synthesis phase, the transcription phase, or the mitosis phase and are therefore considered cell-cycle specific agents.

A problem with the chemotherapeutic treatment of cancer is that normal cells which proliferate rapidly, such as those in bone marrow, hair follicles, and the gastrointestinal tract, are often damaged or killed by the anti-neoplastic agents. This cytotoxicity problem occurs because the metabolism of cancer cells is similar to that of normal cells and anticancer agents lack specificity for cancer cells. Because most of the metabolic differences between normal and neoplastic cells are quantitative, anticancer drugs are usually employed at or near the toxic range in order to obtain satisfactory therapeutic effects.

When cells are injured or killed as a result of a cytotoxic agent, a cytoprotective step is desirable to protect the normal cells from the cytotoxic agent, resuscitate the injured cells, and help produce new healthy cells to replace the dead cells. Injured cells require low levels of oxygen in the initial stages of recovery to suppress oxidative damage and higher levels of oxygen in the later stages of recovery to stimulate cellular viability and proliferation.

U.S. Pat. No. 4,170,821 discloses a disposable razor cartridge comprising a blade seat, a razor blade, a cap, and an integral solid water-soluble shaving aid. The shaving aid is permanently and immovably affixed to the cartridge.

While the above therapeutic wound healing compositions are reported to inhibit the production of reactive oxygen intermediates, none of the above compositions are entirely satisfactory. None of the compositions has the ability to simultaneously decrease cellular levels of hydrogen peroxide production, increase cellular resistance to cytotoxic agents, increase rates of cellular proliferation, and increase cellular viability to protect and resuscitate mammalian cells. The present invention provides such improved therapeutic wound healing compositions without the disadvantages characteristic of previously known compositions. This invention also relates to methods for preparing and using the therapeutic wound healing compositions and the topical and ingestible pharmaceutical products in which the therapeutic compositions may be used.

SUMMARY OF THE INVENTION

This invention pertains to a therapeutic bioadhesive-wound healing composition which comprises a therapeutically effective amount of a bioadhesive agent (X) and a wound healing composition of the present invention. Preferably, the wound healing composition comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

The therapeutic bioadhesive-wound healing compositions may further comprise medicaments which are useful for treating injured mammalian cells such as immunostimulating agents, antiviral agents, antikeratolytic agents, antiinflammatory agents, antifungal agents, tretinoin, sunscreen agents, dermatological agents, topical antihistamine agents, antibacterial agents, other bioadhesive agents, cytotoxic agents, and the like.

The bioadhesive-wound healing compositions of this invention may be utilized in a wide variety of pharmaceutical products. This invention also relates to methods for preparing and using the bioadhesive-wound healing compositions and the pharmaceutical products in which the therapeutic compositions may be used.

DESCRIPTION OF THE DRAWINGS

FIGS. 13A–13D are photographs of the histological results of wounded mice after 3 days of treatment with: no composition (FIG. 13A); Betafectin™ with Preparation H™ with the wound healing composition (FIG. 13B); Betafectin™ (FIG. 13C); live yeast cell derivative containing the wound healing composition (FIG. 13D).

FIG. 18A top portion, is a graph showing the viability of U937 monocytic leukemia tumor cells in a wash-out study, as determined by tritiated thymidine incorporation assay, after 24 hour pretreatment of the cells with 5 mM sodium pyruvate followed by administration of different dosage levels of Doxorubicin.

FIG. 20A is a graph showing the viability of U937 monocytic leukemia tumor cells in a wash-out study, as determined by tritiated thymidine incorporation assay, after 24 hour pretreatment of the cells with 10 U Vitamin E followed by administration of different dosage levels of Doxorubicin.

FIG. 23B is a graph showing the viability of peripheral blood monocytes in a wash-out study, as determined by tritiated thymidine incorporation assay, after 24 hour pretreatment of the cells with 5 mM sodium pyruvate and 10 U Vitamin E followed by administration of different dosage levels of Doxorubicin.

FIG. 25A is a graph showing the viability of U937 monocytic leukemia tumor cells in a wash-out study, as determined by tritiated thymidine incorporation assay, after 24 hour pretreatment of the cells with 10 U Vitamin E and 0.5% fatty acids followed by administration of different dosage levels of Doxorubicin.

FIG. 28A is a graph showing the viability of U937 monocytic leukemia tumor cells in a wash-out study, as determined by tritiated thymidine incorporation assay, after 24 hour pretreatment of the cells with 5 mM sodium pyruvate, 50 U Vitamin E, and 0.5% fatty acids followed by administration of different dosage levels of Doxorubicin.

FIG. 33B is a graph showing the viability of peripheral blood monocytes in a co-culture study, as determined by tritiated thymidine incorporation assay, after 24 hour pretreatment of the cells with 5 mM sodium pyruvate and 0.5% fatty acids followed by administration of different dosage levels of Doxorubicin.

FIG. 34A is a graph showing the viability of U937 monocytic leukemia tumor cells in a co-culture study, as determined by tritiated thymidine incorporation assay, after 24 hour pretreatment of the cells with 5 mM sodium pyruvate and 10 U Vitamin E followed by administration of different dosage levels of Doxorubicin.

FIG. 38A top portion, is a graph showing the viability of U937 monocytic leukemia minor cells in a co-culture study, as determined by tritiated thymidine incorporation assay, after 24 hour pretreatment of the cells with 5 mM sodium pyruvate, 10 U Vitamin E, and 0.5% fatty acids followed by administration of different dosage levels of Doxorubicin.

FIG. 41 is a graph illustrating the lesion area curves for mice infected with herpes simplex virus and treated with acyclovir (ACV, positive) and polyethylene glycol (PEG, negative). The x-axis represents days post infection and the y-axis represents the average lesion area (mm2).

FIG. 42 is a graph illustrating the symptom score curves for mice infected with herpes simplex virus and treated with acyclovir (ACV, positive) and polyethylene glycol (PEG, negative). The x-axis represents days post infection and the y-axis represents the symptom score.

FIG. 43 is a graph illustrating the area under the symptom score curves by group for mice infected with herpes simplex virus. The x-axis represents the groups and the y-axis represents the area under the symptom score curve by day 12. The clinical symptoms for each group are represented as numbers on the x axis and the control groups (polyethylene glycol, base, or Blistex™) are represented by dotted lines.

FIGS. 44A–44B are photographs illustrating the scoring of cold sore lesions in guinea pig. The scorings illustrated are 1.0 and 1.5. The scorings range from 0 to 4, with 4 being the worst.

FIGS. 45A–45B are photographs illustrating the scoring of cold sore lesions in guinea pig. The scorings illustrated are 2.0 and 2.5. The scorings range from 0 to 4, with 4 being the worst.

FIGS. 46A–46B are photographs illustrating the scoring of cold sore lesions in guinea pig. The scorings illustrated are 3.0 and 3.5. The scorings range from 0 to 4, with 4 being the worst.

FIGS. 47A–47B are photographs illustrating the scoring of cold sore lesions in guinea pig. The scorings illustrated are 4.0 and 0.0 (control). The scorings range from 0 to 4, with 4 being the worst.

DETAILED DESCRIPTION OF THE INVENTION

Figure 1:
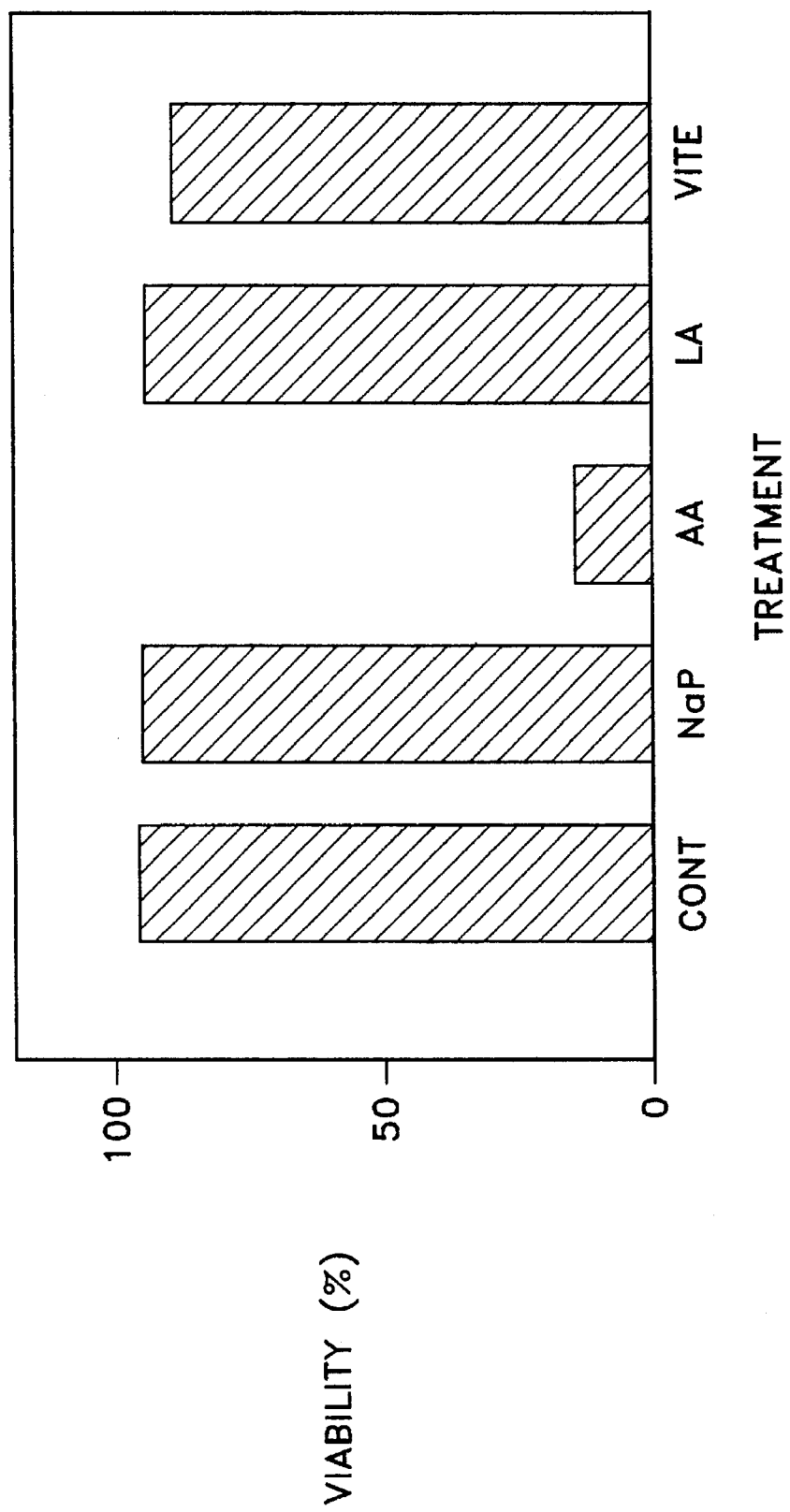
FIG. 1 depicts in bar graph format the viability of U937 monocytic cells following exposure of the cells to various antioxidants (Examples 1–5).

This invention pertains to bioadhesive-wound healing compositions which comprise a bioadhesive agent and a wound healing composition. The bioadhesive agent comprises a water-swellable but water-insoluble fibrous cross-linked material which adheres to live or freshly killed mucous membranes or skin tissues. In one embodiment the wound healing composition and/or its metabolites comprises (a) pyruvate selected from the group consisting of pyruvic acid, pharmaceutically acceptable salts of pyruvic acid, and mixtures thereof; (b) an antioxidant; and (c) a mixture of saturated and unsaturated fatty acids wherein the fatty acids are those fatty acids required for the repair of cellular membranes and resuscitation of mammalian cells.

Applicants have discovered therapeutic wound healing compositions for preventing and reducing injury to mammalian cells and increasing the resuscitation rate of injured mammalian cells. Cells treated with the therapeutic wound healing compositions of the present invention show decreased levels of hydrogen peroxide production, increased resistance to cytotoxic agents, increased rates of proliferation, and increased viability. Cellular cultures containing the therapeutic wound healing compositions showed enhanced differentiation and proliferation over control cultures and rapidly formed attachments or tight junctions between the cells to form an epidermal sheet. Wounded mammals treated with the therapeutic wound healing compositions show significantly improved wound closing and healing over untreated mammals and mammals treated with conventional healing compositions. The wound healing compositions may be used alone or in combination with other medicaments. Applicants have found that the combination of a bioadhesive agent and a wound healing composition results in a therapeutic bioadhesive-wound healing composition which can increase the resuscitation rate of injured mammalian cells and the proliferation rate of new mammalian cells to replace dead cells and thereby reduce the duration and severity of wounds. The bioadhesive-wound healing therapeutic compositions may further comprise medicaments such as immunostimulating agents, antiviral agents, antikeratolytic agents, anti-inflammatory agents, antifungal agents, acne treating agents, sunscreens, agents for treating diaper rash, antihistamines, antibacterials, and the like.

The therapeutic wound healing compositions of this invention are described as Embodiment One. There are several aspects of Embodiment One. In a first aspect of Embodiment One (I.A), the therapeutic wound healing composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition comprises (a) pyruvate selected from the group consisting of pyruvic acid, pharmaceutically acceptable salts of pyruvic acid, and mixtures thereof, Co) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

The term "injured cell" as used herein means a cell that has any activity disrupted for any reason. For example, an injured cell may be a cell that has injured membranes or damaged DNA, RNA, and ribosomes, for example, a cell which has (a) injured membranes so that transport through the membranes is diminished resulting in an increase in toxins and normal cellular wastes inside the cell and a decrease in nutrients and other components necessary for cellular repair inside the cell, (b) an increase in concentration of oxygen radicals inside the cell because of the decreased ability of the cell to produce antioxidants and enzymes, or (c) damaged DNA, RNA, and ribosomes which must be repaired or replaced before normal cellular functions can be resumed. The term "resuscitation" of injured mammalian cells as used herein means the reversal of cytotoxicity, the stabilization of the cellular membrane, an increase in the proliferation rate of the cell, and/or the normalization of cellular functions such as the secretion of growth factors, hormones, and the like. The term "cytotoxicity" as used herein means a condition caused by a cytotoxic agent that injures the cell. Injured cells do not proliferate because injured cells expend all energy on cellular repair. Aiding cellular repair promotes cellular proliferation.

The term "prodrug", as used herein, refers to compounds which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drags, and bioreversible derivatives are used interchangeably. By inference, latentiation implies a time lag element or lime component involved in regenerating the bioactive parent molecule in vivo. The term prodrug is general in that it includes latentiated drug derivatives as well as those substances which are converted after administration to the actual substance which combines with receptors. The term prodrug is a genetic term for agents which undergo biotransformation prior to exhibiting their pharmacological actions. In the case where the administered drag is not the active agent, but rather is biotransformed to the active agent, the term "prodrug" also includes compounds which may not necessarily undergo biotransformation to the administered drag but may undergo biotransformation to the active agent which exhibits the desired pharmacological effect.

The term "metabolite", as used herein, refers to any substance produced by metabolism or by a metabolic process. "Metabolism", as used herein, refers to the various chemical reactions involved in the transformation of molecules or chemical compounds occurring in tissue and the cells therein.

I. Wound Healing Compositions

A. Embodiment One (I.A–D)

The cells which may be treated with the therapeutic wound healing compositions and/or their metabolites in the present invention are mammalian cells. Although applicant will describe the present therapeutic wound healing compositions as useful for treating mammalian epidermal keratinocytes and mammalian monocytes, applicant contemplates that the therapeutic wound healing compositions may be used to protect or resuscitate all mammalian cells. Keratinocytes are representative of normal mammalian cells and are the fastest proliferating cells in the body. The correlation between the reaction of keratinocytes to injury and therapy and that of mammalian cells in general is very high. Monocytes are representative of specialized mammalian cells such as the white blood cells in the immune system and the organ cells in liver, kidney, heart, and brain. The mammalian cells may be treated in vivo and in vitro.

Epidermal keratinocytes are the specialized epithelial cells of the epidermis which synthesize keratin, a scleroprotein which is the principal constituent of epidermis, hair, nails, horny tissue, and the organic matrix of the enamel of teeth. Mammalian epidermal keratinocytes constitute about 95% of the epidermal cells and together with melanocytes form the binary system of the epidermis. In its various successive stages, epidermal keratinocytes are also known as basal cells, prickle cells, and granular cells.

Monocytes are mononuclear phagocytic leukocytes which undergo respiratory bursting and are involved in reactive oxygen mediated damage within the epidermis. Leukocytes are white blood cells or corpuscles which may be classified into two main groups: granular leukocytes (granulocytes) which are leukocytes with abundant granules in the cytoplasm and nongranular leukocytes (nongranulocytes) which are leukocytes without specific granules in the cytoplasm and which include the lymphocytes and monocytes. Phagocyte cells are cells which ingest microorganisms or other cells and foreign particles. Monocytes are also known as large mononuclear leukocytes, and hyaline or transitional leukocytes.

Epidermal keratinocytic cells and monocytic cells have multiple oxygen generating mechanisms and the degree to which each type of mechanism functions differs in each type of cell. In monocytes, for example, the respiratory bursting process is more pronounced than in epidermal keratinocytes. Hence, the components in the therapeutic wound healing compositions of the present invention may vary depending upon the types of cells involved in the condition being treated.

As set out above, in a first aspect of Embodiment One (I.A), the therapeutic wound healing composition for treating mammalian cells, preferably epidermal keratinocytes, comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition for treating mammalian cells, preferably epidermal keratinocytes, comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition for treating mammalian cells, preferably epidermal keratinocytes, comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition for treating mammalian cells, preferably monocytes, comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

Pyruvic acid (2-oxopropanoic acid, Alpha-ketopropionic acid, $CH_3COCOOH$) or pyruvate is a fundamental intermediate in protein and carbohydrate metabolism and in the citric acid cycle. The citric acid cycle (tricarboxylic acid cycle, Kreb's cycle) is the major reaction sequence which executes the reduction of oxygen to generate adenosine triphosphate (ATP) by oxidizing organic compounds in respiring tissues to provide electrons to the transport system. Acetyl coenzyme A ("active acetyl") is oxidized in this process and is thereafter utilized in a variety of biological processes and is a precursor in the biosynthesis of many fatty acids and sterols. The two major sources of acetyl coenzyme A are derived from the metabolism of glucose and fatty acids. Glycolysis consists of a series of transformations wherein each glucose molecule is transformed in the cellular cytoplasm into two molecules of pyruvic acid. Pyruvic acid may then enter the mitochondria where it is oxidized by coenzyme A in the presence of enzymes and cofactors to acetyl coenzyme A. Acetyl coenzyme A can then enter the citric acid cycle.

In muscle, pyruvic acid (derived from glycogen) can be reduced to lactic acid during anerobic metabolism which can occur during exercise. Lactic acid is reoxidized and partially retransformed to glycogen during rest. Pyruvate can also act as an antioxidant to neutralize oxygen radicals in the cell and can be used in the multifunction oxidase system to reverse cytotoxicity.

The pyruvate in the present invention may be selected from the group consisting of pyruvic acid, pharmaceutically acceptable salts of pyruvic acid, prodrugs of pyruvic acid, and mixtures thereof. In general, the pharmaceutically acceptable salts of pyruvic acid may be alkali salts and alkaline earth salts. Preferably, the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, Alpha-ketoglutaric acid, and mixtures thereof. More preferably, the pyruvate is selected from the group of salts consisting of sodium pyruvate, potassium pyruvate, magnesium pyruvate, calcium pyruvate, zinc pyruvate, manganese pyruvate, and the like, and mixtures thereof. Most preferably, the pyruvate is sodium pyruvate.

The amount of pyruvate present in the therapeutic wound healing compositions of the present invention is a therapeutically effective amount. A therapeutically effective amount of pyruvate is that amount of pyrovale necessary for the inventive composition to prevent and reduce injury to mammalian cells or increase the resuscitation rate of injured mammalian cells. The exact amount of pyruvate is a matter of preference subject to such factors as the type of condition being treated as well as the other ingredients in the composition. In a preferred embodiment, pyruvate is present in the therapeutic wound healing composition in an amount from about 10% to about 50%, preferably from about 20% to about 45%, and more preferably from about 25% to about 40%, by weight of the therapeutic wound healing composition.

L-Lactic acid ((S)-2-hydroxypropanoic acid, (+)Alpha-hydroxypropionic acid, $CH_3CHOHCOOH$) or lactate occurs in small quantities in the blood and muscle fluid of mammals. Lactic acid concentration increases in muscle and blood after vigorous activity. Lactate is a component in the cellular feedback mechanism and inhibits the natural respiratory bursting process of cells thereby suppressing the production of oxygen radicals.

The lactate in the present invention may be selected from the group consisting of lactic acid, pharmaceutically acceptable salts of lactic acid, prodrugs of lactic acid, and mixtures thereof. In general, the pharmaceutically acceptable salts of lactic acid may be alkali salts and alkaline earth salts. Preferably, the lactate is selected from the group consisting of lactic acid, lithium lactate, sodium lactate, potassium lactate, magnesium lactate, calcium lactate, zinc lactate, manganese lactate, and the like, and mixtures thereof. More preferably, the lactate is selected from the group consisting of lactic acid, sodium lactate, potassium lactate, magnesium lactate, calcium lactate, zinc lactate, manganese lactate, and mixtures thereof. Most preferably, the lactate is lactic acid.

The amount of lactate present in the therapeutic wound healing compositions of the present invention is a therapeutically effective amount. A therapeutically effective amount of lactate is that amount of lactate necessary for the inventive composition to prevent and reduce injury to mammalian cells or increase the resuscitation rate of injured mammalian cells. For an ingestible composition, a therapeutically effective amount of lactate is that amount necessary to suppress the respiratory bursting process of white blood cells to protect and resuscitate the mammalian cells. In general, a therapeutically effective amount of lactate in an ingestible composition is from about 5 to about 10 times the amount of lactate normally found in serum. The exact amount of lactate is a matter of preference subject to such factors as the type of condition being treated as well as the other ingredients in the composition. In a preferred embodiment, lactate is present in the therapeutic wound healing composition in an amount from about 10% to about 50%, preferably from about 20% to about 45%, and more preferably from about 25% to about 40%, by weight of the therapeutic wound healing composition.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of Vitamin A including retinol and 3,4-didehydroretinol, all forms of carotene such as Alpha-carotene, β-carotene (beta, β-carotene), gamma-carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), β-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, β-carotene, Vitamin E, Vitamin E acetate, and mixtures thereof. More preferably, the antioxidant is Vitamin E or Vitamin E acetate. Most preferably, the antioxidant is Vitamin E acetate.

The amount of antioxidant present in the therapeutic wound healing compositions of the present invention is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound healing composition in an amount from about 0.1% to about 40%, preferably from about 0.2% to about 30%, and more preferably from about 0.5% to about 20%, by weight of the therapeutic wound healing composition.

The mixture of saturated and unsaturated fatty acids in the present invention are those fatty acids required for the repair of mammalian cellular membranes and the production of new cells. Fatty acids are carboxylic acid compounds found in animal and vegetable fat and oil. Fatty acids are classified as lipids and are composed of chains of alkyl groups containing from 4 to 22 carbon atoms and 0–3 double bonds and characterized by a terminal carboxyl group, —COOH. Fatty acids may be saturated or unsaturated and may be solid, semisolid, or liquid. The most common saturated fatty acids are butyric acid ($C_4$), lauric acid ($C_{12}$), palmitic acid ($C_{16}$), and stearic acid ($C_{18}$). Unsaturated fatty acids are usually derived from vegetables and consist of alkyl chains containing from 16 to 22 carbon atoms and 0–3 double bonds with the characteristic terminal carboxyl group. The most common unsaturated fatty acids are oleic acid, linoleic acid, and linolenic acid (all $C_{18}$ acids).

In general, the mixture of saturated and unsaturated fatty acids required for the repair of mammalian cellular membranes in the present invention may be derived from animal and vegetable fats and waxes, prodrugs of saturated and unsaturated fatty acids useful in the present invention, and mixtures thereof. For example, the fatty acids in the therapeutic wound healing composition may be in the form of mono-, di-, or triglycerides, or free fatty acids, or mixtures thereof, which are readily available for the repair of injured cells. Cells produce the chemical components and the energy required for cellular viability and store excess energy in the form of fat. Fat is adipose tissue stored between organs of the body to furnish a reserve supply of energy. The preferred animal fats and waxes have a fatty acid composition similar to that of human fat and the fat contained in human breast milk. The preferred animal fats and waxes may be selected from the group consisting of human fat, chicken fat, cow fat (defined herein as a bovine domestic animal regardless of sex or age), sheep fat, horse fat, pig fat, and whale fat. The more preferred animal fats and waxes may be selected from the group consisting of human fat and chicken fat. The most preferred animal fat is human fat. Mixtures of other fats and waxes, such as vegetable waxes (especially sunflower off), marine oils (especially shark liver oil), and synthetic waxes and oils, which have a fatty acid composition similar to that of animal fats and waxes, and preferably to that of human fats and waxes, may also be employed.

In a preferred embodiment, the mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic, oleic acid, linoleic acid, linolenic acid, arachidic acid, and gadoleic acid. Preferably, butyric acid, caproic acid, caprylic acid, capric acid, lauric acid, myristic acid, myristoleic acid, palmitic acid, palmitoleic acid, stearic, oleic acid, linoleic acid, linolenic acid, arachidic acid, and gadoleic acid are present in the mixture in about the following percentages by weight, respectively (carbon chain number and number of unsaturations are shown parenthetically, respectively): 0.2%–0.4% ($C_4$), 0.1% ($C_6$), 0.3%–0.8% ($C_8$), 2.2%–3.5% ($C_{10}$), 0.9%–5.5% ($C_{12}$), 2.8%–8.5% ($C_{14}$), 0.1%–0.6% ($C_{14:1}$), 23.2%–24.6% ($C_{16}$), 1.8%–3.0% ($C_{16:1}$), 6.9%–9.9% ($C_{18}$), 36.0%–36.5% ($C_{18:1}$), 20%–20.6% ($C_{18:2}$), 7.5–7.8% ($C_{18:3}$), 1.1%–4.9% ($C_{20}$), and 3.3%–6.4% ($C_{20:1}$).

In another preferred embodiment, the mixture of saturated and unsaturated fatty acids is typically chicken fat comprising the following fatty acids: lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid. Preferably, lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid are present in the mixture in about the following percentages by weight, respectively: 0.1% ($C_{12}$), 0.8% ($C_{14}$), 0.2% ($C_{14:1}$), 0.1% ($C_{15}$), 25.3% ($C_{16}$), 7.2% ($C_{16:1}$), 0.1% ($C_{17}$), 0.1% ($C_{17:1}$), 6.5% ($C_{18}$), 37.7% ($C_{18:1}$), 20.6% ($C_{18:2}$), 0.8% ($C_{18:3}$), 0.2% ($C_{20}$), and 0.3% ($C_{20:1}$), all percentages +/−10%.

In another preferred embodiment, the mixture of saturated and unsaturated fatty acids comprises lecithin. Lecithin (phosphatidylcholine) is a phosphatide found in all living organisms (plants and animals) and is a significant constituent of nervous tissue and brain substance. Lecithin is a mixture of the diglycerides of stearic, palmitic, and oleic acids, linked to the choline ester of phosphoric acid. The product of commerce is predominantly soybean lecithin obtained as a by-product in the manufacturing of soybean oil. Soybean lecithin contains palmitic acid 11.7%, stearic 4.0%, palmitoleic 8.6%, oleic 9.8%, linolenic 55.0%, linolenic 4.0%, $C_{20}$ to $C_{22}$ acids (includes arachidonic) 5.5%. Lecithin may be represented by the formula:

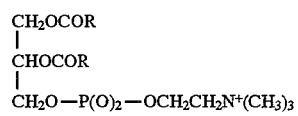

wherein R is selected from the group consisting of stearic, palmitic, and oleic acid.

The above fatty acids and percentages thereof present in the fatty acid mixture are given as an example. The exact type of fatty acid present in the fatty acid mixture and the exact amount of fatty acid employed in the fatty acid mixture may be varied in order to obtain the result desired in the final product and such variations are now within the capabilities of those skilled in the art without the need for undue experimentation.

The amount of fatty acids present in the therapeutic wound healing compositions of the present invention is a therapeutically effective amount. A therapeutically effective amount of fatty acids is that amount of fatty acids necessary for the inventive composition to prevent and reduce injury to mammalian cells or increase the resuscitation rate of injured mammalian cells. The exact amount of fatty acids employed is subject to such factors as the type and distribution of fatty acids employed in the mixture, the type of condition being treated, and the other ingredients in the composition. In a preferred embodiment, the fatty acids are present in the therapeutic wound healing composition in an amount from about 10% to about 50%, preferably from about 20% to about 45%, and more preferably from about 25% to about 40%, by weight of the therapeutic wound healing composition.

In accord with the present invention, the therapeutic wound healing compositions of Embodiment One (I.A–D) for treating mammalian cells may be selected from the group consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells;

(I.C) (a) an antioxidant; and (b) a mixture of saturated and unsaturated fatty acids wherein the fatty acids are those fatty acids required for the repair of cellular membranes and resuscitation of mammalian cells;

(I.D) (a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

Preferably, the wound healing compositions of Embodiment One (I) for treating mammalian cells, preferably epidermal keratinocytes, may be selected from the group consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells; and (I.C) (a) an antioxidant; and (b) a mixture of saturated and unsaturated fatty acids wherein the fatty acids are those fatty acids required for the repair of cellular membranes and resuscitation of mammalian cells.

More preferably, the wound healing compositions of Embodiment One (I) for treating mammalian cells, preferably epidermal keratinocytes, may be selected from the group consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (I.C) (a) an antioxidant; and (b) a mixture of saturated and unsaturated fatty acids wherein the fatty acids are those fatty acids required for the repair of cellular membranes and resuscitation of mammalian cells.

More preferably, the wound healing compositions of Embodiment One for treating mammalian cells, preferably epidermal keratinocytes, may be selected from the group consisting of:

(IA) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells.

Most preferably, the wound healing compositions of Embodiment One (I) for treating mammalian cells, preferably epidermal keratinocytes, comprise:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

Most preferably, the wound healing compositions of Embodiment One (I) for treating mammalian cells, preferably monocytes, comprise:

(I.D) (a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

Throughout this disclosure, applicant will suggest various theories or mechanisms by which applicant believes the components in the therapeutic wound healing compositions and the antiviral agent function together in an unexpected synergistic manner to prevent and reduce injury to mammalian cells, increase the resuscitation rate of injured mammalian cells, and reduce viral titers. While applicant may offer various mechanisms to explain the present invention, applicant does not wish to be bound by theory. These theories are suggested to better understand the present invention but are not intended to limit the effective scope of the claims.

In the first aspect of Embodiment One (I.A), applicant believes that pyruvate can be transported inside a cell where it can act as an antioxidant to neutralize oxygen radicals in the cell. Pyruvate can also be used inside the cell in the citric acid cycle to provide energy to increase cellular viability, and as a precursor in the synthesis of important biomolecules to promote cellular proliferation. In addition, pyruvate can be used in the multifunction oxidase system to reverse cytotoxicity. Antioxidants, especially lipid-soluble antioxidants, can be absorbed into the cell membrane to neutralize oxygen radicals and thereby protect the membrane. The saturated and unsaturated fatty acids in the present invention are those fatty acids required for the resuscitation of mammalian cells and are readily available for the repair of injured cells and the proliferation of new cells. Cells injured by oxygen radicals need to produce unsaturated fatty acids to repair cellular membranes. However, the production of unsaturated fatty acids by cells requires oxygen. Thus, the injured cell needs high levels of oxygen to produce unsaturated fatty acids and at the same time needs to reduce the level of oxygen within the cell to reduce oxidative injury. By providing the cell with the unsaturated fatty acids needed for repair, the need of the cell for unsaturated fatty acids is reduced and the need for high oxygen levels is also reduced.

The combination of pyruvate inside the cell and an antioxidant in the cellular membrane functions in an unexpected synergistic manner to reduce hydrogen peroxide production in the cell to levels lower than can be achieved by use of either type of component alone. The presence of mixtures of saturated and unsaturated fatty acids in the therapeutic wound healing composition significantly enhances the ability of pyruvate and the antioxidant to inhibit reactive oxygen production. By stabilizing the cellular membrane, unsaturated fatty acids also improve membrane function and enhance pyruvate transport into the cell. Hence, the three components in the therapeutic wound healing composition of the first aspect of Embodiment One (I.A) function together in an unexpected synergistic manner to prevent and reduce injury to mammalian cells and increase the resuscitation rate of injured mammalian cells.

In the second aspect of Embodiment One (I.B), lactate is employed instead of an antioxidant. Antioxidants react with, and neutralize, oxygen radicals after the radicals are already formed. Lactate, on the other hand, is a component in the cellular feedback mechanism and inhibits the respiratory bursting process to suppress the production of active oxygen species. The combination of pyruvate to neutralize active oxygen species and lactate to suppress the respiratory bursting process functions in a synergistic manner to reduce hydrogen peroxide production in the cell to levels lower than can be achieved by use of either type of component alone. The presence of mixtures of saturated and unsaturated fatty acids in the therapeutic wound healing composition significantly enhances the ability of pyruvate and lactate to inhibit reactive oxygen production. Hence, the three components in the therapeutic wound healing composition in the second aspect of Embodiment One (I.B) function together in a synergistic manner to protect and resuscitate mammalian cells.

In the third aspect of Embodiment One (I.C), the presence of mixtures of saturated and unsaturated fatty acids in the therapeutic wound healing composition in this embodiment significantly enhances the ability of the antioxidant to inhibit reactive oxygen production. The combination of an antioxidant to neutralize active oxygen species and fatty acids to rebuild cellular membranes and reduce the need of the cell for oxygen functions in a synergistic manner to reduce hydrogen peroxide production in the cell to levels lower than can be achieved by either type of component alone. Hence, the components in the therapeutic wound healing composition in the third aspect of Embodiment One (I.C) function together in a synergistic manner to protect and resuscitate mammalian cells.

In the fourth aspect of Embodiment One (I.D), lactate is employed because the respiratory bursting process is more pronounced in monocytes than in epidermal keratinocytes. The combination of lactate to suppress the respiratory bursting process and an antioxidant to neutralize active oxygen species functions in a synergistic manner to reduce hydrogen peroxide production in the cell to levels lower than can be achieved by either component alone. The presence of mixtures of saturated and unsaturated fatty acids in the therapeutic wound healing composition in this embodiment significantly enhances the ability of lactate and the antioxidant to inhibit reactive oxygen production. Hence, the three components in the therapeutic wound healing composition in the fourth aspect of Embodiment One (I.D) function together in an unexpected synergistic manner to protect and resuscitate mammalian cells.

Accordingly, the combination of ingredients set out in the above embodiments functions together in an enhanced manner to prevent and reduce injury to mammalian cells and increase the resuscitation rate of injured mammalian cells. The therapeutic effect of the combination of the components in each of the above embodiments is markedly greater than that expected by the mere addition of the individual therapeutic components. Hence, applicant's therapeutic wound healing compositions for treating mammalian cells have the ability to decrease intracellular levels of hydrogen peroxide production, increase cellular resistance to cytotoxic agents, increase rates of cellular proliferation, and increase cellular viability.

B. Methods For Making the Therapeutic Wound Healing Compositions of Embodiment One (I.A–D)

The present invention extends to methods for making the therapeutic wound healing compositions of Embodiment One (I.A–D). In general, a therapeutic wound healing composition is made by forming an admixture of the components of the composition. In a first aspect of Embodiment One (I.A), a therapeutic wound healing composition is made by forming an admixture of (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), a therapeutic wound healing composition is made by forming an admixture of (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the repair of cellular membranes and resuscitation of mammalian cells. In a third aspect of Embodiment One (I.C), a therapeutic wound healing composition is made by forming an admixture of (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), a therapeutic wound healing composition is made by forming an admixture of (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

For some applications, the admixture may be formed in a solvent such as water, and a surfactant may be added if required. If necessary, the pH of the solvent is adjusted to a range from about 3.5 to about 8.0, and preferably from about 4.5 to about 7.5, and more preferably about 6.0 to about 7.4. The admixture is then sterile filtered. Other ingredients may also be incorporated into the therapeutic wound healing composition as dictated by the nature of the desired composition as well known by those having ordinary skill in the art. The ultimate therapeutic wound healing compositions are readily prepared using methods generally known in the pharmaceutical arts.

In a preferred embodiment, the invention is directed to a method for preparing a therapeutic wound healing composition (I.A) for preventing and reducing injury to mammalian cells, and increasing the resuscitation rate of injured mammalian cells, which comprises the steps of admixing the following ingredients:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells.

C. Methods For Employing

The Therapeutic Wound Healing Compositions of Embodiment One (I.A–D)

The present invention extends to methods for employing the therapeutic wound healing compositions of Embodiment One (I) in vivo and in vitro. In general, a therapeutic wound healing composition is employed by contacting the therapeutic composition with mammalian cells.

In a first aspect of Embodiment One (I.A), the invention is directed to a method for preventing and reducing injury to mammalian cells, and increasing the resuscitation rate of injured mammalian cells, which comprises the steps of (A) providing a therapeutic wound healing composition which comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells, and (B) contacting the therapeutic wound healing composition with the mammalian cells.

In a second aspect of Embodiment One (I.B), the invention is directed to a method for preventing and reducing injury to mammalian cells, and increasing the resuscitation rate of injured mammalian cells, which comprises the steps of (A) providing a therapeutic wound healing composition which comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the resuscitation of injured mammalian cells, and (B) contacting the therapeutic wound healing composition with the mammalian cells.

In a third aspect of Embodiment One (I.C), the invention is directed to a method for preventing and reducing injury to mammalian cells, and increasing the resuscitation rate of injured mammalian cells, which comprises the steps of (A) providing a therapeutic wound healing composition which comprises (a) an antioxidant, and (b) a mixture of saturated and unsaturated fatty acids wherein the fatty acids are those fatty acids required for the resuscitation of injured mammalian cells, and (B) contacting the therapeutic wound healing composition with the mammalian cells.

In a fourth aspect of Embodiment One (I.D), the invention is directed to a method for preventing and reducing injury to mammalian cells, and increasing the resuscitation rate of injured mammalian cells, which comprises the steps of (A) providing a therapeutic wound healing composition which comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the resuscitation of injured mammalian cells, and (B) contacting the therapeutic wound healing composition with the mammalian cells.

In a preferred embodiment, the invention is directed to a method for healing a wound in a mammal which comprises the steps of:

(A) providing a therapeutic wound healing composition (I.A) which comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells; and (B) contacting the therapeutic wound healing composition with the wound.

The types of wounds which may be healed using the wound healing compositions of Embodiment One (I.A–D) of the present invention are those which result from an injury which causes epidermal damage such as incisions, wounds in which the skin is broken by a cutting instrument, and lacerations, wounds in which the skin is broken by a dull or blunt instrument. The therapeutic compositions may also be used to treat various dermatological disorders such as hyperkeratosis, photo-aging, burns, donor site wounds from skin transplants, ulcers (cutaneous, decubitus, venous stasis, and diabetic), psoriasis, skin rashes, and sunburn photoreactive processes. The topical therapeutic compositions may also be used orally in the form of a mouth wash or spray to protect and accelerate the healing of injured oral tissue such as mouth sores and burns. The topical therapeutic compositions may further be used in ophthalmological preparations to treat wounds such as those which result from corneal ulcers, radialkeratotomy, corneal transplants, epikeratophakia and other surgically induced wounds in the eye. The topical therapeutic compositions may in addition be used in anorectal creams and suppositories to treat such conditions as pruritus and, proctitis, anal fissures, and hemorrhoids. In a preferred embodiment, the therapeutic compositions are used to treat wounds such as incisions and lacerations.

The wound healing compositions of Embodiment One (I.A–D) of the present invention may be utilized in topical products, ingestible products, and tissue culture medium to protect mammalian cells and increase the resuscitation rate of injured mammal/an cells. For example, the therapeutic wound healing compositions may be used in topical skin care products to protect and increase the resuscitation rate of skin tissue such as in the treatment of various dermatological disorders such as hyperkeratosis, photo-aging, and sunburn photoreactive processes. Injury to skin can occur for a variety of reasons. Injury often occurs to individuals who wash their hands often, to individuals who are exposed to stressful environmental conditions (overexposure to sun or chemicals), or to the elderly or individuals with an underlining disease. The addition of the wound healing compositions of the present invention to a lotion provides a source of antioxidants to the skin which would protect the skin from the harmful effects of UV light, chemicals, and severe drying. The wound healing compositions can be used for the following indications: a) Moisturizing and protecting; b) Healing dry cracked skin; c) Treating irritated skin such as diaper rash; d) Healing severe dry skin due to other diseases (venous dermatitis); e) Treating psoriasis and other hyperproliferative diseases; f) Protecting skin from UV light damage (antioxidant skin replacement); g) Treating seborrheic conditions; and h) Treating shaving wounds in an after shave lotion.

The topical therapeutic wound healing compositions may also be used orally in the form of a mouth wash or spray to protect and accelerate the healing of injured oral tissue such as mouth sores and burns. The topical therapeutic wound healing compositions may further be used in ophthalmological preparations such as eye care products to neutralize hydrogen peroxide used in the cleaning of contact lenses. The topical therapeutic wound healing compositions may in addition be used in anorectal creams and suppositories to treat such conditions as pruritus and, proctitis, anal fissures, and hemorrhoids. Initially as white blood cells enter a wound site, the cells release oxygen radicals, depleting the antioxidants at the wound site, thus impairing the healing process. Incorporating the wound healing compositions of the present invention into a wound healing formulation would facilitate healing by providing the site with usable antioxidants, and a source of fatty acids needed for membrane repair. The wound healing compositions can be used for the following indications: a) Healing of cuts and scrapes; b) Burns (heals burns with less scaring and scabbing); c) Decubitus ulcers; d) Bed sores, pressure ulcers; e) Fissures, Hemorrhoids; f) Use in combination with immunostimulators (simulated healing in healing deficient people); g) Post surgical wounds; h) Bandages; i) Diabetic ulcers; j) Venous ulceration; and k) Use in combination with wound cleansing agents.

The therapeutic wound healing compositions may also be used in ingestible products to protect and increase the resuscitation rate of erosions, stomach ulcers, and hemorrhages in the gastric mucosa. Other ingestible therapeutic products include: stroke medications; autoimmune disease medications; arthritis medications; ulcer medications; cancer medications (cytotoxic agents); heart medication to improve regional ventricular function and restore normal heart rate and pressure functions; lung medication to repair injured tissue; liver medication to suppress lipogenesis of alcoholic origin and prevent hepatic steatosis; kidney medication to suppress urinary calculi (kidney stones); detoxification medication to antagonize heavy metal poisoning, cyanide poisoning, sodium sulfide poisoning, other types of poisoning, and reduce and neutralize the production of oxygen radicals which produces injury to tissue, to protect and further enhance the resuscitation rate of the injured mammalian cells. The therapeutic wound healing compositions may be used in ingestible products to treat inflammatory diseases such as hepatitis, gastritis, colitis, esophagitis, arthritis, and pancreatitis.

The therapeutic wound healing compositions of the present invention may also be used in tissue culture media and organ transplant media to prevent and reduce injury to mammalian cells and increase the resuscitation rate of injured mammalian cells. Tissue cultures and transplant organs encounter reactive oxygen species generated in the culture media by the injured cells. Organs particularly susceptible to oxidative damage during transport and transplantation due to reperfusion injury following ischemia are corneas, livers, hearts, and kidneys. The therapeutic wound healing compositions may be useful to abrogate reperfusion injury to such transplant organs.

In a specific embodiment, the invention is directed to a method for preserving mammalian cells in a culture medium which comprises the steps of:

(A) providing a therapeutic wound healing composition selected from the group of consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells;

(I.C) (a) an antioxidant; and (b) a mixture of saturated and unsaturated fatty acids wherein the fatty acids are those fatty acids required for the repair of cellular membranes and resuscitation of mammalian cells;

(I.D) (a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (b) an antioxidant; and (c) a mixture of saturated and unsaturated fatty acids wherein the fatty acids are those fatty acids required for the resuscitation of injured mammalian cells;

(B) providing mammalian cells in a culture medium; and (C) contacting the therapeutic wound healing composition from step (A) with the mammalian cells in the culture medium from step (B).

D. Formulations of the Therapeutic Wound Healing Compositions of Embodiment One (I.A–D)

Once prepared, the inventive therapeutic wound healing compositions of Embodiment One (I.A–D) may be stored for future use or may be formulated in effective amounts with pharmaceutically acceptable carriers to prepare a wide variety of pharmaceutical compositions. Examples of pharmaceutically acceptable carriers are pharmaceutical appliances, topical vehicles (non-oral and oral), and ingestible vehicles.

Examples of pharmaceutical appliances are sutures, staples, gauze, bandages, burn dressings, artificial skins, liposome or micell formulations, microcapsules, aqueous vehicles for soaking gauze dressings, and the like, and mixtures thereof. Non-oral topical compositions employ non-oral topical vehicles, such as creams, gels formulations, foams, ointments and sprays, salves, and films, which are intended to be applied to the skin or body cavity and are not intended to be taken by mouth. Oral topical compositions employ oral vehicles, such as mouthwashes, rinses, oral sprays, suspensions, and dental gels, which are intended to be taken by mouth but are not intended to be ingested. Ingestible compositions employ ingestible or partly ingestible vehicles such as confectionery bulking agents which include hard and soft confectionery such as lozenges, tablets, toffees, nougats, suspensions, chewy candies, and chewing gums.

In one form of the invention, the therapeutic wound healing composition is incorporated into a pharmaceutical appliance which may be in the form of sutures, staples, gauze, bandages, burn dressings, artificial skins, liposome or micell formulations, microcapsules, aqueous vehicles for soaking gauze dressings, and the like, and mixtures thereof. A variety of traditional ingredients may optionally be included in the pharmaceutical composition in effective amounts such as buffers, preservatives, tonicity adjusting agents, antioxidants, polymers for adjusting viscosity or for use as extenders, and excipients, and the like. Specific illustrative examples of such traditional ingredients include acetate and borate buffers; thimerosol, sorbic acid, methyl and propyl paraben and chlorobutanol preservatives; sodium chloride and sugars to adjust the tonicity; and excipients such as mannitol, lactose and sucrose. Other conventional pharmaceutical additives known to those having ordinary skill in the pharmaceutical arts may also be used in the pharmaceutical composition.

In accordance with this invention, therapeutically effective amounts of the therapeutic wound healing compositions of the present invention may be employed in the pharmaceutical appliance. These amounts are readily determined by those skilled in the art without the need for undue experimentation. The exact amount of the therapeutic wound healing composition employed is subject to such factors as the type and concentration of the therapeutic wound healing composition and the type of pharmaceutical appliance employed. Thus, the amount of therapeutic wound healing composition may be varied in order to obtain the result desired in the final product and such variations are within the capabilities of those skilled in the art without the need for undue experimentation. In a preferred embodiment, the pharmaceutical composition will comprise the therapeutic wound healing composition in an amount from about 0.1% to about 5%, by weight of the pharmaceutical composition. In a more preferred embodiment, the pharmaceutical composition will comprise the therapeutic wound healing composition in an amount from about 0.1% to about 3%, by weight of the pharmaceutical composition. In a most preferred embodiment, the pharmaceutical composition will comprise the therapeutic wound healing composition in an amount from about 0.1% to about 1%, by weight of the pharmaceutical composition.

The present invention extends to methods for making the pharmaceutical compositions. In general, a pharmaceutical composition is made by contacting a therapeutically effective amount of a therapeutic wound healing composition with a pharmaceutical appliance and the other ingredients of the final desired pharmaceutical composition. The therapeutic wound healing composition may be in a solvent and may be absorbed onto a pharmaceutical appliance.

Other ingredients will usually be incorporated into the composition as dictated by the nature of the desired composition as well known by those having ordinary skill in the art. The ultimate pharmaceutical compositions are readily prepared using methods generally known in the pharmaceutical arts.

In another form of the invention, the therapeutic wound healing composition is incorporated into a non-oral topical vehicle which may be in the form of a cream, gel, foam, ointment, spray, and the like. Typical non-toxic non-oral topical vehicles known in the pharmaceutical arts may be used in the present invention. The preferred non-oral topical vehicles are water and pharmaceutically acceptable water-miscible organic solvents such as ethyl alcohol, isopropyl alcohol, propylene glycol, glycerin, and the like, and mixtures of these solvents. Water-alcohol mixtures are particularly preferred and are generally employed in a weight ratio from about 1:1 to about 20:1, preferably from about 3:1 to about 20:1, and most preferably from about 3:1 to about 10:1, respectively.

The non-oral topical therapeutic wound healing compositions may also contain conventional additives employed in those products. Conventional additives include humectants, emollients, lubricants, stabilizers, dyes, and perfumes, providing the additives do not interfere with the therapeutic properties of the therapeutic wound healing composition.

Suitable humectants useful in the non-oral topical therapeutic wound healing compositions include glycerin, propylene glycol, polyethylene glycol, sorbitan, fructose, and the like, and mixtures thereof. Humectants, when employed, may be present in amounts from about 10% to about 20%, by weight of the topical therapeutic wound healing composition.

The coloring agents (colors, colorants) useful in the non-oral topical therapeutic wound healing composition are used in amounts effective to produce the desired color. These coloring agents include pigments which may be incorporated in amounts up to about 6% by weight of the non-oral topical therapeutic wound healing composition. A preferred pigment, titanium dioxide, may be incorporated in amounts up to about 2%, and preferably less than about 1%, by weight of the non-oral topical therapeutic wound healing composition. The coloring agents may also include natural food colors and dyes suitable for food, drag and cosmetic applications. These coloring agents are known as F. D. & C. dyes and lakes. The materials acceptable for the foregoing uses are preferably water-soluble. Illustrative nonlimiting examples include the indigoid dye known as F. D. & C. Blue No. 2, which is the disodium salt of 5,5-indigotindisulfonic acid. Similarly, the dye known as F. D. & C. Green No. 1 comprises a triphenylmethane dye and is the monosodium salt of 4-[4-(N-ethyl-p-sulfoniumbenzylamino) diphenylmethylene]-[1-(N-ethyl-N-p-sulfoniumbenzyl)-delta-2,5-cyclohexadieneimine]. A full recitation of all F. D. & C. coloring agents and their corresponding chemical structures may be found in the Kirk-Othmer Encyclopedia of Chemical Technology, 3rd Edition, in volume 5 at pages 857–884, which text is incorporated herein by reference.

In accordance with this invention, therapeutically effective amounts of the therapeutic wound healing compositions of the present invention may be admixed with a non-oral topical vehicle to form a topical therapeutic wound healing composition. These amounts are readily determined by those skilled in the art without the need for undue experimentation. In a preferred embodiment, the non-oral topical therapeutic wound healing compositions will comprise the therapeutic wound healing composition in an amount from about 0.1% to about 10% and a non-oral topical vehicle in a quantity sufficient to bring the total amount of composition to 100%, by weight of the non-oral topical therapeutic wound healing composition. In a more preferred embodiment, the non-oral topical therapeutic wound healing compositions will comprise the therapeutic wound healing composition in an amount from about 0.1% to about 5%, and in a most preferred embodiment, the non-oral topical therapeutic wound healing compositions will comprise the therapeutic wound healing composition in an amount from about 0.1% to about 2%, and a non-oral topical vehicle in a quantity sufficient to bring the total amount of composition to 100%, by weight of the non-oral topical therapeutic wound healing composition.

The present invention extends to methods for preparing the non-oral topical therapeutic wound healing compositions. In such a method, the non-oral topical therapeutic wound healing composition is prepared by admixing a therapeutically effective amount of the therapeutic wound healing composition of the present invention and a non-oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In another form of the invention, the therapeutic wound healing composition is incorporated into an oral topical vehicle which may be in the form of a mouthwash, rinse, oral spray, suspension, dental gel, and the like. Typical non-toxic oral vehicles known in the pharmaceutical arts may be used in the present invention. The preferred oral vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

The oral topical therapeutic wound healing compositions may also contain conventional additives normally employed in those products. Conventional additives include a fluorine providing compound, a sweetening agent, a flavoring agent, a coloring agent, a humectant, a buffer, and an emulsifier, providing the additives do not interfere with the therapeutic properties of the therapeutic wound healing composition.

The coloring agents and humectants, and the amounts of these additives to be employed, set out above as useful in the non-oral topical therapeutic wound healing composition may be used in the oral topical therapeutic wound healing composition.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and di-fluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the present oral topical therapeutic wound healing composition is dependent upon the type of fluorine providing compound employed, the solubility of the fluorine compound, and the nature of the final oral therapeutic wound healing composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the oral topical therapeutic wound healing composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof. Without being limited to particular sweetening agents, representative categories and examples include:

(a) water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-Alpha-aspartyl-N-(2,2,4,4-tetramethyl-3-thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalacto-sucrose derivatives include but are not limited to: 1-chloro-1'-deoxysucrose; 4-chloro-4-deoxy-Alpha-D-galacto-pyranosyl-Alpha-D-fructofuranoside, or 4-chloro-4-deoxygalactosucrose; 4-chloro-4-deoxy-Alpha-D-galacto-pyranoxyl-1-chloro-1-deoxy-β-D-fructo-furanoside, or 4,1'-dichloro-4,1'-dideoxygalactosucrose; 1',6'-dichloro-1',6'-dideoxysucrose; 4-chloro-4-deoxy-Alpha-D-galacto-pyranosyl-1,6-dichloro-1,6-dideoxy-β-D-fructo-furanoside, or 4,1',6'-trichloro-4,1',6'-trideoxygalacto-sucrose; 4,6-dichloro-4,6-dideoxy-Alpha-D-galacto-pyranosyl-6-chloro-6-deoxy-β-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-Alpha-D-galacto-pyranosyl-1,6-dichloro-1,6-di-deoxy-β-D-fructofuranoside, or 4,6,1',6'-tetrachloro-4,6,1',6'-tetradeoxygalacto-sucrose; and 4,6,1',6'-tetrachloro-4,6,1',6'-tetradeoxy-sucrose; and (e) protein based sweeteners such as thaumaoccous danielli (Thaumatin I and II).

In general, an effective amount of sweetening agent is utilized to provide the level of sweetness desired in the particular oral topical therapeutic wound healing composition, and this amount will vary with the sweetener selected and the final oral therapeutic product desired. The amount of sweetener normally present is in the range from about 0.0025% to about 90%, by weight of the oral topical therapeutic wound healing composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the oral topical therapeutic wound healing composition is normally a matter of preference subject to such factors as the type of final oral therapeutic wound healing composition, the individual flavor employed, and the strength of flavor desired. Thus, the amount of flavoring may be varied in order to obtain the result desired in the final product and such variations are within the capabilities of those skilled in the art without the need for undue experimentation. The flavoring agents, when used, are generally utilized in amounts that may, for example, range in amounts from about 0.05% to about 6%, by weight of the oral topical therapeutic wound healing composition.

Suitable buffer solutions useful in the non-oral topical therapeutic wound healing compositions include citric acid-sodium citrate solution, phosphoric acid-sodium phosphate solution, and acetic acid-sodium acetate solution in amounts up to about 1%, and preferably from about 0.05% to about 0.5% by weight of the oral topical therapeutic wound healing composition.

In accordance with this invention, therapeutically effective amounts of the therapeutic wound healing compositions of the present invention may be admixed with an oral topical vehicle to form a topical therapeutic wound healing composition. These amounts are readily determined by those skilled in the art without the need for undue experimentation. In a preferred embodiment, the oral topical therapeutic wound healing compositions will comprise the therapeutic wound healing composition in an amount from about 0.1% to about 10% and a oral topical vehicle in a quantity sufficient to bring the total amount of composition to 100%, by weight of the oral topical therapeutic wound healing composition. In a more preferred embodiment, the oral topical therapeutic wound healing compositions will comprise the therapeutic wound healing composition in an amount from about 0.1% to about 5%, and in a most preferred embodiment, the oral topical therapeutic wound healing compositions will comprise the therapeutic wound healing composition in an amount from about 0.1% to about 2%, and a oral topical vehicle in a quantity sufficient to bring the total amount of composition to 100%, by weight of the oral topical therapeutic wound healing composition.

The present invention extends to methods for preparing the oral topical therapeutic wound healing compositions. In such a method, the oral topical therapeutic wound healing composition is prepared by admixing a therapeutically effective amount of the therapeutic wound healing composition of the present invention and an oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In a preferred embodiment, an oral topical therapeutic wound healing composition is made by first dissolving coloring agents, sweetening agents, and similar additives in water. The therapeutic wound healing composition is then admixed with the aqueous solution. Then sufficient water or ethanol, or mixtures of water and ethanol, are added to the solution with mixing until the final solution volume is reached. In a more preferred embodiment, the therapeutic wound healing composition is added to the solution as the final ingredient. The final oral topical therapeutic wound healing compositions are readily prepared using methods generally known in the pharmaceutical arts.

The oral therapeutic wound healing composition may also be in the form of dental gel. As used herein, the term "gel" means a solid or semisolid colloid which contains considerable quantities of water. The colloid particles in a gel are linked together in a coherent meshwork which immobilizes the water contained inside the meshwork.

The dental gel compositions of the present invention may contain the conventional additives set out above for oral topical therapeutic wound healing compositions such as mouthwashes, rinses, oral sprays, and suspensions and, in addition, may contain additional additives such as a polishing agent, a desensitizing agent, and the like, providing the additional additives do not interfere with the therapeutic properties of the therapeutic wound healing composition.

In a dental gel composition, the oral vehicle generally comprises water, typically in an amount from about 10% to about 90%, by weight of the dental gel composition. Polyethylene glycol, propylene glycol, glycerin, and mixtures thereof may also be present in the vehicle as humectants or binders in amounts from about 18% to about 30%, by weight of the dental gel composition. Particularly preferred oral vehicles comprise mixtures of water with polyethylene glycol or water with glycerin and polypropylene glycol.

The dental gels of the present invention include a gelling agent (thickening agent) such as a natural or synthetic gum or gelatin. Gelling agents such as hydroxyethyl cellulose, methyl cellulose, glycerin, carboxypolymethylene, and gelatin and the like, and mixtures thereof may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 1%, by weight, and sodium citrate may be used in an amount from about 0.3% to about 9%, and preferably from about 0.6% to about 3%, by weight of the dental gel composition.

In accordance with this invention, therapeutically effective amounts of the therapeutic wound healing compositions of the present invention may be admixed into the dental gel compositions. These amounts are readily determined by those skilled in the art without the need for undue experimentation. In a preferred embodiment, the dental gel compositions will comprise the therapeutic wound healing composition in an amount from about 0.1% to about 10% and an oral topical vehicle in a quantity sufficient to bring the total amount of composition to 100%, by weight of the dental gel composition. In a more preferred embodiment, the dental gel compositions will comprise the therapeutic wound healing composition in an amount from about 0.1% to about 5%, and in a most preferred embodiment, the dental gel compositions will comprise the therapeutic wound healing composition in an amount from about 0.1% to about 2%, and an oral topical vehicle in a quantity sufficient to bring the total amount of composition to 100%, by weight of the dental gel composition.

The present invention extends to methods for preparing the therapeutic dental gel compositions. In such a method, the dental gel composition is prepared by admixing a therapeutically effective amount of the therapeutic wound healing composition of the present invention and an oral topical vehicle. The final compositions are readily prepared using methods generally known by those skilled in the dental and pharmaceutical arts. The apparatus useful in accordance with the present invention comprises mixing apparatus well known in the pharmaceutical arts, and therefore the selection of the specific apparatus will be apparent to the artisan.

In a preferred embodiment, a therapeutic dental gel composition is made by first dispersing a gelling agent in a humectant or water, or a mixture of both, then admixing to the dispersion an aqueous solution of the water-soluble additives such as the fluorine providing compound, sweeteners and the like, then adding the polishing agent, and lastly admixing the flavoring agent and the therapeutic wound healing composition. The final gel mixture is then tubed or otherwise packaged. The liquids and solids in a gel product are proportioned to form a creamy or gelled mass which is extrudable from a pressurized container or from a collapsible tube. The final therapeutic wound healing compositions are readily prepared using methods generally known in the pharmaceutical arts. In yet another form of the invention, the therapeutic wound healing composition is incorporated into an ingestible vehicle. The ingestible vehicle may be a confectionery bulking agent in the form of lozenges, tablets, toffees, nougats, suspensions, chewy candies, chewing gums, and the like. The pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular therapeutic confection.

The preparation of confectionery formulations is historically well known and has changed little through the years. Confectionery items have been classified as either "hard" confectionery or "soft" confectionery. The therapeutic wound healing compositions of the present invention can be incorporated into confectionery compositions by admixing the inventive composition into conventional hard and soft confections.

As used herein, the term confectionery material means a product containing a bulking agent selected from a wide variety of materials such as sugar, corn syrup, and in the case of sugarless bulking agents, sugar alcohols such as sorbitol and mannitol and mixtures thereof. Confectionery material may include such exemplary substances as lozenges, tablets, toffee, nougat, suspensions, chewy candy, chewing gum and the like. The bulking agent is present in a quantity sufficient to bring the total amount of composition to 100%. In general, the bulking agent will be present in amounts up to about 99.98%, preferably in amounts up to about 99.9%, and more preferably in amounts up to about 99%, by weight of the ingestible therapeutic wound healing composition.

Lozenges are flavored medicated dosage forms intended to be sucked and held in the mouth. Lozenges may be in the form of various shapes such as flat, circular, octagonal and biconvex forms. The lozenge bases are generally in two forms: hard boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavors, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from 4 to 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets, Volume I* (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agent, coloring agents, preservatives, medicaments, mixtures thereof and the like may be added thereafter also under agitation. A general discussion of the composition and preparation of nougat confections may be found in B. W. Minifie, *Chocolate, Cocoa and Confectionery: Science and Technology*, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The ingestible therapeutic wound healing compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as butylated hydroxyanisole (BHA), butylated hydroxytoluene (BHT), benzoic acid, ascorbic acid, methyl paraben, propyl paraben, tocopherols, and the like, and mixtures thereof. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacias, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltese, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drag and cosmetic applications. These colorants are known as F. D. & C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10%, and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution of the thickener is water soluble;

(B) admix the sweetening agent with water to form a solution;

(C) admix the therapeutic wound healing composition with the thickener-water admixture to form a uniform thickener-therapeutic wound healing composition;

(D) combine the sweetener solution with the thickener-therapeutic wound healing composition and mix until uniform; and (E) admix the optional adjunct materials such as coloring agents, flavoring agents, decolorants, solubilizers, antifoaming agents, buffers and additional water with the mixture of step (D) to form the suspension.

The ingestible therapeutic wound healing compositions of this invention may also be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable therapeutic candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The ingestible therapeutic wound healing composition of the instant invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, *Pharmaceutical Dosage Forms: Tablets Volume* 1, Marcel Dekker, Inc., New York, N.Y. at pages 289 to 466, which disclosure is incorporated herein by reference.

In accordance with this invention, therapeutically effective amounts of the therapeutic wound healing compositions of the present invention may be admixed into the hard and soft confectionery products. These amounts are readily determined by those skilled in the art without the need for undue experimentation. In a preferred embodiment, the ingestible therapeutic wound healing composition will comprise the therapeutic wound healing composition in an amount from about 0.1% to about 10% and an ingestible vehicle, that is a pharmaceutically acceptable carrier, in a quantity sufficient to bring the total amount of composition to 100%, by weight the ingestible therapeutic wound healing composition. In a more preferred embodiment, the ingestible composition will comprise the therapeutic wound healing composition in an mount from about 0.1% to about 5%, and in a most preferred embodiment, the ingestible composition will comprise the therapeutic wound healing composition in an mount from about 0.1% to about 2%, and an ingestible vehicle in a quantity sufficient to bring the total amount of composition to 100%, by weight the ingestible therapeutic wound healing composition.

The present invention extends to methods of making the ingestible therapeutic wound healing compositions. In such methods, an ingestible therapeutic wound healing composition is prepared by admixing a therapeutically effective amount of the therapeutic wound healing composition with a pharmaceutically-acceptable carrier. The apparatus useful in accordance with the present invention comprises mixing and heating apparatus well known in the confectionery arts, and therefore the selection of the specific apparatus will be apparent to the artisan. The final ingestible therapeutic wound healing compositions are readily prepared using methods generally known in the confectionery arts.

The therapeutic wound healing compositions may also be incorporated into chewing gums. In this form of the invention, the chewing gum composition contains a gum base, a bulking agent, the inventive therapeutic wound healing composition, and various additives.

The gum base employed will vary greatly depending upon various factors such as the type of base desired, the consistency of gum desired and the other components used in the composition to make the final chewing gum product. The gum base may be any water-insoluble gum base known in the art, and includes those gum bases utilized for chewing gums and bubble gums. Illustrative examples of suitable polymers in gum bases include both natural and synthetic elastomers and rubbers. For example, those polymers which are suitable as gum bases include, without limitation, substances of vegetable origin such as chicle, crown gum, nispero, rosadinha, jelutong, perillo, niger gutta, tunu, balata, gutta-percha, lechi-capsi, sorva, gutta kay, mixtures thereof and the like. Synthetic elastomers such as butadiene-styrene copolymers, polyisobutylene, isobutylene-isoprene copolymers, polyethylene, mixtures thereof and the like are particularly useful.

The gum base may include a non-toxic vinyl polymer, such as polyvinyl acetate and its partial hydrolysate, polyvinyl alcohol, and mixtures thereof. When utilized, the molecular weight of the vinyl polymer may range from about 2,000 up to and including about 94,000.

The amount of gum base employed will vary greatly depending upon various factors such as the type of base used, the consistency of the gum desired and the other components used in the composition to make the final chewing gum product. In general, the gum base will be present in amounts from about 5% to about 94%, by weight of the final chewing gum composition, and preferably in amounts from about 15% to about 45%, and more preferably in amounts from about 15% to about 35%, and most preferably in amounts from about 20% to about 30%, by weight of the final chewing gum composition.

The gum base composition may contain conventional elastomer solvents to aid in softening the elastomer base component. Such elastomer solvents may comprise terpinene resins such as polymers of Alpha-pinene or β-pinene, methyl, glycerol or pentaerythritol esters of rosins or modified rosins and gums, such as hydrogenated, dimerized or polymerized rosins or mixtures thereof. Examples of elastomer solvents suitable for use herein include the pentaerythritol ester of partially hydrogenated wood or gum rosin, the pentaerythritol ester of wood or gum rosin, the glycerol ester of wood rosin, the glycerol ester of partially dimerized wood or gum rosin, the glycerol ester of polymerized wood or gum rosin, the glycerol ester of tall oil rosin, the glycerol ester of wood or gum rosin and the partially hydrogenated wood or gum rosin and the partially hydrogenated methyl ester of wood or rosin, mixtures thereof, and the like. The elastomer solvent may be employed in amounts from about 5% to about 75%, by weight of the gum base, and preferably from about 45% to about 70%, by weight of the gum base.

A variety of traditional ingredients may be included in the gum base in effective amounts such as plasticizers or softeners such as lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, mixtures thereof, and the like may also be incorporated into the gum base to obtain a variety of desirable textures and consistency properties. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like may also be incorporated into the gum base to obtain a variety of desirable textures and consistency properties. These traditional additional materials are generally employed in amounts up to about 30%, by weight of the gum base, and preferably in amounts from about 3% to about 20%, by weight of the gum base.

The gum base may include effective amounts of mineral adjuvants such as calcium carbonate, magnesium carbonate, alumina, aluminum hydroxide, aluminum silicate, talc, tricalcium phosphate, dicalcium phosphate and the like as well as mixtures thereof. These mineral adjuvants may serve as fillers and textural agents. These fillers or adjuvants may be used in the gum base in various amounts. Preferably the amount of filler when used will be present in an amount up to about 60%, by weight of the chewing gum base.

The chewing gum base may additionally include the conventional additives of coloring agents, antioxidants, preservatives and the like. For example, titanium dioxide and other dyes suitable for food, drug and cosmetic applications, known as F. D. & C. dyes, may be utilized. An antioxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the chewing gum base.

The gum composition may include effective amounts of conventional additives selected from the group consisting of sweetening agents (sweeteners), plasticizers, softeners, emulsifiers, waxes, fillers, bulking agents, mineral adjuvants, flavoring agents (flavors, flavorings), coloring agents (colorants, colorings), antioxidants, acidulants, thickeners, mixtures thereof and the like. Some of these additives may serve more than one purpose. For example, in sugarless gum compositions, the sweetener, e.g., sorbitol or other sugar alcohol or mixtures thereof, may also function as a bulking agent. Similarly, in sugar containing gum compositions, the sugar sweetener can also function as a bulking agent.

The plasticizers, softeners, mineral adjuvants, colorants, waxes and antioxidants discussed above as being suitable for use in the gum base may also be used in the gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants. The fillers when used may be utilized in an amount up to about 60%, by weight of the gum composition.

Bulking agents (carriers, extenders) suitable for use in chewing gums include sweetening agents selected from the group consisting of monosaccharides, disaccharides, polysaccharides, sugar alcohols, and mixtures thereof; polydextrose; maltodextrins; minerals, such as calcium carbonate, talc, titanium dioxide, dicalcium phosphate, and the like. Bulking agents may be used in amounts up to about 90%, by weight of the final gum composition, with amounts from about 40% to about 70%, by weight of the gum composition being preferred, with from about 50% to about 65%, by weight, being more preferred and from about 55% to about 60%, by weight of the chewing gum composition, being most preferred.

The sweetening agent used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as monosaccharides, disaccharides and polysaccharides such as xylose, ribulose, glucose (dextrose), mannose, galactose, fructose (levulose), sucrose (sugar), maltese, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-Alpha-aspartyl-N-(2,2,4,4-tetramethyl-3-thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), known, for example, under the product designation of Sucralose; and (e) protein based sweeteners such as thaumaoccous danielli (Thaumatin I and II).

In general, an effective amount of sweetener is utilized to provide the level of bulk and/or sweetness desired, and this amount will vary with the sweetener selected. This amount of sweetener will normally be present in amounts from about 0.0025% to about 90%, by weight of the gum composition, depending upon the sweetener used. The exact range of amounts for each type of sweetener is well known in the art and is not the subject of the present invention. The amount of sweetener ordinarily necessary to achieve the desired level of sweetness is independent from the flavor level achieved from flavor oils.

Preferred sugar based-sweeteners are sugar (sucrose), corn syrup and mixtures thereof. Preferred sugarless sweeteners are the sugar alcohols, artificial sweeteners, dipeptide based sweeteners and mixtures thereof. Preferably, sugar alcohols are used in the sugarless compositions because these sweeteners can be used in amounts which are sufficient to provide bulk as well as the desired level of sweetness. Preferred sugar alcohols are selected from the group consisting of sorbitol, xylitol, maltitol, mannitol, and mixtures thereof. More preferably, sorbitol or a mixture of sorbitol and mannitol is utilized. The gamma form of sorbitol is preferred. An artificial sweetener or dipeptide based sweetener is preferably added to the gum compositions which contain sugar alcohols.

The coloring agents useful in the gum compositions are used in amounts effective to produce the desired color. These coloring agents include pigments which may be incorporated in amounts up to about 6% by weight of the gum composition. A preferred pigment, titanium dioxide, may be incorporated in amounts up to about 2%, and preferably less than about 1% by weight of the composition. The colorants may also include natural food colors and dyes suitable for food, drug and cosmetic applications. These colorants are known as F. D. & C. dyes and lakes. The materials acceptable for the foregoing uses are preferably water-soluble. Illustrative nonlimiting examples include the indigoid dye known as F. D. & C. Blue No. 2, which is the disodium salt of 5,5-indigotindisulfonic acid. Similarly, the dye known as F. D. & C. Green No. 1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F. D. & C. colorants and their corresponding chemical structures may be found in the Kirk-Othmer *Encyclopedia of Chemical Technology*, 3rd Edition, in volume 5 at pages 857-884, which text is incorporated herein by reference.

Suitable oils and fats usable in gum compositions include partially hydrogenated vegetable or animal fats, such as coconut off, palm kernel off, beef tallow, lard, and the like. These ingredients when used are generally present in amounts up to about 7%, by weight, and preferably up to about 3.5%, by weight of the gum composition.

In accordance with this invention, therapeutically effective amounts of the therapeutic wound healing compositions of the present invention may be admixed into a chewing gum. These amounts are readily determined by those skilled in the art without the need for undue experimentation. In a preferred embodiment, the final chewing gum composition will comprise the therapeutic wound healing composition in an amount from about 0.1% to about 10% and a chewing gum composition in a quantity sufficient to bring the total amount of composition to 100%, by weight of the chewing gum composition. In a more preferred embodiment, the final chewing gum composition will comprise the therapeutic wound healing composition in an amount from about 0.1% to about 5%, and in a most preferred embodiment, the final chewing gum composition will comprise the therapeutic wound healing composition in an amount from about 0.1% to about 2%, and a chewing gum composition in a quantity sufficient to bring the total amount of composition to 100%, by weight of the chewing gum composition.

The present invention extends to methods of making the therapeutic chewing gum compositions. The therapeutic wound healing compositions may be incorporated into an otherwise conventional chewing gum composition using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

For example, a gum base is heated to a temperature sufficiently high enough to soften the base without adversely effecting the physical and chemical make up of the base. The optimum temperatures utilized may vary depending upon the composition of the gum base used, but such temperatures are readily determined by those skilled in the art without undue experimentation. The gum base is conventionally melted at temperatures that range from about 60° C. to about 120° C. for a period of time sufficient to render the base molten. For example, the gum base may be heated under these conditions for a period of about thirty minutes just prior to being admixed incrementally with the remaining ingredients of the base such as the plasticizer, fillers, the bulking agent and/or sweeteners, the softener and coloring agents to plasticize the blend as well as to modulate the hardness, viscoelasticity and formability of the base. The chewing gum base is then blended with the therapeutic wound healing composition of the present invention which may have been previously blended with other traditional ingredients. Mixing is continued until a uniform mixture of gum composition is obtained. Thereafter the gum composition mixture may be formed into desirable chewing gum shapes.

In a specific embodiment, the invention is directed to a therapeutic pharmaceutical composition for preventing and reducing injury to mammalian cells, and increasing the resuscitation rate of injured mammalian cells, which comprises:

(A) a therapeutically effective amount of a therapeutic wound healing composition of Embodiment One (I) selected from the group consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells;

(I.C) (a) an antioxidant; and (b) a mixture of sainted and unsaturated fatty acids wherein the fatty acids are those fatty acids required for the repair of cellular membranes and resuscitation of mammalian cells;

(I.D) (a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (B) a pharmaceutically acceptable carrier.

The pharmaceutically acceptable carrier may be selected from the group consisting of pharmaceutical appliances, topical vehicles, and ingestible vehicle.

In another specific embodiment, the invention is directed to a method for preparing a therapeutic pharmaceutical composition for preventing and reducing injury to mammalian cells, and increasing the resuscitation rate of injured mammalian cells, which comprises the steps of:

(A) providing a therapeutically effective amount of a therapeutic wound healing composition of Embodiment One (I.A-D) selected from the group consisting of:

(I.A) (a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(I.B) (a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells;

(I.C) (a) an antioxidant; and (b) a mixture of saturated and unsaturated fatty acids wherein the fatty acids are those fatty acids required for the repair of cellular membranes and resuscitation of mammalian cells;

(I.D) (a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (B) providing a pharmaceutically acceptable carrier; and (C) admixing the therapeutic wound healing composition from step (A) and the pharmaceutically acceptable carrier from step (B) to form a therapeutic pharmaceutical composition.

Throughout this application, various publications have been referenced. The disclosures in these publications are incorporated herein by reference in order to more fully describe the state of the art.

II. Bioadhesive-Wound Healing Compositions

A. Embodiment Two (I.A-D+X)

Applicant has discovered therapeutic bioadhesive-wound healing compositions (I.A-D+X) which comprise a bioadhesive agent (X) and the wound healing compositions of Embodiment One (I.A-D). Preferably, the wound healing composition (I.A) comprises (a) pyruvate, (b) an antioxidant, and (c) a mixture of saturated and unsaturated fatty acids. The bioadhesive agent comprises a water-swellable but water-insoluble fibrous cross-linked material which adheres to live or freshly killed mucous membranes or skin tissues. Applicants have found that the combination of a bioadhesive agent and a wound healing composition results in a therapeutic bioadhesive-wound healing composition which can increase the resuscitation rate of injured mammalian cells and the proliferation rate of new mammalian cells to replace dead cells and thereby reduce the duration and severity of wounds. The bioadhesive-wound healing therapeutic compositions may further comprise medicaments such as immunostimulating agents, cytotoxic agents, antiviral agents, antikeratolytic agents, anti-inflammatory agents, antifungal agents, tretinoin, sunscreen agents, dermatological agents, topical antihistamine agents, antibacterial agents, and the like.

Gingivitis is caused by supragingival plaque which releases toxins and microbial products that attack the gingiva and result in inflammation of the gingival tissues. Inflammation in the connective tissue results in pocket formation and may ultimately result in periodontitis. The wound healing compositions of the present invention and other medicaments such as immunostimulating agents, antiviral agents, antikeratolytic agents, anti-inflammatory agents, antifungal agents, topical antihistamine agents, antibacterial agents, and the like, may help decrease inflammation and improve healing of the damaged tissues. The use of suitable bioadhesive agents may improve coating, prolong duration of action, and improve patient's comfort and compliance. Suitable dosage forms for the bioadhesive-wound healing therapeutic compositions are solution, suspension, gel, paste, dental floss, microcapsules, nanoparticles, liposomes, mono- and multilaminated strips and patches, mono- and multilayered tablets and other suitable bioadhesive delivery dosage forms. The formulation may be delivered non-specifically to the buccal cavity or locally to the gingiva, gum, gingival pockets, between teeth or other suitable target areas.

The combination of a bioadhesive agent and the wound healing compositions of the present invention provides a bioadhesive agent-wound healing composition useful for treating wounds and having an enhanced ability to prevent and reduce injury to mammalian cells and further increase the resuscitation rate of injured mammalian tells. The tissue damage associated with wounds is believed to be caused by the production of cellular produced active oxygen species. Combination of a bioadhesive agent and the wound healing compositions may suppress such reactive oxygen-linked tissue injury.

The bioadhesive agents which may be employed in the bioadhesive agent-wound healing composition of the present invention are materials which adhere to live or freshly killed mucous membranes or skin tissues. The bioadhesive agents may be selected from a wide variety of water-swellable but water-insoluble fibrous cross-linked materials. Bioadhesives generally comprise a mucoadhesive hydrogel such as a polyacrylic acid cross linked by a polyhydroxy compound such as a carbohydrate (sugar, cyclitols) to form a substantially water-insoluble hydrogel. Other bioadhesives include carboxymethylcellulose (CMC), methylcellulose, guar gum, and polycarbophils which are high molecular weight polymers of acrylic acid such as Carbopol™ commercially available from BF Goodrich Company, Cleveland, Ohio. Bioadhesives are discussed in more detail in, for example, European patent application no. 0410696A1, to Kellaway et al., and U.S. Pat. No. 4,615,697, issued to Robinson, which disclosures are incorporated herein by reference.

The amount of bioadhesive agent used in the bioadhesive agent-wound healing compositions of the present invention may vary depending upon the type of bioadhesive employed and the particular properties desired. In general, the amount of bioadhesive agent present is the ordinary dosage required to obtain the desired result. Such dosages are known to the skilled practitioner in-the medical arts and are not a part of the present invention. In a preferred embodiment, the bioadhesive agent in the bioadhesive-wound healing composition is present in an amount from about 0.01% to about 90%, preferably from about 0.1% to about 50%, and more preferably from about 1% to about 2%, by weight.

b. Methods for Making the Bioadhesive-Wound Healing Compositions of Embodiment Two (IA–D+X)

The present invention extends to methods for making the therapeutic bioadhesive-wound healing compositions (I.A–D+X). In general, a therapeutic bioadhesive-wound healing composition is made by forming an admixture of the wound healing components of Embodiment One (I.A–D) and a bioadhesive agent. In a first aspect of Embodiment Two (I.A+X), a bioadhesive-wound healing therapeutic composition is made by forming an admixture of a bioadhesive agent and a wound healing composition comprising (a) a pyruvate, (b) an antioxidant, and (c) a mixture of saturated and unsaturated fatty acids. In a second aspect of Embodiment Two (I.B+X), a bioadhesive-wound healing therapeutic composition is made by forming an admixture of a bioadhesive agent and a wound healing composition comprising (a) a pyruvate, (b) a lactate, and (c) a mixture of saturated and unsaturated fatty acids. In a third aspect of Embodiment Two (I.C+X), a bioadhesive-wound healing therapeutic composition is made by forming an admixture of a bioadhesive agent and a wound healing composition comprising (a) an antioxidant, and (b) a mixture of saturated and unsaturated fatty acids. In a fourth aspect of Embodiment Two (I.D+X), a bioadhesive-wound healing therapeutic composition is made by forming an admixture of a bioadhesive agent and a wound healing composition comprising (a) a lactate, (13) an antioxidant, and (c) a mixture of saturated and unsaturated fatty acids.

In a preferred embodiment, the invention is directed to a method for preparing a therapeutic bioadhesive-wound healing composition (I.A+X) which comprises the steps of admixing the following ingredients:

(A) a therapeutically effective amount of a bioadhesive agent; and (B) a wound healing composition which comprises:
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells.

c. Methods for Employing the Bioadhesive-Wound Healing Compositions of Embodiment Two (I.A–D+X)

The present invention extends to methods for employing the therapeutic bioadhesive-wound healing compositions (I.A–D+X). In general, a therapeutic composition is employed by contacting the therapeutic composition with a wound. In a preferred embodiment, the invention is directed to a method for treating a wound in a mammal with a bioadhesive-wound healing composition (I.A+X) which comprises the steps of:

(A) providing a therapeutic bioadhesive-wound healing composition which comprises:

(1) a therapeutically effective amount of a bioadhesive agent; and (2) a wound healing composition which comprises:
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells; and (B) contacting the bioadhesive-wound healing composition with the itching wound.

d. Augmented Bioadhesive-Wound Healing Compositions of Embodiment Two (I.A–D+X+M)

In another aspect of Embodiment Two, the therapeutic bioadhesive-wound healing compositions (I.A–D+X) of the present invention may be further combined with medicaments useful for treating wounds (M) to form augmented bioadhesive-wound healing compositions (I.A–D+X+M). In this embodiment, the combination of the bioadhesive-wound healing composition of the present invention and the medicament useful for treating wounds provides an augmented bioadhesive-wound healing composition having an enhanced ability to increase the proliferation and resuscitation rate of mammalian cells. For example, the therapeutic compositions of the present invention may be used in combination with medicaments useful for treating wounds such as immunostimulating agents (Betafectin™), antiviral agents, antikeratolytic agents, anti-inflammatory agents, antifungal agents, tretinoin, sunscreen agents, dermatological agents, topical antihistamine agents, antibacterial agents, other bioadhesive agents, respiratory bursting inhibitors (lactic acid, adenosine), inhibitors of prostaglandin synthesis (ibuprofen, aspirin, indomethacin, meclofenomic acid, retinoic acid, padimate O, meclomen, oxybenzone), steroidal anti-inflammatory agents (corticosteroids including synthetic analogs), antimicrobial agents (neosporin ointment, silvadine), antiseptic agents, anesthetic agents (pramoxine hydrochloride, lidocaine, benzocaine), cell nutrient media, burn relief medications, sun burn medications, acne preparations, insect bite and sting medications, wound cleansers, wound dressings, scar reducing agents (vitamin E), and the like, and mixtures thereof, to further enhance the proliferation and resuscitation rate of mammalian cells. Preferably, the medicament useful for treating wounds is selected from the group consisting of immunostimulating agents, antiviral agents, antikeratolytic agents, anti-inflammatory agents, antifungal agents, tretinoin, sunscreen agents, dermatological agents, topical antihistamine agents, antibacterial agents, bioadhesive agents, respiratory bursting inhibitors, inhibitors of prostaglandin synthesis, antimicrobial agents, cell nutrient media, scar reducing agents, and mixtures thereof. More preferably, the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, and mixtures thereof.

In a preferred embodiment, the invention is directed to an augmented bioadhesive-wound healing composition (I.A+X+M) which comprises:

(A) a therapeutic bioadhesive-wound healing composition which comprises:
  (1) a therapeutically effective amount of a bioadhesive agent; and
  (2) a wound healing composition which comprises:
    (a) pyruvate selected from the group consisting of pyruvic acid, pharmaceutically acceptable salts of pyruvic acid, and mixtures thereof;
    (b) an antioxidant; and
    (c) a mixture of saturated and unsaturated fatty acids wherein the fatty acids are those fatty acids required for the repair of cellular membranes and resuscitation of mammalian cells; and
(B) a medicament useful for treating wounds.

In a first aspect of this embodiment, the augmented bioadhesive-wound healing composition is an immunostimulating bioadhesive-wound healing composition (I.A–D+X+M1) which comprises an immunostimulating agent (M1), a bioadhesive agent, and a wound healing composition. Immunostimulating agents can stimulate the immune system in a patient to kill an infecting organism but do not promote the wound healing process. Applicants have found that the combination of an immunostimulating agent, a bioadhesive agent, and a wound healing composition results in a therapeutic immunostimulating bioadhesive-wound healing composition which acts synergistically to enhance wound repair in both the upper and lower portions of the skin.

In a second aspect of this embodiment, the augmented bioadhesive-wound healing composition is an antiviral bioadhesive-wound healing composition (I.A–D+X+M2) which comprises an antiviral agent (M2), a bioadhesive agent, and a wound healing composition. Antiviral agents can reduce virus liters in a patient but do not promote the wound healing process. Applicants have found that the combination of an antiviral agent, a bioadhesive agent, and a wound healing composition results in a therapeutic antiviral bioadhesive-wound healing composition which reduces the size, duration, and severity of oral and vaginal wounds suffered from viruses such as herpes.

In a third aspect of this embodiment, the augmented bioadhesive-wound healing composition is an antikeratolytic bioadhesive-wound healing composition (I.A–D+X+M3) which comprises an antikeratolytic agent (M3), a bioadhesive agent, and a wound healing composition. Antikeratolytic agents can reduce scaling and dryness in a patient but do not promote the wound healing process. Applicants have found that the combination of an antikeratolytic agent, a bioadhesive agent, and a wound healing composition results in a therapeutic antikeratolytic bioadhesive-wound healing composition which reduces the duration and severity of keratolysis type diseases such as psoriasis.

In a fourth aspect of this embodiment, the augmented bioadhesive-wound healing composition is an anti-inflammatory bioadhesive-wound healing composition (I.A–D+X+M4) which comprises anti-inflammatory bioadhesive-wound healing composition which comprises an anti-inflammatory agent (M4), a bioadhesive agent, and a wound healing composition. And-inflammatory agents can reduce inflammation in a patient but do not promote the wound healing process. Applicants have found that the combination of an anti-inflammatory agent, a bioadhesive agent, and a wound healing composition results in a therapeutic anti-inflammatory bioadhesive-wound healing composition which reduces the duration and severity of inflammation.

In a fifth aspect of this embodiment, the augmented bioadhesive-wound healing composition is an antifungal bioadhesive-wound healing composition (I.A–D X+M5) which comprises a first antifungal agent (M5), a bioadhesive agent, and a wound healing composition. The first antifungal agent is lactic acid or sorbic acid. Antifungal agents can treat fungal infections in a patient but do not promote the wound healing process. Applicants have found that the combination of an antifungal agent, a bioadhesive agent, and a wound healing composition results in a therapeutic antifungal bioadhesive-wound healing composition which reduces the duration and severity of fungal infections. The therapeutic antifungal bioadhesive-wound healing compositions may further comprise a second antifungal agent and an anti-inflammatory agent.

In a sixth aspect of this embodiment, the augmented bioadhesive-wound healing composition is an acne treating bioadhesive-wound healing composition (I.A–D X+M6) which comprises tretinoin (M6), a bioadhesive agent, and a wound healing composition. Tretinoin is useful for the topical treatment of acne vulgaris but is known to induce excessive redness, edematous blistering or crusting, and severe local erythema and peeling at the site of application. Applicants have found that the combination of tretinoin, a bioadhesive agent, and a wound healing composition results in a therapeutic acne treating bioadhesive-wound healing composition which reduces the duration and severity of acne vulgaris and the irritation associated with tretinoin. This invention also relates to methods for employing the therapeutic acne treating bioadhesive-wound healing compositions to treat wrinkles.

In a seventh aspect of this embodiment, the augmented bioadhesive-wound healing composition is a sunscreen treating bioadhesive-wound healing composition (I.A–D+X+M7) which comprises a bioadhesive and a therapeutically effective amount of a sunscreen agent and an anti-inflammatory agent (sunscreen agent and anti-inflammatory agent collectively referred to as M7) and the wound healing compositions of the present invention. Sunscreen agents can help prevent sunburn by screening ultra violet light but do not heal injured mammalian cells. Wound healing compositions can increase the resuscitation rate of injured mammalian cells and the proliferation rate of new mammalian cells to replace dead cells. Wound healing compositions can also minimize oxygen radical damage from ultra violet light. Applicants have found that the combination of a bioadhesive agent, a sunscreen agent, an anti-inflammatory agent, and a wound healing composition results in a therapeutic sunscreen bioadhesive-wound healing compositions useful for minimizing and treating sunburn damage. The sunscreen bioadhesive-wound healing compositions may optionally contain a therapeutically effective amount of a topical anesthetic to further reduce the severity of sunburn.

In an eighth aspect of this embodiment, the augmented bioadhesive-wound healing composition is a dermatological bioadhesive-wound healing composition (I.A–D+X+M8) useful to minimize and treat diaper dermatitis. The dermatological bioadhesive,-wound healing compositions comprise a bioadhesive and a therapeutically effective amount of (1) a buffering agent to maintain the pH of the dermatitis in a range from about 5 to about 8 and an anti-inflammatory agent (buffering agent and anti-inflammatory agent collectively referred to as M8) and the wound healing compositions of the present invention. Applicants have found that the combination of a bioadhesive, a buffering agent, an anti-inflammatory agent, and a wound healing composition results in a therapeutic dermatological bioadhesive-wound healing compositions useful for minimizing and treating diaper dermatitis. The dermatological bioadhesive-wound healing compositions may optionally contain a therapeutically effective amount of a topical antiseptic to further reduce the duration and severity of diaper dermatitis.

In a ninth aspect of this embodiment, the augmented bioadhesive-wound healing composition is an antihistamine bioadhesive-wound healing composition (I.A–D+X+M9) useful to minimize and treat itching associated with skin irritations. The antihistamine bioadhesive-wound healing compositions comprise a therapeutically effective amount of a bioadhesive, a topical antihistamine, and the wound healing compositions of the present invention. Topical antihistamines are useful for the topical treatment of skin irritations but are potentially sensitizing. Wound healing compositions can increase the resuscitation rate of injured mammalian cells and the proliferation rate of new mammalian cells to replace dead cells. Applicants have found that the combination of a bioadhesive, a topical antihistamine, and a wound healing composition results in a therapeutic antihistamine bioadhesive-wound healing composition which reduces the duration and severity of itching associated with skin irritations and the sensitizing effect associated with topical antihistamines.

In a tenth aspect of this embodiment, the augmented bioadhesive-wound healing composition is an antibacterial bioadhesive-wound healing composition (I.A–D+X+M10) which comprises a bioadhesive agent, an antibacterial agent (M10), and a wound healing composition. Antibacterial agents can treat bacterial infections in a patient but do not promote the wound healing process. Applicants have found that the combination of a bioadhesive agent, an antibacterial agent, and a wound healing composition results in a therapeutic antibacterial bioadhesive-wound healing composition which reduces the duration and severity of bacterial infections.

In an eleventh aspect of this embodiment, the augmented bioadhesive-wound healing composition is a cytoprotective bioadhesive-wound healing composition (I.A–D+X+X) for protecting mammalian cells from a medicament having cytotoxic properties which comprises a cytotoxic agent (X), a bioadhesive agent, and a wound healing composition. Cells treated with the cytoprotective compositions of the present invention show decreased levels of hydrogen peroxide production, increased resistance to cytotoxic agents, increased rates of proliferation, and increased viability. Cytoprotective-wound healing composition are discussed in detail below.

The medicaments useful for treating wounds which may be employed in the augmented bioadhesive-wound healing therapeutic compositions, such as the immunostimulating agents, antiviral agents, antikeratolytic agents, anti-inflammatory agents, antifungal agents, tretinoin, sunscreen agents, dermatological agents, topical antihistamine agents, antibacterial agents, and the like, and the amounts which may be employed, have been described above in detail.

The present invention extends to methods for making the augmented bioadhesive-wound healing compositions. In general, the augmented compositions are made by admixing the therapeutic bioadhesive-wound healing composition with the medicament useful for treating wounds to prepare the augmented bioadhesive-wound healing composition.

The present invention also extends to methods for employing the augmented bioadhesive-wound healing compositions. In general, an augmented bioadhesive-wound healing composition is employed by contacting the composition with a wound. In a preferred embodiment, the invention is directed to a method for treating a wound in a mammal with an augmented bioadhesive-wound healing composition (I.A+X+M) which comprises the steps of:

(A) providing a therapeutic augmented bioadhesive-wound healing composition which comprises:

(1) a therapeutically effective amount of a bioadhesive agent;

(2) a wound healing composition which comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (3) providing a medicament useful for treating wounds; and (B) contacting the augmented bioadhesive-wound healing composition with the wound.

The types of wounds which may be healed using the bioadhesive-wound healing compositions and the augmented bioadhesive-wound healing compositions of the present invention are wounds such as those caused by viral infection, keratolysis, inflammation, fungal infections, and the like. The therapeutic compositions may be used topically to protect and accelerate the healing of injured tissue.

Methods for treating a wound comprise topically administering the compositions of the present invention directly to a wound site to increase the healing rate of the wound. The composition is maintained in contact with the wound for a period of time sufficient to increase the proliferation and resuscitation rate of the cells.

e. Formulations of the Bioadhesive-Wound Healing Compositions of Embodiment Two (I.A–D+X) and (I.A–D+X+M)

Once prepared, the inventive therapeutic bioadhesive-wound healing compositions and augmented bioadhesive-wound healing compositions may be stored for future use or may be formulated in effective amounts with pharmaceutically acceptable carriers such as pharmaceutical appliances and topical vehicles (oral and non-oral) to prepare a wide variety of pharmaceutical compositions. The pharmaceutically acceptable carriers which may be employed and the methods used to prepare the pharmaceutical compositions have been described above in connection with the formulations of the wound healing compositions of Embodiment One (I.A–D).

In a preferred embodiment, the invention is directed to a bioadhesive-wound healing pharmaceutical composition which comprises:

(A) a therapeutic bioadhesive-wound healing composition (I.A+X) which comprises:

(1) a therapeutically effective amount of a bioadhesive agent; and (2) a wound healing composition which comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (B) a pharmaceutically acceptable carrier selected from the group consisting of pharmaceutical appliances, bioadhesives, and occlusive vehicles.

In another preferred embodiment, the invention is directed to a method for preparing a pharmaceutical composition for increasing the proliferation and resuscitation rate of mammalian cells, which comprises the steps of:

(A) providing a therapeutically effective amount of a bioadhesive-wound healing composition (I.A+X) which comprises:

(1) a bioadhesive agent; and (2) a wound healing composition comprising:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells;

(B) providing a pharmaceutically acceptable carrier; and (C) admixing the bioadhesive-wound healing composition from step (A) and the pharmaceutically acceptable carrier from step (B) to form a pharmaceutical composition.

The present invention is further illustrated by the following examples which are not intended to limit the effective scope of the claims. All parts and percentages in the examples and throughout the specification and claims are by weight of the final composition unless otherwise specified.

E. EXAMPLES

1. Examples of the Therapeutic Wound Healing Compositions of Embodiment One (I.A–D)

a. Study 1

This study demonstrates a comparison of the viability of U937 monocytic cells after exposure of the cells to various antioxidants and combinations of antioxidants. This study also demonstrate a comparison of the levels of hydrogen peroxide produced by U937 monocytic cells and mammalian epidermal keratinocytes after exposure of the cells to various antioxidants and combinations of antioxidants. The results of this study are illustrated in FIGS. 1–4 and examples 1–26 below.

Mammalian epidermal keratinocytes and monocytes were employed to examine the ability of various antioxidants to reduce levels of hydrogen peroxide in these cells. Hydrogen peroxide was measured after the cells were exposed to ultraviolet light in the wavelength range from 290 to 320 nm (UV-B) or to the inflammatory compound 12-0-tetradecanoyl-phorbol-13-acetate (TPA). Sodium pyruvate was tested at various concentrations to determine the effect of concentrations of this antioxidant on the hydrogen peroxide production by epidermal cells and monocytes. Magnesium pyruvate, calcium pyruvate, zinc pyruvate, and combinations of sodium pyruvate with ascorbic acid, lactic acid, and Vitamin E were then tested to determine the effect of these salts and combinations of antioxidants on the hydrogen peroxide production by epidermal cells and monocytes.

Mammalian epidermal keratinocytes were isolated by trypsinization of epithelial sheets and grown in modified basal MCDB 153 medium supplemented with epidermal growth factor, bovine pituitary extract, and hydrocortisone. Cells were maintained in a humidified incubator with 5% carbon dioxide at 37° C. Keratinocytes were seeded in 60 mm culture dishes at a cell density of $3 \times 10^5$ cells per dish and the cultures were exposed to 1 M.E.D. dose of ultraviolet-B light (100 mJ/cm$^2$) or treated with 100 ng/ml of TPA.

U937 monocytic cells are a cultured cell line grown in RPMI media with 10% fetal calf serum. Cells were maintained in a 60 mm culture dish at 5% carbon dioxide at 37° C. at a seeding density not exceeding $1 \times 10^6$ cells per dish.

Sodium pyruvate, lactic acid, ascorbic acid, and Vitamin E were dissolved in distilled water, with sufficient surfactant. The concentrations of the sodium pyruvate solutions prepared were 1 mM, 10 mM, 50 mM, 100 mM, and 200 mM. The concentrations of the lactic acid solutions prepared were 1.0%, 0.1%, and 0.05%. The concentrations of the ascorbic acid solutions prepared were 1.0%, 0.1%, 0.05%, and 0.025%. The concentrations of the Vitamin E solutions prepared were 1 U, 10 U, 50 U, and 100 U. The test solutions were adjusted to a pH value of 7.4 with 1.0N sodium hydroxide solution and then sterile filtered. The appropriate concentration of test solution or combination of test solutions was added to the cells immediately prior to exposure of the cells to ultraviolet light-B or TPA [100 ng/ml]. Stock solutions were prepared so that the vehicle did not constitute more than 1% of the total volume of the culture media.

Intracellular hydrogen peroxide production by mammalian epidermal keratinocytes and U937 monocytes was measured using dichlorofluorescein diacetate (DCFH-DA, Molecular Probes, Eugene, Oreg.). DCFH-DA is a non-polar non-fluorescent compound that readily diffuses into cells where it is hydrolyzed to the polar non-fluorescent derivative DCFH which then becomes trapped within the cells. In the presence of intracellular hydrogen peroxide, DCFH is oxidized to the highly fluorescent compound DCF. Hence, cellular fluorescence intensity is directly proportional to the level of intracellular hydrogen peroxide produced. Cellular fluorescence intensity can be monitored by fluorimetry and by flow cytometry.

Mammalian epidermal keratinocytes and U937 cultured monocytes ($1 \times 10^6$ per dish) were incubated at 37° C. with 5 uM of DCFH-DA. Production of hydrogen peroxide was measured using a Coulter Profile analytical flow cytometer. Linear and log intensity of green fluorescence data was collected. For each analysis, a quantity of 10,000 to 20,000 events was accumulated. Optical alignment for the instrument was performed daily. Coefficients of variation for forward angle light scatter and integrated green fluorescence were generally less than two. Each analysis was repeated three times and the quantitation of fluorescence was expressed in terms of femtomoles (fmol, $10^{-15}$ moles) of DCF oxidized per cell, which is a direct measure of the intracellular hydrogen peroxide produced. Alternatively, in the saturated and unsaturated fatty acid examples in examples 27–52, fluorimetry was used to assess the DCF oxidation per cell.

Figure 2:
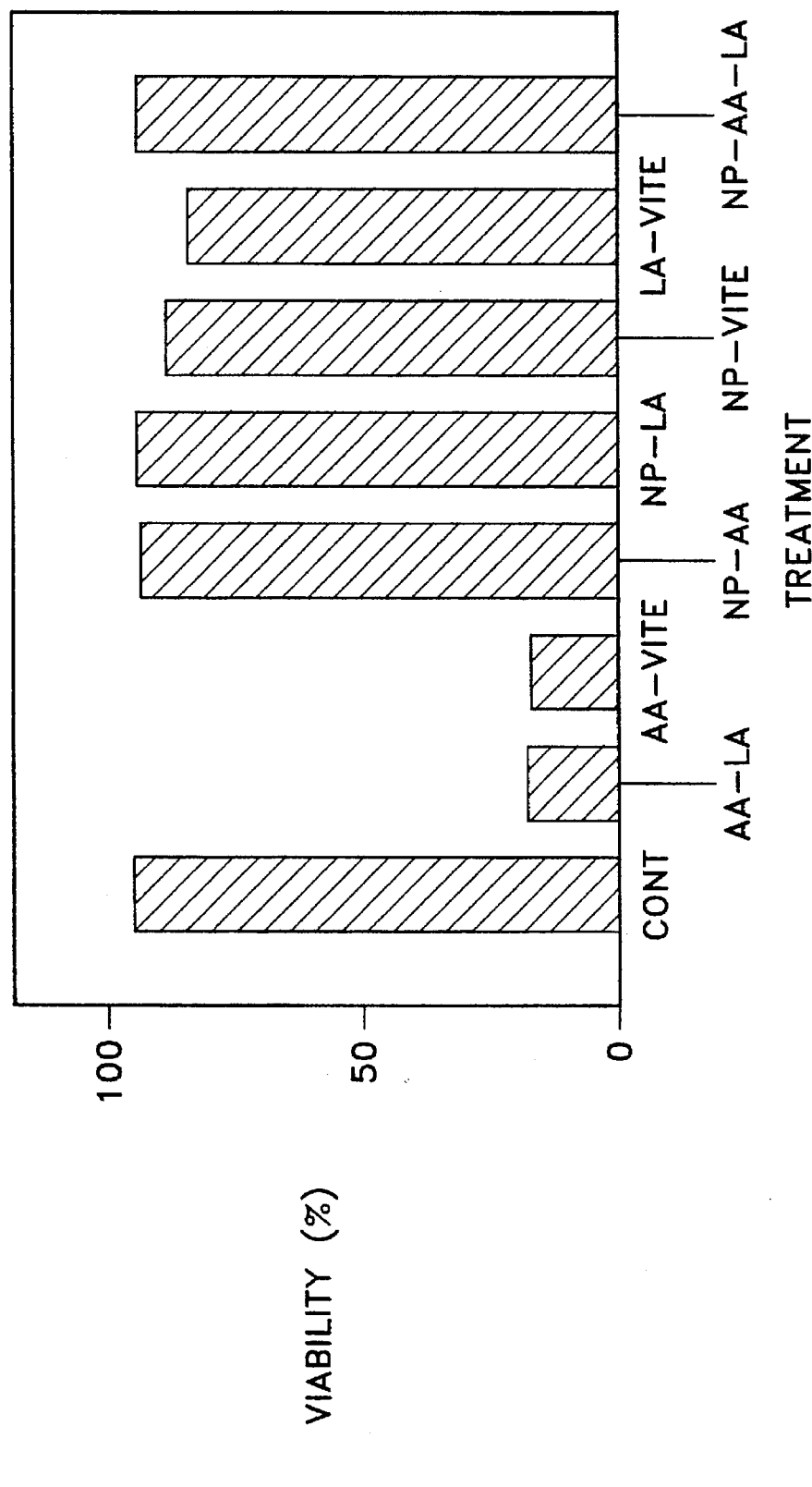
FIG. 2 depicts in bar graph format the viability of U937 monocytic cells following exposure of the cells to various combinations of antioxidants (Examples 6–13).

The viability of the U937 monocytic cells after exposure of the cells to various antioxidants for 24 hours was measured. The viability of the cells was determined by exposing the cells to the dye propidium iodide. Permeable cell membranes which absorbed the dye were not considered viable. The viability of the cells was represented as the percentage of cells that excluded propidium iodide. FIG. 1 depicts in bar graph format the viability of U937 monocytic cells after exposure of the cells to no antioxidant (Example 1, control), to sodium pyruvate (Example 2), to ascorbic acid (Example 3), to lactic acid (Example 4), and to Vitamin E (Example 5). FIG. 2 depicts in bar graph format the viability of U937 monocytic cells after exposure of the cells to various combinations of antioxidants. Specifically, the viability of U937 monocytic cells was measured after exposure to no antioxidant (Example 6, control), to ascorbic acid and lactic acid (Example 7), to ascorbic acid and Vitamin E (Example 8), to sodium pyruvate and ascorbic acid (Example 9), to sodium pyruvate and lactic acid (Example 10), to sodium pyruvate and Vitamin E (Example 11), to lactic acid and Vitamin E (Example 12), and to sodium pyruvate, ascorbic acid, and lactic acid (Example 13).

FIG. 1 shows that ascorbic acid is cytotoxic to monocytes at concentrations as low as 0.25%. FIG. 2 shows that the cytotoxicity of ascorbic acid was reversed by the addition of 10 mM of sodium pyruvate. FIGS. 1 and 2 show that the viability rate of 15% to 20% of the cells when treated with ascorbic acid was increased to 95% to 98% upon addition of sodium pyruvate. Lactic acid and Vitamin E did not reverse the cytotoxicity of ascorbic acid.

Sodium pyruvate was then tested at various concentrations to determine the effect of concentrations of this antioxidant on the hydrogen peroxide production by epidermal cells and monocytes. Mammalian epidermal keratinocytes and monocytes were exposed to (a) 1 M.E.D. dose of ultraviolet light-B and (b) 100 ng/ml of 12-O-tetradecanoylphorbol-13-acetate (TPA) in the presence of sodium pyruvate at the following concentrations: 200 mM, 100 mM, 50 mM, 10 mM, 1 mM.

The optimum concentration of sodium pyruvate to reduce the hydrogen peroxide production by epidermal cells and monocytes was found to be 10 mM. Concentrations of sodium pyruvate of 50 mM and above were cytotoxic to both epidermal keratinocytes and monocytes.

Magnesium pyruvate, calcium pyruvate, zinc pyruvate, ascorbic acid, lactic acid, and Vitamin E, and combinations of sodium pyruvate with ascorbic acid, lactic acid, and Vitamin E were then tested to determine the effect of these salts and combinations of antioxidants on the hydrogen peroxide production by epidermal cells and monocytes. The following test solutions were prepared.

(a) sodium pyruvate [10 mM]; zinc salt [10 mM];

(c) magnesium salt [10 mM];

(d) calcium salt [10 mM];

(e) sodium pyruvate [10 mM] and ascorbic acid [0.025%];

(f) sodium pyruvate [10 mM] and lactic acid [0.05%];

(g) sodium pyruvate [10 mM], lactic acid, [0.05%], and ascorbic acid [0.025%];

(h) lactic acid [1.0%, 0.1%, and 0.05%];

(i) ascorbic acid [1.0%, 0.1% 0.05%, and 0.025%];

(j) Vitamin E [1 U, 10 U, 50 U, and 100 U]; and (k) vehicle solvent controls.

There was no significant difference among the zinc, magnesium, and calcium salts of pyruvic acid on the hydrogen peroxide production by epidermal cells and monocytes. The zinc and calcium salts of pyruvic acid induced differentiation of keratinocytes. For convenience, the sodium salt was used in subsequent tests.

The optimum concentration of lactic acid to reduce the hydrogen peroxide production by epidermal cells and monocytes was found to be 0.05%. The optimum concentration of ascorbic acid was found to be 0.025%. The higher concentrations of both of these compounds were found to be cytotoxic to both types of cells. The optimum concentration of Vitamin E was found to be 50 U.

Figure 3:
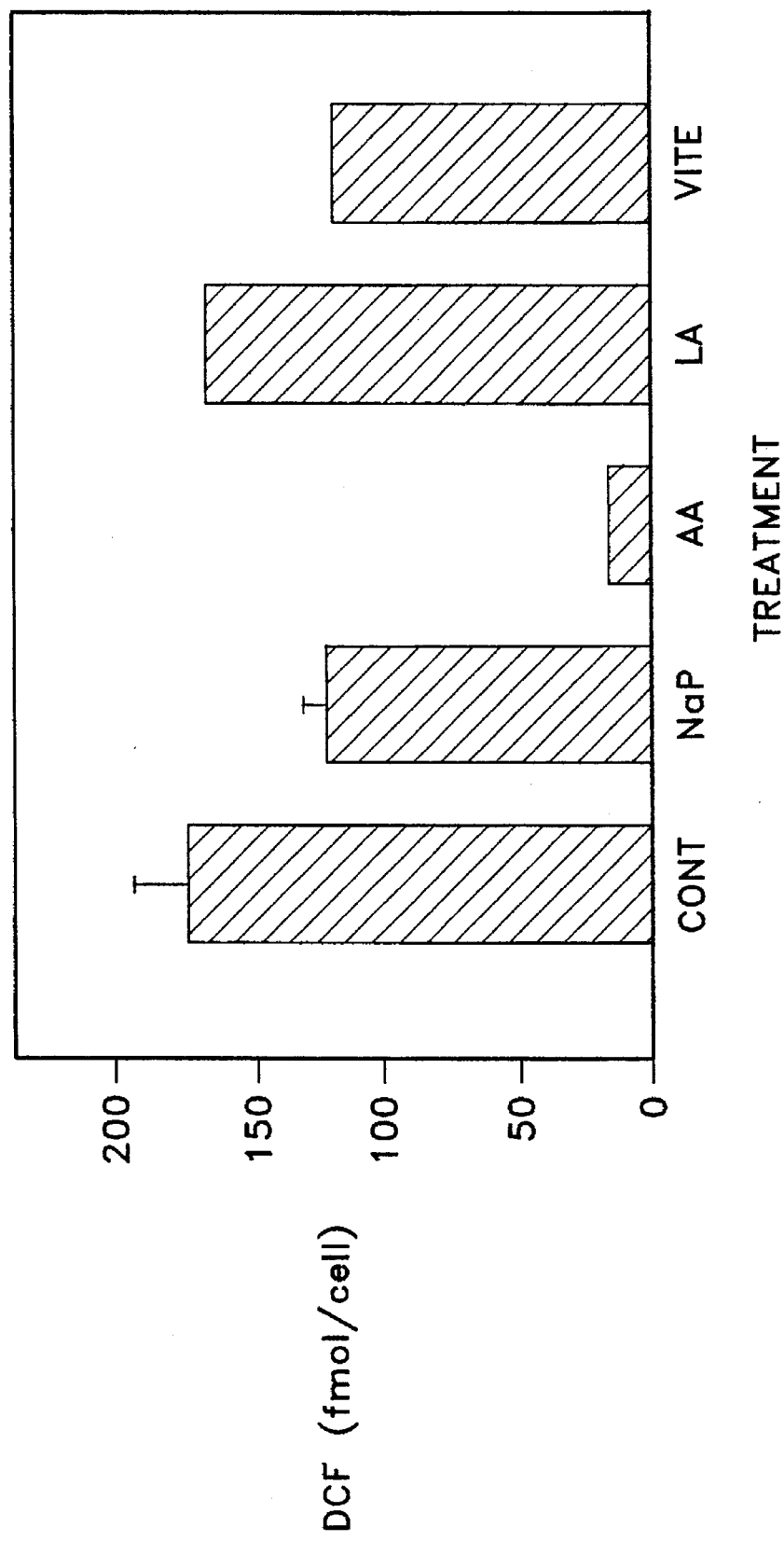
FIG. 3 depicts in bar. graph format the levels of hydrogen peroxide produced by U937 monocytic cells following exposure of the cells to various antioxidants (Examples 14–18).

FIG. 3 depicts in bar graph format the levels of hydrogen peroxide produced by U937 monocytic cells after exposure of the cells to no antioxidant (Example 14, control), to sodium pyruvate (Example 15), to ascorbic acid (Example 16), to lactic acid (Example 17), and to Vitamin E (Example 18). Sodium pyruvate and Vitamin E significantly reduced the hydrogen peroxide production by monocytes.

Figure 4:
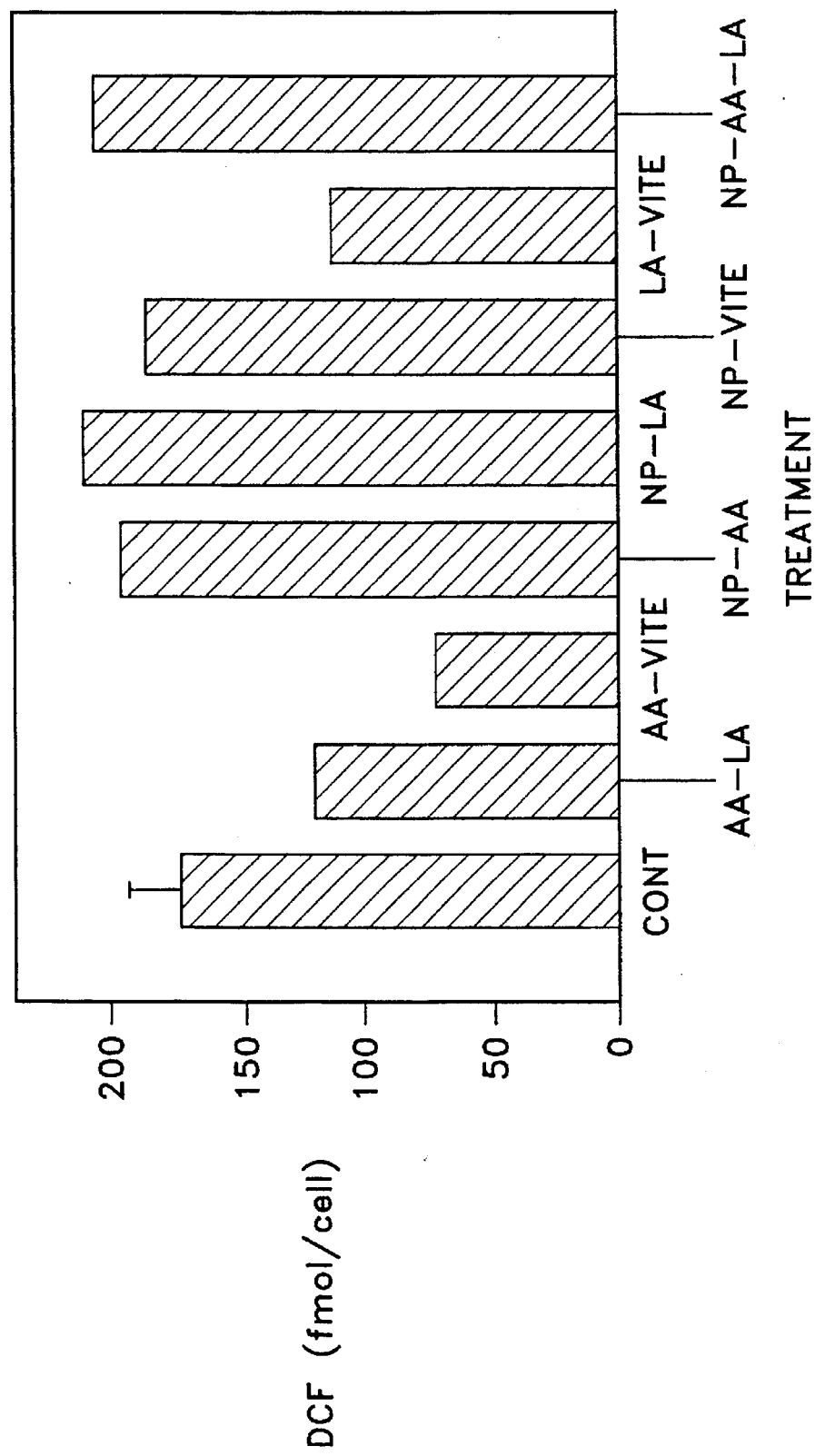
FIG. 4 depicts in bar graph format the levels of hydrogen peroxide produced by U937 monocytic cells following exposure of the cells to various combinations of antioxidants (Examples 19–26).

FIG. 4 depicts in bar graph format the levels of hydrogen peroxide produced by U937 monocytic cells after exposure of the cells to various combinations of antioxidants. Specifically, the levels of hydrogen peroxide produced by U937 monocytic cells were measured after exposure to no antioxidant (Example 19, control), to ascorbic acid and lactic acid (Example 20), to ascorbic acid and Vitamin E (Example 21), to sodium pyruvate and ascorbic acid (Example 22), to sodium pyruvate and lactic acid (Example 23), to sodium pyruvate and Vitamin E (Example 24), to lactic acid and Vitamin E (Example 25), and to sodium pyruvate, ascorbic acid, and lactic acid (Example 26). The combination of lactic acid (0.05%) and Vitamin E (50 U) significantly reduced the hydrogen peroxide production by monocytes.

The morphological alterations in epidermal keratinocytes were observed in control cultures and in cultures exposed to ultraviolet-B. Cells in the layer closest to the dermis are basal keratinocytes. These cells proliferate and migrate into the spinous and granular layers of the epidermis where the cells begin to differentiate. The differentiation pattern results in cells enucleating and forming cornified envelopes at the uppermost portion of the epidermis, the statum corneum. The differentiation of keratinocytes is controlled by the levels of calcium; magnesium; and other elements in the medium. Cells in culture systems promoting differentiation appear as an epidermal sheet forming attachments or tight junctions with each other. Keratinocytes that become non-adherent or float in the media were considered responding to a cytotoxic event.

The following morphological alterations in the mammalian epidermal keratinocytes were observed for the following control cultures:

10 mM Sodium Pyruvate: Tight junctions of cells were formed and the proliferation rate of the cells was higher than the rate of the control cells.

0.025% Ascorbic Acid: Cells were floating in a cytotoxic response to ascorbic acid.

0.025% Ascorbic acid and 10 mM Sodium pyruvate: Few tight junctions of cells were observed and cells appeared similar to the cells in the sodium pyruvate culture.

0.05% Lactic Acid: Cells appeared dramatically altered as an epidermal sheet and as flat granular cells.

0.05% Lactic Acid and 10 mM Sodium Pyruvate: Cells formed an epidermal sheet but appeared smaller than the cell in the lactic acid culture.

50 U Vitamin E: Cells appeared the same as the cells in the control culture.

50 U Vitamin E and 10 mM Sodium Pyruvate: Cells increased in number and changed in appearance resembling the cells in the sodium pyruvate culture.

The following morphological alterations in the mammalian epidermal keratinocytes were observed for the corresponding cultures exposed to ultraviolet light-B, 100 mJoules, for 24 hours:

10 mM Sodium Pyruvate: Cells proliferated more rapidly than the cells in the control culture:

0.025% Ascorbic Acid: Cells were nonadherent and floating in a cytotoxic response to ascorbic acid greater than the cytotoxic response of the corresponding cells without ultraviolet-B light exposure.

0.05% Lactic Acid: Cells formed an epidermal sheet and were more granular than cells in the control culture without ultraviolet-B light exposure.

50 U Vitamin E: Cell growth was inhibited but cells appeared similar to cells in the control culture without ultraviolet-B light exposure.

50 U Vitamin E and 10 mM Sodium Pyruvate: Cells appeared similar to cells in the control culture and proliferated to a greater extent than cells in the control cultures without ultraviolet-B light exposure.

Morphological alterations in the U937 monocytic cell line were also observed for control cultures and cultures exposed to ultraviolet light-B, 100 mJoules, for 24 hours. The following compounds and combination of compounds, at the concentrations set out below, significantly inhibited the levels of hydrogen peroxide produced by U937 monocytic cells Sodium pyruvate at 10 mM and 50 mM;
Vitamin E at 50 U and 100 U; and
Lactic acid at 0.05% and Vitamin E at 50 U.

b. Study 2

Figure 5:
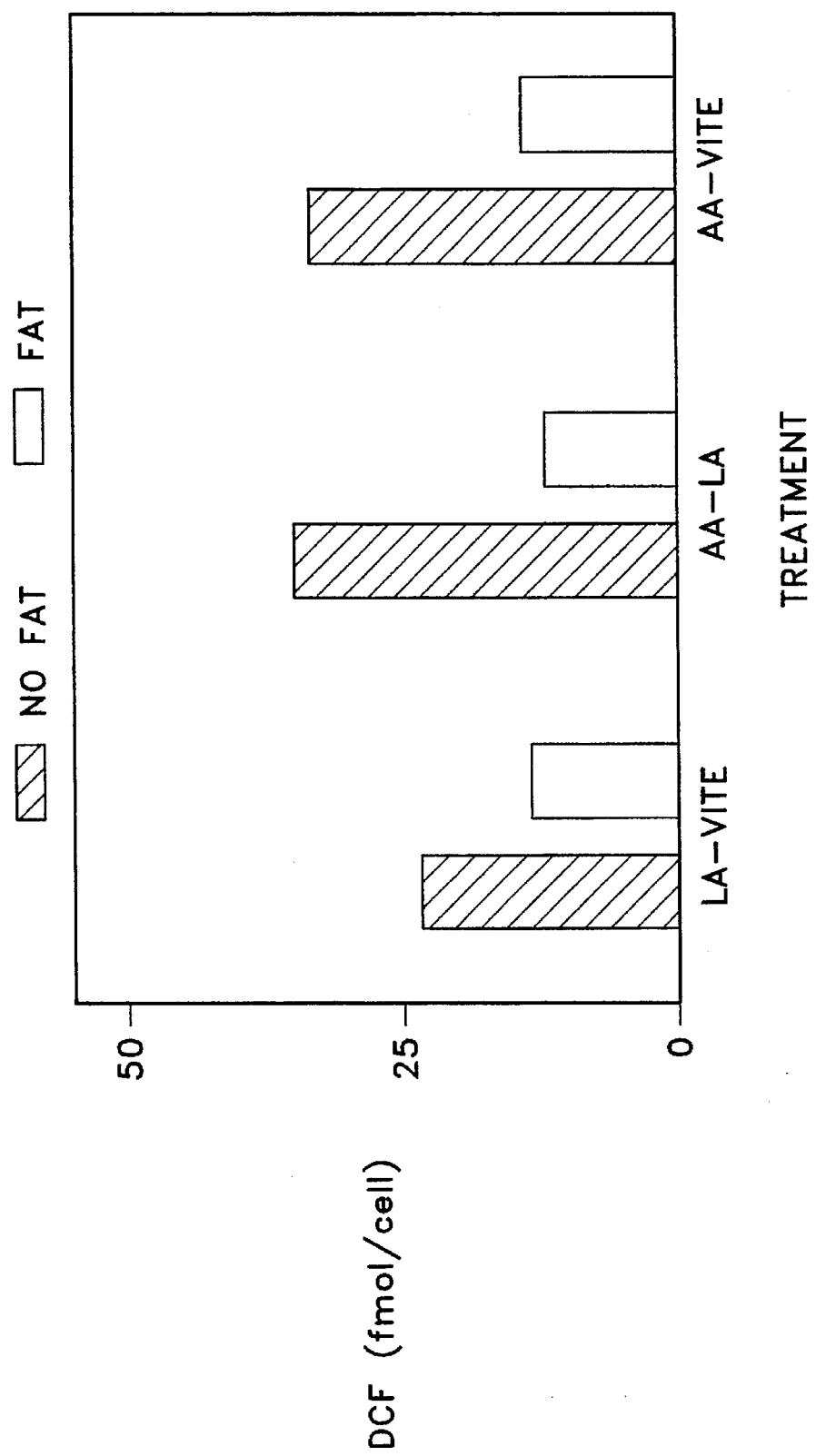
FIG. 5 depicts in bar graph format the levels of hydrogen peroxide produced by U937 monocytic cells following exposure of the cells to various combinations of antioxidants with and without a mixture of saturated and unsaturated fatty acids (Examples 27–32).
Figure 6:
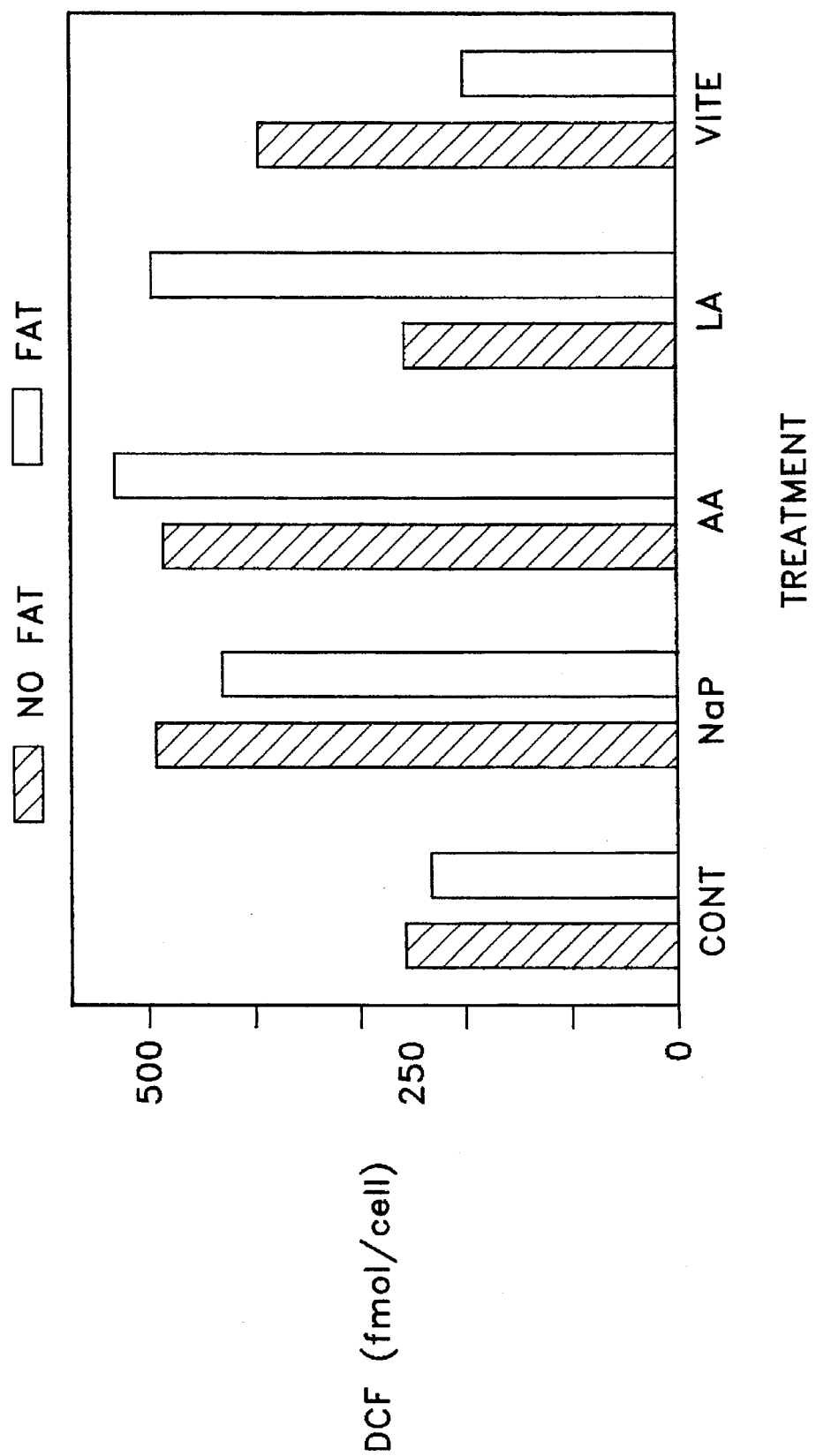
FIG. 6 depicts in bar graph format the levels of hydrogen peroxide produced by epidermal keratinocytes following exposure of the cells to various antioxidants with and without a mixture of saturated and unsaturated fatty acids (Examples 33–42).
Figure 7:
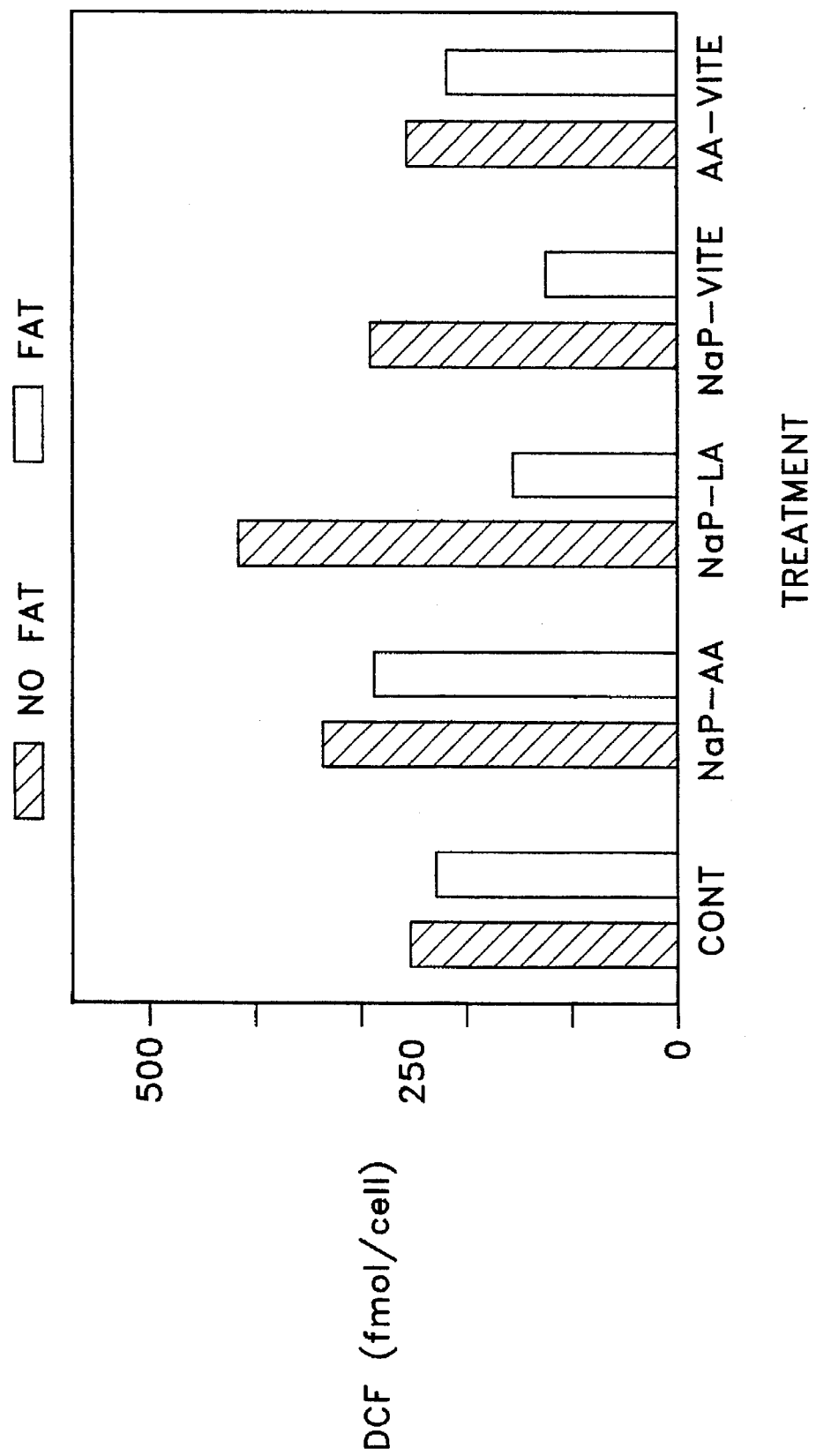
FIG. 7 depicts in bar graph format the levels of hydrogen peroxide produced by epidermal keratinocytes following exposure of the cells to various combinations of antioxidants with and without a mixture of saturated and unsaturated fatty acids (Examples 43–52).

This study demonstrates a comparison of the levels of hydrogen peroxide produced by U937 monocytic cells and epidermal keratinocytes after exposure of the cells to various combinations of antioxidants with and without a mixture of saturated and unsaturated fatty acids. The results of this study are illustrated in FIGS. 5–7 and examples 27–52 below.

Mammalian epidermal keratinocytes and U937 monocytic cells and the test solutions of sodium pyruvate, lactic acid, ascorbic acid, and Vitamin E were prepared as describe above for Examples 1–26. Intracellular hydrogen peroxide production by the mammalian epidermal keratinocytes and U937 monocytes was also measured as described above.

A mixture of fatty acids derived from chicken fat was prepared for addition to the cultured cells by mixing 0.1% of the chicken fat with the culture media. At the temperature of the culture media, 37° C., the chicken fat was miscible. This chicken fat mixture was added to cultures of cells prior to exposure of the cells to ultraviolet-B light or TPA treatment.

As set out in examples 1–26, mammalian epidermal keratinocytes and monocytes were exposed to (a) 1 M.E.D. dose of ultraviolet light-B and (b) 100 ng/ml of 12-O-tetradecanoylphorbol-13-acetate in the presence of various antioxidants and combinations of antioxidants with and without a mixture of saturated and unsaturated fatty acids [0.1%, 0.5%, and 1.0% chicken fat].

FIG. 5 depicts in bar graph format the levels of hydrogen peroxide produced by U937 monocytic cells after exposure of the cells to various combinations of antioxidants with and without a mixture of saturated and unsaturated fatty acids. Specifically, the levels of hydrogen peroxide produced by U937 monocytic cells were measured after exposure to lactic acid and Vitamin E without fatty acids (Example 27) and with fatty acids (Example 28), to ascorbic acid and lactic acid without fatty acids (Example 29) and with fatty acids (Example 30), and to ascorbic acid and Vitamin E without fatty acids (Example 31) and with fatty acids (Example 32). The ability of the combinations of lactic acid and Vitamin E, ascorbic acid and lactic acid, and ascorbic acid and Vitamin E to reduce the hydrogen peroxide production by monocytes was increased in the presence of fatty acids. The most effective combination to reduce the hydrogen peroxide production of monocytes was lactic acid (0.05%) and Vitamin E (50 E) in the presence of a mixture of saturated and unsaturated fatty acids (0.5%).

FIG. 6 depicts in bar graph format the levels of hydrogen peroxide produced by epidermal keratinocytes after exposure of the cells to various antioxidants with and without a mixture of saturated and unsaturated fatty acids. Specifically, the levels of hydrogen peroxide produced by epidermal keratinocytes were measured afar exposure to no antioxidant without fatty acids (Example 33, control) and with fatty acids (Example 34), to sodium pyruvate without fatty acids (Example 35) and with fatty acids (Example 36), to ascorbic acid without fatty acids (Example 37) and with fatty acids (Example 38), to lactic acid without fatty acids (Example 39) and with fatty acids (Example 40), and to Vitamin E without fatty acids (Example 41) and with fatty acids (Example 42). The ability of sodium pyruvate and Vitamin E to reduce the hydrogen peroxide production by epidermal keratinocytes was increased in the presence of fatty acids. The most effective combinations to reduce the hydrogen peroxide production of epidermal keratinocytes were sodium pyruvate in combination with a mixture saturated and unsaturated fatty acids and Vitamin E in combination with a mixture of saturated and unsaturated fatty acids.

FIG. 7 depicts in bar graph format the levels of hydrogen peroxide produced by epidermal keratinocytes after exposure of the cells to various combinations of antioxidants with and without a mixture of saturated and unsaturated fatty acids. Specifically, the levels of hydrogen peroxide produced by epidermal keratinocytes were measured after exposure to no antioxidant without fatty acids (Example 43, control) and with fatty acids (Example 44), to sodium pyruvate and ascorbic acid without fatty acids (Example 45) and with fatty acids (Example 46), to sodium pyruvate and lactic acid without fatty acids (Example 47) and with fatty acids (Example 48), to sodium pyruvate and Vitamin E without fatty acids (Example 49) and with fatty acids (Example 50), and to ascorbic acid and Vitamin E without fatty acids (Example 51) and with fatty acids (Example 52). The ability of all combinations of antioxidants to reduce the hydrogen peroxide production by epidermal keratinocytes was increased in the presence of fatty acids. In order of potency, the most effective combinations to reduce the hydrogen peroxide production of epidermal keratinocytes were sodium pyruvate and Vitamin E, sodium pyruvate and lactic acid, and Vitamin E, each in combination with a mixture of saturated and unsaturated fatty acids (0.5%).

Because of the cytotoxicity of cells towards ascorbic acid described above, the ascorbic acid combinations without sodium pyruvate were not considered significantly different from the control test solution.

Summary Analysis of the Data From Studies 1 and 2

Human epidermal keratinocytes were isolated by trypsinization of epithelial sheets and grown in modified base MCDB 153 medium supplemented with epidermal growth factor and bovine pituitary extract. Cells were seeded in culture dishes at a density of $3 \times 10^5$/dish. Prior to exposure to UV B light (100 mJ/cm$^2$) or treatment with 100 ng/ml TPA, the cultures were treated with the appropriate concentration of wound healing components. Intracellular production of hydrogen peroxide was measured using DCFH-DA, a nonpolar compound that readily diffuses into cells, hydrolyzed to a nonpolar derivative. In the presence of intracellular hydrogen peroxide, DCFH is oxidized to a highly fluorescent compound DCF. Thus, cellular fluorescence intensity is directly proportional to levels of hydrogen peroxide produced and can be monitored by flow cytometry. Hydrogen peroxide is cytotoxic, therefore lower levels of hydrogen peroxide production is desirable for cellular viability.

In all cases, the three component wound healing composition surpassed the predicted outcomes, clearly demonstrating unpredicted synergy.

| | Results | | | |
|---|---|---|---|---|
| 1 | | 2 | 3 | 4 |
| 1- Control | | 250 | 250 | 0 |
| 2- Fatty Acids (0.5%) | | 250 | 230 | −20 |
| 3- Sodium pyruvate (10 mM) | | 250 | 490 | +240 |
| 4- Vitamin E (50 units) | | 250 | 400 | +150 |
| 5- Pyruvate & Fatty Acids | | 250 | 430 | +180 |
| 6- Vitamin E & Fatty Acids | | 250 | 200 | −50 |
| 7- Pyruvate & Vitamin E | | 250 | 290 | +40 |
| 8- Pyruvate & Vitamin E & Fatty Acids | | 250 | 120 | −130 |

Column 1 shows the different treatment groups.
Column 2 shows the production of $H_2O_2$ in control cells (fmol/cell).
Column 3 shows the production of $H_2O_2$ after treatment with wound healing components.
Column 4 shows the difference in production of $H_2O_2$ from control after the treatment.

Figure 8:
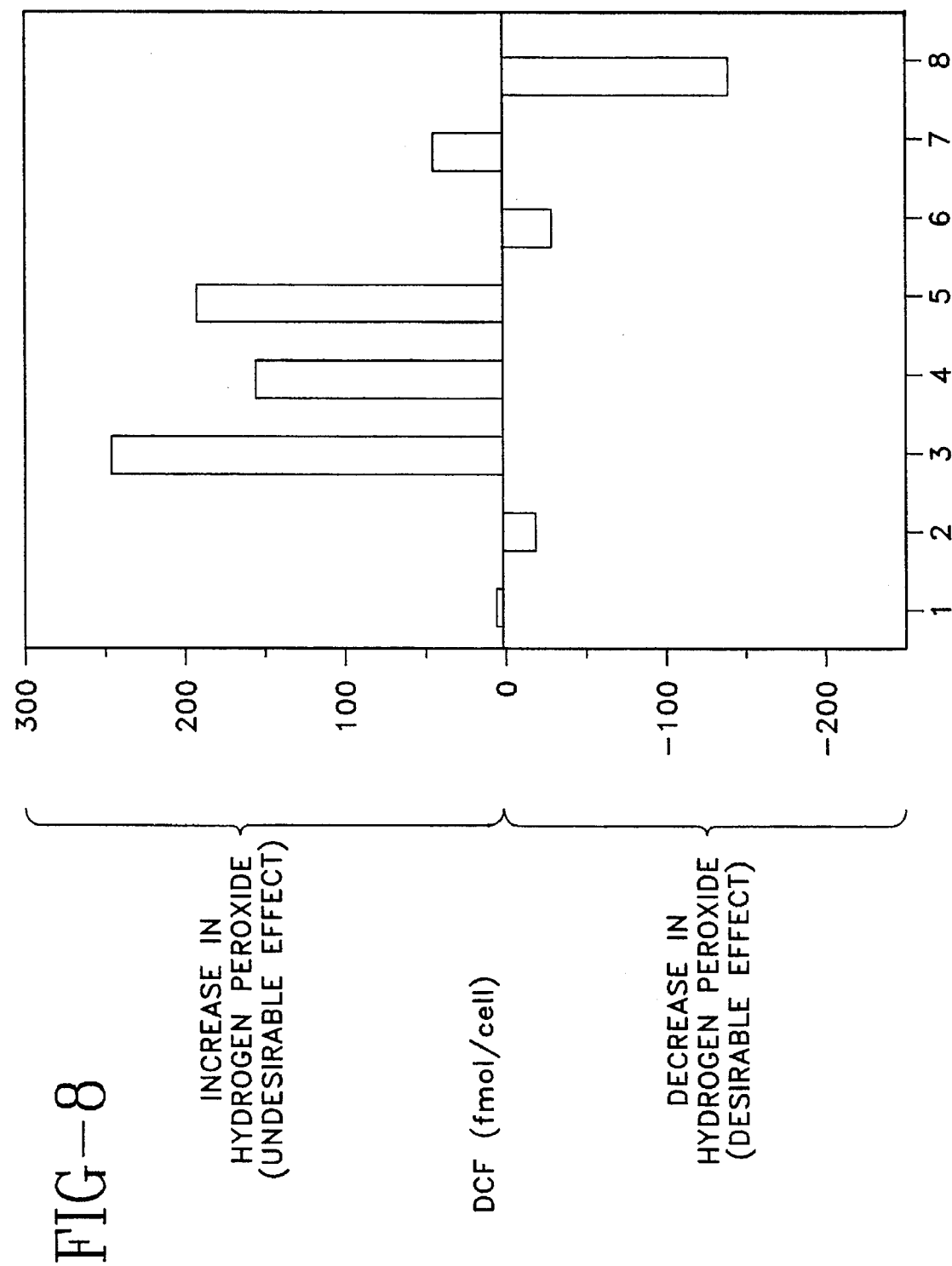
FIG. 8 depicts in bar graph format a summary analysis of the levels of hydrogen peroxide produced by epidermal keratinocytes following exposure of the cells to the individual components of the wound healing composition, to various combinations of the wound healing composition, and to the wound healing composition.
Figure 9A:
FIGS. 9A–9D are photographs of wounded mice after 4 days of treatment with: no composition (FIG. 9A, control); a petrolatum base formulation containing live yeast cell derivative, shark oil, and a mixture of sodium pyruvate, vitamin E, and chicken fat (FIG. 9B); a petrolatum base formulation containing live yeast cell derivative and shark oil (FIG. 9C); and Preparation H™ (FIG. 9D).
Figure 9B:
Figure 9C:
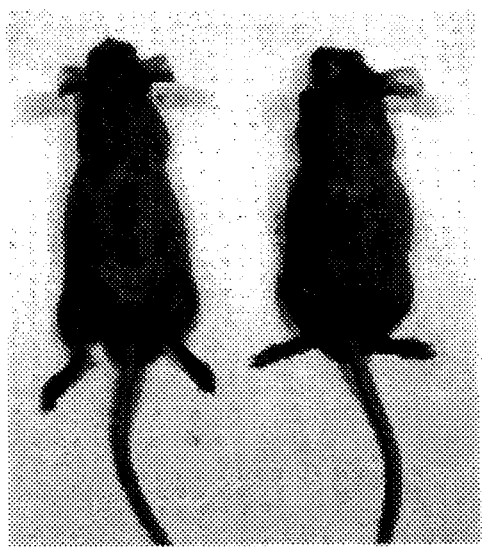
Figure 9D:

All comparisons were assessed against the controls, which produced 250 $H_2O_2$ fmol/cell. The positive numbers represent $H_2O_2$ production in excess of the control and the negative numbers represent $H_2O_2$ production below the control. These results are set out in FIG. 8.

Combination of Single Ingredient Effects

Fatty Acids (−20) & Vitamin E (+150) & Pyruvate (+240)
  +370 Is The Predicted Three Component Effect
  −130 Is The Wound healing composition Actual Effect
  500 Is The Difference Between Predicted Effect minus Actual effect
  (Synergy)

Combination of Paired and Single Ingredients

Pyruvate & Fatty Acids (+180) & vitamin E (+150)
  +330 Is The Predicted Three Component Effect
  −130 Is The Wound healing composition Actual Effect
  460 Is The Difference between Predicted Effect minus Actual Effect
  (Synergy)

Vitamin E & Fatty Acids (−50) & Pyruvate (+240)
  +190 Is The Predicted Three Component Effect
  −130 Is The Wound healing composition Actual Effect
  320 Is The Difference between Predicted Effect minus Actual Effect
  (Synergy)

Pyruvate & Vitamin E (+40) & Fatty Acids (−20)
  +20 Is The Predicted Three Component Effect
  −130 Is The Wound healing composition Actual Effect
  150 Is The Difference between Predicted Effect minus Actual Effect
  (Synergy)

In all cases, the three component wound healing composition surpassed the predicted outcomes clearly demonstrating unpredicted synergy.

c. Study 3

This study demonstrates a comparison of the wound healing abilities of the therapeutic wound healing compositions of the present invention versus conventional wound healing compositions. The results of this study are illustrated in examples A–D.

The wound healing compositions of Examples A–D were prepared having the compositions set out in Table A.

| | Examples | | | |
|---|---|---|---|---|
| Ingredient | A Prep-H ™ | B | C | D |
| sodium pyruvate | — | 2% | — | — |
| vitamin E | — | 1% | — | — |
| chicken fat | — | 2% | — | — |
| LYCD | 2000 U* | 2400 U | 2400 U | — |

-continued

| Ingredient | Examples | | | |
|---|---|---|---|---|
| | A Prep-H™ | B | C | D |
| shark liver oil | 3%* | 3% | 3% | — |
| petrolatum | in | 64% | 66.5% | 68% |
| mineral oil | amounts | 22.53% | 25.03% | 26.8% |
| paraffin | totaling | 5% | 5% | 5% |
| emulsifier | 100% | 0.2% | 0.2% | 0.2% |

*These components are present in Preparation H™

Wound healing composition A was commercially available Preparation H™. Wound healing composition B was a petrolatum base formulation containing live yeast cell derivative, shark oil, and a mixture of sodium pyruvate, vitamin E, and chicken fat. Wound healing composition C was a petrolatum base formulation containing live yeast cell derivative and shark oil. Wound healing composition D was a petrolatum base formulation only.

Wound healing studies were carried out using hairless mice (SKR-1, Charles River) 6–8 weeks in age. One group of mice were untreated as a control group and were referred to as Example E. In each group there were 6 mice for evaluation at either day 3 or day 7 for a total number of 60 animals in the study. The mice were anesthetized with ether and a midline 3 cm full thickness longitudinal incision was made with a number 10 scalpel blade. Incisions were closed using steel clips at 1 cm intervals. Formulations A–D set out above were applied in a randomized blinded study to the wounds on day 0 at 2 hours following wounding and reapplied at 24 hour intervals during the 7 days of the study. The wounds were examined daily and scored on a basis of 0–5 for closure on each day of the study, with a score of 5 representing the wound best healed.

The animals were sacrificed on day 3 and day 7 using cervical dislocation. The dorsal skin including the incision was dissected without the subcutaneous tissue. The skin was placed in neutral buffered formalin and subsequently sectioned and stained with hematoxylin and eosin. The wounds were examined microscopically and representative tissue sections were photographed.

On each day of the experiment, the score and rank order of the formulations for closure of wounds and speed of healing were as follows:

B (5)>>D (4)>>C (2)>/=E, Control (2)>A (1)

Figure 10:
FIG. 10 is a photograph of a wounded mouse after 4 days of treatment with a petrolatum base formulation only (Example D).

Photographs of the wounded mice on day 4 are set out in FIGS. 9 and 10.

FIGS. 9A–9D and 10 show that Formulation B, which was a petrolatum base formulation containing live yeast cell derivative, shark oil, and a mixture of sodium pyruvate, vitamin E, and chicken fat, was a significantly better wound healing agent than the other formulations. These results are supported by the subjective grading of the wound closures and the speed of healing on each day (1–7) of the experiment as well as on the objective histological examination of tissue sections to measure the extent of inflammatory cell infiltrate within the wound and the extent of epithelialization at the wound edges. The final result was that less scar tissue was present at day 7 on the mice treated with Formulation B.

Formulation D, which was a white petrolatum formulation only, was judged to be significantly more effective to promote healing than either Formulation C, which was a petrolatum base formulation containing shark liver oil and live yeast cell derivative, or Formulation A, which was Preparation H™. The superior ability of Formulation D over Formulation C to improve healing may result from a delay in the healing process caused when the live yeast cell derivative is depleted and the cells shift to an alternative nutrient source. The presence of the mixture of sodium pyruvate, vitamin E, and chicken fat in Formulation B apparently offsets the depletion of the live yeast cell derivative.

Formulation C, which was a petrolatum base formulation containing live yeast cell derivative and shark oil, was judged comparable to the control (untreated wound) in speed of wound closure and extent of healing. Formulation A, which was Preparation H™, appeared to be the least effective healing formulation by both subjective grading of wound healing and by objective examination of tissue sections. The superior ability of Formulation D and Formulation C over Formulation A to improve healing may be due to their ability to act as an occlusive wound dressing that prevents transepidermal water loss and thus promotes healing and wound closure. The poor ability of Formulation A to improve healing may be due to the potential cytotoxicity of phenylmercuric nitrate present in Preparation H™ as a preservative.

These results show that the wound healing compositions of the present invention which comprise a mixture of sodium pyruvate, vitamin E, and chicken fat increase the proliferation and resuscitation rate of mammalian cells. The wound healing compositions mediate low levels of oxygen in the initial stages of healing to suppress oxidative damage and higher levels of oxygen in the later stages of healing to promote collagen formation.

2. Examples of Immunostimulating Wound-Healing Compositions

This study demonstrates a comparison of the wound healing abilities of the therapeutic wound healing compositions of the present invention in infected and noninfected mice versus conventional wound healing compositions.

The wound healing studies were carried out using hairless mice. Five formulations were examined in a randomized double blind study. There were 6 mice in each study group for evaluation at either day three or day seven. A midline, 3 cm, full thickness longitudinal incision was made on the anesthetized mice. The creams were applied 2 hours following the wounding and reapplied at 24 hour intervals during the 7 day study. Betafectin™, the immunostimulating agent, was applied 20 minutes before the application of the creams. Wounds were examined daily and scored for closure on a scale of 0–5 with 5 indicating the most healed. The animals were sacrificed and the tissue samples were examined histologically. Both infected and noninfected wounds were used. Regardless of the presence of infection, the compositions with Betafectin™ with live yeast cell derivative (LYCD) and the wound healing composition were significantly better as wound healing agents then the other tested formulas. This wound healing ability was demonstrated by subjective grading of healing through wound closure and objective histological examinations of tissue sections. The order for wound healing efficacy following the Betafectin™ with live yeast cell derivative and wound healing composition was as follows: 2) Betafectin; (3) wound healing composition with live yeast cell derivative; 4) Neosporin and wound healing composition; and 5) untreated control.

A detailed summary of studies is provided below that were performed to establish that formulations including Betafectin™, the immunostimulating agent, alone and in combination with formulations including Preparation H™ or a Neosporin base with live yeast cell derivative (LYCD) and the wound healing composition of compounds, sodium pyruvate, Vitamin E (alpha-tocopherol) and fatty acids enhance wound healing.

There were 9 groups of mice, with N=6 per group, and the groups had the following treatment: A) wounded, no treatment (control); B) Betafectin™ alone, 2 μg/mouse per day, added topically in Phosphate Buffered Saline (PBS); C) Preparation H™ with wound healing composition; D) Preparation H™ with Betafectin™; and E) Neosporin formulation with wound healing composition. Groups F–I consisted of groups of 6 mice each that were treated with a culture of $10^7$ Staphylococcus 30 minutes after wounding and 2 hours prior to treatment with any formulation. Groups F–I constituted the infection model to determine the ability of Betafectin™ as well as the Neosporin formulation to enhance wound healing in the presence of an infection.

Studies were carried out using hairless SKH-1 inbred mice, 6–8 weeks of age. Mice were placed in cages of 6 each. Mice were anesthetized with ether and a midline 3 cm full thickness longitudinal incision was made with a number 10 scalpel blade, producing a full thickness wound that did not penetrate the underlying fascia. Incisions were closed using steel clips at 1 centimeter intervals. Formulations were applied 30 minutes following wounding and reapplied at 24 hours intervals during the 7 day post-operative period. Wounds were examined daily and rank ordered for effectiveness of formulation for enhancement of visual based wound healing each day.

Animals were photographed at day 3 or 4 of the experimental protocol for documentation of visible effects of the treatments. Animals were sacrificed using ether euthanasia on day 3 and day 7. The dorsal skin including the incision was dissected without the subcutaneous tissue. The skin was placed in neutral buffered formalin and subsequently sectioned and stained with hematoxylin and eosin. Microscopic examination of the wounds was performed and representative tissue sectioned photographed.

The Treatment Groups were as follows:

A. Control-wounded, no treatment.

B. Freshly prepared Preparation H™ formulation containing live yeast cell derivative (LYCD) and the wound healing composition of sodium pyruvate, Vitamin E, and 1% fatty acids.

C. Neosporin formulation with the wound healing composition.

D. Betafectin™ in a solution of Phosphate Buffered Saline, added topically to the wound.

E. Betafectin™ and Preparation H™ with the wound healing composition. The Betafectin™ was added topically in an aqueous solution 20 minutes prior to the application of the formulation with wound healing composition and live yeast cell derivative.

F–I. These groups were treated as set out above, but with the addition of 107 *Staphylococcus aureus* as a bacterial infection agent applied 2 hours prior to the formulations to be tested.

Photographs of the wounded mice are set out in FIGS. 11A–14.

Figure 11A:
FIGS. 11A–11D are photographs of wounded mice after 3 days of treatment with: no composition (FIG. 11A); Betafectin™ with Preparation H™ with the wound healing composition (FIG. 11B); Betafectin™ (FIG. 11C); live yeast cell derivative containing the wound healing composition (FIG. 11D).
Figure 11B:
Figure 11C:
Figure 11D:

FIGS. 11A–11D are photographs of wounded mice after 3 days of treatment with: no composition (FIG. 11A); Betafectin ™ with Preparation H™ with the wound healing composition (FIG. 11B); Betafectin™ (FIG. 11C); live yeast cell derivative containing the wound healing composition (FIG. 11D).

Figure 12:
FIG. 12 is a photograph of a wounded mouse after 3 days of treatment with neosporin containing the wound healing composition.

FIG. 12 is a photograph of a wounded mouse after 3 days of treatment with Neosporin™ containing the wound healing composition.

Figure 13C:
Figure 13D:

FIGS. 13A–13D are photographs of the histological results of wounded mice after 3 days of treatment with: no composition (FIG. 13A); Betafectin ™ with Preparation H™ with the wound healing composition (FIG. 13B); Betafectin™ (FIG. 13C); live yeast cell derivative containing the wound healing composition (FIG. 13D).

Figure 14:
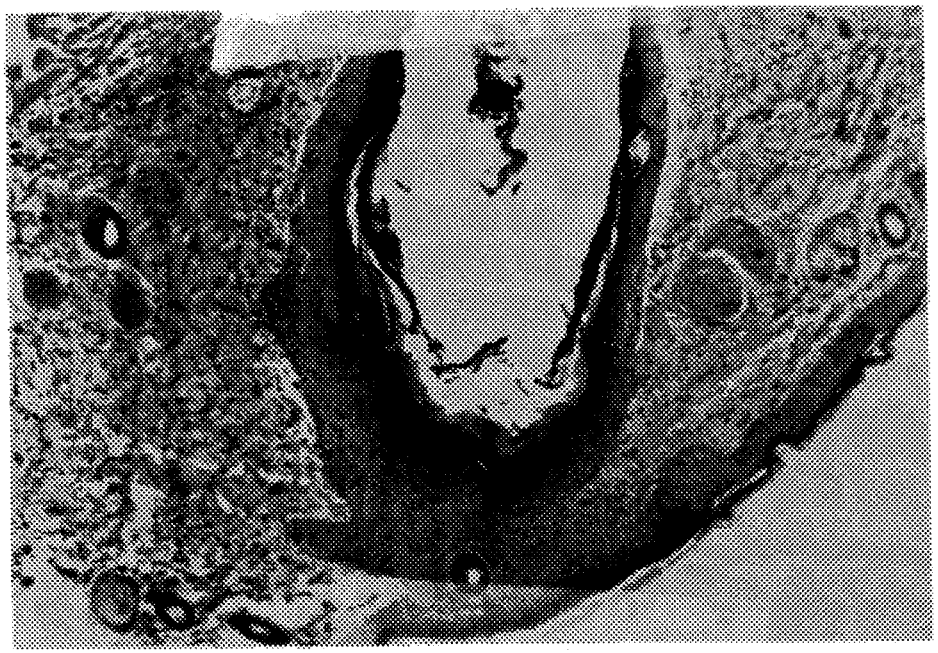
FIG. 14 is a photograph of the histological results of a wounded mouse after 3 days of treatment with neosporin containing the wound healing composition (D).

FIG. 14 is a photograph of the histological results of a wounded mouse after 3 days of treatment with neosporin containing the wound healing composition (D).

Results: Regardless of the presence of infection, the rank order for wound healing efficacy (wound healing and closure, as well as histological correlation of rate of wound healing) was:

(E) wound healing composition and Betafectin™>(D) Betafectin™>(B) wound healing composition=(C) Neosporin>>Untreated.

Histological Description of Wounded Tissue at Day 3 From Each of the Treatment Groups A) Control: Wounded-No Treatment: Lower portion of the wounded area, i.e., dermis has heavy infiltration with both lymphocytes and monocytes/macrophages. The re-epithelialization that occurs at the outer most layer of the skin, the epidermal layer, is not complete. The tissue section shows that the dermal tissue is weak, in that the tissue integrity was not maintained when it was sectioned.

B) Preparation H™ formulation with wound healing composition: From the thicker outer layer of the epidermis, the re-epithelialization process has progressed further than was apparent in the untreated control wounded tissue. Although there is infiltration of the dermis with monocytes and lymphocytes, it does not appear to be as diffuse or as heavy as with the control untreated wound tissue.

C) Neosporin formulation with the wound healing composition: The results with this formulation show that the re-epithelialization was extensive and rapid. In contrast, the infiltration of the macrophages and lymphocytes within the dermis was less than observed in either the control untreated wound tissue or the wound tissue treated with the Preparation H™ containing the wound healing composition combination of agents. It appears that the formulations containing the combination of Vitamin E, sodium pyruvate, and fatty acids stimulates proliferation of the outer layer of the epidermis.

D) Betafectin™ in phosphate buffered saline: The histology of the wounded tissue isolated from mice treated for 3 days with Betafectin™ show that there is a heavy infiltration of macrophages and lymphocytes and that there is apparently greater integrity of the tissue than that observed with any of the other treatments. The re-epithelialization is not, however, comparable to that observed with either the Neosporin or the Preparation H™ formulations that contain the wound healing composition.

E) Betafectin™ and Preparation H™ wound healing composition formulation: The histological sections isolated from tissue taken from mice treated with this formulation was by far superior in terms of both the extent of re-epithelialization as well as the extent of tissue integrity and leukocyte infiltration in the lower portion of the skin, the dermis. It is apparent that this combination of ingredients is able to act synergistically to enhance wound repair in both the upper and lower portions of the skin.

The combination of Betafectin™ and Preparation H™ wound healing composition stimulated both an increase in wound healing within the lower portion of the wound, within the dermal layer, as well as stimulated the re-epithelialization of the outer layer of the wound. These two activities resulted in a rapidly healed wound at day 3 following wounding. The difference in the activities of the other formulations is because complete and rapid healing of wounds requires stimulation of healing in the outer and lower areas of the skin. From histological examination of the wounds, it is apparent that both the Betafectin™ alone as well as the wound healing composition alone stimulated the dermal area for wound healing. In contrast, the Neosporin formulation stimulated the re-epithelialization, that is Stimulated the outer components of the skin to enhance wound closure. The combination of Betafectin™ with the wound healing composition in a Preparation H™ like formulation resulted in a synergistic enhancement of wound healing that was significantly better than any of the agents alone.

The mice that were infected with S. aureus and not treated with any agents were sacrificed at day 3, since the infection was not treated with antibiotics and remained purulent. The histology of tissue isolated from wounds that were treated with formulations of Betafectin™, Preparation H™, and wound healing composition or neosporin and wound healing composition, did not appear to differ with any of the treatments except for the presence of polymorphonuclear cells within the dermis, where in normal uninfected tissue, the predominant cell type was monocytes and lymphocytes.

In summary, these studies show that there are several components necessary to prepare an effective formulation to enhance wound healing: (1) enhance the activity of the epithelial cells within the outer layer of the skin so that re-epithelialization occurs at a rapid and efficient manner; (2) stimulate the activity of the inflammatory and immune cells that come into the lower part of the skin, the dermis, in the early portion of the wound healing process; (3) prepare a stable formulation that is compatible with the Betafectin™ and the wound healing composition combination with live yeast cell derivative.

3. Examples of Cytoprotective-Wound Healing Compositions

Study 1

This study demonstrates the cytoprotective abilities of the therapeutic cytoprotective-wound healing compositions of the present invention.

Methods

Isolation of Peripheral Blood Monocytes

Peripheral blood was obtained from a normal healthy volunteer by venipuncture using an EDTA-containing Vacutainer (Becton Dickinson Mountain View, Calif.). A total of 10 ml of peripheral blood was mixed in a ratio of 1:1 with Dulbecco's Minimal Essential Medium (DMEM, Grand Island Biologicals, GIBCO, Grand Island, N.Y.). The mixture was divided into 2 ml portions and each portion was layered onto 6 ml of Ficoll-Hypaque gradient mixture (Pharmacy, Inc., Piscataway, N.J.) and centrifuged in a Beckman T-J6 refrigerated centrifuge for 30 minutes at 1500 rpm and 4° C. After the cells were washed twice with phosphate buffered saline, the cells were resuspended in Hank's Balanced Salt Solution without $Ca^{++}/Mg^{++}$ (GIBCO).

Culture of U937 and Peripheral Blood Monocytes

Peripheral blood monocytes and U937 monocytic leukemia tumor cells were placed in sterile culture flasks and maintained in culture using Dulbecco's Minimal Essential Medium, with 10% fetal calf serum, supplemented with 2 mM glutamine and Pen/Strep. The cytotoxicity of the cytotoxic agent on the cells was analyzed by propidium iodide exclusion techniques and flow cytometric quantitation. Viability of the cells was quantified as the number of cells that excluded the vital dye trypan blue.

Preparation of Chemicals

Sodium pyruvate was dissolved in distilled water and the solution was adjusted to pH 7.4 with 1N sodium hydroxide solution. Solutions were sterile filtered. Stock solutions were prepared so that the vehicle would not be more than 1% of the total volume of the culture media.

A mixture of fatty acids derived from chicken fat was prepared by mixing 0.1% chicken fat with mineral oil to form an emulsified solution. Tween 80 was added to separate cultures of cells at similar concentrations and to examine possible vehicle effects. Alpha-Tocopherol phosphate (Sigma Chemical Company, St. Louis, Mo.) was added directly to the culture medium:

$^3$H-Thymidine Radiosotopic Incorporation Measurement of Cytotoxity

Cells were plated into 96 well dishes at a concentration of $10^6$ cells/well. Tritiated thymidine (1 uCi/well) was added and the cells were incubated for 4 hours at which time the cells were harvested using a Cambridge cell harvester. The samples were then placed in scintillation vials containing scintillation fluid and counted. These studies yielded a measure of the ability of the cells to proliferate, which is a measure of viability.

The results from the tritiated thymidine incorporation assay, a measure of DNA synthesis and cellular proliferation, correlated directly with the results from the dye exclusion viability assay. Because the tritiated thymidine incorporation assay is a more quantitative assay, the tritiated thymidine incorporation assay was used for the remainder of the studies.

Figure 15A:
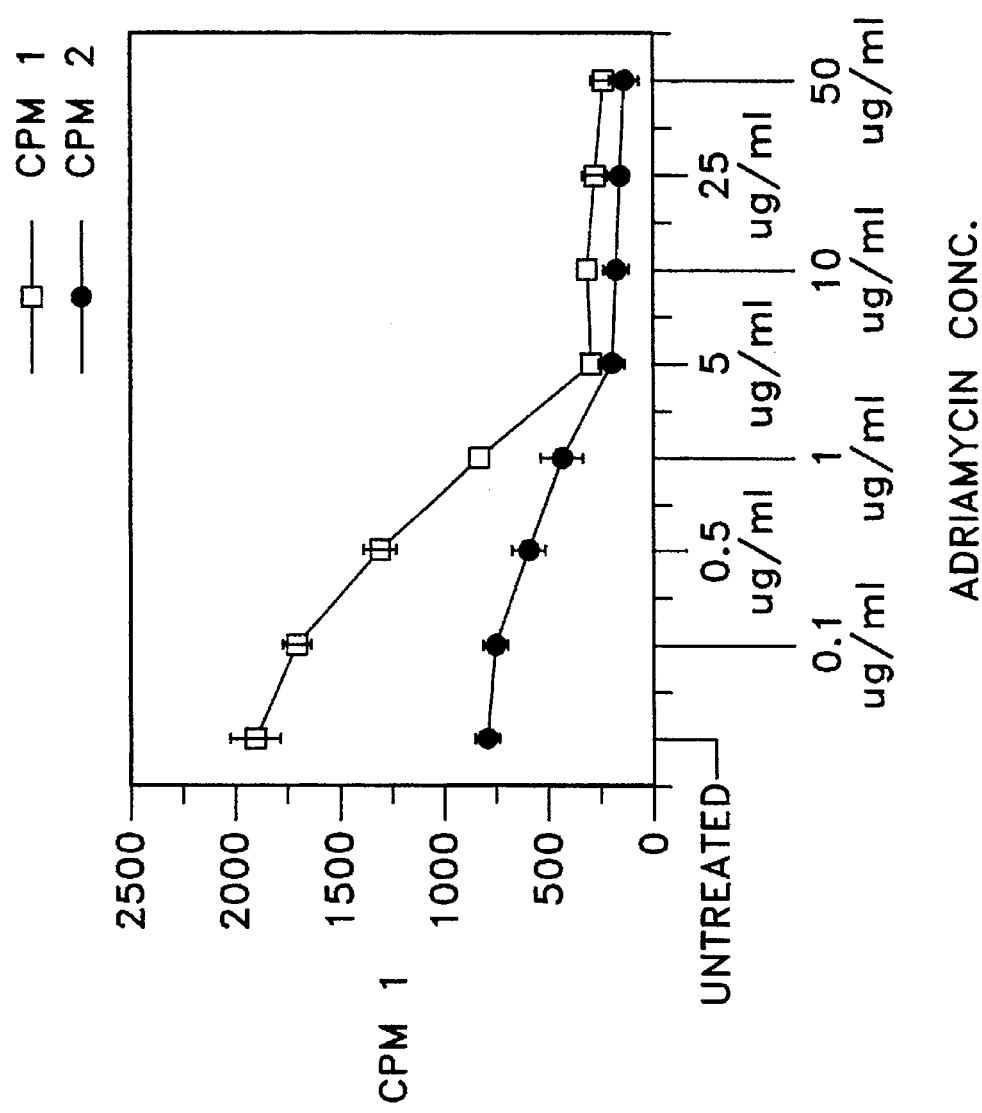
FIG. 15A is a graph showing the viability of U937 monocytic leukemia minor cells after 24 hours, as determined by tritiated thymidine incorporation assay, following treatment of the cells with different dosage levels of Doxorubicin.
Figure 15B:
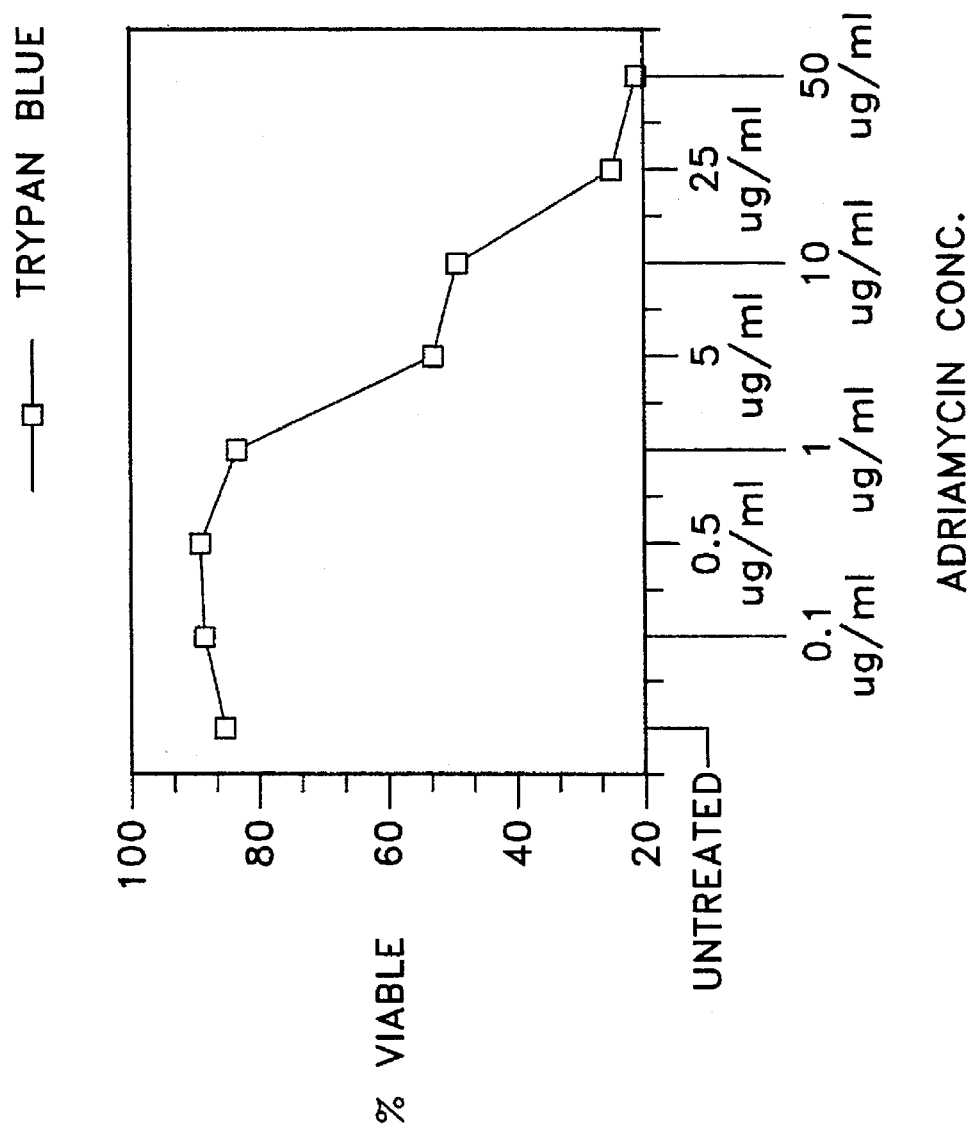
FIG. 15B is a graph showing the viability of U937 monocytic leukemia tumor cells after 24 hours, as determined by exclusion of the vital dye trypan blue assay, following treatment of the cells with different dosage levels of Doxorubicin.
Figure 16:
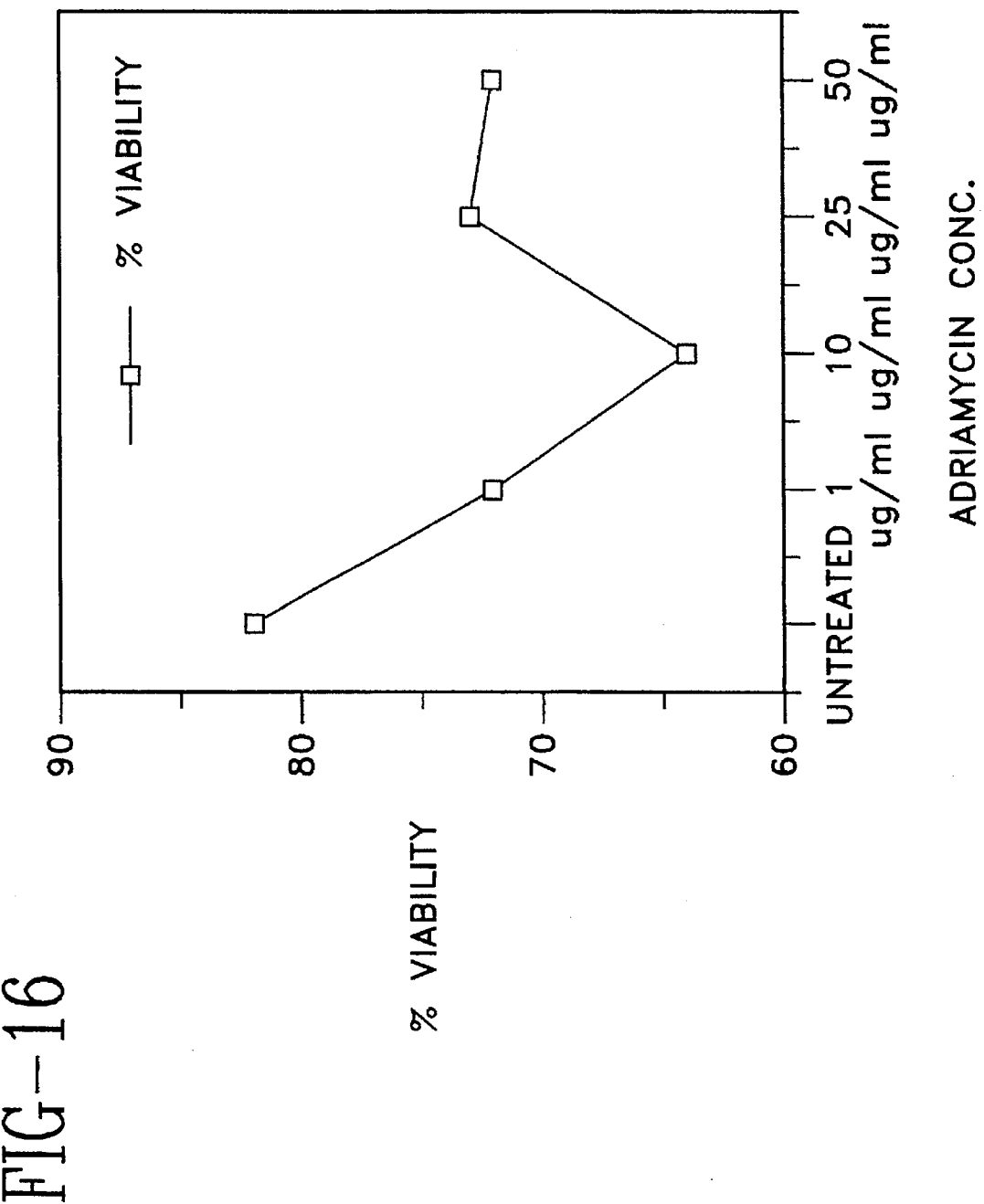
FIG. 16 is a graph showing the viability of U937 monocytic leukemia tumor cells after 1 hour, as determined by exclusion of the vital dye trypan blue assay, following treatment of the cells with different dosage levels of Doxorubicin.

A dose response curve for Doxorubicin (Adriamycin™) alone was constructed. Doxorubicin is an anthracycline antibiotic used as a first line agent in a number of neoplastic conditions and is a well characterized cytotoxic agent. Doses and times examined ranged from 0.1, 0.5, 1, 5, 10, 25, and 50 ug/ml of Doxorubicin for 20–60 minutes and 24 hours. The range of optimal concentrations for cytotoxity of Doxorubicin was established for U937 monocytic minor cells to be 0.5, 1 and 5 ug at 24 hours and 10 ug at 1–2 hours, see FIGS. 15 and 16.

Figure 17:
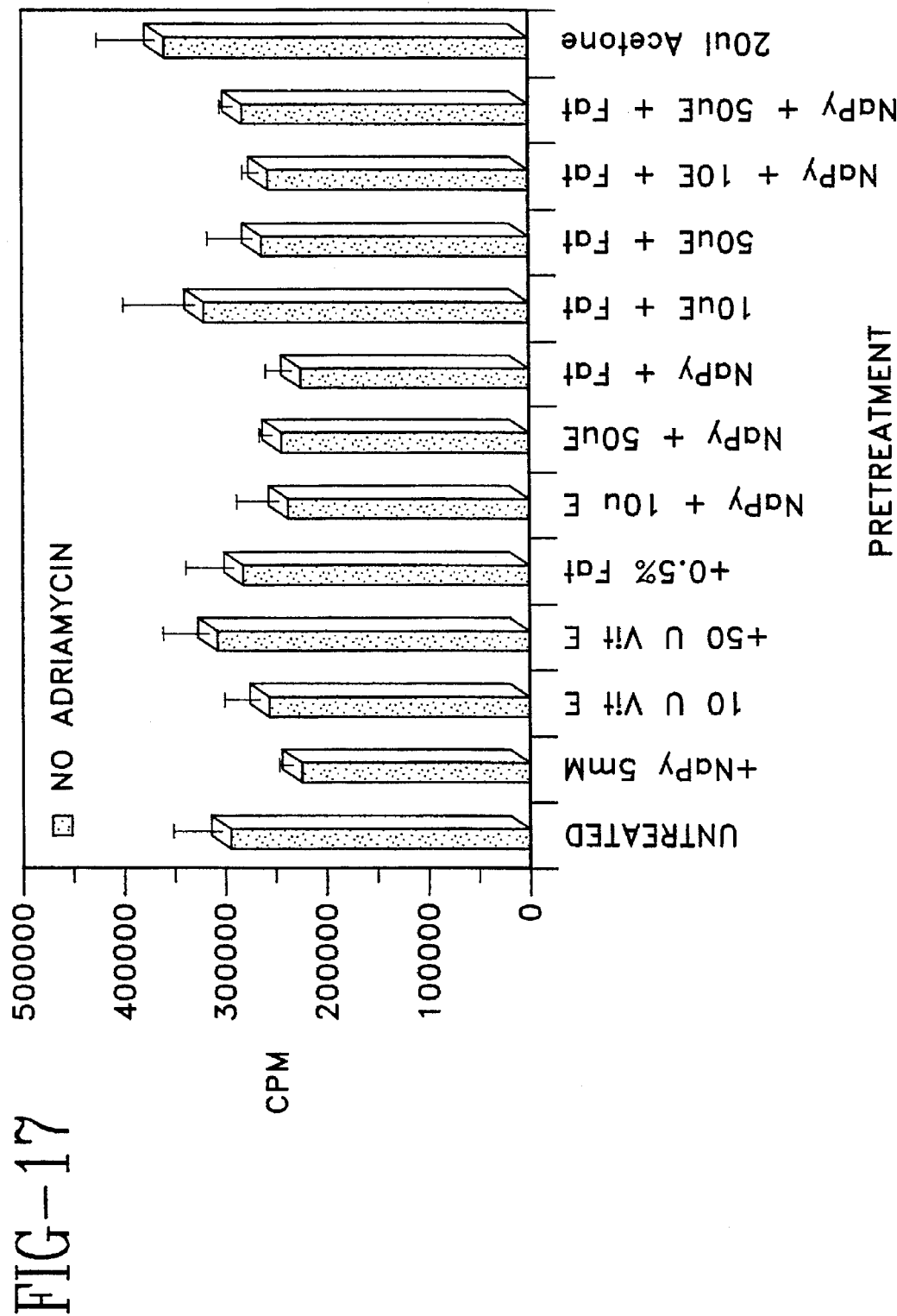
FIG. 17 is a graph showing the viability of U937 monocytic leukemia minor cells after 24 hours, as determined by tritiated thymidine incorporation assay, following treatment of the cells with the cytoprotective components of the present invention, alone and in combinations, at different dosage levels.
Figure 18B:
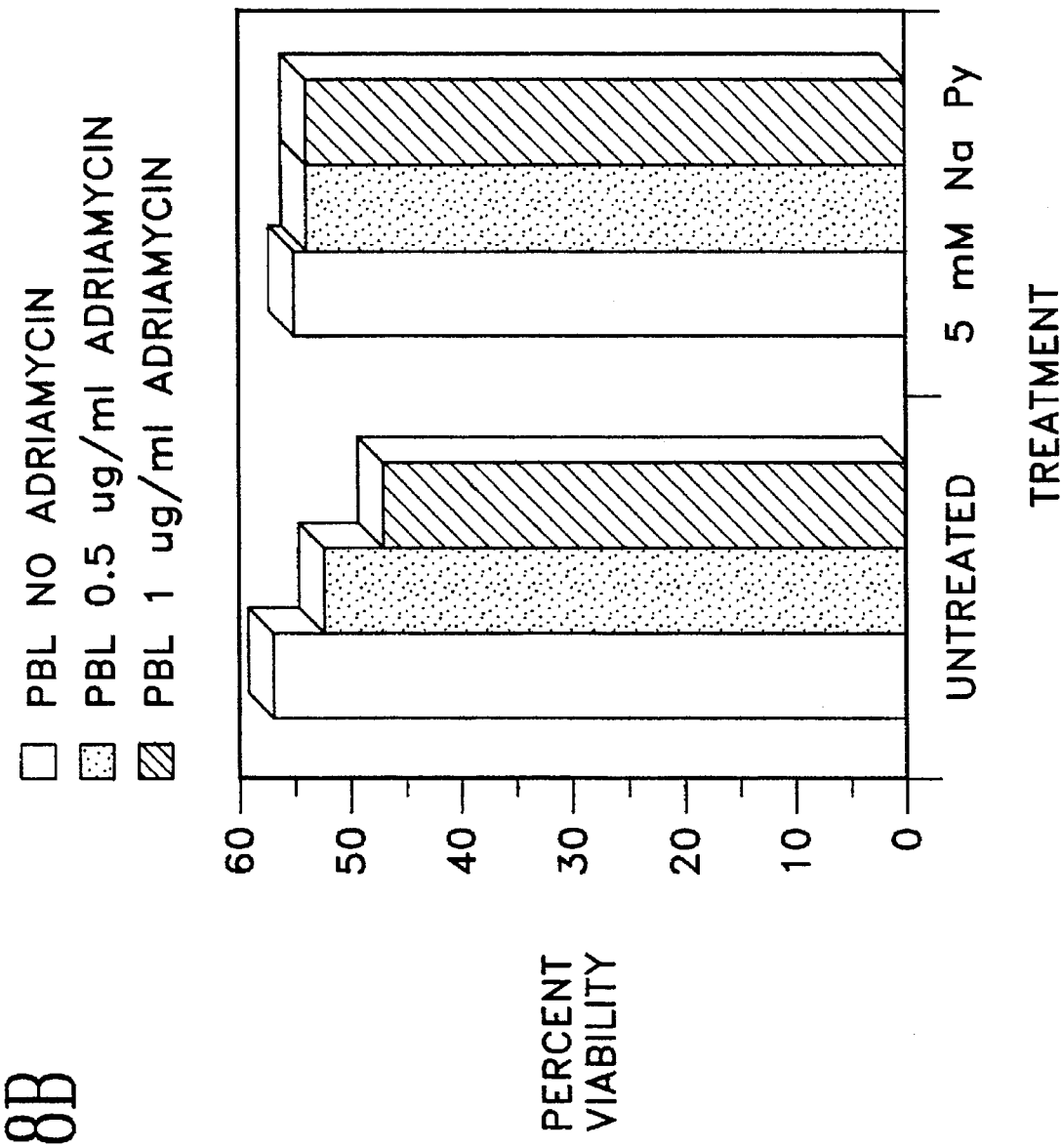
FIG. 18B is a graph showing the viability of peripheral blood monocytes in a wash-out study, as determined by tritiated thymidine incorporation assay, after 24 hour pretreatment of the cells with 5 mM sodium pyruvate followed by administration of different dosage levels of Doxorubicin.
Figure 19A:
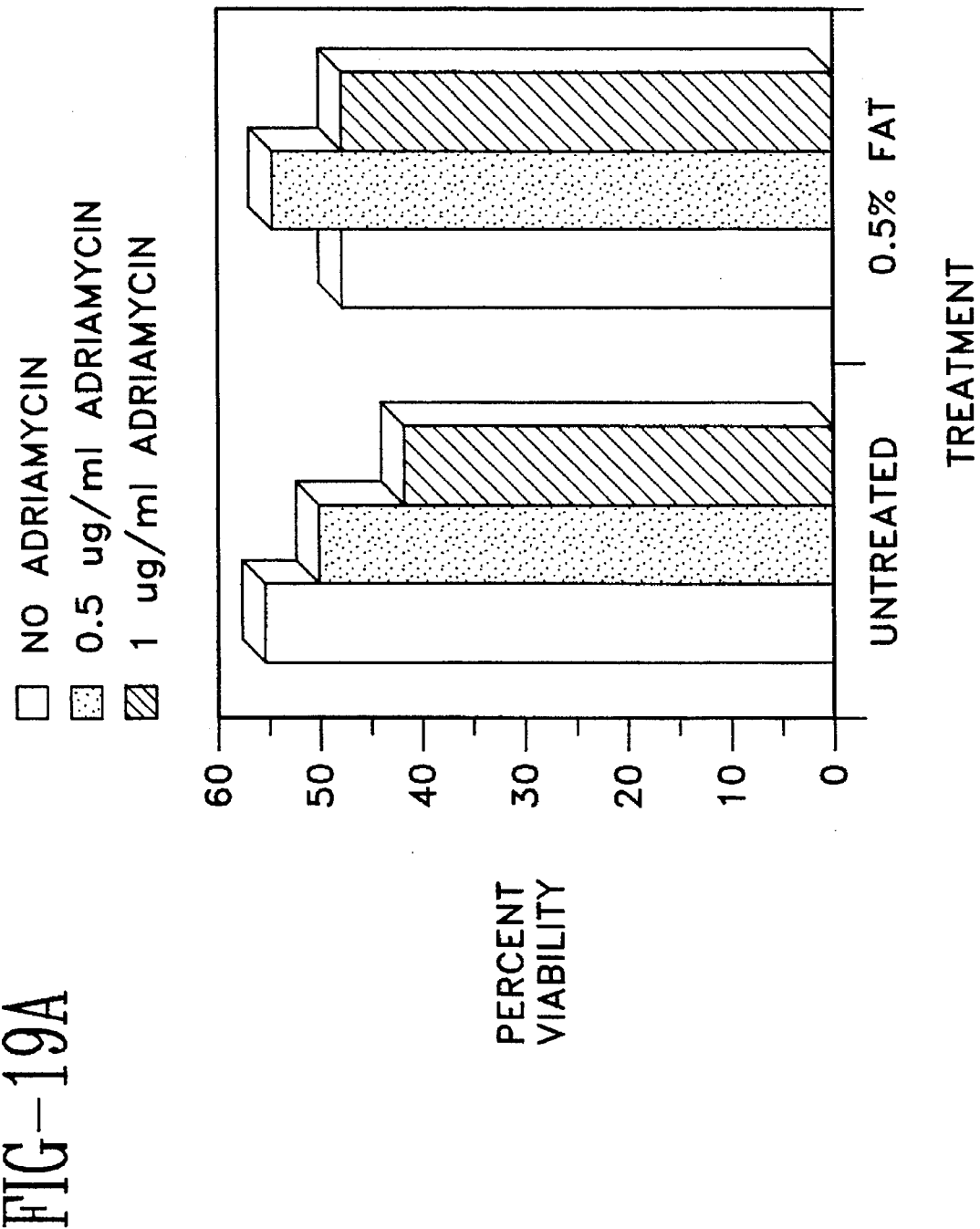
FIG. 19A is a graph showing the viability of U937 monocytic leukemia minor cells in a wash-out study, as determined by tritiated thymidine incorporation assay, after 24 hour pretreatment of the cells with 0.5% fatty acids followed by administration of different dosage levels of Doxorubicin.
Figure 19B:
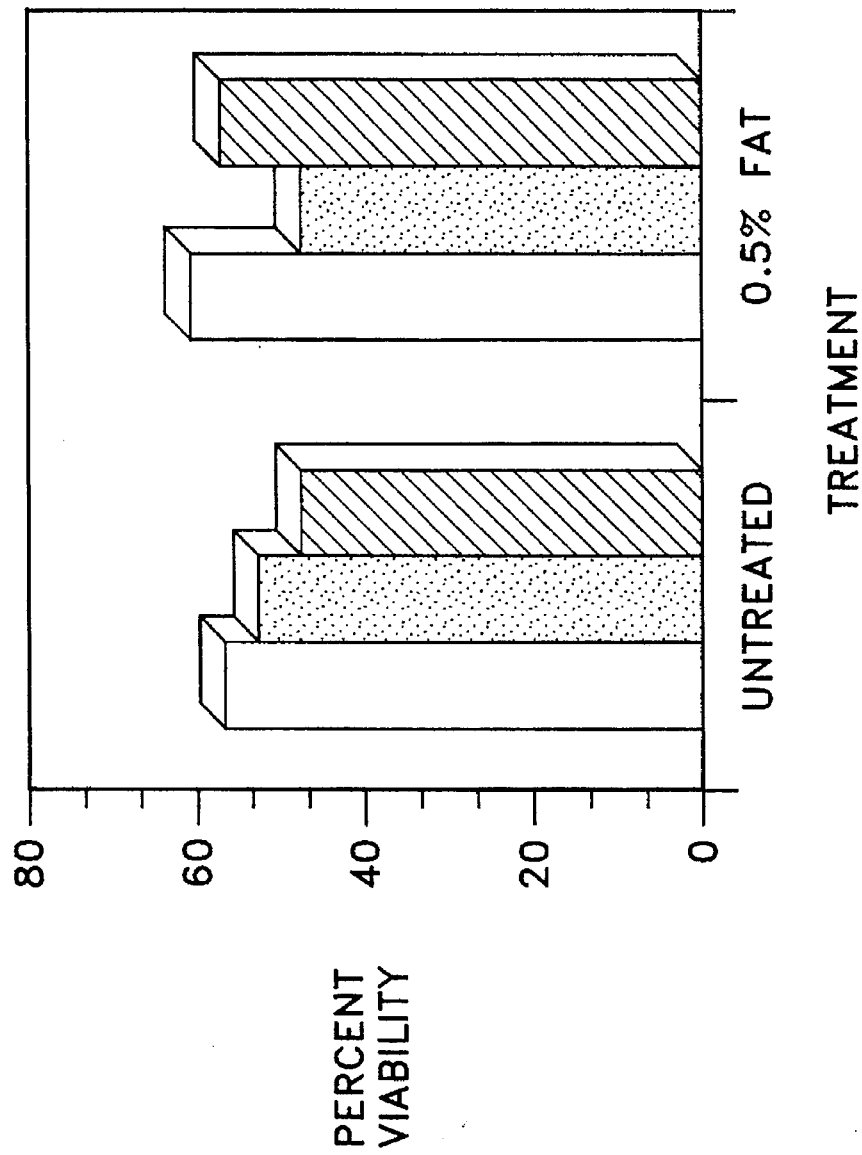
FIG. 19B is a graph showing the viability of peripheral blood monocytes in a wash-out study, as determined by tritiated thymidine incorporation assay, after 24 hour pretreatment of the cells with 0.5% fatty acids followed by administration of different dosage levels of Doxorubicin.
Figure 20B:
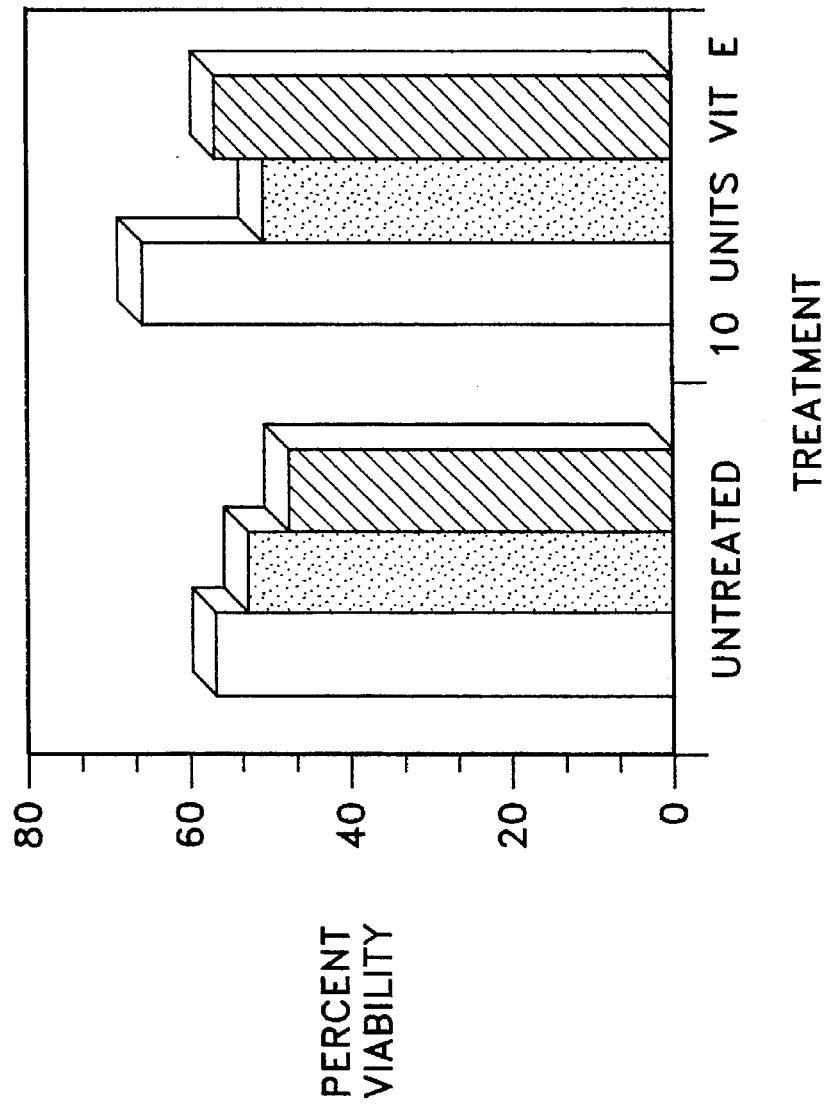
FIG. 20B is a graph showing the viability of peripheral blood monocytes in a wash-out study, as determined by tritiated thymidine incorporation assay, after 24 hour pretreatment of the cells with 10 U Vitamin E followed by administration of different dosage levels of Doxorubicin.

The cytoprotective agents (sodium pyruvate, Vitamin E, and fatty acids; wound healing composition) alone, and in combination, were examined for their ability to decrease the cytotoxity of Doxorubicin to U937 monocytic leukemia cells and normal peripheral blood monocytes. Optimal concentrations of the single ingredients of sodium pyruvate, Vitamin E, and fatty acids were examined. The optimal concentrations of the agents that were able to protect cells against Doxorubicin induced cytotoxicity were as follows: 10–50 U Vitamin E, 0.5% fatty acids, and 5 mM of sodium pyruvate, see FIG. 17.

Window of susceptibility studies were conducted to determine the optimal treatment time of the cells with the cytoprotective agents prior to treatment of the cells with the cytotoxic agent. The normal cells and U937 leukemic tumor cells were pretreated separately in "wash out" studies with the single agents alone, and in combination, at the optimal concentration described above for various time periods, washed with fresh medium to remove the agents, and treated with the cytotoxic agent. The co-culture of normal and U937 leukemic tumor cells was treated essentially in the same manner except that the cells were not treated separately, but co-cultured. The optimal pretreatment time of the cells with the cytoprotective agents was found to be 24 hours prior to treatment of the cells with Doxorubicin. The cells were then placed in culture medium without the protective agents. The length of time that the cytoprotection lasted was 24 hours following Doxorubicin treatment. At this time, peripheral cell viability is a limiting factor because these cells are normal cells and do not remain in culture for extended periods of time.

Normal and U937 minor cells were co-cultured and the cytotoxity of Doxorubicin on the cells was determined by viability assays which examined the differential ability of the cytoprotective compositions alone, and in combinations, to protect the normal cells from the cytotoxity of the chemotherapeutic agent.

The cells were isolated and examined for morphological evidence of cytotoxicity or prevention of cytotoxicity. These studies determined the cytoprotective effect of the single agents and the combination of agents on the normal and minor cells. DNA synthesis studies using 3H-thymidine (1 uCi/well) were carried out 4 hours prior to termination of the experiment to determine the effect of the formulations on the proliferation of the cells as a measure of the prevention of cytotoxicity and the extent of Doxorubicin-induced cytotoxicity. Propidium iodide exclusion analysis was carried out for direct quantitation of the cytotoxicity and the prevention of cytotoxicity. Each set of studies was performed in triplicate so that statistical analysis of the significant differences between the treatment groups could be conducted.

The effect of the cytoprotective agents on the co-culture of tumor and normal cells was very different from the effect of these agents on the individual cell types alone. An interaction between the normal cells and the tumor cells must cause the viability of the minor cells to be significantly diminished. The cytoprotective combination of 5 mM sodium pyruvate, 0.5% fatty acids, and 10 U Vitamin E provided significant protection to the normal peripheral monocytes and did not protect the minor cells from the effects of the cytotoxic agent.

Wash-out studies were conducted to determine viability of the peripheral blood monocytes co-cultured with U937 monocytic leukemia cells after 24 hour pretreatment of the cells with the cytoprotective agents followed by administration of Doxorubicin. With no Doxorubicin treatment, the viability of the control normal peripheral cells was enhanced from 55% to 68% with the use of 5 mM sodium pyruvate and 0.5% fatty acids, see FIG. 17. With no Doxorubicin treatment, the viability of the control U937 cells was enhanced from 43% to 62% with the use of the combination of the cytoprotective composition, 5 mM sodium pyruvate, 10 U Vitamin E, and 0.5% fatty acids, see FIG. 17.

Figure 21A:
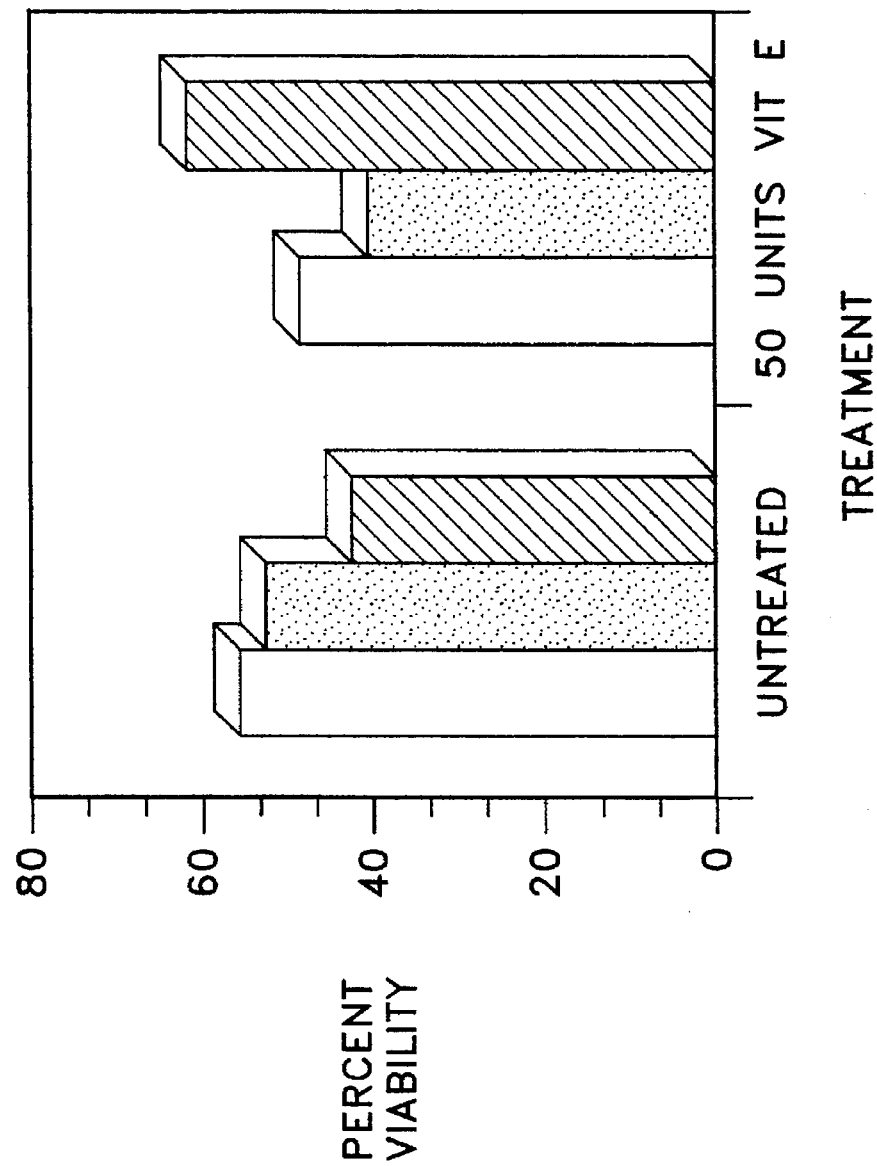
FIG. 21A is a graph showing the viability of U937 monocytic leukemia tumor cells in a wash-out study, as determined by tritiated thymidine incorporation assay, after 24 hour pretreatment of the cells with 50 U Vitamin E followed by administration of different dosage levels of Doxorubicin.
Figure 21B:
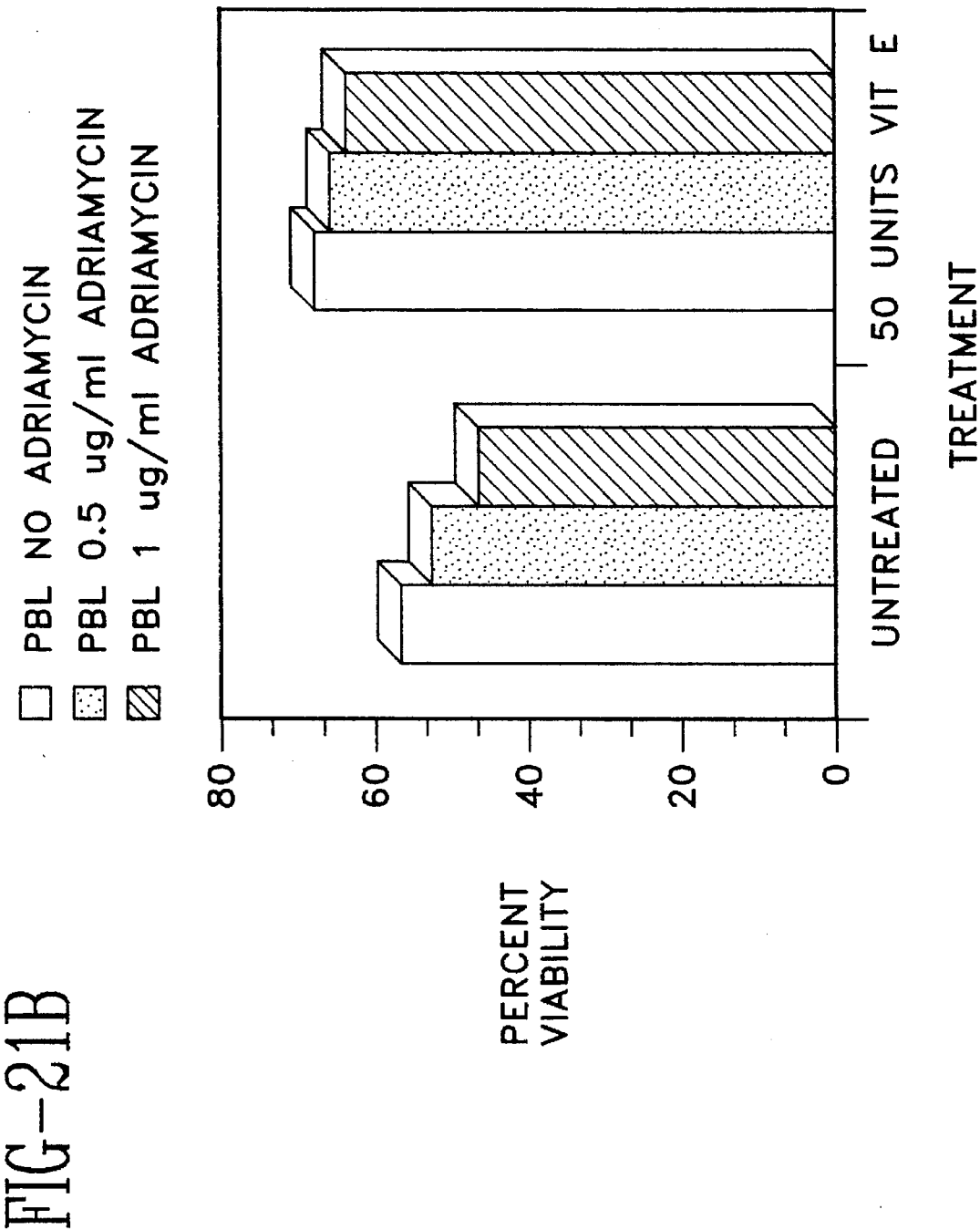
FIG. 21B is a graph showing the viability of peripheral blood monocytes in a wash-out study, as determined by tritiated thymidine incorporation assay, after 24 hour pretreatment of the cells with 50 U Vitamin E followed by administration of different dosage levels of Doxorubicin.
Figure 22A:
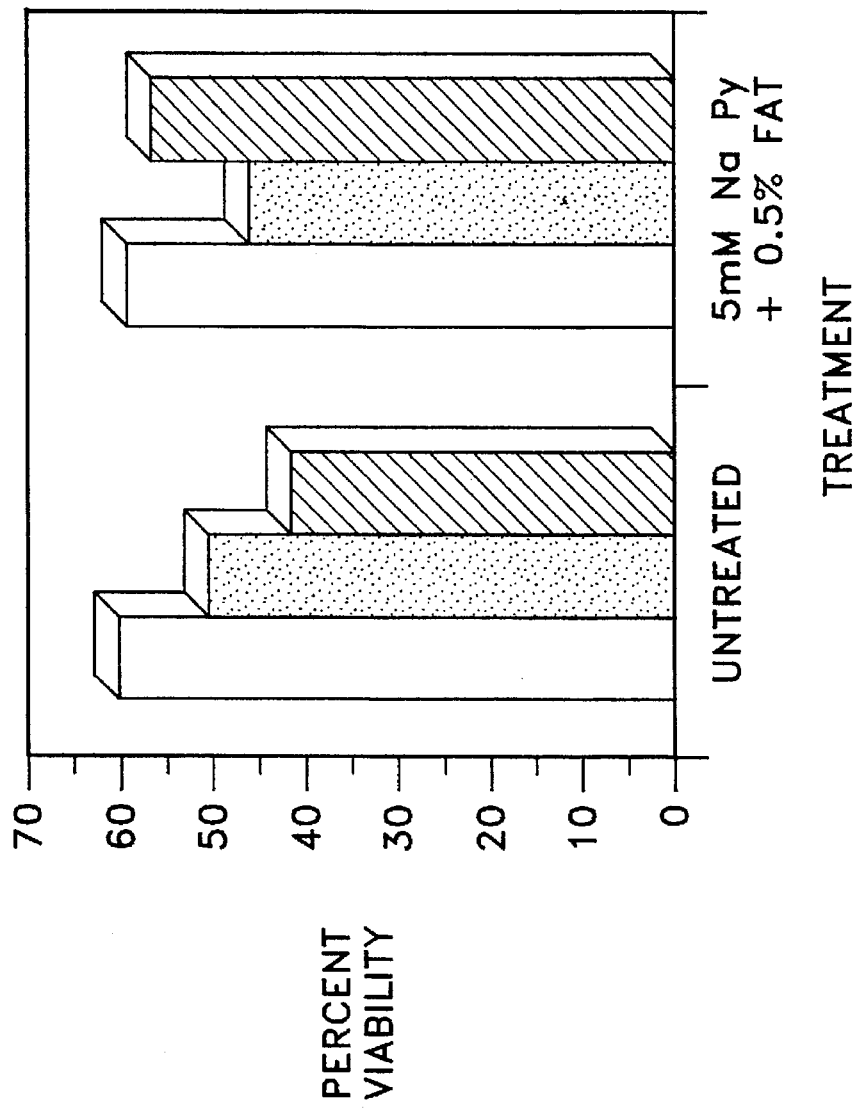
FIG. 22A is a graph showing the viability of U937 monocytic leukemia tumor cells in a wash-out study, as determined by tritiated thymidine incorporation assay, after 24 hour pretreatment of the cells with 5 mM sodium pyruvate and 0.5% fatty acids followed by administration of different dosage levels of Doxorubicin.
Figure 22B:
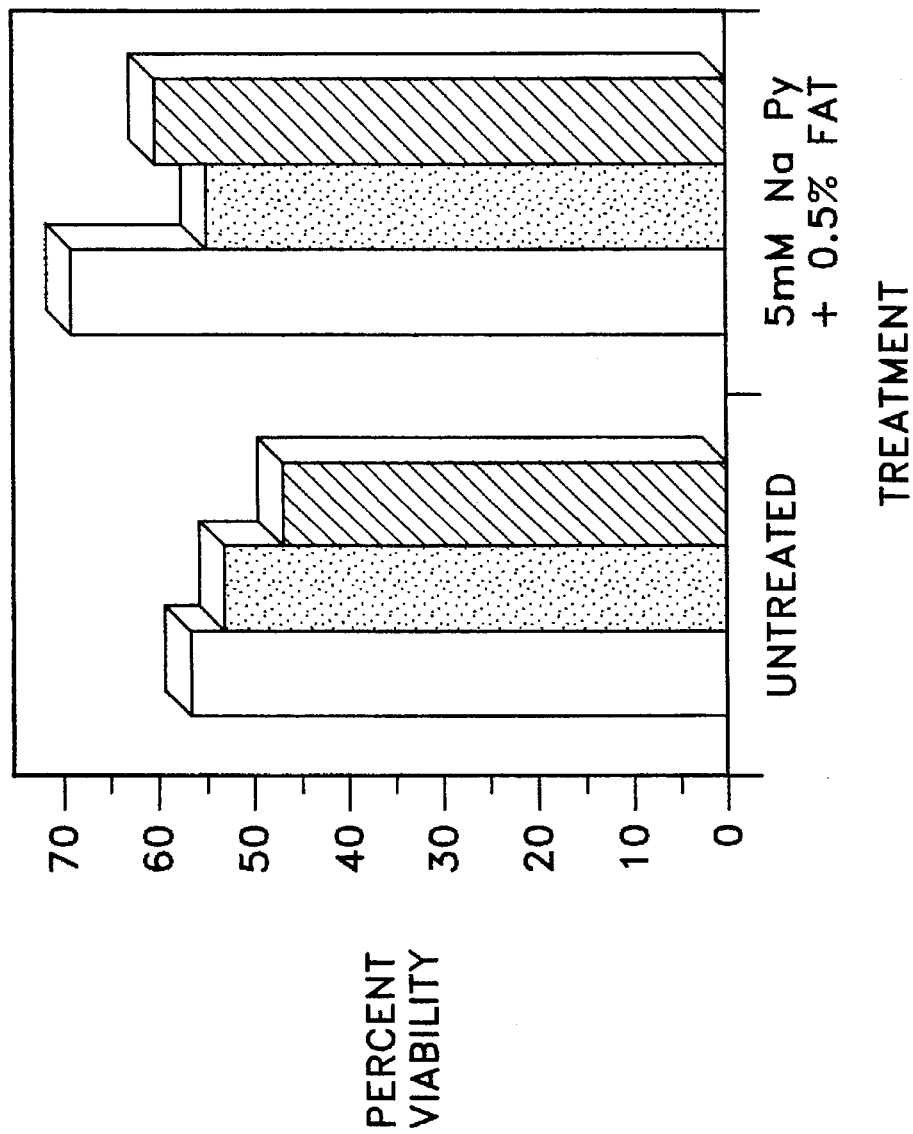
FIG. 22B is a graph showing the viability of peripheral blood monocytes in a wash-out study, as determined by tritiated thymidine incorporation assay, after 24 hour pretreatment of the cells with 5 mM sodium pyruvate and 0.5% fatty acids followed by administration of different dosage levels of Doxorubicin.
Figure 23A:
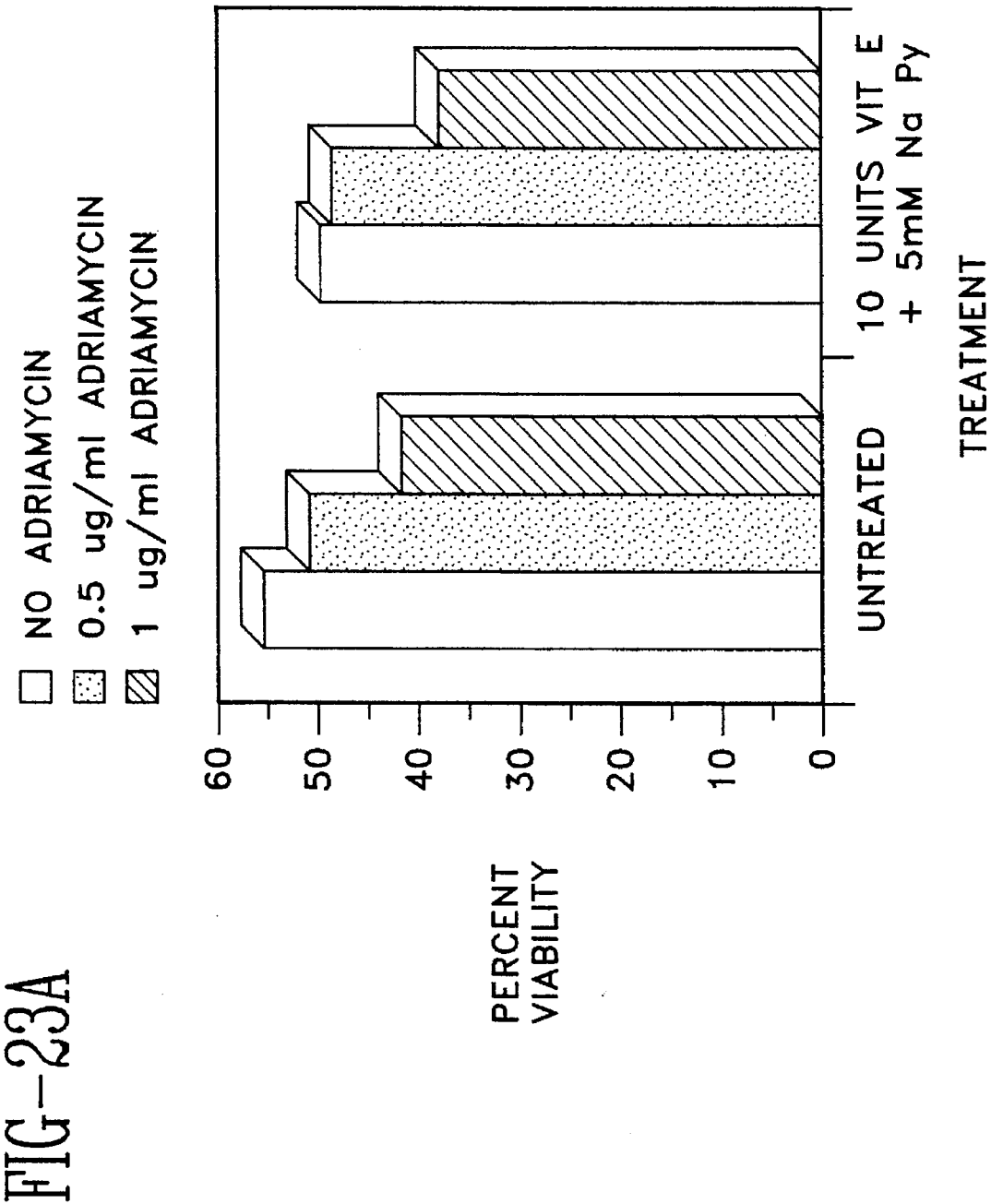
FIG. 23A is a graph showing the viability of U937 monocytic leukemia minor cells in a wash-out study, as determined by tritiated thymidine incorporation assay, after 24 hour pretreatment of the cells with 5 mM sodium pyruvate and 10 U Vitamin E followed by administration of different dosage levels of Doxorubicin.
Figure 24A:
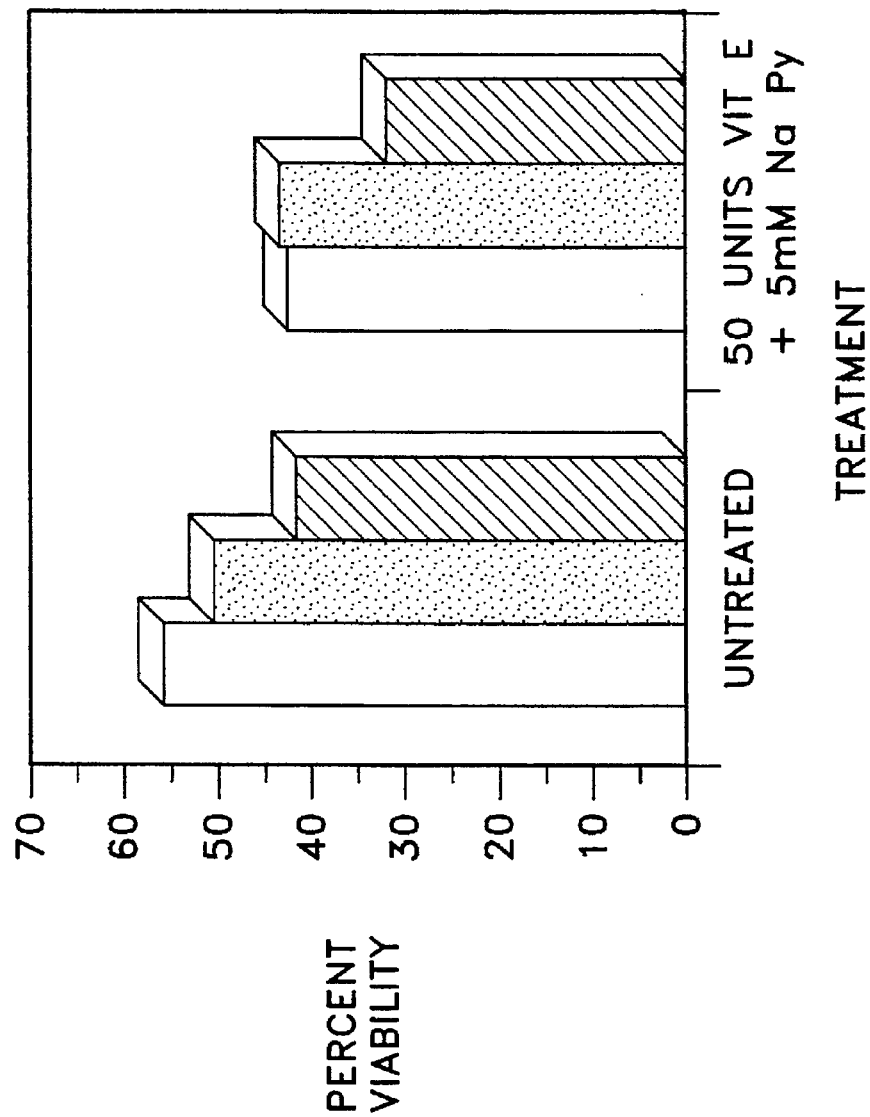
FIG. 24A is a graph showing the viability of U937 monocytic leukemia tumor cells in a wash-out study, as determined by tritiated thymidine incorporation assay, after 24 hour pretreatment of the cells with 5 mM sodium pyruvate and 50 U Vitamin E followed by administration of different dosage levels of Doxorubicin.
Figure 24B:
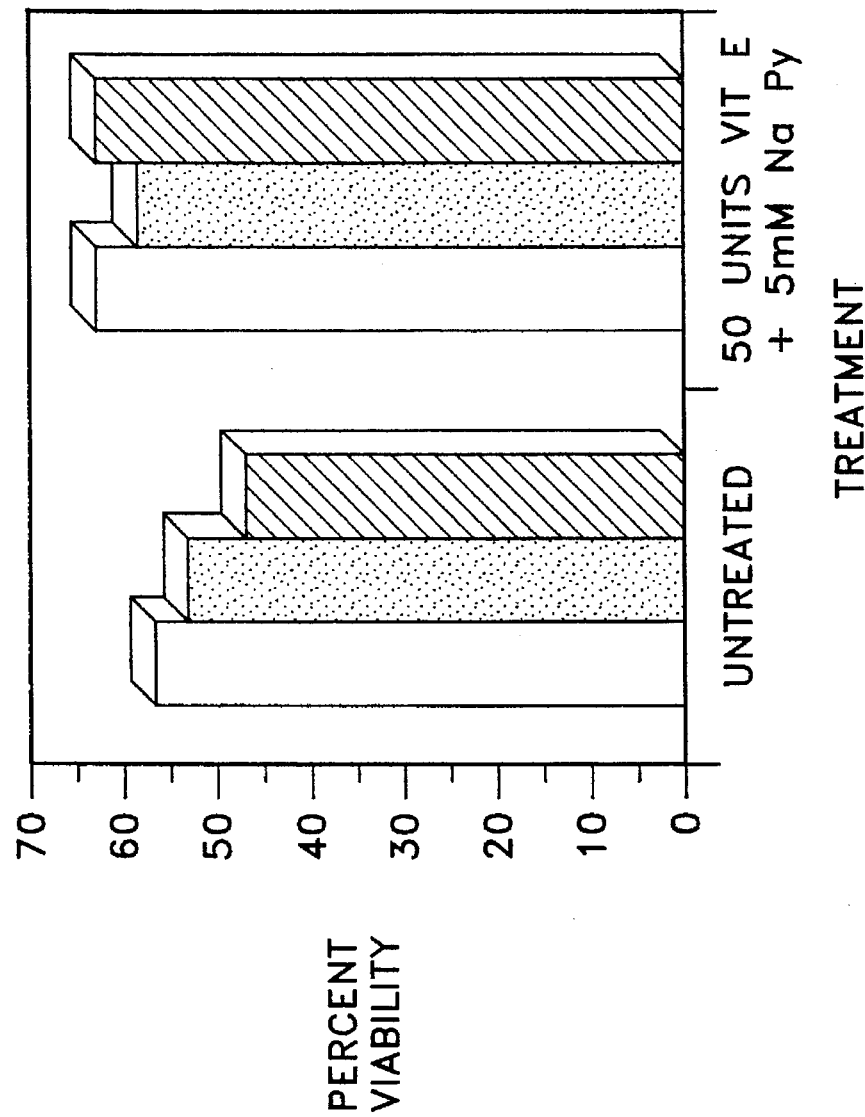
FIG. 24B is a graph showing the viability of peripheral blood monocytes in a wash-out study, as determined by tritiated thymidine incorporation assay, after 24 hour pretreatment of the cells with 5 mM sodium pyruvate and 50 U Vitamin E followed by administration of different dosage levels of Doxorubicin.

Pretreatment with a combination of 10 U Vitamin E and 5 mM sodium pyruvate prevented cytotoxity to normal peripheral blood monocytes with a concentration of 0.5 ug/ml Doxorubicin (53% to 68% viable), see FIGS. 23A–23B. Pretreatment with a combination of 5 mM sodium pyruvate, 10 U Vitamin E, and 0.5% fatty acids prevented cytotoxity to peripheral blood monocytes with a concentration of 1 ug/ml Doxorubicin (47% to 69% viable), see FIGS. 27A–27B. Pretreatment with the single agent 50 U Vitamin E prevented cytotoxity to U937 tumor cells induced by 1 ug/ml Doxorubicin (42% to 62% viable), see FIGS. 21A–21B.

Figure 27A:
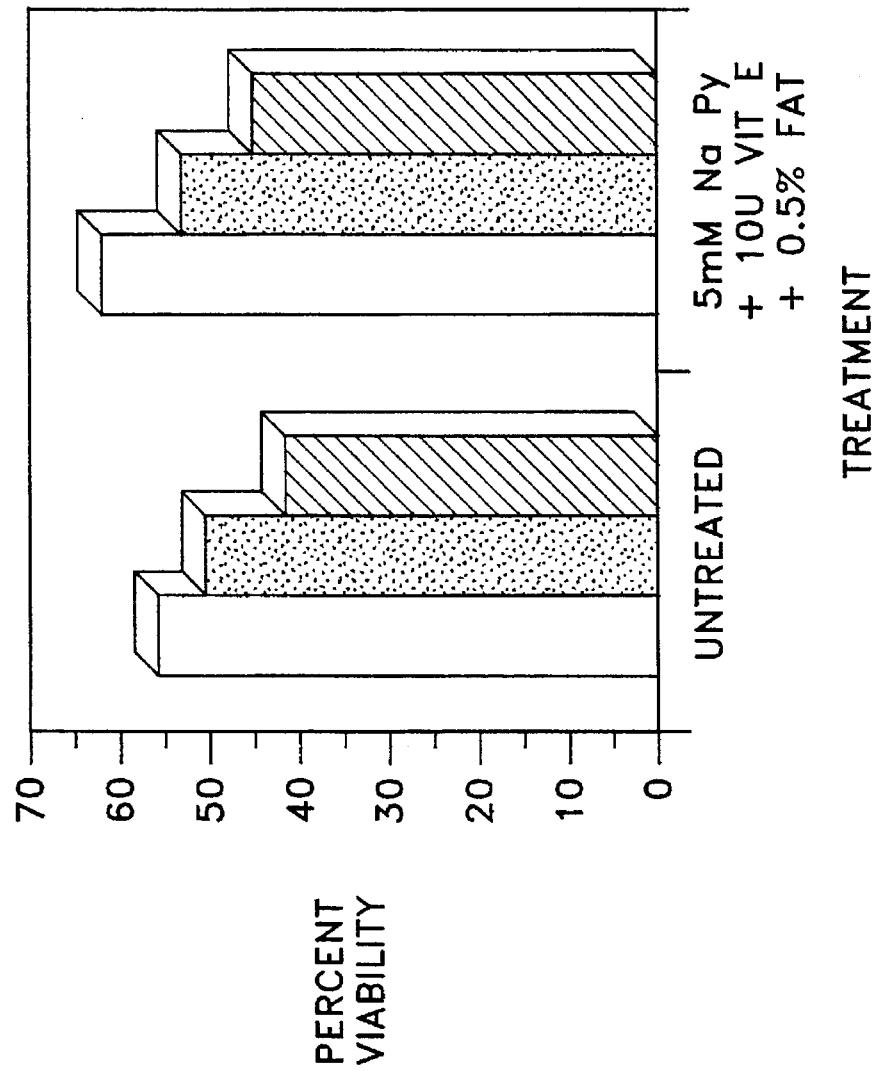
FIG. 27A is a graph showing the viability of U937 monocytic leukemia tumor cells in a wash-out study, as determined by tritiated thymidine incorporation assay, after 24 hour pretreatment of the cells with 5 mM sodium pyruvate, 10 U Vitamin E, and 0.5% fatty acids followed by administration of different dosage levels of Doxorubicin.
Figure 27B:
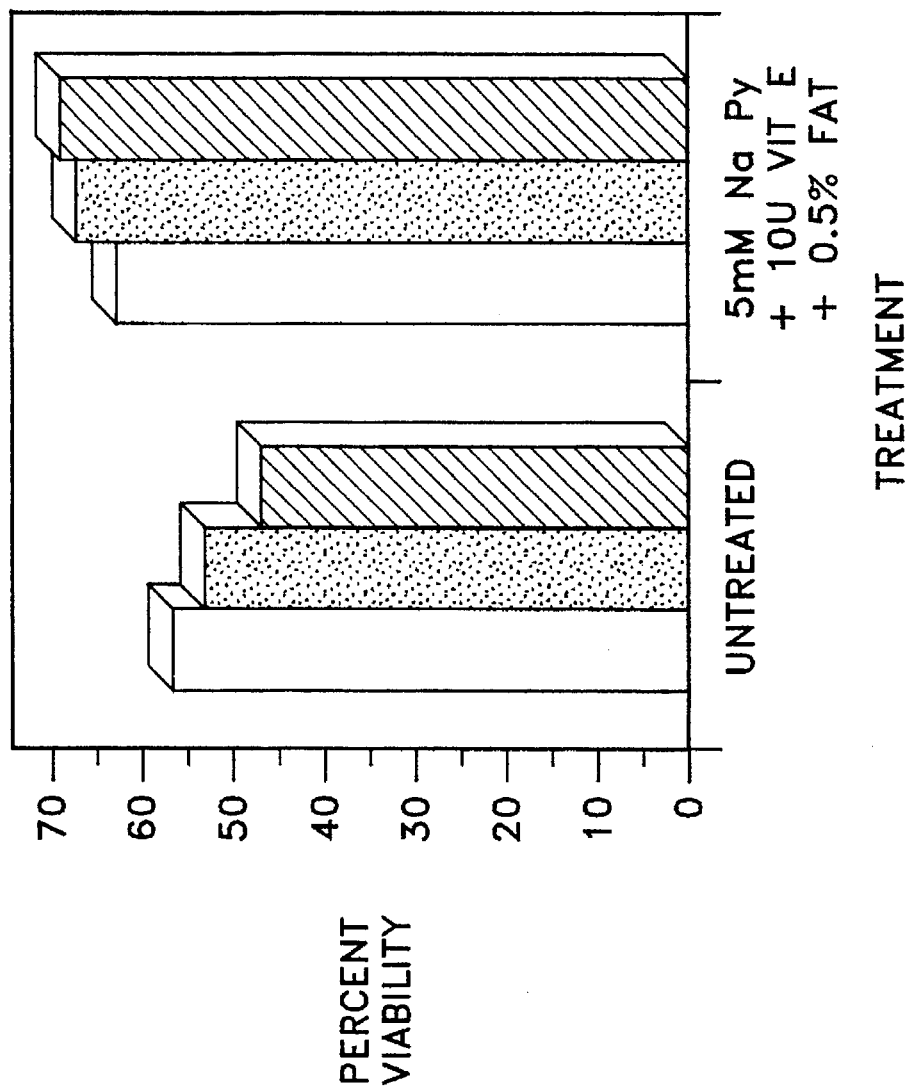
FIG. 27B is a graph showing the viability of peripheral blood monocytes in a wash-out study, as determined by tritiated thymidine incorporation assay, after 24 hour pretreatment of the cells with 5 mM sodium pyruvate, 10 U Vitamin E, and 0.5% fatty acids followed by administration of different dosage levels of Doxorubicin.
Figure 28B:
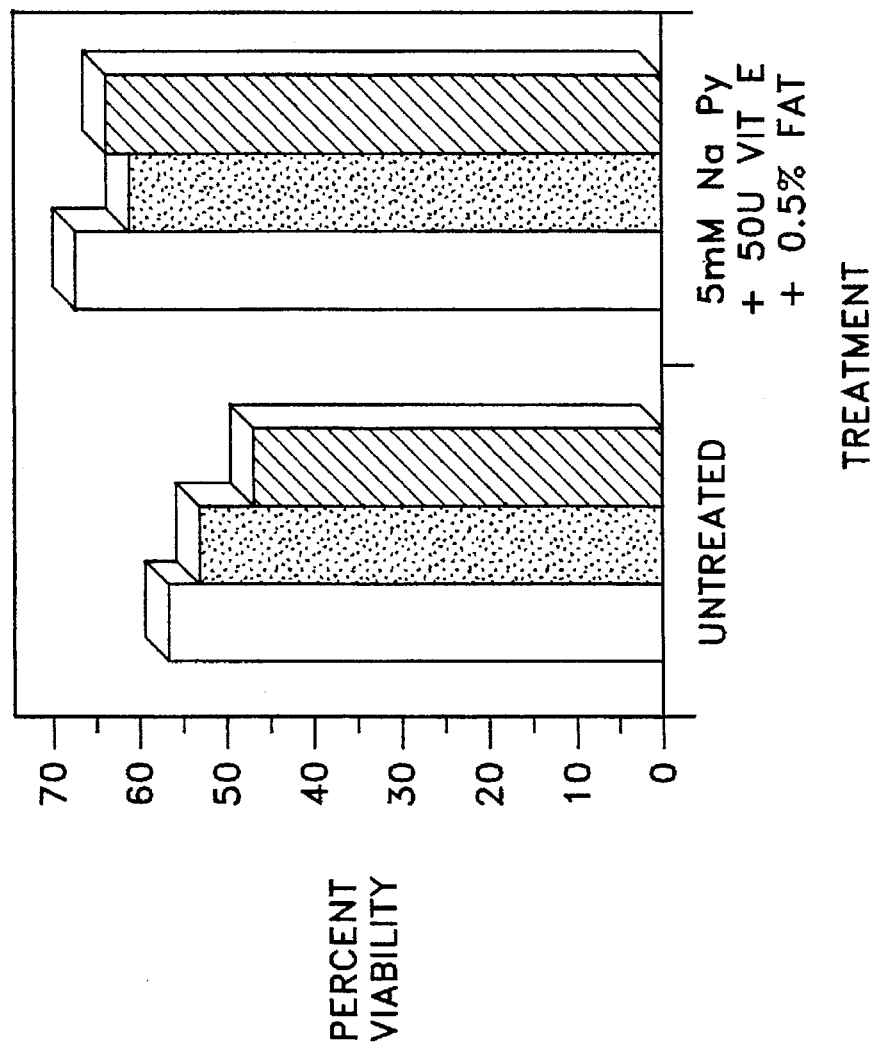
FIG. 28B is a graph showing the viability of peripheral blood monocytes in a wash-out study, as determined by tritiated thymidine incorporation assay, after 24 hour pretreatment of the cells with 5 mM sodium pyruvate, 50 U Vitamin E, and 0.5% fatty acids followed by administration of different dosage levels of Doxorubicin.
Figure 29A:
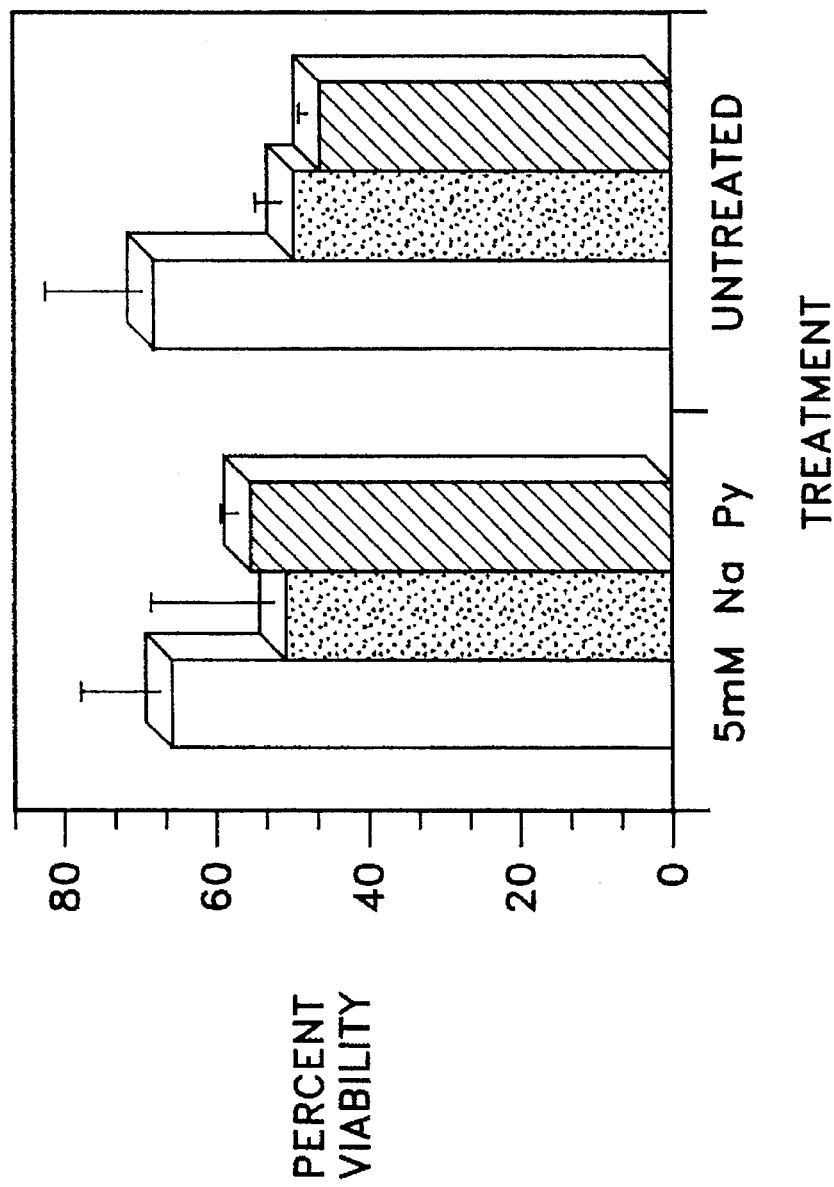
FIG. 29A is a graph showing the viability of U937 monocytic leukemia tumor cells in a co-culture study, as determined by tritiated thymidine incorporation assay, after 24 hour pretreatment of the cells with 5 mM sodium pyruvate followed by administration of different dosage levels of Doxorubicin.
Figure 29B:
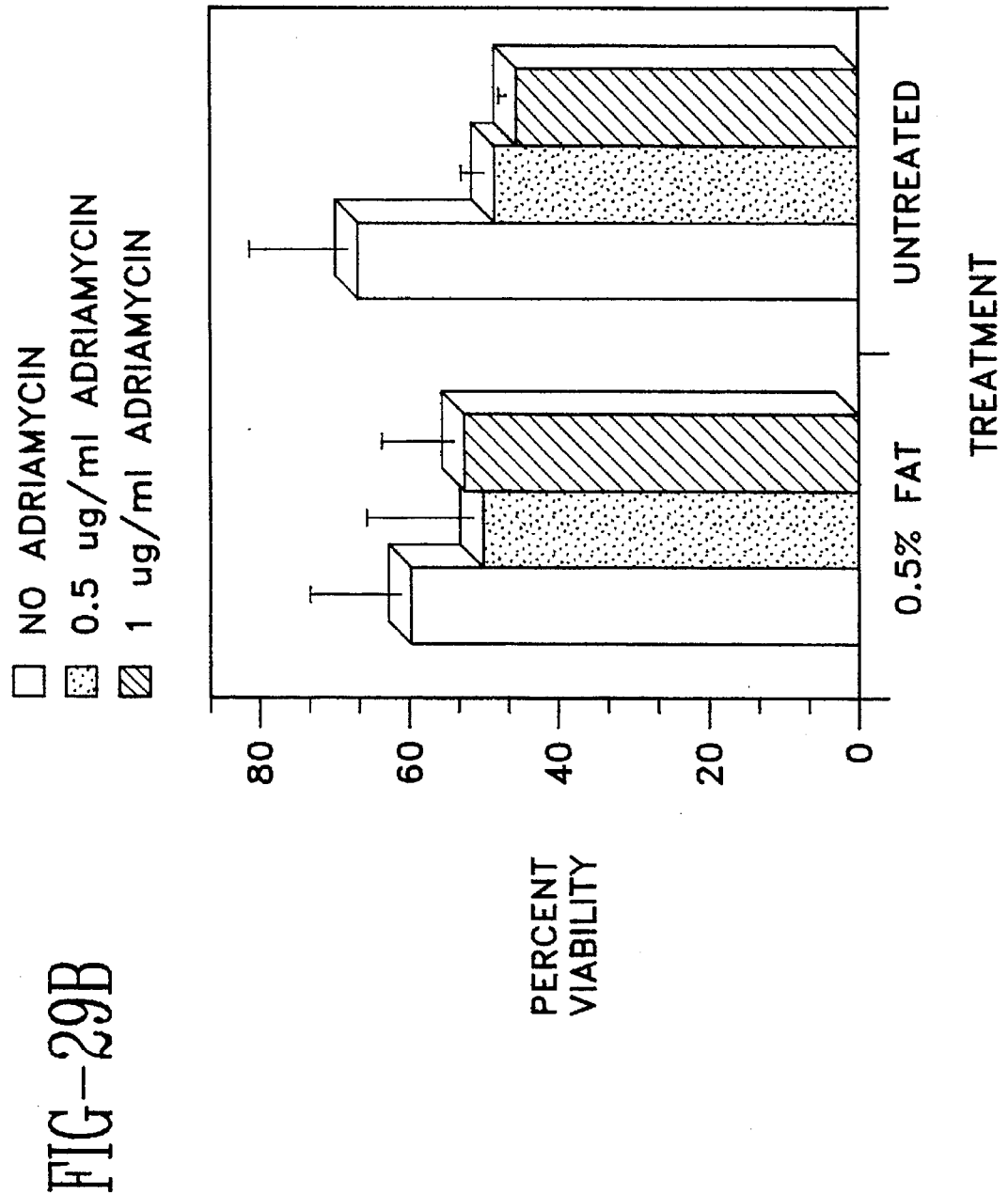
FIG. 29B is a graph showing the viability of peripheral blood monocytes in a co-culture study, as determined by tritiated thymidine incorporation assay, after 24 hour pretreatment of the cells with 5 mM sodium pyruvate followed by administration of different dosage levels of Doxorubicin.
Figure 30A:
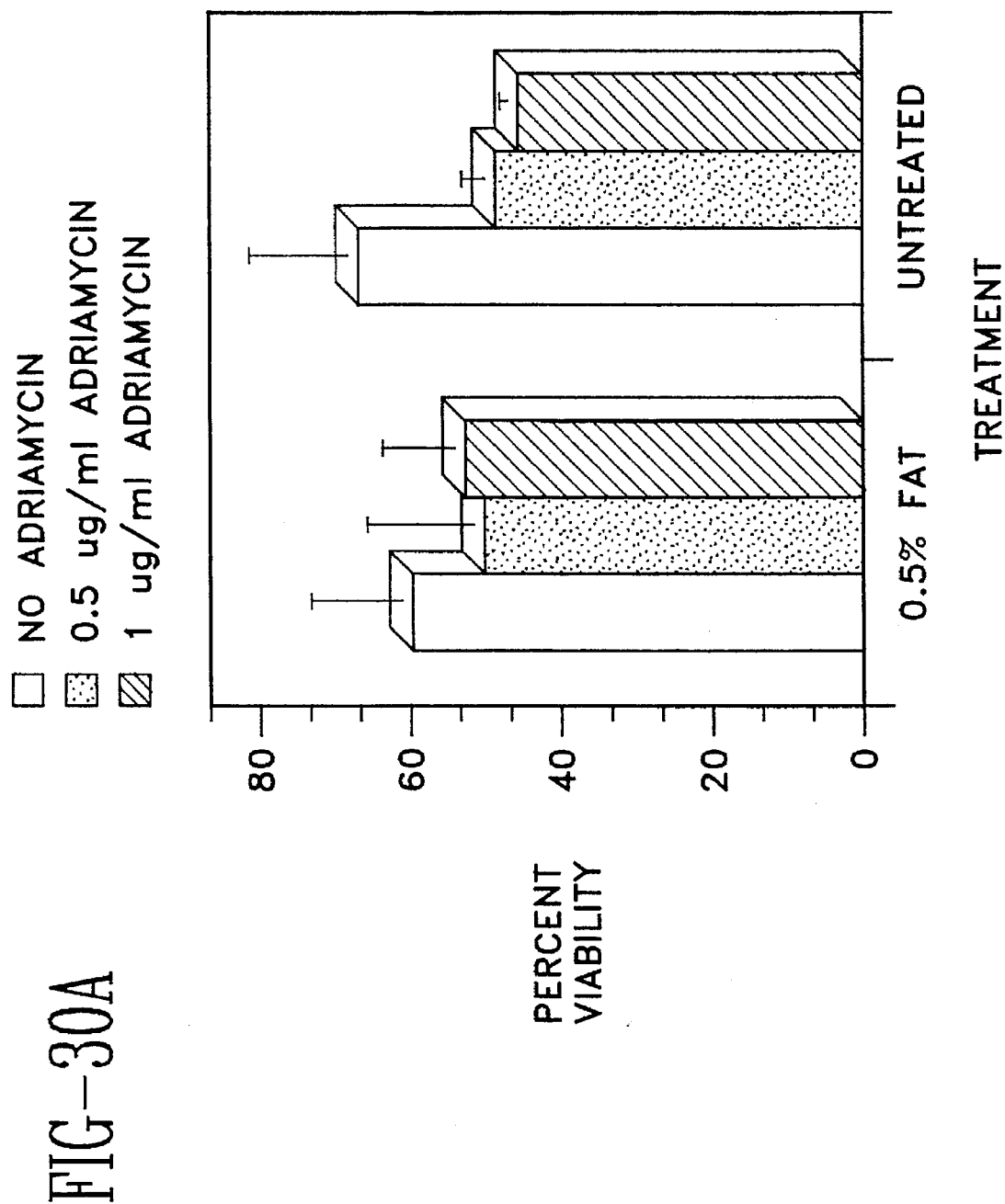
FIG. 30A is a graph showing the viability of U937 monocytic leukemia tumor cells in a co-culture study, as determined by tritiated thymidine incorporation assay, after 24 hour pretreatment of the cells with 0.5% fatty acids followed by administration of different dosage levels of Doxorubicin.
Figure 30B:
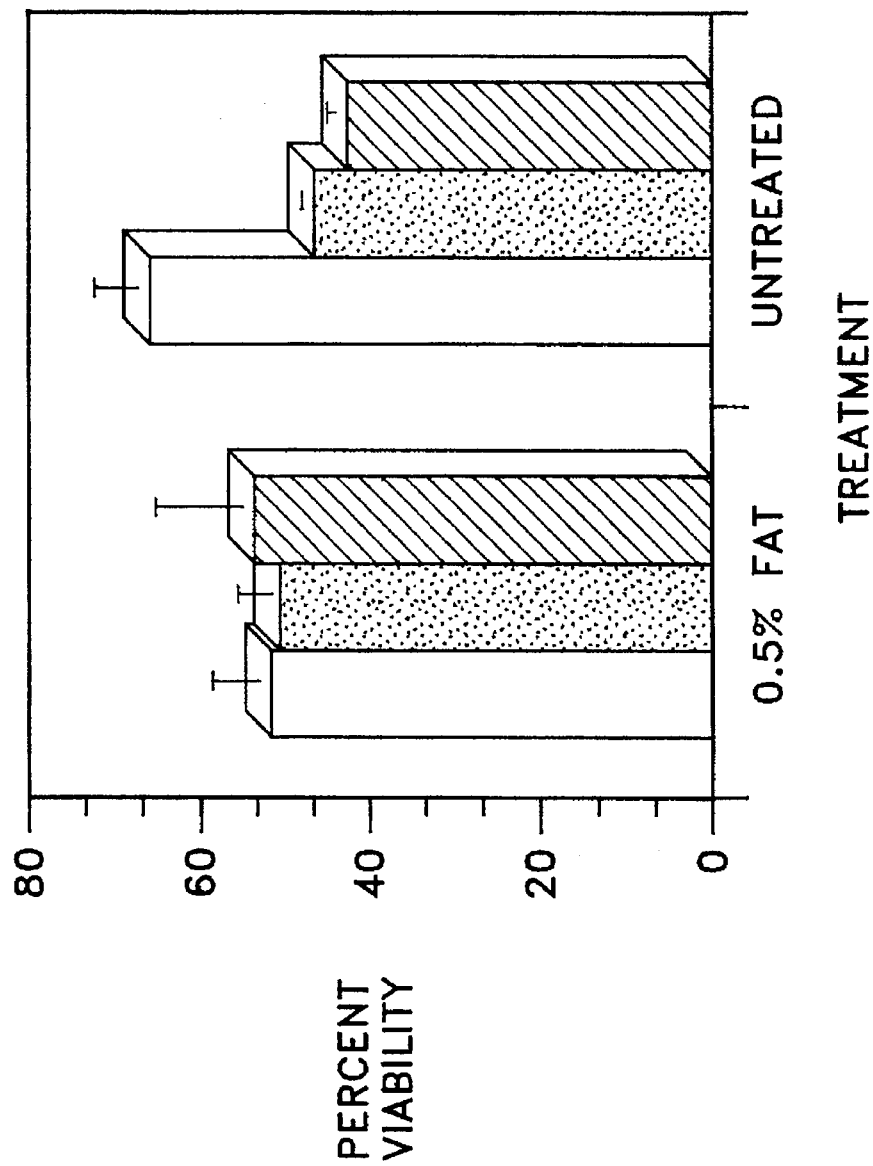
FIG. 30B is a graph showing the viability of peripheral blood monocytes in a co-culture study, as determined by tritiated thymidine incorporation assay, after 24 hour pretreatment of the cells with 0.5% fatty acids followed by administration of different dosage levels of Doxorubicin.
Figure 31A:
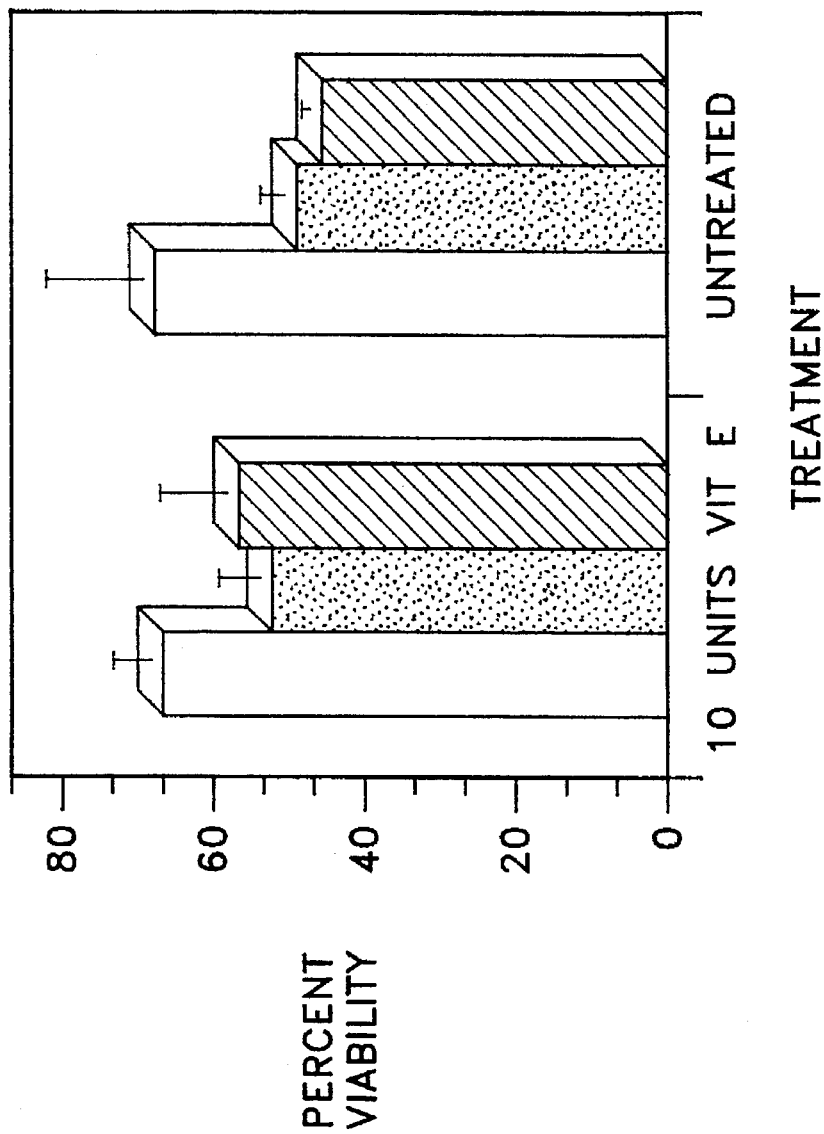
FIG. 31A is a graph showing the viability of U937 monocytic leukemia tumor cells in a co-culture study, as determined by tritiated thymidine incorporation assay, after 24 hour pretreatment of the cells with 10 U Vitamin E followed by administration of different dosage levels of Doxorubicin.
Figure 31B:
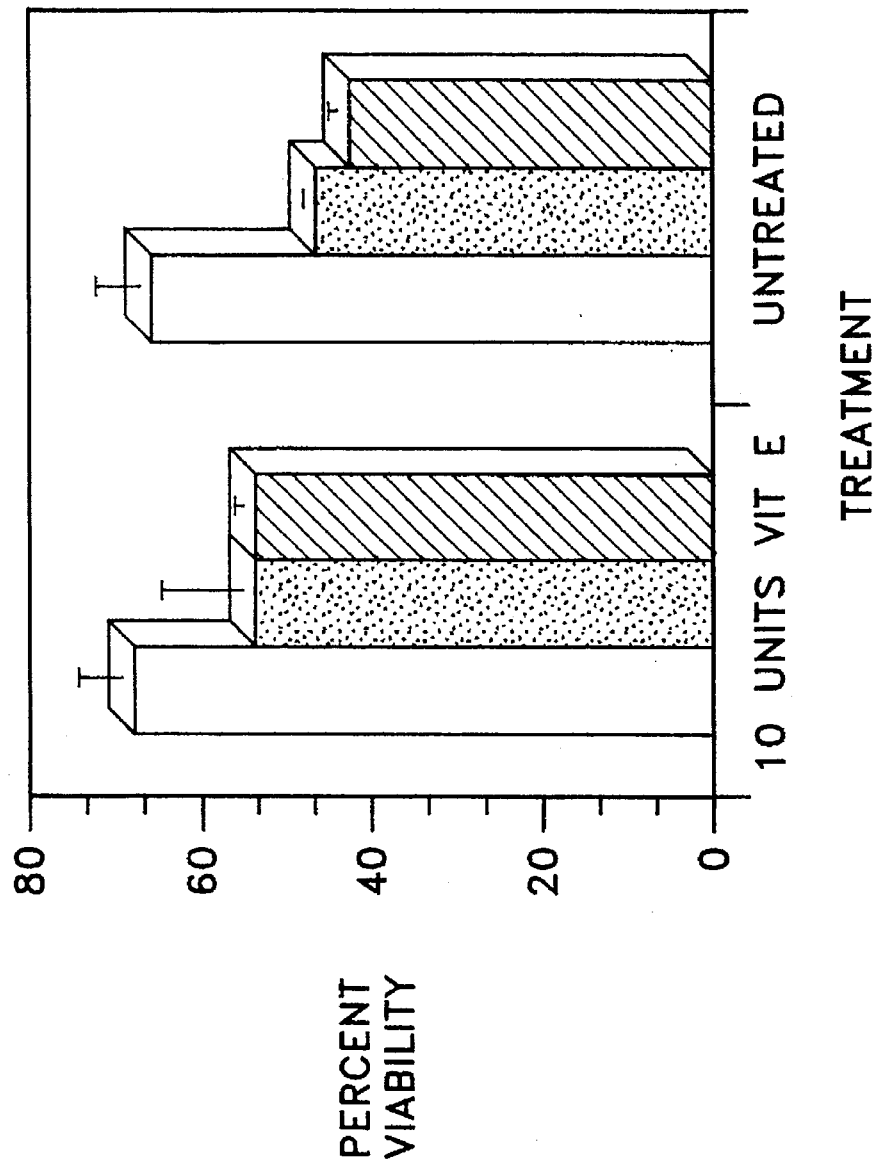
FIG. 31B is a graph showing the viability of peripheral blood monocytes in a co-culture study, as determined by tritiated thymidine incorporation assay, after 24 hour pretreatment of the cells with 10 U Vitamin E followed by administration of different dosage levels of Doxorubicin.
Figure 32A:
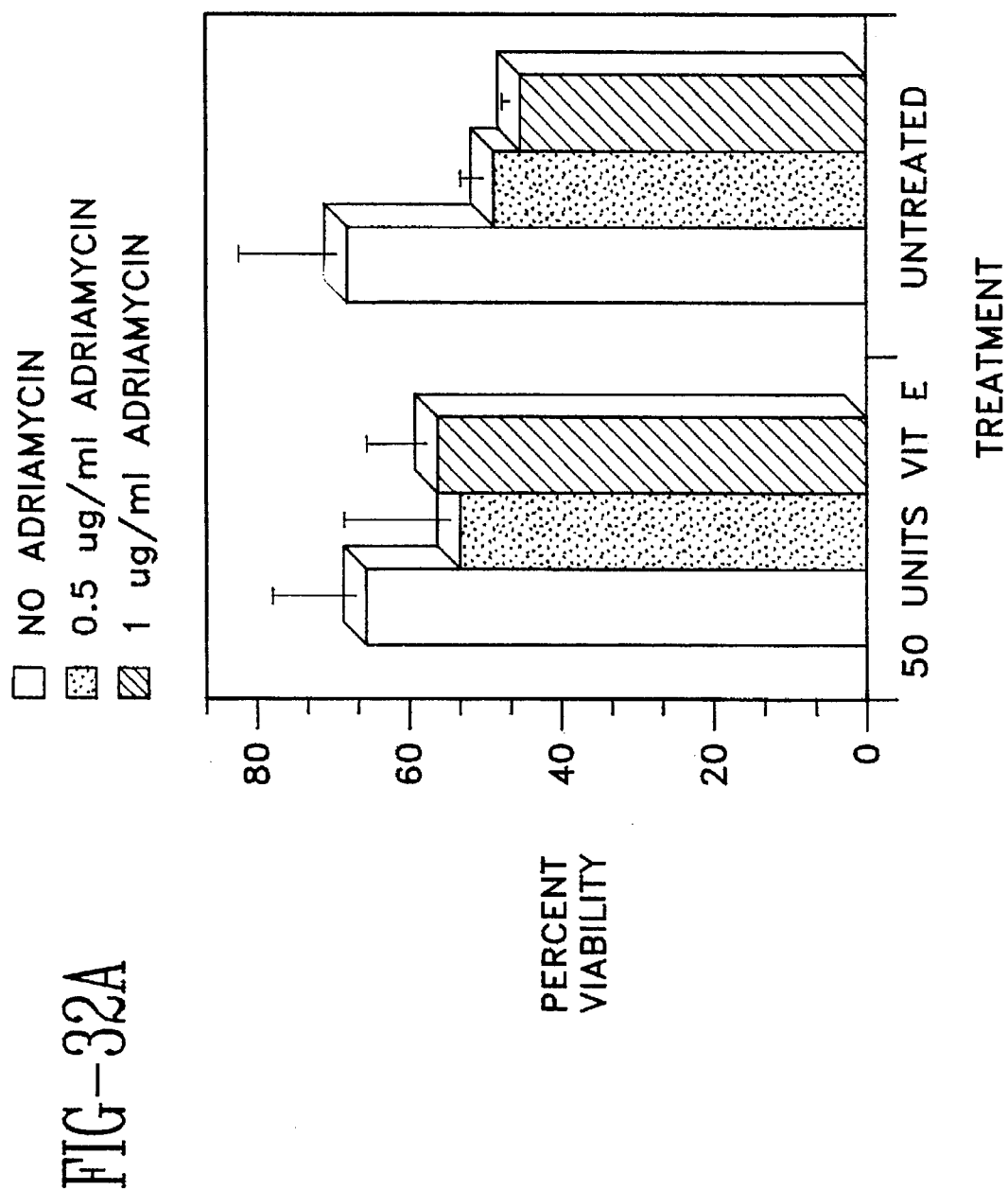
FIG. 32A is a graph showing the viability of U937 monocytic leukemia tumor cells in a co-culture study, as determined by tritiated thymidine incorporation assay, after 24 hour pretreatment of the cells with 50 U Vitamin E followed by administration of different dosage levels of Doxorubicin.
Figure 32B:
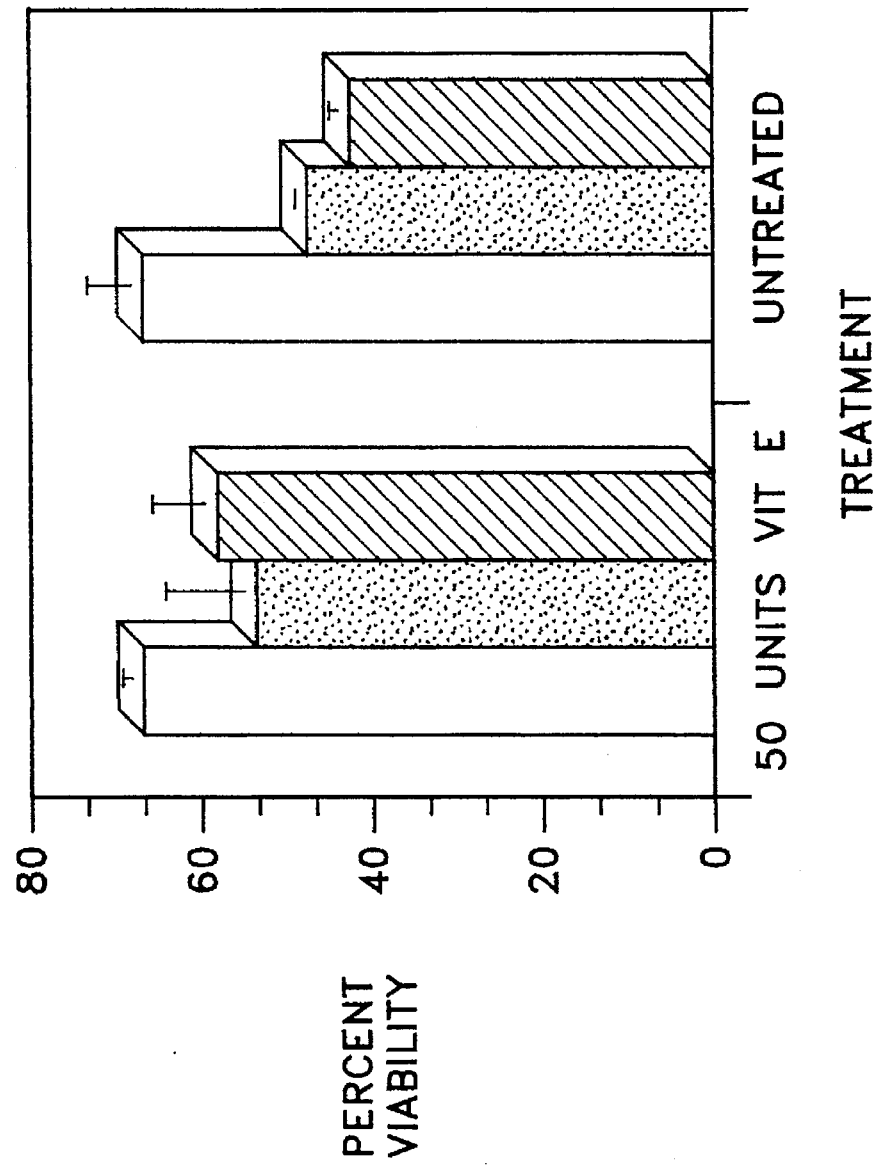
FIG. 32B is a graph showing the viability of peripheral blood monocytes in a co-culture study, as determined by tritiated thymidine incorporation assay, after 24 hour pretreatment of the cells with 50 U Vitamin E followed by administration of different dosage levels of Doxorubicin.
Figure 33A:
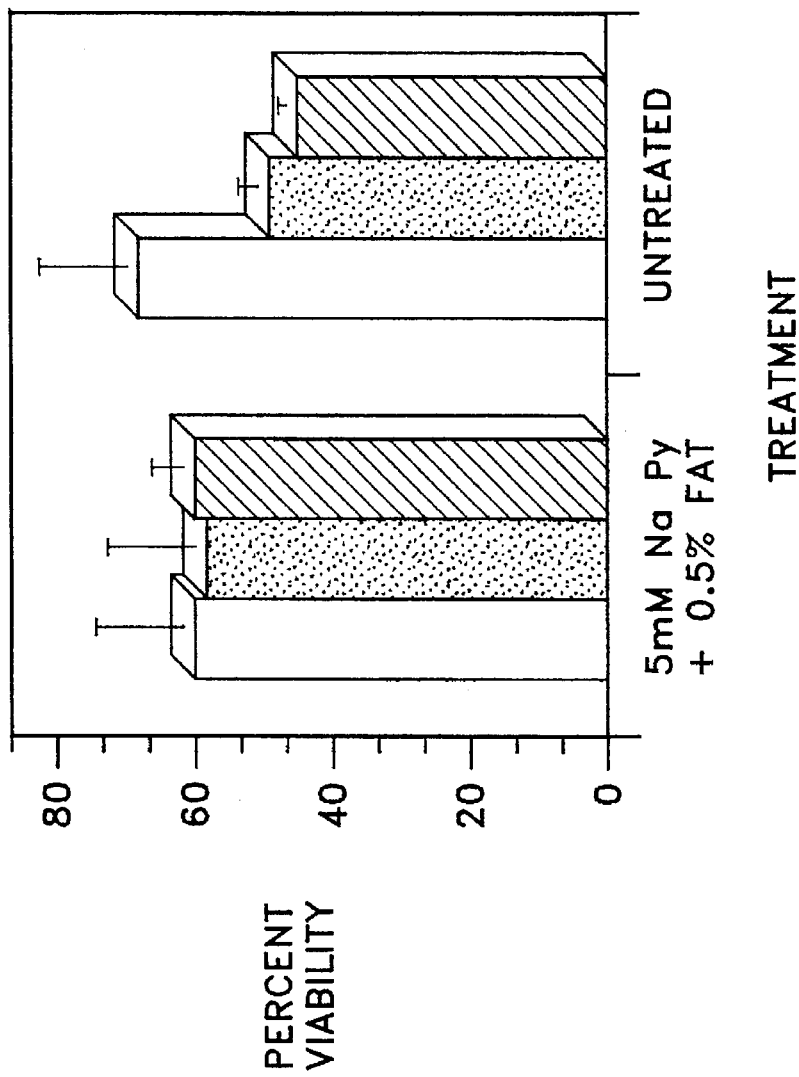
FIG. 33A is a graph showing the viability of U937 monocytic leukemia tumor cells in a co-culture study, as determined by tritiated thymidine incorporation assay, after 24 hour pretreatment of the cells with 5 mM sodium pyruvate and 0.5% fatty acids followed by administration of different dosage levels of Doxorubicin.
Figure 34B:
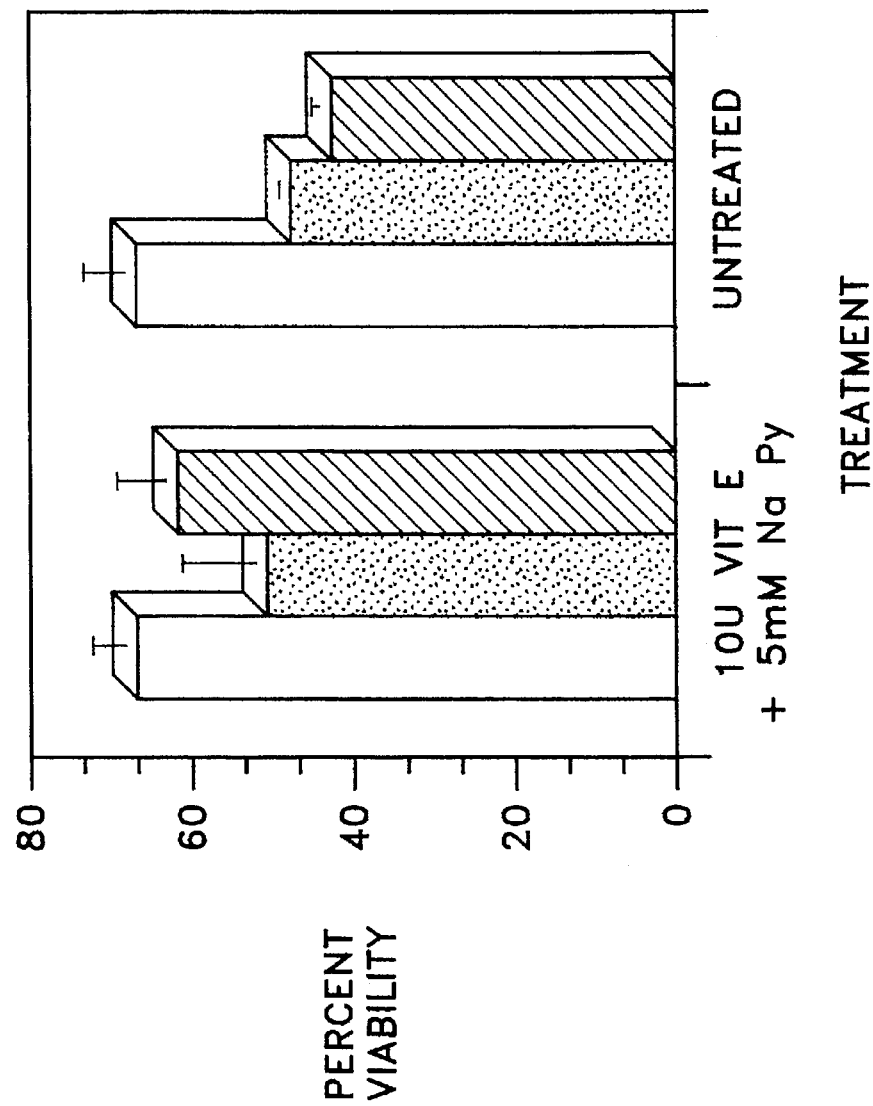
FIG. 34B is a graph showing the viability of peripheral blood monocytes in a co-culture study, as determined by tritiated thymidine incorporation assay, after 24 hour pretreatment of the cells with 5 mM sodium pyruvate and 10 U Vitamin E followed by administration of different dosage levels of Doxorubicin.
Figure 35A:
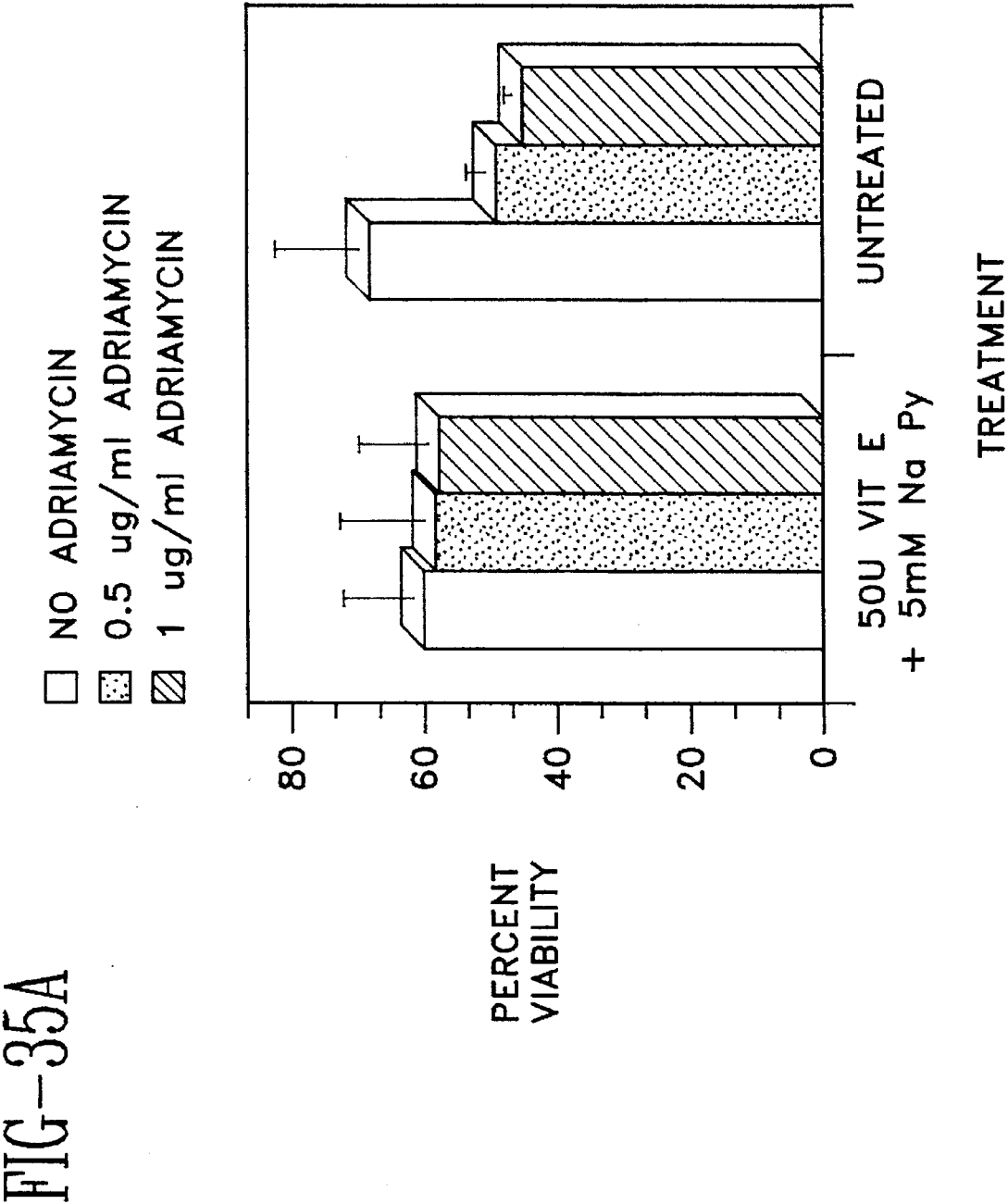
FIG. 35A is a graph showing the viability of U937 monocytic leukemia tumor cells in a co-culture study, as determined by tritiated thymidine incorporation assay, after 24 hour pretreatment of the cells with 5 mM sodium pyruvate and 50 U Vitamin E followed by administration of different dosage levels of Doxorubicin.
Figure 35B:
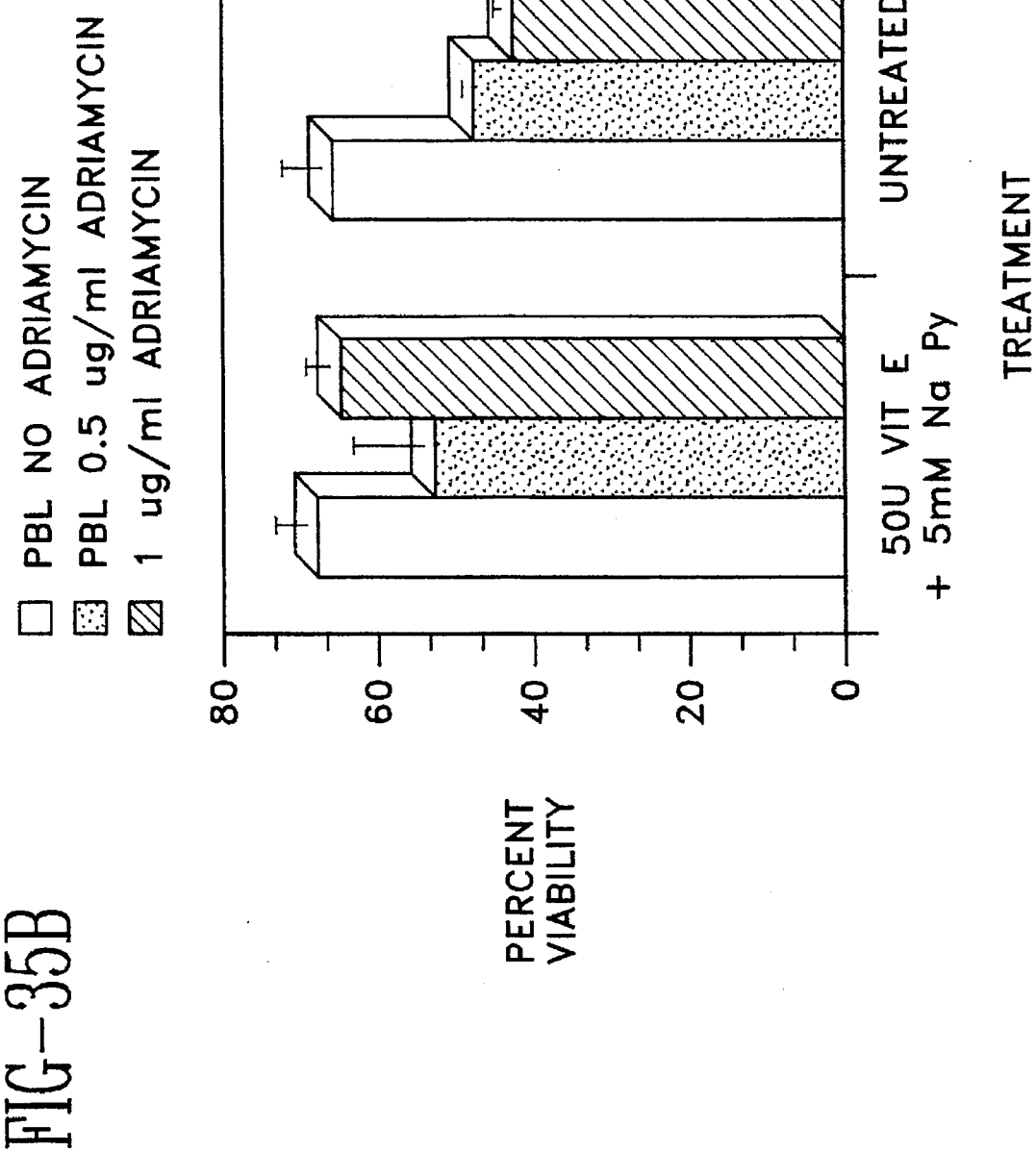
FIG. 35B is a graph showing the viability of peripheral blood monocytes in a co-culture study, as determined by tritiated thymidine incorporation assay, after 24 hour pretreatment of the cells with 5 mM sodium pyruvate and 50 U Vitamin E followed by administration of different dosage levels of Doxorubicin.
Figure 36A:
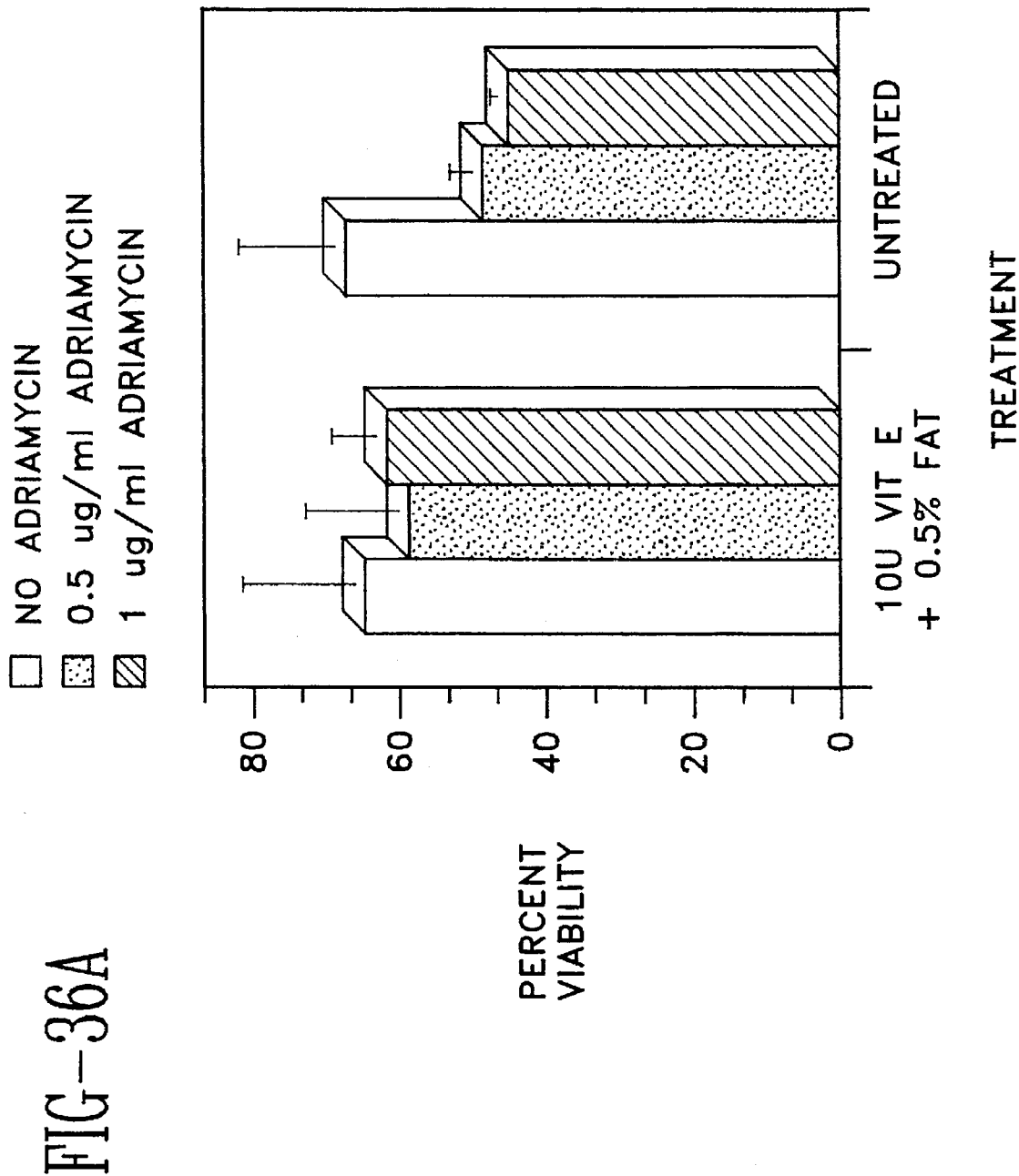
FIG. 36A is a graph showing the viability of U937 monocytic leukemia tumor cells in a co-culture study, as determined by tritiated thymidine incorporation assay, after 24 hour pretreatment of the cells with 10 U Vitamin E and 0.5% fatty acids followed by administration of different dosage levels of Doxorubicin.
Figure 36B:
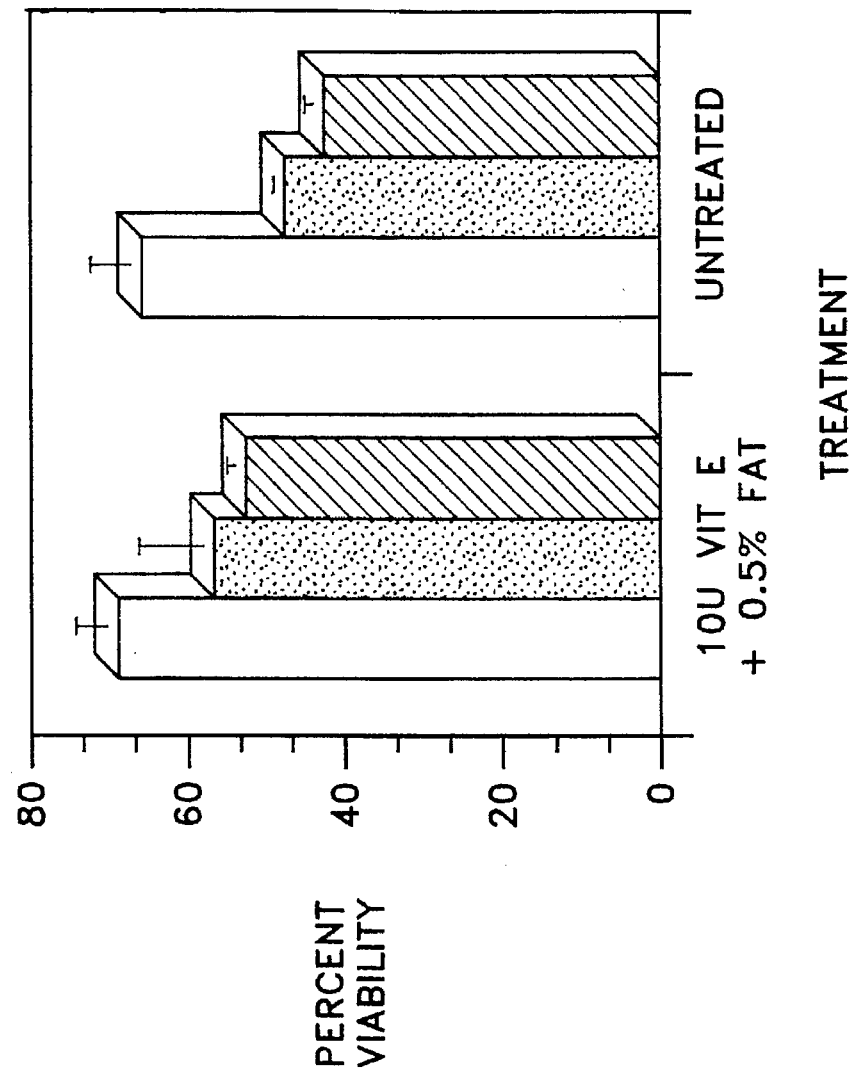
FIG. 36B is a graph showing the viability of peripheral blood monocytes in a co-culture study, as determined by tritiated thymidine incorporation assay, after 24 hour pretreatment of the cells with 10 U Vitamin E and 0.5% fatty acids followed by administration of different dosage levels of Doxorubicin.
Figure 37A:
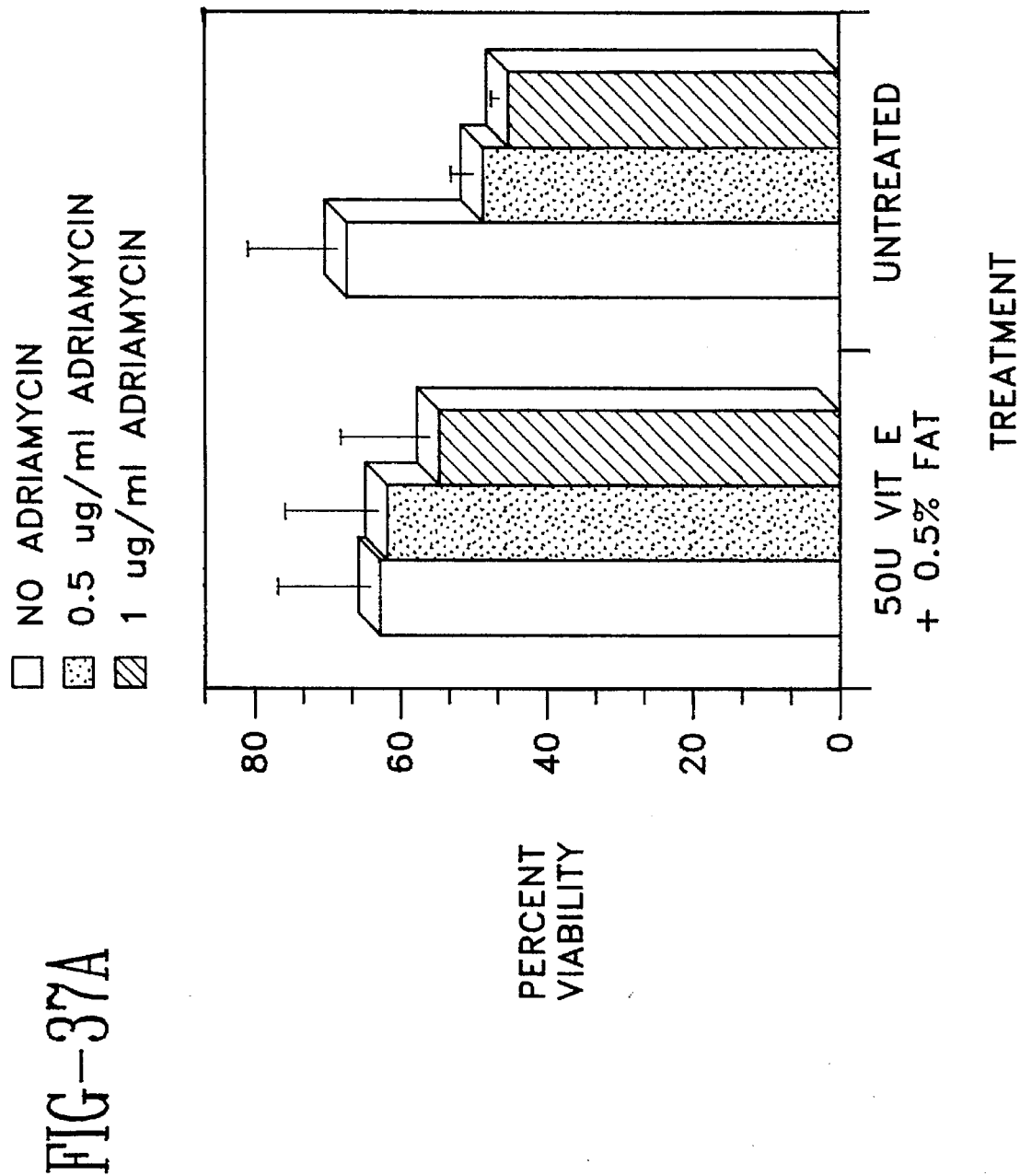
FIG. 37A is a graph showing the viability of U937 monocytic leukemia tumor cells in a co-culture study, as determined by tritiated thymidine incorporation assay, after 24 hour pretreatment of the cells with 50 U Vitamin E and 0.5% fatty acids followed by administration of different dosage levels of Doxorubicin.
Figure 37B:
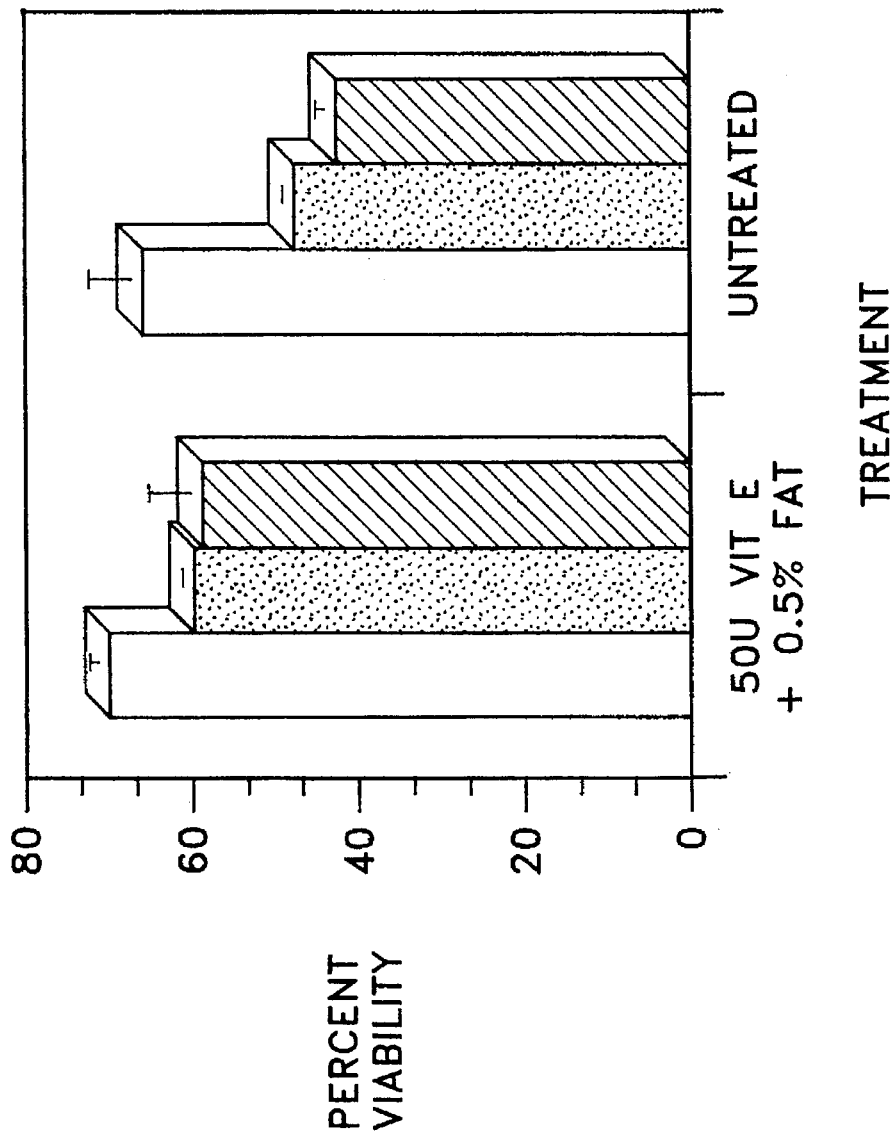
FIG. 37B is a graph showing the viability of peripheral blood monocytes in a co-culture study, as determined by tritiated thymidine incorporation assay, after 24 hour pretreatment of the cells with 50 U Vitamin E and 0.5% fatty acids followed by administration of different dosage levels of Doxorubicin.

The viability of cultured peripheral monocytes without Doxorubicin was 66% and increased to 75% with the cytoprotective combination of 5 mM sodium pyruvate, 10 U Vitamin E, and 0.5% fatty acids, see FIGS. 27A–27B. The viability of cultured peripheral monocytes treated with 0.5 ug/ml Doxorubicin was 47% and increased to 63.5% when pretreated with the cytoprotective combination of 5 mM sodium pyruvate, 10 U Vitamin E, and 0.5% fatty acids, see FIGS. 27A–27B. The viability of cultured peripheral monocytes treated with 1 ug/ml Doxorubicin was 42% and increased to 66% when pretreated with the cytoprotective combination of 5 mM sodium pyruvate, 10 U Vitamin E, and 0.5% fatty acids, see FIGS. 27A–27B.

Figure 25B:
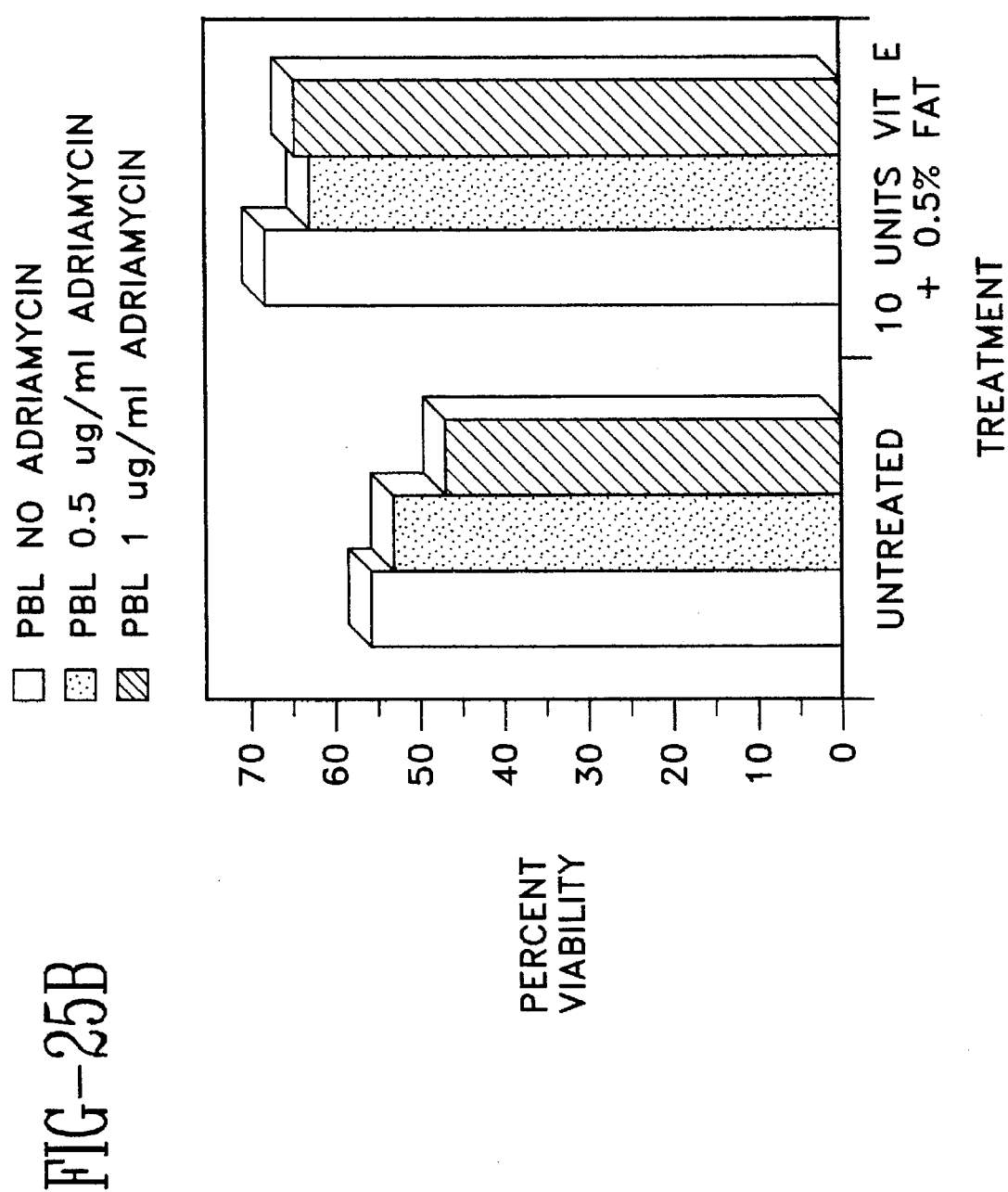
FIG. 25B is a graph showing the viability of peripheral blood monocytes in a wash-out study, as determined by tritiated thymidine incorporation assay, after 24 hour pretreatment of the cells with 10 U Vitamin E and 0.5% fatty acids followed by administration of different dosage levels of Doxorubicin.
Figure 26A:
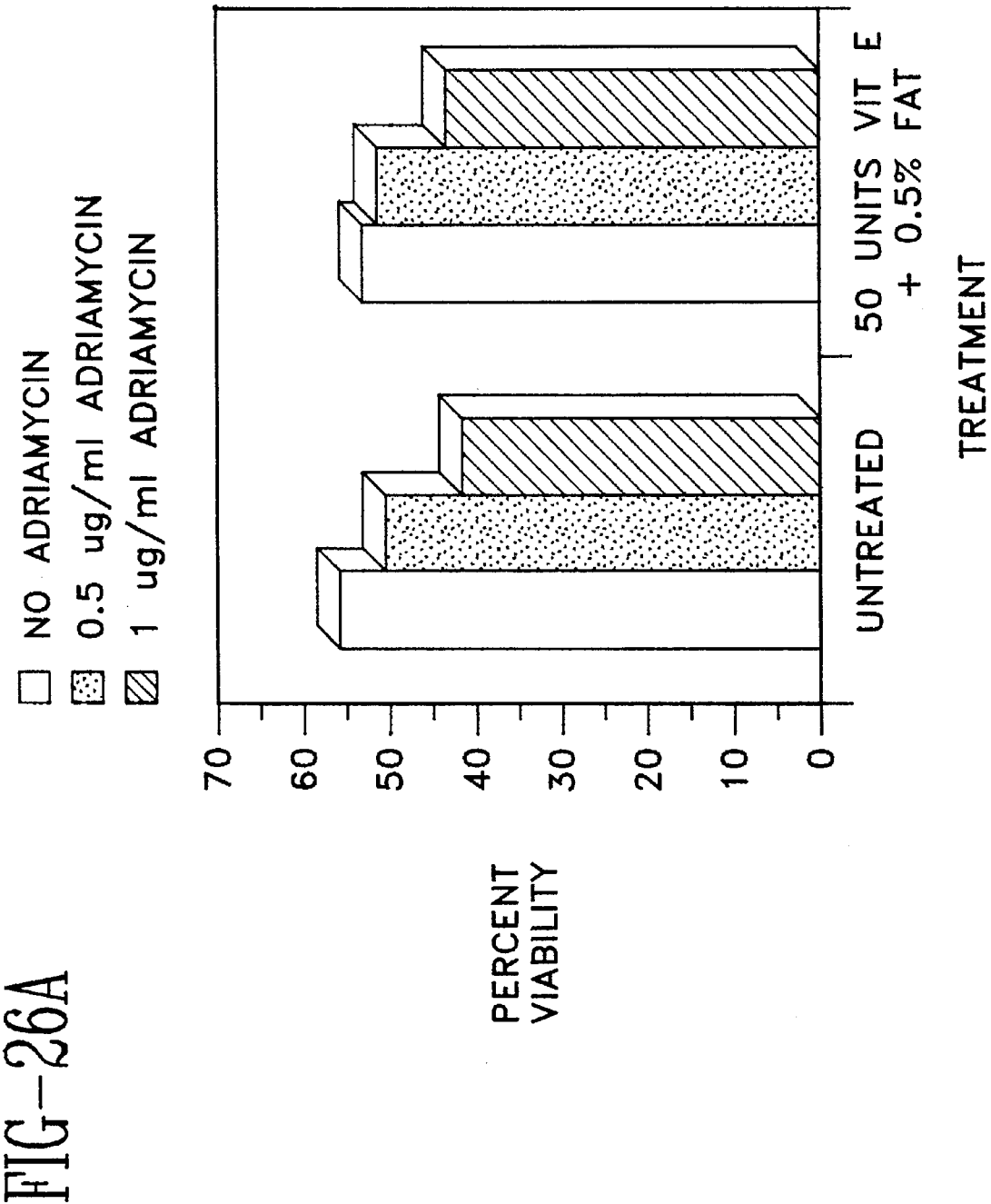
FIG. 26A is a graph showing the viability of U937 monocytic leukemia tumor cells in a wash-out study, as determined by tritiated thymidine incorporation assay, after 24 hour pretreatment of the cells with 50 U Vitamin E and 0.5% fatty acids followed by administration of different dosage levels of Doxorubicin.
Figure 26B:
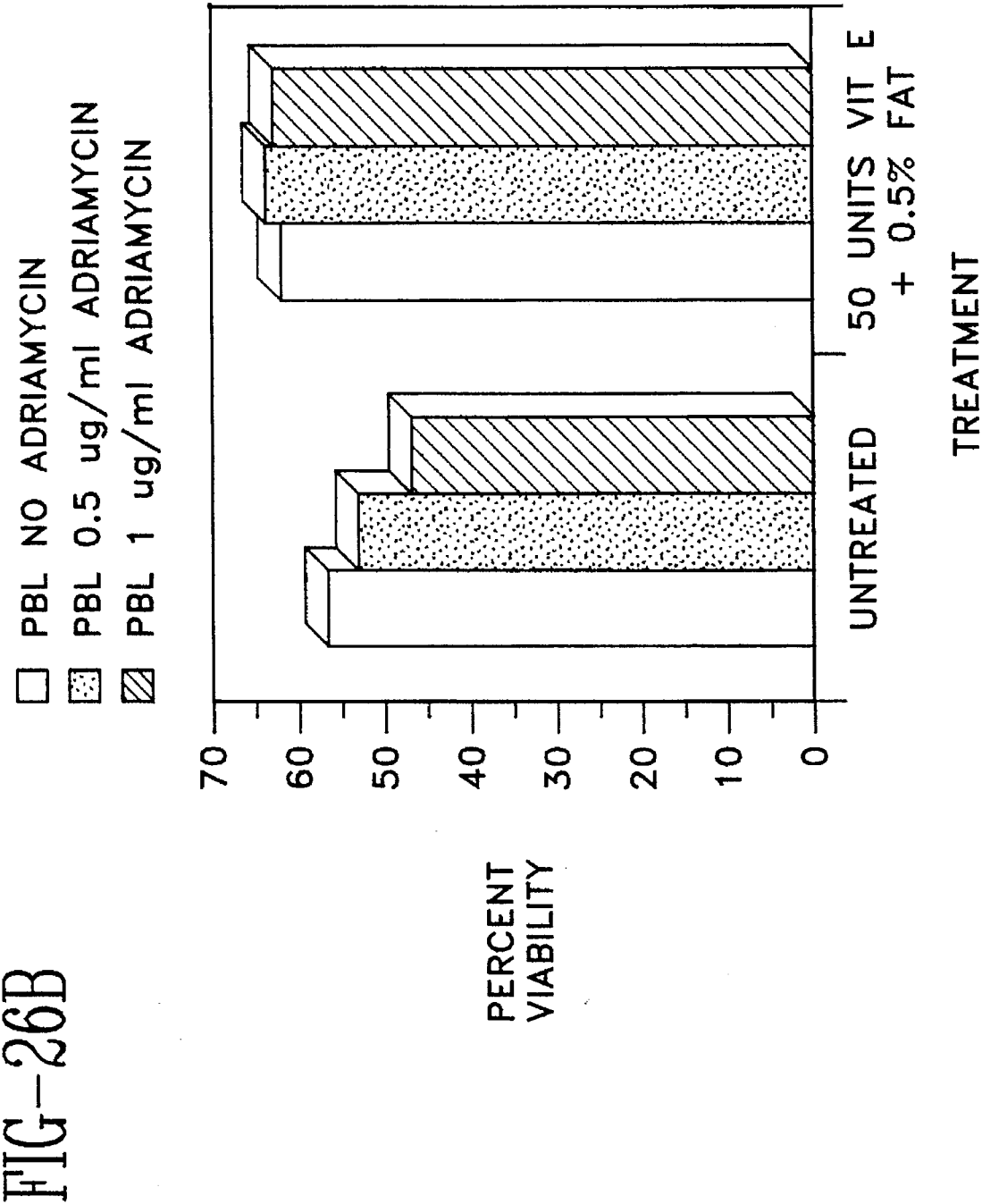
FIG. 26B is a graph showing the viability of peripheral blood monocytes in a wash-out study, as determined by tritiated thymidine incorporation assay, after 24 hour pretreatment of the cells with 50 U Vitamin E and 0.5% fatty acids followed by administration of different dosage levels of Doxorubicin.

The viability of cultured U937 tumor cells without Doxorubicin was 67% and did not increase when treated with any of the agents, see FIGS. 27A–27B. The viability of cultured U937 tumor cells with 0.5 ug/ml Doxorubicin treatment was 47% and the highest increase in viability occurred with pretreatment of 50 U Vitamin E and 0.5% fatty acids, see FIGS. 26A–26B. The viability of cultured U937 tumor cells with 1 ug/ml Doxorubicin treatment was 45% and the highest increase in viability occurred with pretreatment of 10 U Vitamin E and 0.5% fatty acids, see FIGS. 25A–25B.

Figure 38B:
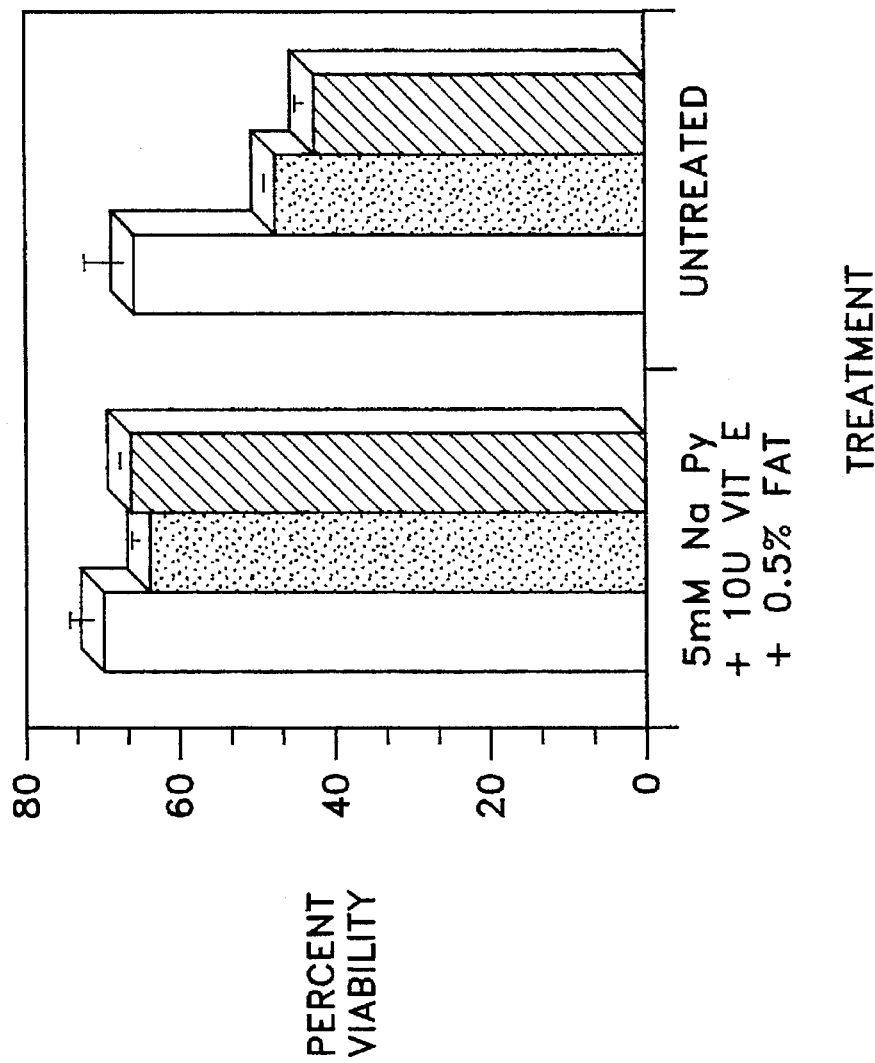
FIG. 38B is a graph showing the viability of peripheral blood monocytes in a co-culture study, as determined by tritiated thymidine incorporation assay, after 24 hour pretreatment of the cells with 5 mM sodium pyruvate, 10 U Vitamin E, and 0.5% fatty acids followed by administration of different dosage levels of Doxorubicin.
Figure 39A:
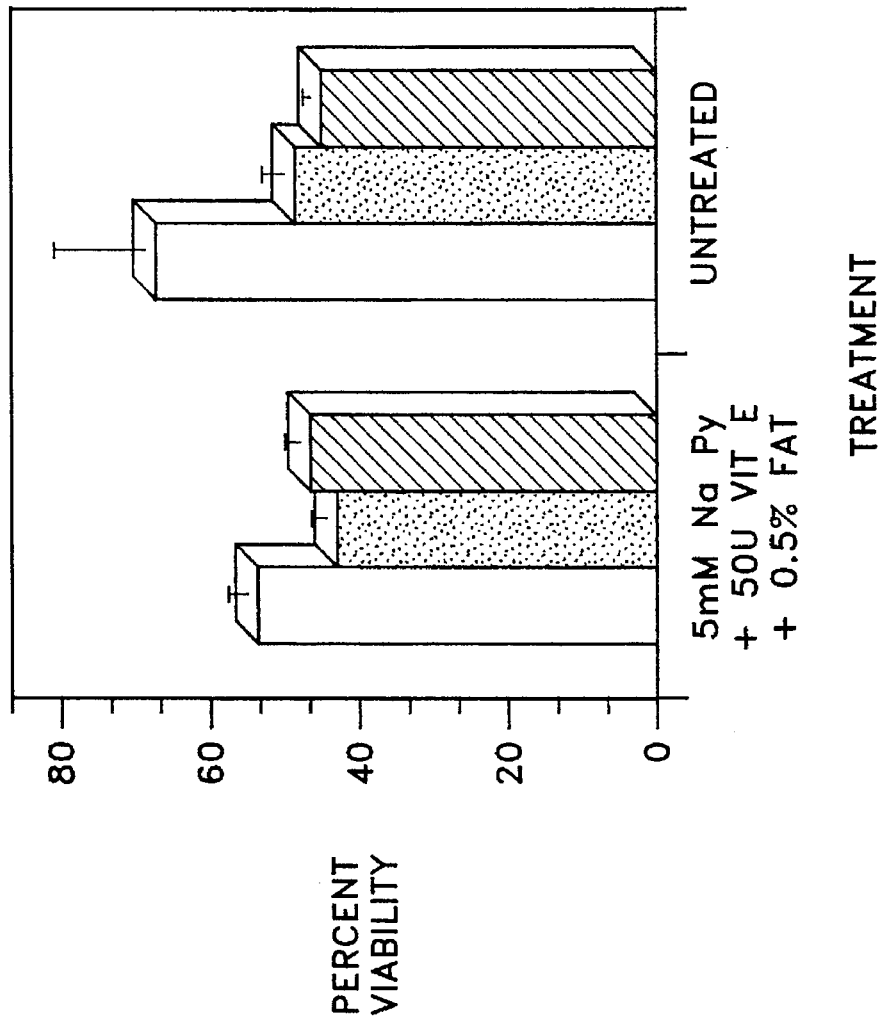
FIG. 39A is a graph showing the viability of U937 monocytic leukemia tumor cells in a co-culture study, as determined by tritiated thymidine incorporation assay, after 24 hour pretreatment of the cells with 5 mM sodium pyruvate, 50 U Vitamin E, and 0.5% fatty acids followed by administration of different dosage levels of Doxorubicin.
Figure 39B:
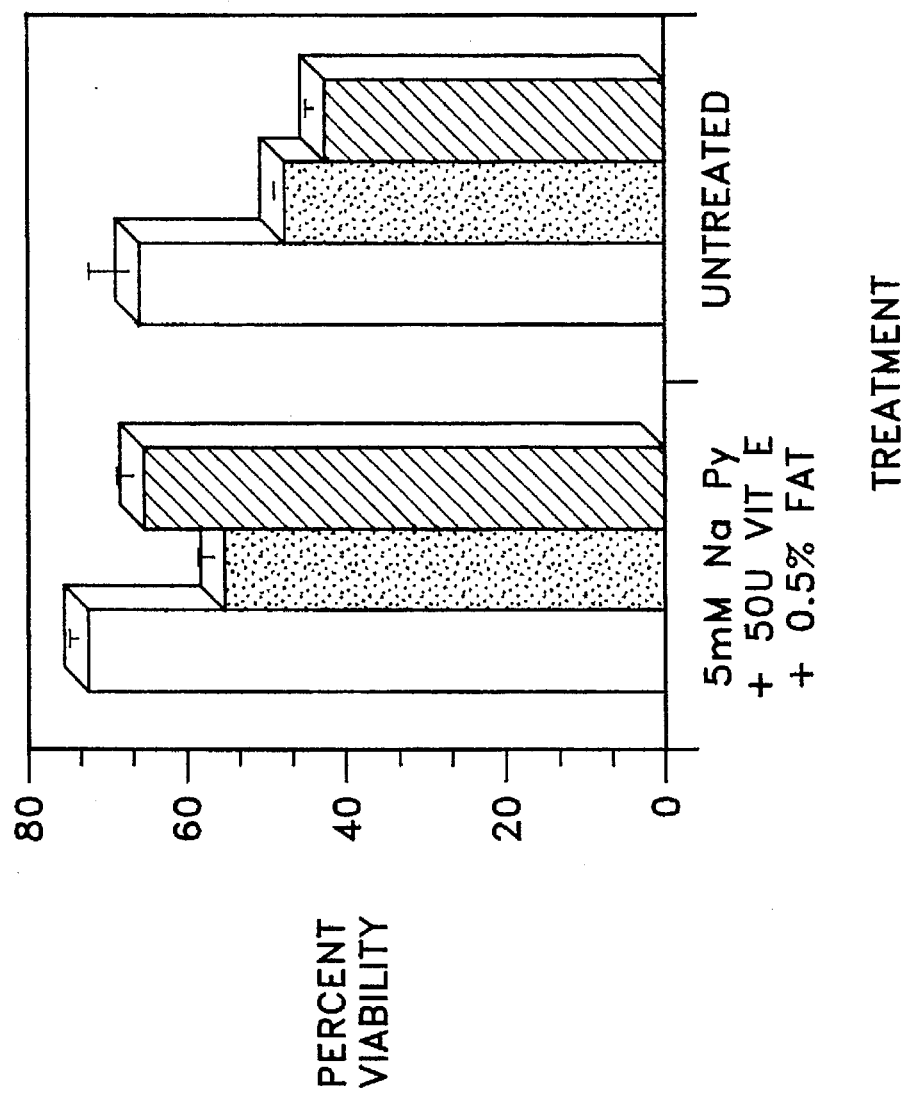
FIG. 39B is a graph showing the viability of peripheral blood monocytes in a co-culture study, as determined by tritiated thymidine incorporation assay, after 24 hour pretreatment of the cells with 5 mM sodium pyruvate, 50 U Vitamin E, and 0.5% fatty acids followed by administration of different dosage levels of Doxorubicin.

Optimal concentrations of the cytoprotective agents to prevent Doxorubicin-induced cytotoxicity were found to be 5 mM sodium pyruvate, 10–50 U Vitamin E, and 0.5% fatty acids. In wash-out studies, the cytoprotective combination of sodium pyruvate, Vitamin E, and fatty acids and the combination of 5 mM sodium pyruvate and 10 U Vitamin E protected the normal peripheral blood monocytes from Doxorubicin-induced cytotoxicity, see FIGS. 27A–27B. Vitamin E alone and fatty acids alone prevented the cytotoxicity of Doxorubicin in U937 cells, see FIGS. 19A–19B and 20A–20B. When normal peripheral blood monocytes were co-cultured with U937 monocytic leukemia tumor cells, the cytoprotective combination of 5 mM sodium pyruvate, 0.5% fatty acids, and 10 U Vitamin E provided significant protection to the normal peripheral monocytes from Doxorubicin-induced cytotoxicity and did not protect the minor cells from the effects of the cytotoxic agent, see FIGS. 38A–38B.

These results show that the combination of agents 5mM sodium pyruvate, 0.5% fatty acids, and 10 U and 50 U Vitamin E are useful as selective cytoprotective agents for use with compounds that are toxic to normal cells as well as minor cells.

Summary Analysis of the Data From Study 1

This is a summary analysis of the examples illustrating cytoprotective-wound healing compositions set out above to show the synergistic effects of the wound healing components.

Peripheral blood monocytes were exposed to 0.51 g/ml Adriamycin™ and treated wth wound healing composition components (Sodium Pyruvate, Vitamin E, and Fatty Acids) to determine their effect on cellular viability. Adriamycin™, an anthracycline antibiotic is cytotoxic to cells. Adriamycin™ decreases cellular viability and produces cellular death. The wound healing composition components were tested individually and in combination to determine if they could reverse cellular damage caused by Adriamycin™ and increase cellular vitality. Measurements were made using $^3$H-thymidine radioisotopic incorporation, which is a measure of DNA synthesis, i.e., cellular viability. The measure of cellular viability is the presence of living cells in the sample after treatment.

Figure 40:
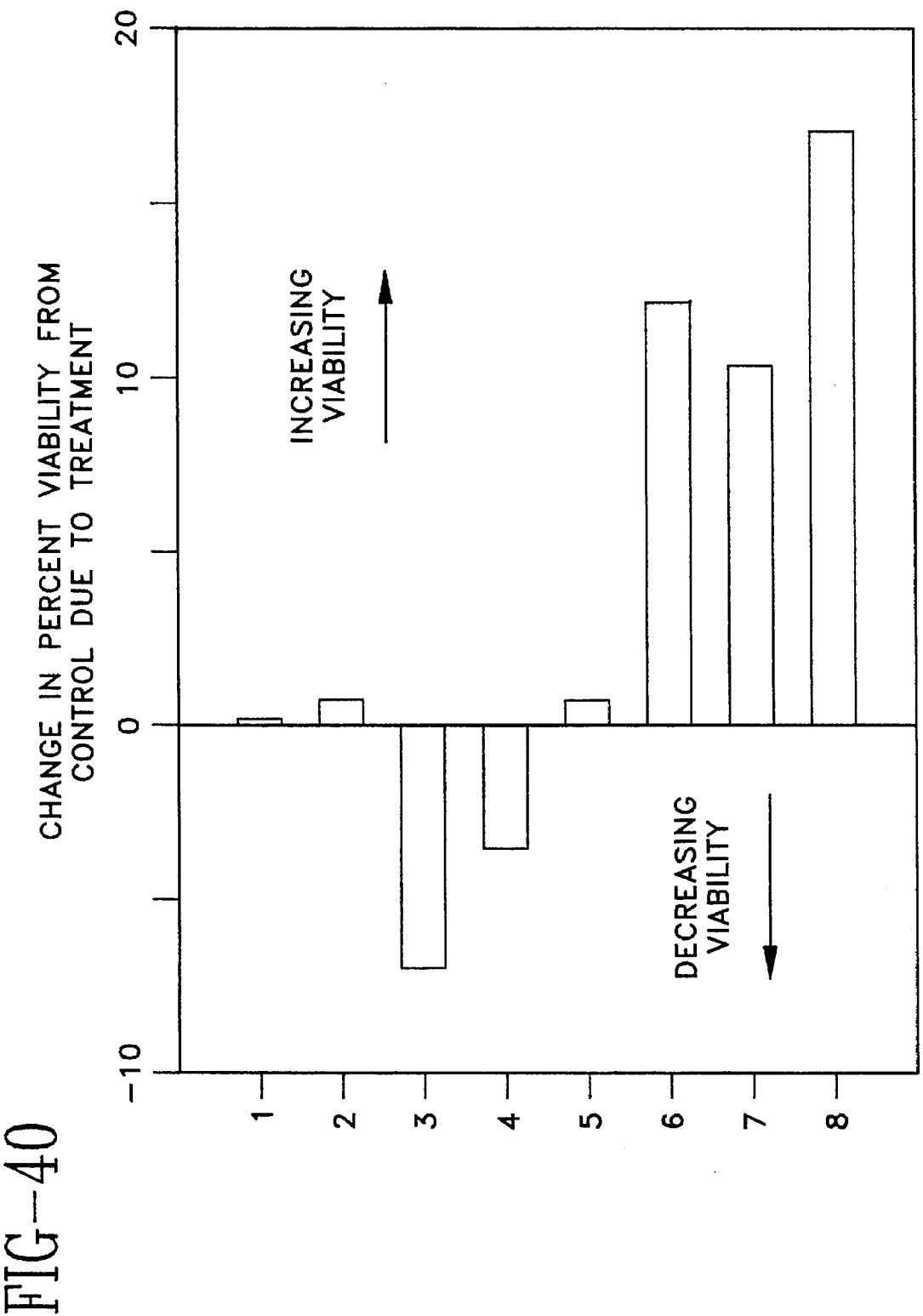
FIG. 40 is a graph summarizing the percent viability from control due to various treatments.

In all cases, the three component wound healing composition surpassed predicted outcomes, clearly demonstrating unpredicted synergy. These results are set out in FIG. 40.

4. Examples of Antiviral-Wound Healing Compositions

Study 1

This study demonstrates a comparison of the wound healing abilities of the therapeutic antiviral-wound healing compositions of the present invention versus conventional

| | | Results | | |
|---|---|---|---|---|
| | 1 Treatment Adriamycin™ Groups Viability | 2 0.5 µg/ml Adriamycin™ Difference in Treatment - Percent Viability of Controls Wound Healing Components | 3 Treatment - Percent Viability of Cells with | 4 0.5 µg/ml Cellular |
| 1- | Control | 54 | 54 | 0 |
| 2- | Fatty Acids (0.5%) | 54 | 47 | −7 |
| 3- | Vitamin E (10 units) | 53 | 50 | −3 |
| 4- | Sodium Pyruvate (5 mm) | 54 | 55 | +1 |
| 5- | Pyruvate & Fatty Acids | 54 | 55 | +1 |
| 6- | Vitamin E & Fatty Acids | 54 | 64 | +10 |
| 7- | Pyruvate & Vitamin E | 55 | 68 | +13 |
| 8- | Pyruvate & Vitamin E & Fatty Acids (wound healing composition) | 47 | 64 | +17 |

Column 1 shows the different treatment groups.
Column 2 shows the percent of living cells (viability) present when the monocytes are treated with the cytotoxic agent, Adriamycin™.
Column 3 shows the viability of cells treated with Adriamycin™ and the treatment.
Column 4 shows the change in viability from control due to the treatment.

Analysis

Combination of Single Ingredient Effects

Fatty Acids (−7) & Vitamin E (−3) & Pyruvate (+1)
  −9 Is The Predicted Three Component Effect
  +17 Is The Wound healing composition Actual Effect
  26 Is The Difference Between Predicted Effect minus Actual effect
  (Synergy)

Combination of Paired and Single Ingredients

Pyruvate & Fatty Acids (+1) & vitamin E (−3)
  −2 Is The Predicted Three Component Effect
  +17 Is The Wound healing composition Actual Effect
  19 Is The Difference between Predicted Effect minus Actual Effect
  (Synergy)

Vitamin E & Fatty Acids (+10) & Pyruvate (+1)
  +11 Is The Predicted Three Component Effect
  +17 Is The Wound healing composition Actual Effect
  6 Is The Difference between Predicted Effect minus Actual Effect
  (Synergy)

Pyruvate & Vitamin E (+13) & Fatty Acids (−7)
  +6 Is The Predicted Three Component Effect
  +17 Is The Wound healing composition Actual Effect
  11 Is The Difference between Predicted Effect minus Actual Effect
  (Synergy)

In all cases, the three component wound healing composition surpassed the predicted outcomes clearly demonstrating unpredicted Synergy.

wound healing compositions. The results of this study are illustrated in examples 1–21.

Two animal models were used to examine the ability of the wound healing components to reduce lesion development, duration, and severity. Mathematical modeling was used to determine the ratio and concentrations of wound healing components used in the animal models. In the guinea pig model, formulas #11 and #17 reduced lesion development, duration, and severity scores significantly compared to the vehicle control, Blistex™, and Acyclovir. Acyclovir was the only compound that reduced viral titers significantly. In the mouse model, formulas #1, #15, and #16 reduced clinical symptoms compared to the vehicle and Blistex™. Acyclovir, in the mouse model, reduced lesion development, duration and severity, producing the best results. Statistical analysis of the data have confirmed the results. In both models, the best formulas contain an equal ratio of Vitamin E and pyruvate and the higher levels of fatty acids. In the guinea pig model, formulas #11 and #17 contained 0.5% of both Vitamin E and pyruvate. In the mouse model, formulas #1 and #16 contained 4.75% of the same actives. Deviation from these ratios reduced the herpes lesion healing efficacy for both models.

Guinea Pig Studies

The purpose of these studies was to evaluate the activity of various antioxidant preparations administered topically in a primary genital HSV-2 infection of guinea pigs. Eighteen different preparations containing varying concentrations of three agents (vitamin E, pyruvic acid and fatty acids) were evaluated. Treatment was initiated at 48 hours post-infection, which is 1–2 days before external genital lesions begin to appear. The commercial preparations of 5% acyclovir (ACV)-polyethylene glycol (PEG) and medicated Blistex™ for cold sores were utilized as internal controls.

Materials and Methods

I. Medications

The experiment was placebo-controlled and the preparations were tested in a coded fashion (except for the ACV and Blistex™).

I. Genital HSV-2 Infection of Guinea Pigs

A. Description of Model

Intravaginal inoculation of weanling guinea pigs with HSV-2 results in a primary genital infection characterized by initial replication of virus in the vaginal tract followed by the development of external vesicular lesions. Virus liters peak on days one to three in the vaginal tract and gradually clears by days 7–10. The external genital lesions first appear on day four, peak lesion severity occurs on days 6–8, and the lesions generally heal by days 15–18.

B. Virus and Vital Inoculation

The MS strain of HSV-2 was utilized for animal inoculation. Female Hartley guinea pigs (Charles River, Kingston, N.Y.) weighing 250–300 g were inoculated intravaginally (i.vag.) with approximately $1.2 \times 10^5$ plaque forming units one hour after being swabbed for removal of vaginal secretions. Vital inoculation was accomplished by inserting a swab soaked with virus into the vaginal tract and rotating about six times.

C. Treatment of Guinea Pigs

Groups of 6 guinea pigs were run in duplicate, consecutive experiments (with the exception of group 21, which was run only once). The guinea pigs were treated on the external genital skin with 0.1 ml of each preparation, four times daily for ten days beginning 48 hours post-viral inoculation.

D. Sample Collection and Virus Assays

To determine the effect of treatment on HSV-2 replication in lesions, swabs of lesions were obtained during the primary infection on days 3, 4, 5, 6, 7, and 10 after HSV-2 inoculation. The swabs were placed in tubes containing 2.0 ml of media, and frozen at $-70°$ C. until titrated for HSV. To identify the number of animals that became infected, vaginal swabs were obtained from all animals on day 5 and handled as above. When all samples were collected, they were thawed, vortexed, diluted serially, and HSV-2 titers determined in rabbit kidney cells using a microtiter CPE assay.

E. Scoring of External Lesions

To determine the effect of therapy on the development, spread, and healing of external genital lesions, lesion severity was scored on a 0–5+scale through the primary infection (Table 7 and FIGS. 44A–48B).

F. Evaluation of Efficacy

The data for each of the two experiments were first analyzed separately, then the results were combined and reanalyzed.

Peak lesion scores, peak lesion virus liters, areas under lesion score-day, and areas under the virus titer-day curves between placebo-treated and drug-treated animals were compared using the Mann-Whitney U rank sum test. A p-value of 0.05 or less was considered significant.

Hairless Mouse Studies

This model was used to assess the ability of various anti-oxidant compounds, applied topically to the infected area, to modify the clinical course of the infection.

Materials and Methods

Mice: six to eight week old male SKH-1 hairless mice (Charles River) were infected with HSV-1 virus, McIntyre swain. Infection was achieved under general anesthesia (Ketamine, Xylazine) by the abrasion of a 1 cm square area (using a 25 gauge needle) centrally located on the dorsal surface of a mouse. Virus was then applied directly onto the abraded area (10 µl of a $1 \times 10^9$ PFU/ml virus stock). Following inoculation of $10 \times 10^6$ PFU of HSV-1 McIntyre strain by scarification of the epidermis, herpetic lesions developed by day 5 and persisted through day 12 post infection (p.i.). The viral lesions spread in a zosteriform pattern from the site of inoculation (midline on the back) to the abdominal area. By day 10, lesions were crusted over and complete healing generally occurred by day 12 p.i. (post infection).

Individual mice were treated with test compounds starting on the afternoon of the infection day, and treatment was continued for 14 days. Treatments were administered at 7 a.m. and 4 p.m. each day and involved the use of a sterile cotton tipped applicator in such a manner that the affected area was evenly coated with the test compound. If no lesions were visible, only the site of infection was treated. Data, including lesion scores, number of lesions, and lesion areas were recorded during the 7 a.m. treatment session. Each animal was recorded as having one of five possible scores: 0, no signs; 1, redness and swelling; 2, single lesion; 3, multiple lesions; 4, a spread of lesions in a dermatome pattern (see FIGS. 49A–49D). In addition, the actual lesion area on the skin was measured using a micrometer (x and y axial values for each lesion were obtained in millimeters and then multiplied together to give the lesion area). For analysis, the individual lesions scores or areas within a treatment group were averaged on a daily basis.

Nineteen compounds with varying amounts of anti-oxidant compounds were tested. Control compounds included Zovirax ointment, Blistex™, and polyethylene glycol m.w. 400. Each experimental compound was tested on a total of eight to sixteen mice.

Statistical Evaluation Product Design/Product Group Allocation of the Guinea Pig and Mouse Models The purpose of this study was to convey the product groups and the allocations of the animals necessary to evaluate the optimal combination of the wound healing components (vitamin E, unsaturated fatty acids, and sodium pyruvate) in the presence of phenol and lidocaine both at 0.5% by weight. The range of the three components in the wound healing, all from 0.5% to 9.0% by weight, were incorporated in the experimental design. The design is a two-cubed factorial with six star points and one center point with the "control groups" Blistex™, Acyclovir and untreated. The product groups are listed in a random order in the attachments (Table 8). This order was random and was not changed.

The experimental variance is important for estimating the number of animals per product group (sample size) so that the resulting study will have sufficient power to detect a clinically meaningful effect. An estimate of this variance for the mouse study was obtained from the range of the clinical symptom scale. The use of eight (8) mice per product group should be sufficient to achieve 80% power to detect an effect of 0.5 units when conducting a two-sided t test at the 0.05 level of significance. The sample size for the mouse study was approximated using only the clinical symptoms scale. The power for detecting a clinically meaningful effect of the lesion size (total vesicular area) was not known.

The allocation of product in mice (Table 8) contains eight (8) mice per product group, except for the second use of Product Group Number 14 which contains four (4) mice. There are two uses of Product Group Number 1. The numbers of the products groups in this table are the same as those identified in Table 1 and were not changed, since the order of these product groups have been randomized. The side receiving the listed product group was also randomized. The person scoring the clinical symptoms and measuring the lesion size did not know which product group was used on which animal (blinding).

An estimate of the experimental variance for the guinea pig study was obtained from the range of the lesion severity scale. The use of twelve (12) guinea pigs per product group should be sufficient to achieve 80% power to detect an effect of 0.5 units when conducting a two-sided t test at the 0.05 level of significance. The sample size for the guinea pig study was approximated using only the lesion severity scale. The powers for detecting clinically meaningful effects in the viral liter, time to healing, and other measures over time (days) were unknown.

The allocation of the guinea pigs to the product groups is given in Table 9 in two blocks of six (6) guinea pigs per product group. Notice that there are two uses of Product Group Numbers 1 and 14. The members of the product groups in this table are the same as those identified in Table 1 and were not changed, since the order of these product groups have been randomized. The person making the observations did not know which product group was used on which animal (blinding).

If the actual experimental variance is less than the estimate used, then the study will be more powerful than stated. Alternatively, if the actual experimental variance is more than the estimate used, then the study will be less powerful than stated. The design and sample size calculations in this memorandum have been guided by information provided by the investigator.

Guinea Pig Model Results and Discussion

I. Effect of Topical Antioxidants on Lesion Vital Replication in Guinea Pigs: First Study The effect of topical antioxidants on lesion virus titers are shown in Table 1. There were no significant differences observed in lesion virus titer-day areas under the curve (AUC) between drug and placebo-treated animals.

I. Effect of Topical Antioxidants on Lesion Development in Guinea Pigs: First Study The effect of topical antioxidants on lesion development are summarized in Table 2. Only group 9 exhibited a significant reduction in the lesion score-day AUC when compared to the vehicle treated animals (group 8). Groups 14a, 1a, 7, 18, 8, 10, 1b, 5, 4 (Blistex™), 2, 19, 15, 16 and 20 had significantly greater lesion score-day AUC's when compared to the appropriate control group (group 13 or 8).

II. Effect of Topical Antioxidants on Lesion Viral Replication in Guinea Pigs: Second Study The effect of topical antioxidants on lesion virus titers are shown in Table 3. Significant differences were observed in lesion virus titer-day AUC's in groups 6 (ACV) and 20. It should be noted that group 20 had only 4 out of 6 animals with positive vaginal virus liters. Moderate reductions in lesion AUC's were also observed with groups 12 and 2 (p-values of 0.06 and 0.0–7, respectively).

IV. Effect of Topical Antioxidants on Lesion Development In Guinea Pigs: Second Study The effect of topical antioxidants on lesion development are summarized in Table 4. Groups 11, 17, and 20 exhibited significant reductions in the lesion score-day AUC when compared to the vehicle treated animals (group 8). Groups 14a, 1a, 18, 9, 5, 4 (Blistex™), 2, 15, 16, 3 and 21 had significantly greater lesion score-day AUC's when compared to the vehicle treated animals (group 8). Groups 10 and 1b had moderately greater lesion AUC's (p-values of 0.07 and 0.06, respectively).

V. Effect of Topical Antioxidants on Lesion Replication in Guinea Pigs: Combined Results The effect of topical antioxidants on lesion virus titers from the combined results of the first and second studies are shown in Table 5. The only significant difference observed in lesion virus titer-day AUC's was with group 6 (ACV). A moderate reduction in the lesion titer AUC was shown with group 21 (p-value of 0.07).

VI. Effect of Topical Antioxidants on Lesion Development In Guinea Pigs: Combined Resales The effect of topical antioxidants on lesion development from the combined results of the first and second studies are summarized in Table 6. Only groups 11 and 17 exhibited a significant reduction in the lesion score-day AUC when compared to the vehicle treated animals (group 8). Groups 14a, 1a, 18, 8, 9, 10, 1b, 5, 4 (Blistex™), 2, 19, 15, 16, 3 and 21 had significantly greater lesion score-day AUC's when compared to the appropriate control animals (groups 13 and 8).

VI. Discussion of Guinea Pig Results

Because of the large number of samples to be tested (22) and the need to compare directly all of the samples at one time, the study was conducted as two identical experiments with six animals per group. The genital infection of guinea pigs is a natural infection and like any biological system, there is variability from animal to animal in the natural history of the disease and the rate of progression through the various stages of the primary infection. Due to this variability, a minimum group size of 10 guinea pigs per group was established in order to minimize the variability within each group.

In the first second and combined studies, there was excellent correlation for effect of treatment on virus liters in lesions. In fact, only the 5% ACV preparation significantly reduced vital replication in external genital lesions.

The effect of treatment with the various compounds on the development and severity of lesions on the external genital skin was more variable between the two experiments, however, almost all of the preparations resulted in more severe lesions than the untreated control, the vehicle control, or the group treated with ACV. One of the reference compounds (Blistex™, group 4) was consistently worse than the vehicle control. Groups 11 and 17 were the only preparations that significantly reduced the lesion score compared with the vehicle control. Groups 7, 12, 20 and 14b were neutral preparations in that they did not decrease or increase the severity of the genital lesions. In contrast, groups 18, 10, 1b, 5, 4, 2, 15, 16, 3 and 21 clearly resulted in significantly more severe disease than those that were untreated, treated with vehicle alone, or with ACV-PEG. Analysis of the various components in each of the formulations identifies those materials that contribute to healing or exacerbation of disease severity and the information obtained will be used to construct a more optimal formulation.

Mouse Model Results and Discussion

All groups contained at least 8 animals by the conclusion of the study, however, as many as 16 animals at minimum, were infected for each treatment. Mice that did not show clinical signs for at least two consecutive days following inoculation of the virus, were considered to be uninfected and were excluded from the study (the Acyclovir control was an exception as this positive control was expected to prevent viral replication and reduce clinical signs). The infection rate varied from 60% to 100% over the course of experiments.

By taking daily measurements of the lesions, a disease curve was constructed which consisted of 3 phases of the infection: incubation, log, and resolution. The data, presented as the average lesion area (in sq. mm) for the-positive (Acyclovir) and negative (PEG) drag treatment controls from a representative experiment, are shown in FIG. 41. The incubation period for this infection spanned day 0 to day 5 p.i. Measurable herpetic lesions developed in the PEG-treated group between 5 and 6 days p.i. The severity of the lesions continued to increase in the log phase of the infection through day 7 pi., and peak clinical signs occurred on day 8 p.i. The resolution phase of the infection occurred from day 9 through day 12 p.i. Mice treated with acyclovir showed minimum clinical signs, only 2 out of a total of 18 HSV-infected mice developed clinical signs.

In addition to measuring the lesion area on a daily basis, symptom scores from 0 to 4 (see Materials and Methods section) were also recorded (FIG. 42). As seen in FIG. 42, this curve tended to have a more broad pattern. This was due to the fact that infected mice had clinical signs of infection, such as erythema and swelling, prior to the development of the actual herpetic lesions The "area under the curves" for the lesions area and the clinical symptoms was also calculated. These data proved a useful way of expressing the dynamics of the infectious disease process. In FIG. 43, the "area under the curve" (y axis) for the clinical symptoms for each group (numbers on the x axis) and the control groups (PEG, Base or Blistex™), represented by the dotted lines, was compared. Data points below the dotted lines had lower average clinical symptom scores than the controls. This analysis showed that compounds 1, 15 and 16 had the most reduced clinical symptoms compared to the control groups.

Summary of Mouse and Guinea Pig Studies

In summary, the guinea pig model produced statistically and clinically significant results, while the mouse model provided clinically but not statistically significant results. The guinea pig study showed that the concentration of wound healing components in formulas #11 and #17 reduced lesion development, duration, and severity. Acyclovir reduced vital liters, but its effect on vital lesion development, duration, and severity was worse than groups 11 and 17. In the mouse model, groups 1, 15, and 16 reduced clinical symptoms compared to the control group. Acyclovir reduced lesion development, duration, and severity, producing the best results. The mouse model which is generally used as a screen for antiviral compounds, was modified in an attempt to broaden its sensitivity to differentiate among the test formula. Unfortunately, lesion size variations increased within each test group, producing non-statistically significant results for that parameter. In spite of these unforeseen problems, some meaningful data was obtained from the mouse model experiment. In both models the best formulas contained an equal ratio of Vitamin E and pyruvate and the higher levels of fatty acids. In the guinea pig model, formulas #11 and #17 contained 0.5% of both Vitamin E and pyruvate. In the mouse model, formulas #1 and #16 contained 4.75% of the both actives therefore suggesting that equal but higher concentrations of the actives were needed for skin penetration, healing and cell resuscitation. Variation from these ratios reduced the healing efficacy of the formulas in both models. Both animal studies confirmed previous results attained on the efficacy of wound healing compositions to accelerate wound healing.

FIG. 41 is a graph illustrating the lesion area curves for mice infected with herpes simplex virus and treated with acyclovir (ACV, positive) and polyethylene glycol (PEG, negative). The x-axis represents days post infection and the y-axis represents the average lesion area ($mm^2$).

FIG. 42 is a graph illustrating the symptom score curves for mice infected with herpes simplex virus and treated with acyclovir (ACV, positive) and polyethylene glycol (PEG, negative). The x-axis represents days post infection and the y-axis represents the symptom score.

FIG. 43 is a graph illustrating the area under the symptom score curves by group for mice infected with herpes simplex virus. The x-axis represents the groups and the y-axis represents the area under the symptom score curve by day 12. The clinical symptoms for each group are represented as numbers on the x axis and the control groups (polyethylene glycol, base, or Blistex™) are represented by dotted lines.

FIGS. 44A–44B are photographs illustrating the scoring of cold sore lesions in guinea pig. The scorings illustrated are 1.0 and 1.5. The scorings range from 0 to 4, with 4 being the worst.

FIGS. 45A–45B are photographs illustrating the scoring of cold sore lesions in guinea pig. The scorings illustrated are 2.0 and 2.5. The scorings range from 0 to 4, with 4 being the worst.

FIGS. 46A–46B are photographs illustrating the scoring of cold sore lesions in guinea pig. The scorings illustrated are 3.0 and 3.5. The scorings range from 0 to 4, with 4 being the worst.

FIGS. 47A–47B are photographs illustrating the scoring of cold sore lesions in guinea pig. The scorings illustrated are 4.0 and 0.0 (control). The scorings range from 0 to 4, with 4 being the worst.

Figure 48A:
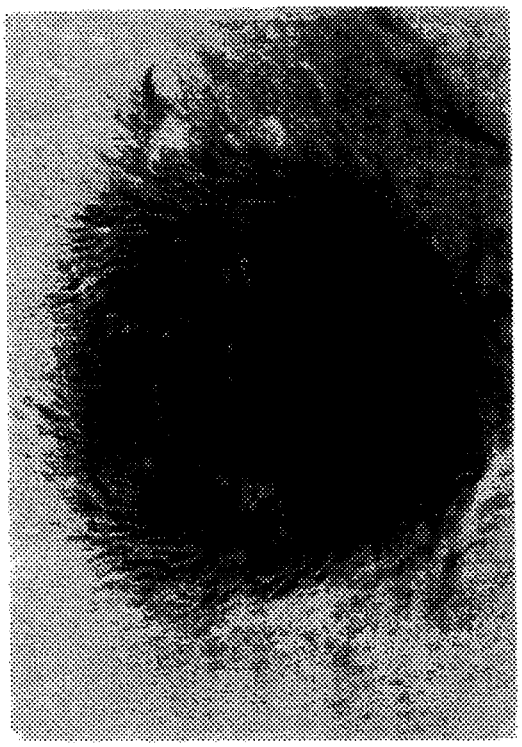
FIGS. 48A–48B are photographs illustrating the scoring of cold sore lesions in guinea pig. Animals in FIG. 48A were treated with formulas 11 or 17. Animals in FIG. 48B were treated with Blistex™. The scorings range from 0 to 4, with 4 being the worst.
Figure 48B:
Figure 49A:
FIGS. 49A–49D are photographs illustrating the scoring of cold sore lesions in hairless mice. The scorings illustrated are 1.0, 2.0, 3.0 and 4.0, respectively. The scorings range from 0 to 4, with 4 being the worst.
Figure 49B:
Figure 49C:
Figure 49D:
Figure 50:
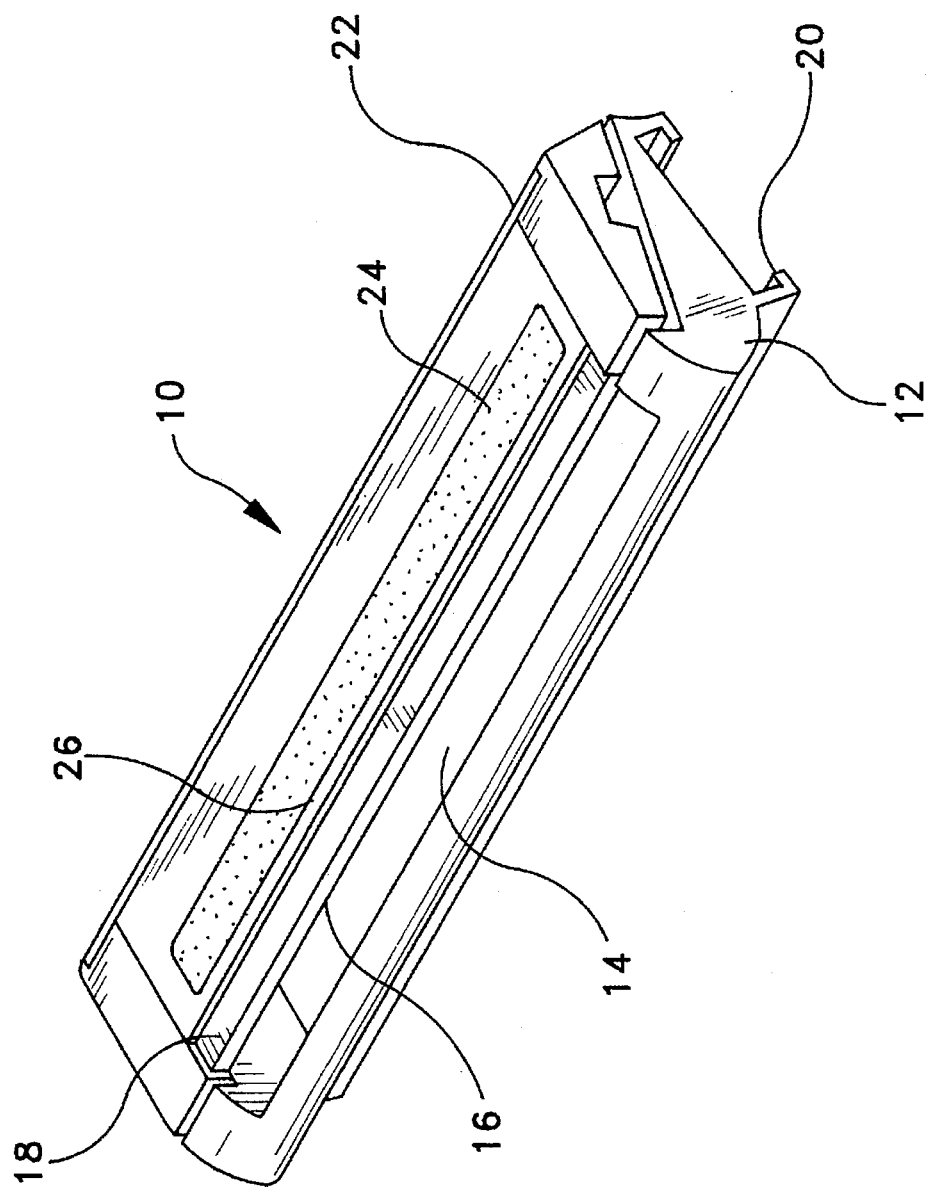
FIG. 50 is a view of a razor cartridge incorporating an embodiment of the present invention. For clarity, double cross-hatching has been used to depict portions of the razor cartridge which contain an integral wound healing composition delivery system affixed to the cartridge.

FIGS. 48A–48B are photographs illustrating the scoring of cold sore lesions in guinea pig. Animals in FIG. 19A were treated with formulas 11 or 17. Animals in FIG. 19B were treated with BLISTEX™. The scorings range from 0 to 4, with 4 being the worst.

FIGS. 49A–49D are photographs illustrating the scoring of cold sore lesions in hairless mice. The scorings illustrated are 1.0, 2.0, 3.0 and 4.0, respectively. The scorings range from 0 to 4, with 4 being the worst.

TABLE 1

Evaluation of Topical Antioxidants on Lesion Virus Titers in a Primary Genital HSV-2 Infection in Guinea Pigs: First Study

| Treatment[a] | # Vaginal Virus Positive/ # Inoculated | Lesion Virus Titer-Day Area Under Curve | P-Value[b] | Mean Peak Lesion Virus Titer | P-Value[b] |
|---|---|---|---|---|---|
| Group 13 (untreated) | 6/6 | 16.5 | — | 3.9 | — |
| Group 11 | 6/6 | 18.2 | NS[c] | 4.2 | NS |
| Group 14[a] | 6/6 | 16.6 | NS | 3.7 | NS |
| Group 1[a] | 6/6 | 18.1 | NS | 3.7 | NS |
| Group 7 | 6/6 | 15.9 | NS | 4.1 | NS |
| Group 12 | 6/6 | 17.7 | NS | 3.9 | NS |
| Group 18 | 6/6 | 18.7 | NS | 4.1 | 0.08[d] |
| Group 6 (5% ACV/PEG) | 6/6 | 9.9 | NS | 4.0 | NS |
| Group 8 | 6/6 | 19.5 | NS | 4.5 | NS |
| Group 9 | 6/6 | 15.6 | NS | 3.8 | NS |
| Group 10 | 6/6 | 17.0 | NS | 3.8 | NS |
| Group 1[b] | 6/6 | 18.4 | NS | 4.4 | NS |
| Group 5 | 6/6 | 18.6 | NS | 4.1 | 0.08 |
| Group 4 (BLISTEX ™) | 6/6 | 16.1 | NS | 4.0 | 0.07 |
| Group 2 | 6/6 | 20.0 | NS | 4.4 | NS |
| Group 19 | 6/6 | 17.4 | NS | 3.9 | 0.07 |
| Group 15 | 6/6 | 19.1 | NS | 4.3 | NS |
| Group 16 | 6/6 | 19.2 | NS | 4.3 | NS |
| Group 17 | 6/6 | 17.3 | NS | 4.2 | NS |
| Group 3 | 6/6 | 20.0 | NS | 4.8 | NS |
| Group 20 | 6/6 | 19.4 | NS | 4.4 | NS |
| Group 14[b] | 6/6 | 19.2 | NS | 4.4 | NS |

[a]Treatment was initiated at 48 hours post-inoculation. Animals were treated 4 times per day for 10 days with 0.1 ml applied topically on external genitalia.
[b]All groups were compared with group 8 (vehicle only), except for group 8 which was compared with the untreated control animals (group 13).
[c]Not significantly different from group 8 or group 13.
[d]Lesion titer was decreased compared to vehicle treated animals (group 8).

TABLE 2

Evaluation of Topical Antioxidants on Lesion Severity in a Primary Genital HSV-2 Infection of Guinea Pigs: First Study

| Treatment[a] | Lesion Score Day Area Area Under Curve | P-Value[b] | Mean Peak Lesion Score | P-Value[b] |
|---|---|---|---|---|
| Group 13 (untreated) | 23.3 | — | 2.7 | — |
| Group 11 | 26.2 | NS[c] | 2.8 | NS |
| Group 14[a] | 38.6 | <0.05[d] | 3.9 | NS |
| Group 1[a] | 38.5 | <0.01 | 3.5 | NS |
| Group 7 | 37.3 | <0.01 | 3.2 | NS |
| Group 12 | 28.4 | NS | 3.0 | NS |
| Group 18 | 46.8 | <0.001 | 3.9 | NS |
| Group 6 (5% ACV/PEG) | 31.6 | NS | 3.2 | NS |
| Group 8 | 30.5 | <0.01[e] | 3.5 | NS |
| Group 9 | 22.8 | <0.05 | 2.8 | NS |
| Group 10 | 40.0 | <0.01 | 3.4 | |
| Group 1[b] | 45.1 | <0.01 | 4.1 | NS |
| Group 5 | 40.2 | <0.01 | 3.5 | NS |
| Group 4 (BLISTEX ™) | 37.4 | <0.05 | 3.5 | NS |
| Group 2 | 40.8 | <0.01 | 3.5 | NS |
| Group 19 | 40.2 | <0.01 | 3.3 | <0.05 |
| Group 15 | 46.4 | <0.01 | 4.3 | <0.05 |
| Group 16 | 42.4 | <0.001 | 3.7 | NS |
| Group 17 | 25.2 | NS | 3.2 | NS |
| Group 3 | 34.7 | NS | 3.4 | NS |
| Group 20 | 47.9 | <0.01 | 4.0 | NS |
| Group 14[b] | 25.7 | NS | 3.0 | NS |

[a]Treatment was initiated at 48 hours post-inoculation. Animals were treated 4 times per day for 10 days with 0.1 ml applied topically on external genitalia.
[b]All groups were compared with group 8 (vehicle only), except for group 8 which was compared with the untreated control animals (group 13).
[c]Not significantly different from group 8 or group 13.
[d]Lesion severity was increased significantly compared to the appropriate control animals (group 8 or group 13).
[e]Lesion severity was decreased significantly compared to vehicle treated animals (group 8).

TABLE 3

Evaluation of Topical Antioxidants on Lesion Virus Titers in a Primary Genital HSV-2 Infection in Guinea Pigs: Second Study

| Treatment[a] | # Vaginal Virus Positive/ # Inoculated | Lesion Virus Titer-Day Area Under Curve | P-Value[b] | Mean Peak Lesion Virus Titer | P-Value[b] |
|---|---|---|---|---|---|
| Group 13 (untreated) | 6/6 | 9.8 | — | 2.7 | — |
| Group 11 | 6/6 | 10.6 | NS[c] | 2.7 | NS |
| Group 14[a] | 6/6 | 13.4 | NS | 3.6 | NS |
| Group 1[a] | 6/6 | 9.5 | NS | 3.0 | NS |
| Group 7 | 6/6 | 10.3 | NS | 2.9 | NS |
| Group 12 | 6/6 | 8.6 | 0.06[d] | 3.1 | NS |
| Group 18 | 6/6 | 13.8 | <0.001 | 3.3 | 0.07 |
| Group 6 (5% ACV/PEG) | 6/6 | 2.3 | NS | 1.6 | 0.06[e] |
| Group 8 | 6/6 | 11.9 | NS | 3.6 | NS |
| Group 9 | 6/6 | 9.8 | NS | 2.8 | NS |
| Group 10 | 6/6 | 10.9 | NS | 2.8 | NS |
| Group 1[b] | 6/6 | 11.1 | NS | 3.0 | NS |
| Group 5 | 6/6 | 12.8 | NS | 3.3 | NS |
| Group 4 (BLISTEX ™) | 6/6 | 9.5 | 0.07 | 2.9 | NS |
| Group 2 | 6/6 | 8.9 | NS | 2.6 | <0.05 |
| Group 19 | 6/6 | 11.6 | NS | 3.2 | NS |
| Group 15 | 6/6 | 13.1 | NS | 3.6 | NS |
| Group 16 | 6/6 | 11.9 | NS | 2.7 | 0.07 |
| Group 17 | 6/6 | 9.1 | NS | 2.7 | 0.07 |
| Group 3 | 6/6 | 9.4 | NS | 2.3 | <0.05 |
| Group 20 | 6/6 | 5.7 | <0.01 | 2.2 | NS |
| Group 14[b] | 6/6 | 12.7 | NS | 3.2 | NS |
| Group 21 | 12/12 | 10.5 | NS | 3.0 | NS |

[a]Treatment was initiated at 48 hours post-inoculation. Animals were treated 4 times per day for 10 days with 0.1 mls applied topically to external genitalia.
[b]All groups were compared with group 8 (vehicle only), except for group 8 which was compared with the untreated control animals (group 13).
[c]Not significantly different from group 8 or group 13.
[d]Lesion titer was decreased compared to vehicle treated animals (group 8).
[e]Lesion titer was increased compared to untreated control animals (group 13).

TABLE 4

Evaluation of Topical Antioxidants on Lesion Severity in a Primary Genital HSV-2 Infection of Guinea Pigs: Second Study

| Treatment[a] | Lesion Score Day Area Area Under Curve | P-Value[b] | Mean Peak Lesion Score | P-Value[b] |
|---|---|---|---|---|
| Group 13 (untreated) | 21.7 | — | 2.4 | — |
| Group 11 | 16.5 | <0.05[c] | 2.0 | 0.08 |
| Group 14[a] | 28.7 | <0.05[d] | 3.0 | NS[e] |
| Group 1[a] | 38.6 | NS | 3.8 | <0.05 |
| Group 7 | 24.5 | NS | 2.5 | NS |
| Group 12 | 28.8 | NS | 2.7 | NS |
| Group 18 | 35.0 | <0.01 | 3.0 | NS |
| Group 6 (5% ACV/PEG) | 24.0 | NS | 2.2 | NS |
| Group 8 | 25.0 | NS | 2.8 | NS |
| Group 9 | 41.6 | <0.001 | 3.5 | NS |
| Group 10 | 29.1 | <0.07 | 3.0 | NS |
| Group 3[b] | 28.5 | <0.06 | 2.7 | NS |
| Group 5 | 37.8 | 0.001 | 3.3 | NS |
| Group 4 (BLISTEX ™) | 39.5 | 0.001 | 3.8 | NS |
| Group 2 | 37.9 | <0.001 | 3.4 | NS |
| Group 19 | 27.0 | NS | 2.4 | NS |
| Group 15 | 50.7 | <0.001 | 4.3 | 0.01 |
| Group 16 | 32.7 | <0.01 | 3.1 | NS |
| Group 17 | 10.3 | <0.001 | 1.7 | <0.01 |
| Group 3 | 36.5 | 0.001 | 3.3 | NS |
| Group 20 | 11.6 | <0.001 | 1.5 | 0.06 |
| Group 14[b] | 28.5 | NS | 2.8 | NS |
| Group 21 | 35.6 | <0.01 | 3.2 | NS |

[a]Treatment was initiated at 48 hours post-inoculation. Animals were treated 4 times per day for 10 days with 0.1 ml applied topically on genitalia.
[b]All groups were compared with group 8 (vehicle only), except for group 8 which was compared with the untreated control animals (group 13).
[c]Lesion severity was decreased significantly compared to vehicle animals (group 8).
[d]Lesion severity was increased significantly compared to vehicle animals (group 8).
[e]Not significantly different from group 8 or group 13.

TABLE 5

Evaluation of Topical Antioxidants on Lesion Virus Titers
in a Primary Genital HSV-2 Infection in Guinea Pigs:
Combination of Results From the First and Second Studies

| Treatment[a] | # Vaginal Virus Positive/ # Inoculated | Lesion Virus Titer-Day Area Under Curve | P-Value[b] | Mean Peak Lesion Virus Titer | P-Value[b] |
|---|---|---|---|---|---|
| Group 13 (untreated) | 12/12 | 13.1 | — | 3.3 | — |
| Group 11 | 12/12 | 14.4 | NS[c] | 3.5 | NS |
| Group 14[a] | 12/12 | 15.0 | NS | 3.7 | NS |
| Group 1[a] | 12/12 | 13.8 | NS | 3.3 | 0.07 |
| Group 7 | 12/12 | 13.1 | NS | 3.5 | NS |
| Group 12 | 12/12 | 13.1 | NS | 3.5 | NS |
| Group 18 | 12/12 | 16.3 | NS | 3.7 | NS |
| Group 6 (5% ACV/PEG) | 12/12 | 6.1 | <0.01[d] | 2.8 | 0.05 |
| Group 8 | 12/12 | 15.7 | NS | 4.1 | <0.05[e] |
| Group 9 | 12/12 | 12.7 | NS | 3.3 | 0.05 |
| Group 10 | 12/12 | 14.0 | NS | 3.3 | NS |
| Group 1[b] | 12/12 | 14.7 | NS | 3.7 | NS |
| Group 5 | 12/12 | 15.7 | NS | 3.7 | NS |
| Group 4 (BLISTEX ™) | 12/12 | 12.8 | NS | 3.5 | 0.07 |
| Group 2 | 12/12 | 14.5 | NS | 3.5 | NS |
| Group 19 | 12/12 | 14.5 | NS | 3.5 | NS |
| Group 15 | 12/12 | 16.1 | NS | 4.0 | NS |
| Group 16 | 12/12 | 15.6 | NS | 3.5 | NS |
| Group 17 | 12/12 | 13.2 | NS | 3.4 | NS |
| Group 3 | 12/12 | 14.7 | NS | 3.6 | NS |
| Group 20 | 12/12 | 12.6 | NS | 3.3 | NS |
| Group 14[b] | 12/12 | 15.8 | NS | 3.7 | NS |
| Group 21 | 12/12 | 10.5 | 0.07 | 3.0 | <0.01 |

[a]Treatment was initiated at 48 hours post-inoculation. Animals were treated 4 times per day for 10 days with 0.1 ml applied topically on external genitalia.
[b]All groups were compared with group 8 (vehicle only), except for group 8 which was compared with the untreated control animals (group 13).
[c]Not significantly different from group 8 or group 13.
[d]Lesion titer was decreased compared to vehicle treated animals (group 8).
[e]Lesion titer was increased compared to untreated control animals (group 13).

TABLE 6

Evaluation of Topical Antioxidants on Lesion Severity
in a Genital Primary HSV-2 Infection of Guinea Pigs:
Combination of Results From the First and Second Studies

| Treatment[a] | Lesion Score Day Area Area Under Curve | P-Value[b] | Mean Peak Lesion Score | P-Value[b] |
|---|---|---|---|---|
| Group 13 (untreated) | 22.5 | — | 2.5 | — |
| Group 11 | 21.1 | <0.05[c] | 2.4 | 0.07 |
| Group 14[a] | 33.4 | <0.05[d] | 3.5 | NS[e] |
| Group 1[a] | 38.5 | <0.01 | 3.5 | NS |
| Group 7 | 30.5 | NS | 2.8 | NS |
| Group 12 | 28.6 | NS | 2.8 | NS |
| Group 18 | 40.9 | <0.001 | 3.5 | NS |
| Group 6 (5% ACV/PEG) | 27.8 | NS | 2.7 | NS |
| Group 8 | 27.4 | <0.05 | 3.1 | NS |
| Group 9 | 32.7 | <0.05 | 3.2 | NS |
| Group 10 | 34.9 | <0.01 | 3.2 | NS |
| Group 1[b] | 37.4 | <0.01 | 3.4 | NS |
| Group 5 | 39.0 | 0.001 | 3.4 | NS |
| Group 4 (BLISTEX ™) | 38.6 | <0.01 | 3.7 | NS |

TABLE 6-continued

Evaluation of Topical Antioxidants on Lesion Severity
in a Genital Primary HSV-2 Infection of Guinea Pigs:
Combination of Results From the First and Second Studies

| Treatment[a] | Lesion Score Day Area Area Under Curve | P-Value[b] | Mean Peak Lesion Score | P-Value[b] |
|---|---|---|---|---|
| Group 2 | 39.4 | <0.001 | 3.5 | NS |
| Group 19 | 32.9 | <0.05 | 2.9 | <0.001 |
| Group 15 | 48.6 | <0.001 | 4.3 | NS |
| Group 16 | 36.7 | <0.01 | 3.4 | 0.06 |
| Group 17 | 17.6 | <0.01 | 2.4 | NS |
| Group 3 | 35.6 | <0.01 | 3.4 | NS |
| Group 20 | 28.8 | NS | 2.8 | NS |
| Group 14[b] | 27.3 | NS | 2.9 | NS |
| Group 21 | 35.6 | <0.01 | 3.2 | NS |

[a]Treatment was initiated at 48 hours post-inoculation. Animals were treated 4 times per day for 10 days with 0.1 ml applied topically on external genitalia.
[b]All groups were compared with group 8 (vehicle only), except for group 8 which was compared with the control animals (group 13).
[c]Not significantly different from group 8 or group 13.
[d]Lesion severity was increased significantly compared to the appropriate control animals (group 8 or group 13).
[e]Lesion severity was decreased significantly compared to vehicle treated animals (group 8).

TABLE 7

Lesion Scoring System for a
Primary Genital HSV Infection in Guinea Pigs

| Score | Description |
|---|---|
| 0.0 | Nothing, normal genital skin |
| 0.5 | Distinct erythema |
| 1.0 | 1–2 lesions |
| 1.5 | 3–5 lesions |
| 2.0 | More than 5 lesions |
| 2.5 | More than 5 lesions with some coalesced |
| 3.0 | Half of the area covered with coalesced lesions |
| 3.5 | Greater than half the area covered with coalesced lesions |
| 4.0 | As above with some ulceration (less than half the area ulcerated) |
| 4.5 | Half of the area ulcerated |
| 5.0 | Greater than half the area ulcerated |
| 4.5 | As above but with less than half the area crusted (scabbed over) |
| 4.0 | Greater than half of the area crusted/scabbed |
| 3.5 | As above but with loss of crust on less than half the area |
| 3.0 | Loss of crust on half to ¾ of the area |
| 2.5 | Some distinct (larger patches) crust still left |
| 2.0 | Less than above but greater than 5 small areas of crust |
| 1.5 | 3–5 small areas of crust left |
| 1.0 | 1–2 small areas of crust left |
| 0.5 | Distinct erythema |
| 0.0 | Nothing, normal genital skin |

TABLE 8

Cold Sore Product Groups In Mice and Guinea Pigs
Amount in Product (%)

| Product Group | Vitamin E | Unsaturated Fatty Acids | Sodium Pyruvate | Phenol | Lidocaine |
|---|---|---|---|---|---|
| 1 | 4.75 | 4.75 | 4.75 | 0.5 | 0.5 |
| 2 | 9.00 | 9.00 | 9.00 | 0.5 | 0.5 |
| 3 | 0.50 | 0.50 | 9.00 | 0.5 | 0.5 |
| 4 | | | Blistex ™ | | |
| 5 | 9.00 | 0.50 | 0.50 | 0.5 | 0.5 |
| 6 | | | Acyclovir | | |
| 7 | 4.7 | 0.00 | 4.75 | 0.5 | 0.5 |
| 8* | 0.00 | 0.00 | 0.00 | 0.0 | 0.0 |
| 9 | 0.50 | 9.00 | 9.00 | 0.5 | 0.5 |
| 10 | 4.75 | 4.75 | 0.00 | 0.5 | 0.5 |
| 11 | 0.50 | 0.50 | 0.50 | 0.5 | 0.5 |
| 12 | 9.92 | 4.75 | 4 75 | 0.5 | 0 5 |
| 13 | | | Untreated | | |
| 14 | 0.00 | 0.00 | 0.00 | 0.5 | 0.5 |
| 15 | 4.75 | 4.75 | 9.92 | 0.5 | 0.5 |
| 16 | 4.75 | 9.92 | 4.75 | 0.5 | 0 5 |
| 17 | 0.50 | 9.00 | 0.50 | 0.5 | 0.5 |
| 18 | 9.00 | 9.00 | 0.50 | 0.5 | 0.5 |
| 19 | 9.00 | 0.50 | 9.00 | 0.5 | 0.5 |
| 20 | 0.00 | 4.75 | 4.75 | 0.5 | 0.5 |

*base

TABLE 9

Cold Sore Product Guinea Pig Allocation

| Block | Product Group | Guinea Pig Number |
|---|---|---|
| 1 | 13 | 1–6 |
| | 11 | 7–12 |
| | 14 | 13–18 |
| | 1 | 19–24 |
| | 7 | 25–30 |
| | 12 | 31–36 |
| | 18 | 37–42 |
| | 6 | 43–48 |
| | 8 | 49–54 |
| | 9 | 55–60 |
| | 10 | 61–66 |
| | 1 | 67–72 |
| | 5 | 73–78 |
| | 4 | 79–84 |
| | 2 | 85–90 |
| | 19 | 91–96 |
| | 15 | 97–102 |
| | 16 | 103–108 |
| | 17 | 109–114 |

TABLE 9-continued

Cold Sore Product Guinea Pig Allocation

| Block | Product Group | Guinea Pig Number |
|---|---|---|
|   | 3  | 115–120 |
|   | 20 | 121–126 |
|   | 14 | 127–132 |
| 2 | 13 | 133–138 |
|   | 11 | 139–144 |
|   | 14 | 145–150 |
|   | 1  | 151–156 |
|   | 7  | 157–162 |
|   | 12 | 163–168 |
|   | 18 | 169–174 |
|   | 6  | 175–180 |
|   | 8  | 181–186 |
|   | 9  | 187–192 |
|   | 10 | 193–198 |
|   | 1  | 199–204 |
|   | 5  | 205–210 |
|   | 4  | 211–216 |
|   | 2  | 217–222 |
|   | 19 | 223–228 |
|   | 15 | 229–234 |
|   | 16 | 235–240 |
|   | 17 | 241–246 |
|   | 3  | 247–252 |
|   | 20 | 253–258 |
|   | 14 | 259–264 |

Statistical Analysis

The product (treatment) groups necessary to evaluate the optimal combination of the components of wound healing (vitamin E, unsaturated fatty acids, and sodium pyruvate) in the presence of phenol and lidocaine both at 0.5% by weight are incorporated in the experimental design. The design is a two-cubed factorial with six star points and one center point with the "control groups" Blistex™, Acyclovir, and untreated. The ranges of the three components in wound healing are all from 0.5% to 9.0% by weight. The product groups are listed in the random order presented to the investigator by member without any other identification.

The measures of efficacy considered for statistical analyses are the area under the lesion score "curve", the peak lesion score, the time to resolution of the lesions, the area under the viral liter "curve", and the peak viral titer. For each of these measures, the following statistical procedure was used. The treatment groups involving wound healing were all compared to the treatment groups Blistex™, Acyclovir, and base (Treatment Groups 4, 6, and 14, respectively). The factorial portion of the treatment groups were then investigated to determine a response model for the components of wound healing. The model was then used to predict what response could be expected for combinations of the wound healing components that were not statistically different from the minimum response.

Statistical Analysis of the Guinea Pig Model

The guinea pigs were allocated to the product groups in a random order to two blocks of six (6) guinea pigs per product group with repeats of Product Group Numbers 1 and 14 (design center point and base, respectively). The lesion scores for guinea pigs were recorded daily on days 3 through 19 on a scale of 0 to 5 in half-unit increments in increasing severity, while the titers were recorded on days 3, 4, 5, 6, 7, and 10 as actually measured on a continuous scale. The areas under the lesion and titer "curves" were calculated with the application of the trapezoidal role. Any missing values were considered as zero values on both scales. The peaks are the maximum values over the days observed. The time to resolution (healing time) of the lesions was defined as midway between the last day of non-zero responses and zero responses. If no resolution occurred in the time frame of the study, the time to resolution was the last day plus a half day.

For area under the lesion score "curve", Treatment Groups 11 and 17 were statistically different from Blistex™ (4) (p values of 0.0160 and 0.0034, respectively), Treatment Group 17 was almost statistically different from base (14) (p value of 0.0502), and no treatment groups were statistically different from Acyclovir (6). For peak lesion score, Treatment Groups 6, 7, 11, 12, 17, and 20 were statistically different from Blistex™ (p values of 0.0178, 0.0479, 0.0031, 0.0479, 0.0031, and 0.0297, respectively), Treatment Groups 11 and 17 were statistically different from base (p values of 0.0347 and 0.0347, respectively), and no treatment groups were statistically different from Acyclovir, except Blistex™. For time to lesion resolution, Treatment Groups 11, 17, and 20 were statistically different from Blistex™ (p values of 0.0185, 0.0099, and 0.0283, respectively), Treatment Groups 11, 17, and 20 were statistically different from base (p values of 0.0001, 0093, and 0.0312, respectively), and no treatment groups were statistically different from Acyclovir. For area under the viral titer "curve", no treatment groups were statistically different from Blistex™ and base, except Acyclovir, and all treatment groups were statistically different from Acyclovir. For peak viral titer, no treatment groups were statistically different from Blistex™ and base, and Treatment Groups 1, 3, 5, 8, 12, 14, 15, 18, 19, and 21 were statistically different from Acyclovir (p values of 0.0195, 0.0342, 0.0128, 0.0005, 0.0479, 0.0035, 0.0009, 0.0098, 0.0383, and 0.0174, respectively).

Statistical Analysis of the Mouse Model

The mice were planned to be allocated to the treatment (product) groups in a random order to one block of eight (8) mice per product group with repeats of Product Group Numbers 1 and 14 (design center point and base, respectively). The lesion scores for mice were recorded daily on days 1 through 14 on a scale of 0 to 4 in half-unit increments in increasing severity and the lesion areas were measured on a continuous scale on these same days. The areas under the lesion area and score "curves" were calculated with the application of the trapezoidal rule. Any missing values were considered as zero on both scales. The peaks are the maximum values over the days observed. The time to resolution of the lesions was defined as midway between the last day of non-zero lesion scores and zero lesion scores. If no resolution occurred in the time frame of the study, the time to resolution was the last day plus a half day. The actual allocation of the mice to the treatment groups was accomplished on four (4) exposure dates. This resulted in an unbalanced design across exposure days. The means presented in this report are adjusted for this unbalance, probably resulting in an increase in expected variation of the measures.

For area under the lesion area "curve", no treatment groups were statistically different from Blistex™ and base, except Acyclovir, and all treatment groups except Treatment Groups 5 and 15 were statistically different from Acyclovir. For peak lesion area, no treatment groups were statistically different from Blistex™ and base, except Acyclovir, and all treatment groups except Treatment Groups 17 and 19 were statistically different from Acyclovir. For area under the lesion score "curve", no treatment groups were statistically different from Blistex™ and base, except Acyclovir, and all treatment groups were statistically different from Acyclovir. For peak lesion score, no treatment groups were statistically different from Blistex™ and base, except Acyclovir, and all treatment groups were statistically different from Acyclovir. For time to resolution of lesion scores, no treatment groups were statistically different from Blistex™ and base, and all treatment groups were statistically different from Acyclovir (6).

Conclusions

Various combinations of the components of wound healing in the neighborhood of 9% unsaturated fatty acids, 0.5% sodium pyruvate, and 0.5% vitamin E statistically reduced the severity, intensity, and duration of coldsore lesions in the guinea pig model in comparison to Blistex™, Acyclovir, and base. Only Acyclovir statistically reduces these measures of efficacy in the mouse model.

Summary Analysis of The Data From

Study 1

Six to eight week old male SKH-1 hairless mice (Charles River) were infected with HSV-1 virus, McIntyre strain. Infection was achieved under general anesthesia (Ketamine, Xylazine) by the abrasion of a 1 cm square area (using a 25 gauge needle) centrally located on the dorsal surface of a mouse. Virus was then applied directly onto the abraded area (10 µl of a 1×10⁹ PFU/ml virus stock). Following inoculation of 10×10⁶ PFU of HSV-1 McIntyre strain by scarification of the epidermis, herpetic lesions developed by day 5 and persisted through day 12 post infection (p.i.). The viral lesions spread in a zosteriform pattern from the site of inoculation (middle of the back) to the abdominal area. By day 10, lesions were crusted over and complete healing generally occurred by day 12 p.i.

Individual mice were treated with test compounds starting on the afternoon of the infection day, and treatment was continued for 14 days. Treatments were administered at 7 a.m. and 4 p.m. each day and involved the use of a sterile cotton tipped applicator in such a manner that the affected area was evenly coated with the test compound. If no lesions were visible, only the site of infection was treated. Data including lesion scores, number of lesions, and lesion areas were recorded during the 7 a.m. treatment session. Each animal was recorded as having one of five possible scores:

0, no signs; 1, redness and swelling; 2, single lesion; 3, multiple lesions; 4, a spread of lesions in a dermatome pattern. In addition, the actual lesion area on the skin was measured using a micrometer (x and y axial values for each lesion were obtained in millimeters and then multiplied together to give the lesion area). For analysis, the individual lesion scores or areas within a treatment group were averaged on a daily basis. The scores are set out in the Table below.

| 1<br>Treatment<br>Groups | 2<br>Lesion<br>Size<br>(mm²) | 3<br>Mean Lesion<br>Peak Area<br>Severity<br>(mm²) | 4<br>Sum of Lesion<br>Peaks 0–4<br>Scale | 5<br>Mean Peak<br>Averages<br>Severity | 6<br>Days to<br>Healing |
|---|---|---|---|---|---|
| 1 - Control | 130.8 | 51.1 | 17.5 | 3.38 | 12 |
| 2 - Pyruvate & Vitamin E | 110.4 | 40.9 | 18.5 | 3.14 | 12 |
| 3 - Vitamin E & Fatty Acids | 100.2 | 36.9 | 16.8 | 3.43 | 11.8 |
| 4 - Pyruvate & Fatty Acids | 128.7 | 48.3 | 18.1 | 3.24 | 12 |
| 5 - Pyruvate & Vitamin E & Fatty Acids (wound healing composition) | 87.8 | 32.2 | 15.2 | 3.01 | 11.9 |

Table of Results

Inspection of the results clearly shows that the three component wound healing composition treatment achieved the best results in four of the five measures (lesion size, lesion severity, sum of lesion peaks, and lesion peak severity).

The following proposed model was established to determine unexpected results from the wound healing composition.

Change from control=Vitamin E+Fatty Acids+Sodium Pyruvate+ Synergy where Vitamin E represents the single component contribution of Vitamin E, Fatty Acids is the single component effect of Fatty Acids, Sodium Pyruvate is the single component effect of Sodium Pyruvate, and Synergy is the unexplained wound healing composition synergy effect of the three components together.

Applying the data set out above in column 2 of the Table of Results (LA–D+M) in this model provides the following results.

| Lesion Size From (Column 2) in the Table of Results. | |
|---|---|
| Vitamin E + Sodium Pyruvate | = 110.4–130.8 mm² |
| Vitamin E + Fatty Acids | = 100.2–130.8 mm² |
| Fatty Acids + Sodium Pyruvate | = 128.7–130.8 mm² |
| Vitamin E + Fatty Acids + Sodium Pyruvate + Synergy | = 87.8–130.8 mm² |

This model now provides a linear equation system with four equations and four unknowns, which can be solved by standard mathematical techniques to give:

| | |
|---|---|
| Vitamin E | = −24.5 |
| Sodium Pyruvate | = +4 |
| Fatty Acids | = −6.1 |
| Synergy | = −16.4 |

Solving for the remaining columns of the Table of Results in this model provides the following results.

Table of Results of Contribution of Each Component

| 1<br>Individual<br>Effects | 2<br>Lesion<br>Size<br>(mm²) | 3<br>Mean Lesion<br>Peak Area<br>Severity<br>(mm²) | 4<br>Sum of Lesion<br>Peaks 0–4<br>Scale | 5<br>Mean Peak<br>Averages<br>Severity | 6<br>Days to<br>Healing |
|---|---|---|---|---|---|
| 1 - Vitamin E | −24.5 | −10.8 | −0.15 | 0.0 | −0.1 |
| 2 - Pyruvate | +4.0 | +0.6 | +1.15 | −0.2 | +0.1 |
| 3 - Fatty Acids | −6.1 | −3.4 | −0.55 | 0.0 | −0.1 |
| 5 - Pyruvate &<br>Vitamin E & Fatty Acids<br>(wound healing composition) | −16.4 | −5.3 | −2.75 | −0.2 | 0.0 |

Comparing the predicted effect of the wound healing composition with the actual effect of wound healing composition gives the difference in effect of wound healing composition and the % synergy difference set out below.

Table of Results Showing Contribution of Wound Relaxing Composition

| 1 | 2<br>Lesion<br>Size<br>(mm²) | 3<br>Mean Lesion<br>Peak Area<br>Severity<br>(mm²) | 4<br>Sum of Lesion<br>Peaks 0–4<br>Scale | 5<br>Mean Peak<br>Averages<br>Severity | 6<br>Days to<br>Healing |
|---|---|---|---|---|---|
| Predicted Effect<br>of Wound Healing<br>Composition | −26.6 | −13.6 | +0.45 | −0.2 | 0 |
| Actual Effect<br>of Wound Healing<br>Composition | −43.0 | −18.9 | −2.3 | −0.4 | +0.1 |
| Difference in Effect<br>of Wound Healing<br>Composition | −16.4 | −5.3 | −2.75 | −0.2 | +0.1 |
| % Synergy Difference | 61% | 39% | 611% | 100% | 0 |

As shown in the Table of Results Showing Contribution of Wound Healing Composition (I.A−D+M2), the wound healing composition reduced four of the five lesion measurements greater than was predicted for the three component effect. The wound healing composition reduced lesion sizes 61% more than was predicted for the three component effect. The wound healing composition reduced mean lesion peak are (severity) 39% greater than was predicted for the three component effect. The wound healing composition reduced the sum of lesion peaks 611% greater than was predicted for the three component effect. The wound healing composition also reduced mean peak averages 100% greater than was predicted for the three component effect. The wound healing composition did not reduce the days to healing in this model because mice require approximately five days to develop lesions, three days to respond (inflammatory phase), leaving only four days to heal. The effect of the wound healing composition to reduce is small in this model because the wound healing composition is not an antiviral agent and can only enhance healing after the inflammatory phase is over. In these examples, the antiviral agent was phenol, which does not effectively reduce viral titers, and lesions do not heal until the viral infection is reduced. In summary, the wound healing composition provided greater results than was predicted for the three component. The wound healing composition was synergistic in reducing viral lesions and severity but did not reduce times to healing in this model.

b. Study 2

This study is a summary of findings from an evaluation of a cold sore treatment product conducted among 20 patients who presented with the onset of symptoms of herpes labialus. The results from this study are illustrated in examples 22–41 below.

Twenty subjects were enrolled and completed the expert study. Each subject was administered a lip balm containing the wound healing composition, 2% sodium pyruvate, 2% vitamin E acetate, and 4% chicken fat, in a Lubriderm lotion base. Enrollment was based on the presence of vesiculation and a positive vital assay for herpes. Treatment with the study product began immediately following the positive viral assay and continued for up to two (2) weeks depending upon when full resolution, i.e, elimination of scabbing, occurred.

Table 1 (not shown) is a summary of daily diary responses which shows that pain, itching, and swelling predominated over the first three (3) days (Baseline, Day 2 and Day 3) after vesicle formation had occurred and thereafter diminished. Pain was no longer present in any subject by Day 7 and in only one (1) subject by Day 5. Itching extended slightly further with four (4) subjects still reporting mild itching by Day 6, two (2) subjects by Days 7 and 8, one (1) subject by Day 9 and no subjects by Day 10. The pattern for swelling closely paralleled that for pain with only one (1) subject reporting mild swelling on Days 6 and 7.

Results of clinical examinations are summarized in Table 2 (not shown). It is important to note in examining these tables that apparent day-to-day fluctuations in data are due to 1) the every-other-day visit schedule and 2) the fact that subjects were not on the same visit schedule. (Depending upon the day of the week on which subjects were enrolled, their return visits would be adjusted to accommodate the weekends). Thus, data can be analyzed only for general trends.

Results show that vesiculation persisted in approximately two-thirds (⅔) of the patients to Day 3 and thereafter diminished significantly. There was no evidence of ulceration occurring with any subject at any interval. Scabbing was present in more than half of the subjects by Day 3 and persisted at a relatively high level through Day 8 after which it diminished significantly. Full resolution was noted for seven (7) subjects on Day 8 with an additional six (6) subjects on Day 9 (two subjects), Day 10 (three subjects) and Day 11 (one subject). The remaining seven (7) subjects were found to be fully resolved on Day 13 (four Subjects), Day 14 (two subjects) and Day 15 (one subject). When asked at their examination visits to assess pain, six (6) subjects reported mild pain on Day 3 with no pain reported by any subject beyond that interval. The severity of pruritus diminished significantly from Baseline (5 moderate and 2 severe) to Day 3 (1 moderate and no severe) with a few subjects reporting mild pruritus between Days 4 and 8.

Table 3 (not shown) is a statuary of the comparison of resolution time as determined by clinical examination and by the patient's recollection of historical resolution time from prior incidence. No advantage in time to cold sore resolution is evident from examination of this data. The number of days required for scabbing to occur was also clinically observed and, in those instances in which the patient defined resolution as scab formation, there still appeared to be no advantage to the study product.

Subjective responses to questionnaires are summarized in Table 4 (not shown). Thirteen (13) of 20 subjects regarded the product as excellent, six (6) as good and one (1) poor. Eleven of the 13 subjects who rated the product as excellent claimed that it worked fast or faster than other medications. Fourteen of the study participants regarded the cold sore as not as bad as normal, five (5) regarded it as about the same and one (1) as worse than normal. Regarding relief of pain, discomfort and/or soreness, 12 of 20 subjects regarded it as excellent and eight (8) as good.

In conclusion, under the conditions employed in this study, there were no apparent increases in healing rate as the result of the use of the study product in the treatment of cold sores. However, the product was perceived by approximately two-thirds (⅔) of the patients to be excellent and to work fast or faster than other medications. In addition, the majority of subjects perceived the cold sore to be not as bad as normal and rated the product as excellent for the relief of pain, discomfort and/or soreness. Finally only one (1) adverse event occurred, namely, one (1) subject who developed an additional cold sore lesion. However, the development of the additional lesion is not regarded as product-related.

5. Examples of Sunscreen-Wound Healing Compositions

Study 1

SUMMARY

This study was conducted to determine the potential of formulations with moisturizers and antioxidants to effectively prevent or reduce solar simulator derived erythema in normal volunteers, and whether the erythema once manifested would be ameliorated with the test product. The concept was to develop a product that could protect and heal skin from UV damage without the use of UV sunscreen blockers, i.e., PABA, oxybenzone, etc. Such protection would be extremely beneficial for cold sores and psoriatic lesions since UV exposure is known to exacerbate these skin diseases.

Two products, a lotion and a cream, were evaluated for their sun protection potential (Phase I) and for product efficacy in the treatment of solar simulator induced erythema (Phase II). Ten subjects completed Phase I of the study. Thirteen subjects completed Phase II of the study. An 8% Homosalate solution served as a control in Phase I.

Under the conditions employed in this study, both the cream and lotion test products provided low level sun protection (SPF values less then 2) and minor improvements in UV-induced erythema as compared with irradiated control sites not treated with test products.

INTRODUCTION

Objective

This study was conducted to determine the potential for two wound healing compositions containing formulations for preventing solar simulator derived erythema in normal volunteers and whether, the erythema once manifested, would be ameliorated with the test wound healing composition product.

Rationale

The demands for sun screen and skin care products make up the fastest growing cosmetics sector in the United States. The growth in sun care products is continuing because overexposure to the sun is believed to produce many ill-effects on the skin. It is known that even high sun protectant factor (SPF-15) products do not fully protect human skin against cumulative skin damage. The nature of this damage is believed to be associated with the presence of various "reactive" oxygen species. A product to reduce the levels of photogenerated reactive oxygen species should provide meaningful long term skin benefits. The purpose of this experiment was to determine whether a formula which contains moisturizers and antioxidants could effectively eliminate or ;educe the damage produced from overexposure to UV light. The objective was also to determine if applying the product before and/or after UV damage would provide beneficial effects to the damaged area.

Background

Two (2) products were submitted for testing in this two phase study. Each study group consisted of ten (10) volunteer subjects. The products were considered reasonably safe for testing on human subjects. The protocol followed for Phase I was that established by the OTC panel and published in the Federal Register, Aug. 25, 1978 (Vol 43, No. 166).

MATERIALS AND METHODS

A sample of each test material(s) was reserved and stored for a period of five (5) years. At the conclusion of the clinical study, the remaining test material(s) was discarded. All information regarding the receipt, storage and disposition of the material(s) was also recorded on a Clinical Material Record form. All test materials were kept in a locked product storage room accessible to clinical staff members only.

Test Materials

| | |
|---|---|
| Product (1) Identification: | Lotion |
| Description: | White Lotion |
| Quantity Provided: | 1 × 6 oz. |
| Amount applied: | 0.1 g/50 cm² |
| Product (2) Identification: | Cream |
| Description: | Yellow Cream |
| Quantity Provided: | 1 × 4 oz. |
| Amount applied: | 0.1 g/50 cm² |

Product (1) was Lubriderm™ Lotion containing 2% sodium pyruvate, 1% vitamin E, and 1% chicken fat. Product (2) was Lubriderm™ Cream containing aquaphor/petrolatum cream with 10% sodium pyruvate, 5% vitamin E, and 5% chicken fat.

EXPERIMENTAL DESIGN

Inclusion Data

Individuals included in the study were eighteen (18) years of age or older; were fair and had uniformly-colored skin on the lower thoracic area of the back which would allow a discernible erythema; were free of any systemic or dermatologic disorder which would interfere with the test results; had completed a phototesting Medical Screening form and a Medical/Personal History form; and had read, understood, and signed an informed consent agreement.

Exclusion Data

Individuals excluded in the study were individuals who had any visible skin disease at the test site which would have interfered with the test results; were receiving systemic or topical drugs or medication such as antihistamines or anti-inflammatories which might have interfered with the test results; were taking medication suspected of causing photobiological reactions (i.e., tetracyclins, thiazides, etc.); had active atopic dermatitis or eczema; had psoriasis; were currently under treatment for asthma; had cataracts; had a history of skin cancer; were pregnant or planning a pregnancy or nursing a child; or has a known sensitivity to cosmetics, skin care products, or topical drugs as related to the products being tested.

Light Source

A Xenon Arc Solar Simulator (150W) was used which has a continuous emission spectrum in the UVA and UVB range (290 to 400 nanometers). Less than 1% of its total energy was composed of "non-solar" wavelengths below 290 nm. The output was monitored daily, using the Robert-Berge meter. Additional measurements of the energy output were taken and recorded as needed.

Definitions of Terms in Clinical Evaluation

MED, Minimal Erythema Dose—The time of light exposure necessary to produce a minimal perceptible erythema (redness) on the skin, discernible sixteen (16) to twenty four (24) hours later.

SPF, Sun Protection Factor—The ultraviolet energy required to produce an MED on protected skin, divided by the ultraviolet energy required to produce an MED on unprotected skin.

PCD, Product Category Designation

1. Minimal Sun Protection Product—Sunscreen products that provide an SPF value of 2 to 4, and offer the least protection from sunburning, but permit suntanning.

2. Moderate Sun Protection Product—Sunscreen products that provide an SPF value of 4 to 6, and offer moderate protection from sunburning, and permit some suntanning.

3. Extra Sun Protection Product—Sunscreen products that provide an SPF value of 6 to 8, and offer extra protection from sunburning, and permit limited suntanning.

4. Maximal Sun Protection Product—Sunscreen products that provide an SPF value of 8 to under 15, and offer maximal protection from sunburning, and permit little or no suntanning.

5. Ultra Sun Protection Product—Sunscreen products that provide an SPF value of 15 or greater, and offer the most protection from sunburning and permit no suntanning.

Phase I—Determination of Minimal Erythemal Dose (MED)

MED is defined as the time of light exposure required to produce a minimal perceptible erythema reaction discernible sixteen (16) to twenty-four (24) hours after irradiation using a standardized ultraviolet light source that emits UVB (290–320 nm) as all or part of its emission spectrum. Subjects who were candidates for this testing have skin types commonly referred to as Fitzpatrick skin types, of Category I, II, or III according to the following definitions:
Category I Always burns easily, never tans.
Category II Always burns easily, tans minimally.
Category III Burns moderately, tans gradually (light brown).
Category IV Burns minimally, always tans well (moderate brown).
Category V Rarely burns, tans very well (moderate brown).
Category VI Never burns, deeply pigmented.

An area, other than the test site, was drawn with a marking pen on the subject's back and divided into five (5) equal sites. The anticipated MED was estimated from skin type (I, II, or III) of the individual and the irradiation size calculated based on energy output of the Xenon lamp. The (5) sites were irradiated on the basis of a geometric progression of 1.25, i.e., each site receiving 25% more exposure than the site to its left. Sixteen (16) to twenty-four (24) hours later, the MED was determined by establishing the site which exhibited the least amount of perceptible erythema.

SPF Determination

The test material was applied as follows:

A 50 cm² area was marked on the back-of the subject Then, a uniform application of 0.1 g or ml or product was applied to the area with careful spreading and gentle but thorough robbing over the entire marked area. The product was permitted to dry for fifteen (15) to thirty (30) minutes.

The MED previously determined on untreated skin was multiplied by the expected SPF of the product. For example, for an MED of twenty-five (25) seconds, and a test product whose SPF is estimated at two (2), the median exposure time for this product would be 2×25 seconds=50 seconds.

The irradiation for site exposure was again calculated on the basis of a geometric progression of 1.25 with the site to the right receiving more irradiation than the site to its left. The sites were then exposed to ultraviolet light from the solar simulator. The procedure was repeated using the control product, an 8% homosalate standard.

In addition, an area of untreated skin was exposed to ultraviolet light from the solar simulator to again determine the MED of unprotected skin. Sixteen (16) to twenty-four (24) hours later, the MED for the treated and untreated skin was determined and the SPF calculated.

Following exposure, all immediate responses were noted for reddening, vesiculation, tanning, darkening of skin, etc.

Study Flow Chart

| Day | |
|---|---|
| 1 | Obtained informed consent; completed medical screening form; conducted UV irradiation for MED determination. |
| 2 | Determined MED; calculated UV exposure times; irradiated test product site, control product site, and untreated sites for second MED determination. |
| 3 | Evaluated all sites; calculated SPF. |

To assure the uniform evaluation of sunscreen products, a standard sunscreen was used concomitantly in the test procedure, specifically in step 2, irradiated control product site. This control product was an eight percent (8%) homosalate preparation.

Rejection of Test Data

There were three (3) reasons for rejection of test data.

1. Sometimes the exposure either failed to elicit an MED response on the treated or unprotected skin sites or elicited responses at all five (5) irradiated sites. In either event, that test was considered a technical failure and had to be discarded. If the subject reacted to one or more exposures on the unprotected control site, but not on the treated site, then a minimal estimate could be obtained. However, this estimate would not be used in assessing the Mean of the SPF values.

2. The response on the treated sites was randomly absent, which indicated the product was not spread evenly. Therefore, no assessment of protection was possible.

3. If the SPF values obtained experimentally were well outside the expected range, the values were discarded.

Phase II—Treatment of Erythema

Ten subjects whose MEDs were determined by the previous method (Phase I) had twelve test site areas delineated on the back: five sites were exposed to one times the MED; five sites were exposed to two times the MED, and two sites were not exposed to UV light. The cream test product was applied (0.1 g/50 cm$^2$) and rubbed into two of the 1×MED sites, two of the 2×MED sites, and to one of the unexposed sites. The lotion test product was applied to two separate 1×MED sites, two separate 1×MED sites, and one separate unexposed site. The two remaining exposed areas (one 1×MED and one 2×MED) served as controls and did not have product applied. All sites were covered, but not occluded, with a gauze dressing. Application of the product to the same sites was repeated approximately six hours later and the following mornings and afternoons for four consecutive days. Evaluation of the test sites was made each afternoon prior to product application by a trained clinical evaluator who had no participation in any other aspect of the study procedure. A final evaluation was made on the morning of Day 8, the last product application having occurred on the previous Friday (Day 4). Evaluations of each test site were made according to the following scale:

0.0—minimal or doubtful erythema 0.5—faint erythema 1.0—distinct, but mild erythema 2.0—moderate erythema

Results and Discussion

Phase I

Two (2) products, a lotion and a cream, were submitted for evaluation of their sun protective potential. A total of ten (10) subjects between the ages of 25 and 54 were enrolled and completed the evaluation of the test products and the homosalate control.

A low level of sun protection was observed; an SPF value of 1.9+0.2 (N=9) was obtained for the cream and a value of 1.7+0.3 (N=8) was obtained for the lotion.

Phase II

The same two (2) products were also evaluated for their product efficacy in the treatment of solar-simulator induced erythema. A total of fifteen (15) subjects between the ages of 20 and 66 were enrolled and thirteen (13) subjects completed the study. Two (2) subjects discontinued for personal reasons.

Product treated sites exposed to two MEDs of irradiation exhibited minor improvements in resolution of erythema as compared to the irradiated non-product treated sites. Comparisons between erythema levels at Day 2 and subsequent evaluation days was used as the basis of analysis. Day 2 was selected as the baseline day since increases in erythema from Day 1 to Day 2 occurred frequently but appeared to have stabilized by Day 2. Comparison of erythema results on Days 3, 4, 5 and 8 to Day 2 suggest a minor acceleration in the resolution of erythema responses. Specifically, in 12 instances among the 52 comparisons (23%), thirteen (13) subjects with 4 comparisons each, comparing Day 2 to Days 3, 4, 5, and 8, reductions in erythema associated with both the cream and the lotion were manifested.

While it is noted with caution that both the proportion and degree of improvement associated with the product test sites were minor, it is also noteworthy that there was only one instance out of the total of one hundred four (104) comparisons for the two products in which the control site showed greater degree of improvement than the test site. Furthermore, this one improvement occurred only for the Day 8/Day 2 comparison.

The cream product showed improvement over the control site in two subjects for all four comparison intervals, in one subject at two of the four intervals, and two other subjects at one of the four intervals. Similarly, the lotion product showed improvement in one subject at all four intervals, in one subject at three intervals, in two subjects at two intervals, and, in one subject at one interval. Conversely, eight of thirteen subjects showed no differences at any of the four intervals in comparisons between the test product sites and the control sites for both the cream and the lotion products. While the effects noted here must again be stressed as minimal, it is, nonetheless, noteworthy that improvements, where noted, favored effects of the test products over the control and not the opposite: twenty-four instances of possible positive effects from the two test products compared to one such possible instance at the control site.

A similar analysis of data associated with the 1×MED sites did not provide the same results due to the low level and variable erythematous responses observed. This is believed to be due to the fact that minor perturbations of ultra violet lamp output are likely to be sufficient to result in sub-erythema and mildly erythema responses even on the same subject at adjoining sites.

In conclusion, under the conditions employed in this clinical study, both the cream and lotion test products provided low-level sun protection and indications of minor improvement in UV-induced erythema as compared with irradiated control sites not treated with test products However, it is clear that these effects are, at best, minor and that verification of efficacy would require a larger proportion of study subjects. Formulation changes (vehicle, level of wound healing composition) or product application (e.g., multiple applications or occlusive conditions) may also be worth exploring.

We claim:

1. A therapeutic bioadhesive-wound healing composition which comprises a therapeutically effective amount of a bioadhesive agent and a wound healing composition, wherein the wound healing composition comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells; wherein components a, b, and c are present in amounts sufficient to synergistically enhance wound healing.

2. The composition according to claim 1, wherein the bioadhesive agent is selected from the group consisting of polyacrylic acids crosslinked with polyhydroxy compounds, carboxymethylcellulose, methylcellulose, guar gum, and polycarbophils.

3. The composition according to claim 2, wherein the bioadhesive agent is a polycarbophil.

4. The composition according to claim 1, wherein the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, pharmaceutically acceptable salts of pyruvic acid, prodrugs of pyruvic acid, and mixtures thereof.

5. The composition according to claim 4, wherein the pyruvate is sodium pyruvate.

6. The composition according to claim 1, wherein the antioxidant is selected from the group consisting of all forms of Vitamin A; all forms of carotene; all forms of Vitamin C; all forms of Vitamin E; Vitamin E esters which readily undergo hydrolysis to Vitamin E; prodrugs of Vitamin A, carotene, Vitamin C, and Vitamin E; pharmaceutically acceptable salts of Vitamin A, carotene, Vitamin C, and Vitamin E; and mixtures thereof.

7. The composition according to claim 6, wherein the antioxidant is Vitamin E acetate.

8. The composition according to claim 1, wherein the mixture of saturated and unsaturated fatty acids comprises animal and vegetable fats and waxes.

9. The composition according to claim 8, wherein the mixture of saturated and unsaturated fatty acids is selected from the group consisting of human fat, chicken fat, cow fat, sheep fat, horse fat, pig fat, and whale fat.

10. The composition according to claim 9, wherein the mixture of saturated and unsaturated fatty acids comprises lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid.

11. The composition according to claim 1, wherein the bioadhesive agent is present in the therapeutic wound healing composition in an amount from about 0.01% to about 90%, by weight of the therapeutic wound healing composition.

12. The composition according to claim 1, wherein pyruvate is present in the therapeutic wound healing composition in an amount from about 10% to about 50%, by weight of the therapeutic wound healing composition.

13. The composition according to claim 1, wherein the antioxidant is present in the therapeutic wound healing composition in an amount from about 0.1% to about 40%, by weight of the therapeutic wound healing composition.

14. The composition according to claim 1, wherein the mixture of saturated and unsaturated fatty acids is present in the therapeutic wound healing composition in an amount from about 10% to about 50%, by weight of the therapeutic wound healing composition.

15. A method for treating a wound in a mammal with comprises administering to a mammal in need thereof:

a therapeutic bioadhesive-wound healing composition which comprises:

(1) a bioadhesive agent; and (2) a therapeutically effective amount of a wound healing composition comprising:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells; wherein components a, b, and c are present in synergistic amounts sufficient to synergistically enhance wound healing.

16. An augmented bioadhesive-wound healing composition which comprises:

(A) a therapeutic bioadhesive-wound healing composition which comprises:

(1) a therapeutically effective amount of a bioadhesive agent; and (2) a wound healing composition which comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and, (B) a medicament useful for treating wounds.

17. The augmented bioadhesive-wound healing composition according to claim 16, wherein the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, respiratory bursting inhibitors, inhibitors of prostaglandin synthesis, antimicrobial agents, antiseptic agents, anesthetic agents, cell nutrient media, burn relief medications, sun burn medications, insect bite and sting medications, wound cleansers, wound dressings, scar reducing agents, and mixtures thereof.

18. The augmented bioadhesive-wound healing composition according to claim 16, wherein the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents.

19. The augmented bioadhesive-wound healing composition according to claim 17, wherein the medicament useful for treating wounds is an immunostimulating agent selected from the group consisting of betafectin™ and Freund's complete adjuvant.

20. The augmented bioadhesive-wound healing composition according to claim 16, wherein the medicament useful for treating wounds is a cytotoxic agent selected from the group consisting of epithelial cell cohesiveness reducers, dermatological abradants, anti-inflammatories, lipid regulating agents, centrally acting anticholinesterases, chemotherapeutic drugs, and gastric irritants.

21. The augmented bioadhesive-wound healing composition according to claim 17, wherein the medicament useful for treating wounds is an antiviral agent selected from the group consisting of acyclovir, foscarnet sodium, ribavirin, vidarabine, ganeiclovir sodium, zidovudine, phenol, amantadine hydrochloride, and interferon alfa-n3.

22. The augmented bioadhesive-wound healing composition according to claim 17, wherein the medicament useful for treating wounds is an antikeratolytic agent selected from the group consisting of salicylic acid, lactic acid, and urea.

23. The augmented bioadhesive-wound healing composition according to claim 17, wherein the medicament useful for treating wounds is an anti-inflammatory agent selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone diproprionate, betamethasone diproprionate, hydrocortisone, cortisone, dexamethasone, prednisone, methyl prednisolone, and prednisolone.

24. The augmented bioadhesive-wound healing composition according to claim 17, wherein the medicament useful for treating wounds is an antifungal agent selected from the group consisting of lactic acid, sorbic acid, miconazole, clotrimazole, tioconazole, terconazole, povidone-iodine, and butoconazole.

25. The augmented bioadhesive-wound healing composition according to claim 17, wherein the medicament useful for treating wounds is tretinoin.

26. The augmented bioadhesive-wound healing composition according to claim 17, wherein the medicament useful for treating wounds is a sunscreen agent selected from the group consisting of ethylhexyl p-methoxycinnamate, octyl methoxycinnamate, octyl dimethyl p-aminobenzoic acid, 2-ethylhexyl salicylate, octyl salicylate, menthyl anthranilate, octocrylene, padimate o, titanium dioxide, urea, and oxybenzone.

27. The augmented bioadhesive-wound healing composition according to claim 17, wherein the medicament useful for treating wounds is a buffering agent to maintain the pH of dermatitis in a range from about 5 to about 8 together with an anti-inflammatory agent.

28. The augmented bioadhesive-wound healing composition according to claim 17, wherein the medicament useful for treating wounds is a topical antihistamine agent selected from the group consisting of diphenhydramine hydrochloride and pramoxine hydrochloride.

29. The augmented bioadhesive-wound healing composition according to claim 17, wherein the medicament useful for treating wounds is an antibacterial agent selected from the group consisting of bismuth compounds, such as bismuth aluminate, bismuth subcitrate, bismuth subgalate, bismuth subsalicylate; the sulfonamides; the nitrofurans, such as nitrofurazone and nitrofurantoin; furazolidone, metronidazole, tinidazole, nimorazole, benzoic acid, the aminoglycosides; such as gentamicin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and chloramphenicol, and clidamycin.

30. A method for treating a wound in a mammal with an augmented bioadhesive-wound healing composition which comprises administering to a mammal in need thereof:
  (A) a therapeutic augmented bioadhesive-wound healing composition which comprises:
    (1) a therapeutically effective amount of a bioadhesive agent;
    (2) a wound healing composition which comprises:
      (a) pyruvate selected from the group consisting of pyruvic acid, pharmaceutically acceptable salts of pyruvic acid, and mixtures thereof;
      (b) an antioxidant; and
      (c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and,
    (3) a medicament useful for treating wounds.

31. The method according to claim 29, wherein the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, bioadhesive agents, respiratory bursting inhibitors, inhibitors of prostaglandin synthesis, antimicrobial agents, antiseptic agents, anesthetic agents, cell nutrient media, burn relief medications, sun burn medications, insect bite and sting medications, wound cleansers, wound dressings, scar reducing agents, and mixtures thereof.

32. A bioadhesive-wound healing pharmaceutical composition which comprises:
  (A) a therapeutic bioadhesive-wound healing composition which comprises:
    (1) a therapeutically effective amount of a bioadhesive agent; and
    (2) a wound healing composition which comprises:
      (a) pyruvate selected from the group consisting of pyruvic acid, pharmaceutically acceptable salts of pyruvic acid, and mixtures thereof;
      (b) an antioxidant; and
      (c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and
  (B) a pharmaceutically acceptable carrier selected from the group consisting of pharmaceutical appliances, bioadhesives, and occlusive vehicles.

* * * * *